US009828360B2

(12) United States Patent
Allen et al.

(10) Patent No.: US 9,828,360 B2
(45) Date of Patent: Nov. 28, 2017

(54) PYRROLIDINYL UREA, THIOUREA, GUANIDINE AND CYANOGUANIDINE COMPOUNDS AS TRKA KINASE INHIBITORS

(71) Applicant: Array BioPharma Inc., Boulder, CO (US)

(72) Inventors: Shelley Allen, Boulder, CO (US); Steven Wade Andrews, Boulder, CO (US); James F. Blake, Boulder, CO (US); Barbara J. Brandhuber, Boulder, CO (US); Kevin Ronald Condroski, San Diego, CA (US); Julia Haas, Boulder, CO (US); Yutong Jiang, Boulder, CO (US); Timothy Kercher, San Diego, CA (US); Gabrielle R. Kolakowski, Boulder, CO (US); Shannon L. Winski, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 46 days.

(21) Appl. No.: 14/442,522

(22) PCT Filed: Nov. 13, 2013

(86) PCT No.: PCT/US2013/069838
§ 371 (c)(1),
(2) Date: May 13, 2015

(87) PCT Pub. No.: WO2014/078378
PCT Pub. Date: May 22, 2014

(65) Prior Publication Data
US 2016/0297796 A1   Oct. 13, 2016

Related U.S. Application Data

(60) Provisional application No. 61/725,936, filed on Nov. 13, 2012.

(51) Int. Cl.
*C07D 401/12* (2006.01)
*C07D 403/12* (2006.01)
*C07D 417/12* (2006.01)
*C07D 401/14* (2006.01)
*C07D 413/12* (2006.01)
*C07D 417/14* (2006.01)

(52) U.S. Cl.
CPC ......... *C07D 401/12* (2013.01); *C07D 401/14* (2013.01); *C07D 403/12* (2013.01); *C07D 413/12* (2013.01); *C07D 417/12* (2013.01); *C07D 417/14* (2013.01)

(58) Field of Classification Search
None
See application file for complete search history.

(56) References Cited

U.S. PATENT DOCUMENTS 5,849,779 A   12/1998   Hirota et al.
5,998,424 A   12/1999   Galemmo, Jr. et al.
(Continued)

FOREIGN PATENT DOCUMENTS

EP   0761658 A1   12/1997
EP   1043995 B1   11/2006
(Continued)

OTHER PUBLICATIONS

Brodeur, Garrett. Clin Cancer Res. 2009 15(10) 3244-3250.*
UCSF Medical Center. Neurological Disorders. (2016) Web: <https://www.ucsfhealth.org/conditions/neurological_disorders/>.*
Infections: MedlinePlus. (2016) Web: < https://www.nlm.nih.gov/medlineplus/infections.html>.*
MedicineNet.com (2004) Web: <http://www.medterms.com.*
Byrn, Stephen. Solid-State Chemistry of Drugs, 2nd Ed. (1999), Ch. 11 Hydrates and Solvates, 233-247.*
Morissette, Sherry. Adv. Drug Delivery Rev. 2004, 56, 275-300.*
Rouhi, A. Maureen. Chem. & Eng. News, (2003), 81(8), 32-35.*
Banker, Gilbert. Modern Pharmaceutics 3rd ed. Marcel Dekker, Inc. New York, 1996.*
Desmet, C. J. Cell. Mol. Life Sci. 63 (2006) 755-759.*
(Continued)

*Primary Examiner* — Deepak Rao
*Assistant Examiner* — Laura Daniel
(74) *Attorney, Agent, or Firm* — Viksnins Harris Padys Malen LLP; Sarah S. Mastous

(57) ABSTRACT

Compounds of Formula (I): or stereoisomers, tautomers, or pharmaceutically acceptable salts, or solvates or prodrugs thereof, where $R^1$, $R^2$, $R^a$, $R^b$, $R^c$, $R^d$, X, Ring B, and Ring C are as defined herein, and wherein Ring B moiety and the NH—C(=X)—NH moiety are in the trans configuration, are inhibitors of TrkA kinase and are useful in the treatment of diseases which can be treated with a TrkA kinase inhibitor such as pain, cancer, inflammation/inflammatory diseases, neurodegenerative diseases, certain infectious diseases, Sjogren's syndrome, endometriosis, diabetic peripheral neuropathy, prostatitis and pelvic pain syndrome.

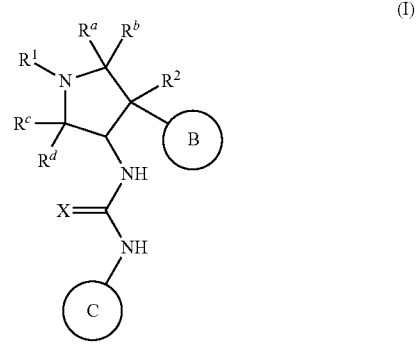

(I)

17 Claims, No Drawings

(56) References Cited

U.S. PATENT DOCUMENTS

| | | | |
|---|---|---|---|
| 6,197,798 | B1 | 3/2001 | Fink et al. |
| 6,410,533 | B1 | 6/2002 | Hirth et al. |
| 7,223,782 | B2 | 5/2007 | Atkinson et al. |
| 7,625,915 | B2 | 12/2009 | Dumas et al. |
| 8,592,454 | B2 | 11/2013 | Shirai et al. |
| 9,163,017 | B2 | 10/2015 | Degoey et al. |

FOREIGN PATENT DOCUMENTS

| | | |
|---|---|---|
| EP | 2033955 A1 | 3/2009 |
| EP | 1451160 B1 | 1/2010 |
| EP | 2336105 B9 | 9/2014 |
| JP | 2005206527 A | 8/2005 |
| WO | 9804521 A1 | 2/1998 |
| WO | 9923091 A1 | 5/1999 |
| WO | 9932110 A1 | 7/1999 |
| WO | 0039116 A1 | 7/2000 |
| WO | 0043384 A1 | 7/2000 |
| WO | 0112188 A1 | 2/2001 |
| WO | 0202525 A2 | 1/2002 |
| WO | 02088101 A2 | 11/2002 |
| WO | 02090326 A1 | 11/2002 |
| WO | 03037274 A2 | 5/2003 |
| WO | 03045920 A1 | 6/2003 |
| WO | 03051275 A2 | 6/2003 |
| WO | 2004005262 A2 | 1/2004 |
| WO | 2004032870 A2 | 4/2004 |
| WO | 2004060305 A2 | 7/2004 |
| WO | 2004060306 A2 | 7/2004 |
| WO | 2004061084 A2 | 7/2004 |
| WO | 2004111009 A1 | 12/2004 |
| WO | 2005024755 A2 | 3/2005 |
| WO | 2005048948 A2 | 6/2005 |
| WO | 2005110994 A2 | 11/2005 |
| WO | 2006014290 A2 | 2/2006 |
| WO | 2006068591 A1 | 6/2006 |
| WO | 2006070198 A1 | 7/2006 |
| WO | 2006071940 A2 | 7/2006 |
| WO | 2006081034 A2 | 8/2006 |
| WO | 2006123257 A2 | 11/2006 |
| WO | 2007008917 A2 | 1/2007 |
| WO | 2007059202 A2 | 5/2007 |
| WO | 2007061882 A2 | 5/2007 |
| WO | 2007064872 A2 | 6/2007 |
| WO | 2008016811 A2 | 2/2008 |
| WO | 2008021859 A1 | 2/2008 |
| WO | 2008033999 A2 | 3/2008 |
| WO | 2008034008 A2 | 3/2008 |
| WO | 2008046003 A2 | 4/2008 |
| WO | 2008131276 A1 | 10/2008 |
| WO | 2008150899 A1 | 12/2008 |
| WO | 2009140128 A2 | 11/2009 |
| WO | 2010032856 A1 | 3/2010 |
| WO | 2010033941 A1 | 3/2010 |
| WO | 2010040663 A1 | 4/2010 |
| WO | 2010048314 A1 | 4/2010 |
| WO | 2010059719 A2 | 5/2010 |
| WO | 2010075376 A2 | 7/2010 |
| WO | 2010077680 A2 | 7/2010 |
| WO | 2010104488 A1 | 9/2010 |
| WO | 2010125799 A1 | 11/2010 |
| WO | 2011006074 A1 | 1/2011 |
| WO | 2011032291 A1 | 3/2011 |
| WO | 2011146336 A1 | 11/2011 |
| WO | 2012158413 A2 | 11/2012 |
| WO | 2013063214 A1 | 5/2013 |
| WO | 2013096226 A1 | 6/2013 |
| WO | 2013176970 A1 | 11/2013 |
| WO | 2014052563 A1 | 4/2014 |
| WO | 2014052566 A1 | 4/2014 |
| WO | 2014078322 A1 | 5/2014 |
| WO | 2014078323 A1 | 5/2014 |
| WO | 2014078325 A1 | 5/2014 |
| WO | 2014078328 A1 | 5/2014 |
| WO | 2014078331 A1 | 5/2014 |
| WO | 2014078372 A1 | 5/2014 |
| WO | 2014078378 A1 | 5/2014 |
| WO | 2014078408 A1 | 5/2014 |
| WO | 2014078417 A1 | 5/2014 |
| WO | 2014078454 A1 | 5/2014 |
| WO | 2015039333 A1 | 3/2015 |
| WO | 2015042085 A2 | 3/2015 |

OTHER PUBLICATIONS

Tsuzuki, Y., et al., Tetrahedron Asymmetry 12 (2001), 2989-2997.
Wadhwa, S., et al., Journal of Biosciences, 2003, 28(2), 181-188.
Wang, T., et al., Expert Opinion in Therapeutic Patents (2009) 19(3)305-319.
Woolf, C.J. et al. (1994) Neuroscience, 62, 327-331.
Yilmaz, T., et al., Cancer Biology and Therapy, 2010, 10(6), 644-653.
Zahn, P.K. et al. (2004) J. Pain, 5, 157-163.
Patent Cooperation Treaty, International Searching Authority, Search Report and Written Opinion for PCT/US2013/069838, May 28, 2015, 8 pages.
Adriaenssens, E., et al. Cancer Res (2008) 68:(2) 346-351.
Asaumi, K., et al., Bone (2000) 26(6) 625-633.
Bardelli, A., Science 2003, 300, 949.
Bhattacharya, S. K., et al., Bioorganic & Medicinal Chemistry Letters (2012) 22(24) 7523-7592.
Bouhana, Karyn S., et al., "Comparison of Analgesic Effects of an Allosteric Inhibitor of TrkA to that of an ATP site Inhibitor of the pan-Trk axis in a Rodent Model of Inflammatory Pain", Gordon Conference, Salve Regina University, Newport, RI, Jun. 7, 2011.
Brodeur, G. M., Nat. Rev. Cancer 2003, 3, 203-216.
Bruno, O., Bioorganic & Medicinal Chemistry (2009) 17, 3379-3387.
Burger, K., et al., Synthesis (1990) vol. 4, 360-365.
Chambers, L. J., et al., Bioorganic & Medicinal Chemistry Letters (2010) 20(10) 3161-3164.
Davidson. B., et al., Clin. Cancer Res. 2003, 9, 2248-2259.
Davies, Stephen G., et al., Asymmetric synthesis of 3,4-anti- and 3,4-syn-substituted aminopyrrolidines via lithium amide conjugate addition, Org. Biomol. Chem., 2007, 5, 1961-1969
Delafoy, L. et al. (2003) Pain 105, 489-497.
Demelo-Jorge, M. et aL., Cell Host & Microbe (2007) 1(4), 251-261.
Dimola, F. F, et. al., Gut (2000) 46(5), 670-678.
Dou, Y.-C., et. al. Archives of Dermatological Research (2006) 298(1), 31-37.
Du, et al., World Journal of Gastroenterology, 2003, 9(7), 1431-1434.
Eguchi, M., et al., Blood 1999, 93 (4), pp. 1355-1363.
El Haddad, M., et al., J. Heterocyclic Chem., (2000) 37, 1247-1252.
Eliav, E. et al., Pain 79, 255-264 (1999).
Euthus, D.M., et al., Cancer Cell 2002, 2 (5), pp. 347-348.
Freund-Michel, V; Frossard, N., Pharmacology & Therapeutics (2008) 117(1), 52-76.
Greco, A., et al., Molecular and Cellular Endocrinology 2010, 321 (1), pp. 44-49.
Gruber-Olipitz, M., et al., Journal of Proteome Research 2008, 7 (5), pp. 1932-1944.
Gwak, Y. S. et al. (2003) Neurosci. Lett. 336, 117-120.
Han, S., et al., J. Biological Chem., (2009), 284(19) 13199-13201.
Herzberg, U. et al., Neuroreport 1997; 8:1613-1618.
Hu, Vivian Y; et al., The Journal of Urology (2005), 173(3), 1016-1021.
Jaggar, S. I. et al., Br. J. Anaesth. (1999) 83, 442-448.
Jin, W., et al., Carcinogenesis (2010) 31 (11), pp. 1939-1947.
Kaymakcioglu, B.K, et al., European Journal of Pharmaceutical Sciences (2005) 26(1), 97-103.
Lamb, K. et al. (2003) Neurogastroenterol. Motil. 15, 355-361.
Li, L. et al. (2003) Mol. Cell. Neurosci. 23, 232-250.
Li, Y.-G., et al., Chinese Journal of Cancer Prevention and Treatment, 2009, 16 (6), pp. 428-430 (with English Abstract).
Ma, Q. P. and Woolf, C. J. NeuroReport (1997) 8, 807-810.
Mantyh, Patrick W., et al., Anesthesiology, vol. 115, No. 1, Jul. 2011, 189-204.

(56) References Cited

OTHER PUBLICATIONS

McCarthy, C. and Walker, E., Expert Opin. Ther. Patents (2014) 24(7):731-744.
McMahon, S.B. et al., (1995) Nat. Med. 1, 774-780.
Meyer, J. et al. (2007) Leukemia, 21(10):2171-2180.
Nakagawara, A. (2001) Cancer Letters 169:107-114.
Patapoutian, A. et al., Current Opinion in Neurobiology, 2001, 11, 272-280.
Pierottia, M.A. and Greco A., (2006) Cancer Letters 232:90-98.
Pinski, J. et al., Cancer Research, (2002) 62:986-989.
Ramer, M. S. and Bisby, M. A. (1999) Eur. J. Neurosci. 11, 837-846.
Raychaudhuri, S. P., et al., J. Investigative Dermatology (2004) 122(3), 812-819.
Ricci A., et al., American Journal of Respiratory Cell and Molecular Biology, 2001, 25(4), pp. 439-446.
Ro, L. S. et al., Pain, Feb. 1999; 79(2-3):265-274.
Shelton, D. L. et al. (2005) Pain, 116, 8-16.
Theodosiou, M. et al. (1999) Pain, 81, 245-255.
Truzzi, F., et al., Dermato-Endocrinology, 2011, 3(1), 32-36.

\* cited by examiner

US 9,828,360 B2

PYRROLIDINYL UREA, THIOUREA, GUANIDINE AND CYANOGUANIDINE COMPOUNDS AS TRKA KINASE INHIBITORS

RELATED APPLICATIONS

This application is a 371 filing of PCT Application No. PCT/US2013/069838, filed Nov. 13, 2013, which claims priority to U.S. Provisional Application Ser. No. 61/725,936, filed Nov. 13, 2012, each of which is incorporated herein by reference in its entirety.

BACKGROUND OF THE INVENTION

The present invention relates to novel compounds, to pharmaceutical compositions comprising the compounds, to processes for making the compounds and to the use of the compounds in therapy. More particularly, it relates to pyrrolidinyl urea, thiourea, guanidine and cyanoguanidine compounds which exhibit TrkA kinase inhibition, and which are useful in the treatment of pain, cancer, inflammation/inflammatory diseases, neurodegenerative diseases, certain infectious diseases, Sjogren's syndrome, endometriosis, diabetic peripheral neuropathy, prostatitis and pelvic pain syndrome.

The current treatment regimens for pain conditions utilize several classes of compounds. The opioids (such as morphine) have several drawbacks including emetic, constipatory and negative respiratory effects, as well as the potential for addictions. Non-steroidal anti-inflammatory analgesics (NSAIDs, such as COX-1 or COX-2 types) also have drawbacks including insufficient efficacy in treating severe pain. In addition, COX-1 inhibitors can cause ulcers of the mucosa. Accordingly, there is a continuing need for new and more effective treatments for the relief of pain, especially chronic pain.

Trk's are the high affinity receptor tyrosine kinases activated by a group of soluble growth factors called neurotrophins (NT). The Trk receptor family has three members: TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Pataoutian, A. et al., *Current Opinion in Neurobiology*, 2001, 11, 272-280).

Inhibitors of the Trk/neurotrophin pathway have been demonstrated to be effective in numerous pre-clinical animal models of pain. For example, antagonistic NGF and TrkA antibodies such as RN-624 have been shown to be efficacious in inflammatory and neuropathic pain animal models (Woolf, C. J. et al. (1994) *Neuroscience* 62, 327-331; Zahn, P. K. et al. (2004) *J. Pain* 5, 157-163; McMahon, S. B. et al., (1995) *Nat. Med.* 1, 774-780; Ma, Q. P. and Woolf, C. J. (1997) *NeuroReport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; Jaggar, S. I. et al. (1999) *Br. J Anaesth.* 83, 442-448) and neuropathic pain animal models (Ramer, M. S. and Bisby, M. A. (1999) *Eur. J. Neurosci.* 11, 837-846; Ro, L. S. et al. (1999); Herzberg, U. et al., *Pain* 79, 265-274 (1997) *Neuroreport* 8, 1613-1618; Theodosiou, M. et al. (1999) *Pain* 81, 245-255; Li, L. et al. (2003) *Mol. Cell. Neurosci.* 23, 232-250; Gwak, Y. S. et al. (2003) *Neurosci. Lett.* 336, 117-120).

It has also been shown that NGF secreted by tumor cells and tumor invading macrophages directly stimulates TrkA located on peripheral pain fibers. Using various tumor models in both mice and rats, it was demonstrated that neutralizing NGF with a monoclonal antibody inhibits cancer related pain to a degree similar or superior to the highest tolerated dose of morphine. Because TrkA kinase may serve as a mediator of NGF driven biological responses, inhibitors of TrkA and/or other Trk kinases may provide an effective treatment for chronic pain states.

Recent literature has also shown that overexpression, activation, amplification and/or mutation of Trk kinases are associated with many cancers including neuroblastoma (Brodeur, G. M., *Nat. Rev. Cancer* 2003, 3, 203-216), ovarian (Davidson. B., et al., *Clin. Cancer Res.* 2003, 9, 2248-2259), colorectal cancer (Bardelli, A., *Science* 2003, 300, 949), melanoma (Truzzi, F., et al., *Dermato-Endocrinology* 2008, 3 (1), pp. 32-36), head and neck cancer (Yilmaz, T., et al., *Cancer Biology and Therapy* 2010, 10 (6), pp. 644-653), gastric carcinoma (Du, J. et al., *World Journal of Gastroenterology* 2003, 9 (7), pp. 1431-1434), lung carcinoma (Ricci A., et al., *American Journal of Respiratory Cell and Molecular Biology* 25 (4), pp. 439-446), breast cancer (Jin, W., et al., *Carcinogenesis* 2010, 31 (11), pp. 1939-1947), Glioblastoma (Wadhwa, S., et al., *Journal of Biosciences* 2003, 28 (2), pp. 181-188), medulloblastoma (Gruber-Olipitz, M., et al., *Journal of Proteome Research* 2008, 7 (5), pp. 1932-1944), secratory breast cancer (Euthus, D. M., et al., *Cancer Cell* 2002, 2 (5), pp. 347-348), salivary gland cancer (Li, Y.-G., et al., *Chinese Journal of Cancer Prevention and Treatment* 2009, 16 (6), pp. 428-430), papillary thyroid carcinoma (Greco, A., et al., *Molecular and Cellular Endocrinology* 2010, 321 (1), pp. 44-49) and adult myeloid leukemia (Eguchi, M., et al., *Blood* 1999, 93 (4), pp. 1355-1363). In preclinical models of cancer, non-selective small molecule inhibitors of TrkA, B and C were efficacious in both inhibiting tumor growth and stopping tumor metastasis (Nakagawara, A. (2001) *Cancer Letters* 169:107-114; Meyer, J. et al. (2007) *Leukemia*, 1-10; Pierottia, M. A. and Greco A., (2006) *Cancer Letters* 232:90-98; Eric Adriaenssens, E., et al. *Cancer Res* (2008) 68:(2) 346-351).

In addition, inhibition of the neurotrophin/Trk pathway has been shown to be effective in treatment of pre-clinical models of inflammatory diseases with NGF antibodies or non-selective small molecule inhibitors of TrkA. For example, inhibition of the neurotrophin/Trk pathway has been implicated in preclinical models of inflammatory lung diseases including asthma (Freund-Michel, V; Frossard, N., *Pharmacology & Therapeutics* (2008) 117(1), 52-76), interstitial cystitis (Hu Vivian Y; et. al. *The Journal of Urology* (2005), 173(3), 1016-21), bladder pain syndrome (Liu, H.-T., et al., (2010) *BJU International*, 106 (11), pp. 1681-1685), inflammatory bowel diseases including ulcerative colitis and Crohn's disease (Di Mola, F. F, et. al., *Gut* (2000) 46(5), 670-678) and inflammatory skin diseases such as atopic dermatitis (Dou, Y.-C., et. al. *Archives of Dermatological Research* (2006) 298(1), 31-37), eczema and psoriasis (Raychaudhuri, S. P., et al., *J. Investigative Dermatology* (2004) 122(3), 812-819).

The TrkA receptor is also thought to be critical to the disease process of the parasitic infection of *Trypanosoma cruzi* (Chagas disease) in human hosts (de Melo-Jorge, M. et al., *Cell Host & Microbe* (2007) 1(4), 251-261).

Trk inhibitors may also find use in treating disease related to an imbalance of the regulation of bone remodeling, such as osteoporosis, rheumatoid arthritis, and bone metastases. Bone metastases are a frequent complication of cancer, occurring in up to 70 percent of patients with advanced breast or prostate cancer and in approximately 15 to 30 percent of patients with carcinoma of the lung, colon, stomach, bladder, uterus, rectum, thyroid, or kidney. Osteolytic metastases can cause severe pain, pathologic fractures, life-threatening hypercalcemia, spinal cord compression, and other nerve-compression syndromes. For these reasons, bone metastasis is a serious and costly complication of cancer. Therefore, agents that can induce apoptosis of proliferating osteoblasts would be highly advantageous. Expression of TrkA receptors has been observed in the bone-forming area in mouse models of bone fracture (K. Asaumi, et al., *Bone* (2000) 26(6) 625-633). In addition, localization of NGF was observed in almost all bone-forming cells (K. Asaumi, et al.). Recently, it was demonstrated that a Trk inhibitor inhibits the signaling activated by neurotrophins binding to all three of the Trk receptors in human hFOB osteoblasts (J. Pinski, et al., (2002) 62, 986-989). These data support the rationale for the use of Trk inhibitors for the treatment of bone remodeling diseases, such as bone metastases in cancer patients.

Trk inhibitors may also find use in treating diseases and disorders such as Sjogren's syndrome (Fauchais, A. L., et al., (2009) Scandinavian Journal of Rheumatology, 38(1), pp. 50-57), endometriosis (Barcena De Arellano, M. L., et al., (2011) Reproductive Sciences, 18(12), pp. 1202-1210; Barcena De Arellano, et al., (2011) Fertility and Sterility, 95(3), pp. 1123-1126; Cattaneo, A., (2010) Current Opinion in Molecular Therapeutics, 12(1), pp. 94-106), diabetic peripheral neuropathy (Kim, H. C., et al., (2009) Diabetic Medicine, 26 (12), pp. 1228-1234; Siniscalco, D., et al., (2011) Current Neuropharmacology, 9(4), pp. 523-529; Ossipov, M. H., (2011) Current Pain and Headache Reports, 15(3), pp. 185-192), and prostatitis and pelvic pain syndrome (Watanabe, T., et al., (2011) BJU International, 108 (2), pp. 248-251; and Miller, L. J., et al., (2002) Urology, 59(4), pp. 603-608).

Several classes of small molecule inhibitors of Trk kinases said to be useful for treating pain or cancer are known (*Expert Opin. Ther. Patents* (2009) 19(3), 305-319).

International application publication WO 2010/032856 describes compounds represented by the formula

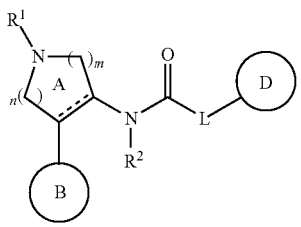

wherein ring B is an aromatic ring, ring D is an aromatic ring, and L is $NR^3$, $NR^3C(R^{4a}R^{4b})$, O or $OC(R^{4a}R^{4b})$, which are asserted to be tachykinin receptor antagonists.

SUMMARY OF THE INVENTION

It has now been found that pyrrolidinyl urea, thiourea, guanidine and cyanoguanidine compounds are inhibitors of TrkA, and useful for treating disorders and diseases such as pain, including chronic and acute pain. Compounds of the invention useful in the treatment of multiple types of pain including inflammatory pain, neuropathic pain, and pain associated with cancer, surgery, or bone fracture. In addition, compounds of the invention are useful for treating cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

More specifically, provided herein are compounds of Formula I:

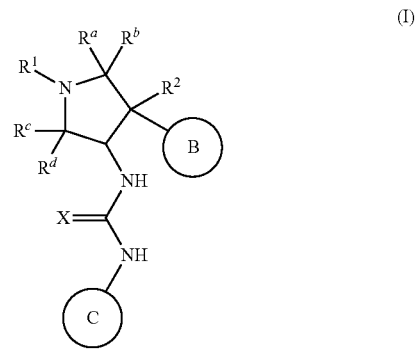

or stereoisomers, tautomers, or pharmaceutically acceptable salts, solvates or prodrugs thereof, wherein Ring B and the NH—C(=X)—NH moiety are in the trans configuration and $R^1$, $R^2$, $R^a$, $R^b$, $R^c$, $R^d$, X, Ring B and Ring C are as defined herein.

Another aspect of the present invention provides methods of treating a disease or disorder modulated by TrkA, comprising administering to a mammal in need of such treatment an effective amount of a compound of this invention or a stereoisomer, solvate or pharmaceutically acceptable salt thereof. In one embodiment, the disease and disorders include chronic and acute pain, including but not limited to inflammatory pain, neuropathic pain, and pain associated with cancer, surgery, or bone fracture. In another embodiment, the disease and disorders include, but are not limited to, cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases. In one embodiment, the treatment includes treating the mammal with a compound of this invention in combination with an additional therapeutic agent.

Another aspect of the present invention provides a pharmaceutical composition comprising a compound of the present invention or a pharmaceutically acceptable salt thereof.

Another aspect of the present invention provides the compounds of the present invention for use in therapy.

Another aspect of the present invention provides the compounds of the present invention for use in the treatment of disease and disorders such as chronic and acute pain, including but not limited to inflammatory pain, neuropathic pain, and pain associated with cancer, surgery, or bone fracture. Another aspect of the present invention provides the compounds of the present invention for use in the treatment of disease and disorders selected from cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Another aspect of the present invention provides the use of a compound of this invention in the manufacture of a medicament for the treatment of disease and disorders such as chronic and acute pain including, but not limited to, inflammatory pain, neuropathic pain, and pain associated with cancer, surgery, or bone fracture.

Another aspect of the present invention provides the use of a compound of this invention in the manufacture of a medicament for the treatment of disease and disorders selected from cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Another aspect of the present invention provides intermediates for preparing compounds of Formula I.

Another aspect of the present invention includes methods of preparing, methods of separation, and methods of purification of the compounds of this invention.

DETAILED DESCRIPTION OF THE INVENTION

Provided herein are compounds, and pharmaceutical formulations thereof, that are useful in the treatment of diseases, conditions and/or disorders modulated by TrkA.

A representative compound of the invention (See Table B below), was found to be highly selective for TrkA over a panel of about 230 other kinases at 10 μM concentration. In addition, compounds of the invention such as those shown in Table A below, were found to be at least 1000 fold more selective for TrkA versus p38α.

One embodiment provides a compound of Formula I:

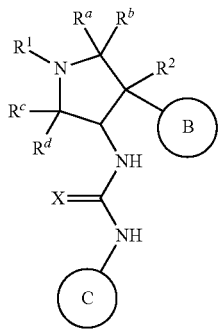

(I)

or stereoisomers, tautomers, or pharmaceutically acceptable salts, solvates or prodrugs thereof, wherein:

Ring B and the NH—C(=X)—NH moiety are in the trans configuration;

$R^a$, $R^b$, $R^c$ and $R^d$ are independently selected from H and (1-3C)alkyl, or $R^c$ and $R^d$ are independently selected from H and (1-3C)alkyl, and $R^a$ and $R^b$ together with the atom to which they are attached form a cyclopropyl ring;

X is O, S, NH or N—CN;

$R^1$ is (1-3C alkoxy)(1-6C)alkyl, (trifluoromethoxy)(1-6C) alkyl, (1-3C sulfanyl)(1-6C)alkyl, monofluoro(1-6C)alkyl, difluoro(1-6C)alkyl, trifluoro(1-6C)alkyl, tetrafluoro(2-6C) alkyl, pentafluro(2-6C)alkyl, cyano(1-6C)alkyl, aminocarbonyl(1-6C)alkyl, hydroxy(1-6C)alkyl, dihydroxy(2-6C) alkyl, (1-6C)alkyl, (1-3Calkylamino)(1-3C)alkyl, (1-4C alkoxycarbonyl)(1-6C)alkyl, amino(1-6C)alkyl, hydroxy(1-3C alkoxy)(1-6C)alkyl, di(1-3C alkoxy)(1-6C)alkyl, (1-3C alkoxy)trifluoro(1-6C)alkyl, hydroxytrifluoro(1-6C)alkyl, (1-4C alkoxycarbonyl)(1-3C alkoxy)(1-6C)alkyl, or hydroxycarbonyl(1-3C alkoxy)(1-6C)alkyl;

$R^2$ is H, F, or OH;

Ring B is $Ar^1$ or $hetAr^1$;

$Ar^1$ is phenyl optionally substituted with one or more substituents independently selected from halogen, $CF_3$, $CF_3O$—, (1-4C)alkoxy, hydroxy(1-4C)alkyl, (1-6C)alkyl and CN;

$hetAr^1$ is a 5-6 membered heteroaryl having 1-3 ring heteroatoms independently selected from N, S and O, and optionally substituted with one or more groups independently selected from (1-6C)alkyl, halogen, OH, $CF_3$, $NH_2$ and hydroxy(1-2C)alkyl;

Ring C is selected from formulas C-1 through C-13:

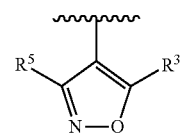

C-1

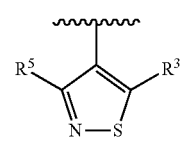

C-2

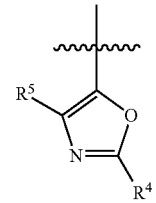

C-3

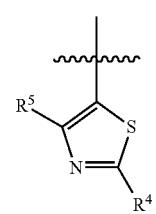

C-4

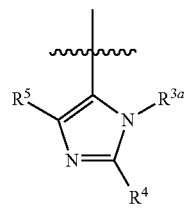

C-5

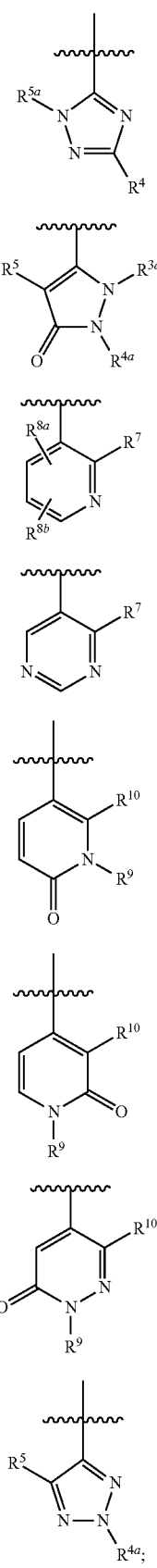

R³ is H, NH₂, CN, halogen, (1-3C)alkyl [optionally substituted with 1 to 3 fluoros], H₂NC(=O)—, (1-3Calkyl)NHC(=O)—, di(1-3Calkyl)NHC(=O)—, hydroxy(1-3C)alkyl, CH₃OCH₂CH₂, (3-4C)cycloalkyl or (1-3C)alkoxy;

R³ᵃ is H, (1-3C)alkyl, CF₃CH₂CH₂, HCF₂CH₂CH₂, H₂FCCH₂CH₂, CF₃CH₂, HOCH₂CH₂, MeOCH₂CH₂ or (3-4C)cycloalkyl;

R⁴ is H, OH, (1-6C)alkyl [optionally substituted with 1-5 fluoros], cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr³ (1-6C)alkyl, Ar³ (1-6C)alkyl, (1-6C)alkoxy [optionally substituted with 1-5 fluoros], cyano(1-6C)alkoxy, hydroxy(1-6C)alkoxy, dihydroxy(2-6C)alkoxy, amino(2-6C)alkoxy, hydroxyl-carbonyl(1-6C)alkoxy, hetCyc²(1-6C)alkoxy, hetAr³(1-6C)alkoxy, Ar³ (1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], hetAr⁴, hetAr⁴—O—, Ar⁴, hetCyc²(O)CH₂—, (1-4C alkoxycarbonyl)(1-6C)alkoxy, hydroxycarbonyl(1-6C)alkoxy, aminocarbonyl(1-6C)alkoxy, hetCyc²C(=O)(1-6C)alkoxy, hydroxy(1-3C alkoxy)(1-6C)alkoxy, hydroxytrifluoro(1-6C)alkoxy, (1-3C)alkylsulfonamido(1-6C)alkoxy, (1-3C)alkylamido(1-6C)alkoxy, di(1-3C alkyl)amino-carboxy, hetCyc²C(=O)O—, hydroxydifluoro(1-6C)alkyl, (1-4C alkylcarboxy)(1-6C)alkyl, (1-6C)alkoxycarbonyl, hydroxylcarbonyl, aminocarbonyl, (1-3C alkoxy)aminocarbonyl, hetCyc³, halogen, CN, trifluoromethylsulfonyl, N-(1-3C alkyl)oxadiazolonyl, or hetAr⁵;

R⁴ᵃ is H, (1-6C)alkyl, CF₃CH₂CH₂, HCF₂CH₂CH₂, H₂FCCH₂CH₂, CF₃CH₂, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr³ (1-6C)alkyl, Ar³ (1-6C)alkyl, (3-6C)cycloalkyl [optionally substituted with F, OH, (1-6C alkyl), (1-6C) alkoxy, or (1-3C alkoxy)(1-6C)alkyl], hetAr⁴, Ar⁴, hydroxydifluoro(1-6C)alkyl, (1-4C alkylcarboxy)(1-6C)alkyl, hetCyc³, N-(1-3C alkyl)oxadiazolonyl, or hetAr⁵;

hetCyc² is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, and (1-6C)acyl;

hetCyc³ is a 4-7 membered heterocycle having 1-2 ring heteroatoms independently selected from N and O and optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl;

hetAr³ is a 5-membered heteroaryl ring having 1-3 ring atoms independently selected from N, O and S and optionally substituted with (1-6C)alkyl;

Ar³ is phenyl optionally substituted with (1-4C)alkoxy;

hetAr⁴ is independently a 5-6 membered heteroaryl ring having 1-3 ring heteroatoms independently selected from N, S and O and optionally substituted with one or more substituents independently selected from (1-6C)alkyl [optionally substituted with 1-3 fluoros], halogen, CN, hydroxy(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy), fluoro (1-6C alkyl)amino, difluoro(1-6C alkyl)amino, trifluoro(1-6C alkyl)amino, and (3-4C cycloalkyl)amino;

hetAr$^5$ is a group selected from the structures:

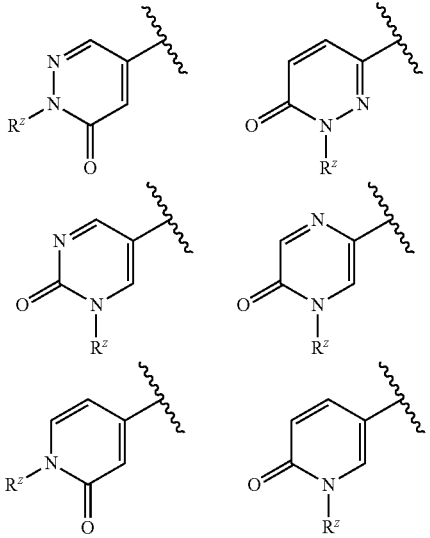

where R$^z$ is (3-4C)cycloalkyl or (1-3C)alkyl (optionally substituted with 1-3 fluoros), wherein each of said hetAr$^5$ groups is optionally further substituted with one or more groups independently selected from F and (1-3C)alkyl optionally substituted with 1-3 fluoros;

Ar$^4$ is phenyl optionally substituted with one or more groups independently selected from (1-6C)alkyl, halogen, CN, CF$_3$, CF$_3$O—, (1-6C)alkoxy, (1-6Calkyl)OC(=O)—, aminocarbonyl, (1-6C)alkylthio, hydroxy(1-6C)alkyl, (1-6C alkyl)SO$_2$—, HOC(=O)— and (1-3C alkoxy)(1-3C alkyl)OC(=O)—;

R$^5$ is H, (1-6C)alkyl [optionally substituted with 1-5 fluoros], halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl [optionally substituted with one or more groups independently selected from halogen, (1-6C)alkyl and (1-6C)alkoxy];

R$^{5a}$ is H, (1-6C)alkyl, CF$_3$CH$_2$CH$_2$, HCF$_2$CH$_2$CH$_2$, H$_2$FCCH$_2$CH$_2$, CF$_3$CH$_2$, hydroxy(1-4C)alkyl, (1-3C alkoxy)(1-4C)alkyl, (3-4C)cycloalkyl, or phenyl [optionally substituted with one or more groups independently selected from halogen, (1-6C)alkyl and (1-6C)alkoxy];

R$^7$ is (1-6C)alkyl, (3-6C)cycloalkyl, or phenyl [optionally substituted with one or more groups independently selected from halogen, (1-6C)alkyl, (1-6C)alkoxy, (3-4C)cycloalkyl, amino, aminocarbonyl, and trifluoro(1-3C)alkylamido];

R$^{8a}$ and R$^{8b}$ are independently H, halogen, CN, NH$_2$, (1-6C)alkyl [optionally substituted with 1-5 fluoros], (1-6C)alkoxy, (1-3C alkoxy)(1-6C)alkyl, (1-3C alkoxy)(1-6C)alkoxy, (1-6C alkyl)sulfonyl, (3-6C cycloalkyl)sulfonyl, (3-4C)cycloalkyl, amino, (1-6Calkyl)NH—, phenyl [optionally substituted with (1-6C alkyl)SO$_2$—] or hetAr$^4$, wherein only one of R$^{8a}$ and R$^{8b}$ can be phenyl [optionally substituted with (1-6C alkyl)SO$_2$—] or hetAr$^4$;

R$^9$ is H, (1-6C)alkyl, CF$_3$CH$_2$—, CF$_3$CH$_2$CH$_2$—, (1-3Calkoxy)(1-6C)alkyl or (3-4C)cycloalkyl; and R$^{10}$ is (3-6C)cycloalkyl or phenyl [optionally substituted with one or more substituents independently selected from halogen, (1-6C)alkyl, (1-6C)alkoxy, (3-4C)cycloalkyl, amino, aminocarbonyl and trifluoro(1-3C alkyl)amido].

It is to be understood that in instances where two or more radicals are used in succession to define a substituent attached to a structure, the first named radical is considered to be terminal and the last named radical is considered to be attached to the structure in question. Thus, for example, the radical "alkoxyalkyl" is attached to the structure in question by the alkyl group.

The terms "(1-6C)alkyl", "(1-4C)alkyl" and "(1-3C)alkyl" as used herein refer to saturated linear monovalent hydrocarbon radicals of one to six carbon atoms, one to four carbon atoms, and one to three carbon atoms, respectively, or a branched saturated monovalent hydrocarbon radical of three to six carbon atoms, three to four carbon atoms, or three carbon atoms, respectively. Examples include, but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

"(1-4C)Alkoxy", "(1-3C)alkoxy", "(1-6C)alkoxy" and "(2-6C)alkoxy" refer to an —OR radical where R is (1-4C)alkyl, (1-3C)alkyl, (1-6C)alkyl, or (2-6C)alkyl, respectively, as defined above. Examples include methoxy, ethoxy, and the like.

"(1-6C)Acyl" means a RC(=O)— radical where R is a linear saturated monovalent hydrocarbon radical of one to five carbon atoms or a branched saturated monovalent hydrocarbon radical of three to five carbon atoms, e.g., methylcarbonyl, and the like.

"(1-3C Alkoxy)(1-6C)alkyl" and "(1-3C alkoxy)(1-4C)alkyl" mean a linear saturated monovalent hydrocarbon radical of one to six carbon atoms or one to four carbon atoms, or a branched saturated monovalent hydrocarbon radical of three to six carbon atoms or three to four carbon atoms, respectively, wherein one of the carbon atoms is substituted with one (1-3C)alkoxy group as defined herein.

"(1-3C Alkoxy)(1-6C)alkoxy" means a (1-6C)alkoxy group as defined herein, wherein one of the carbon atoms is substituted with a (1-3C)alkoxy group as defined herein. Examples include methoxymethoxy, methoxyethoxy, and the like.

"(1-3C Alkoxy)aminocarbonyl" means a (1-3C alkyl)-O—NH—C(=O)— group.

"(1-6C)Alkoxycarbonyl" and "(1-4C)alkoxycarbonyl" mean a (1-6C)—O—C(=O)— and (1-4C)—O—C(=O)— group, respectively.

(1-4C Alkoxycarbonyl)(1-6C)alkyl means a (1-6C)alkyl group as defined herein, wherein one of the carbons is substituted with a (1-4C alkoxy)carbonyl group as defined herein.

"(1-3C Alkoxy)trifluoro(1-6C)alkyl" means a (1-6C)alkyl group as defined herein, wherein one of the carbons is substituted with three fluoros, and another carbon is substituted with a (1-3C)alkoxy group as defined herein.

"(1-4C Alkoxycarbonyl)(1-6C alkoxy)" means a (1-6C) alkoxy group as defined herein wherein one of the carbon atoms is substituted with one (1-4C alkoxy)carbonyl group, i.e., an alkyl-O—C(=O)— group.

"(1-4C Alkoxycarbonyl)(1-3C alkoxy)(1-6C)alkyl" means a (1-3C alkoxy)(1-6C)alkyl group as defined herein wherein one of the carbon atoms is substituted with one (1-4C alkoxycarbonyl group, i.e., an alkyl-O—C(=O)— group.

"(1-3C Alkoxy)hydroxycarbonylalkyl" means a hydroxycarbonylalkyl group as defined herein wherein one of the carbon atoms is substituted with one (1-3C alkoxy) group.

"Amino" means a —NRR' group where R and R' are independently selected from hydrogen or (1-3C)alkyl as defined herein. Examples include $H_2N$—, $CH_3NH$—, $(CH_3)_2$ N, and the like.

"Amino(1-6C)alkyl" means a linear saturated monovalent hydrocarbon radical of one to six carbon atoms or a branched saturated monovalent hydrocarbon radical of three to six carbon atoms, wherein one of the carbon atoms is substituted with one —NRR' group where R and R' are independently selected from hydrogen or (1-3C)alkyl as defined herein. Examples include aminomethyl, methylaminoethyl, 2-ethylamino-2-methylethyl, and the like.

"Amino(2-6C)alkoxy" means a (2-6C)alkoxy group as defined herein, wherein one of the carbon atoms is substituted with one —NRR' group where R and R' are independently selected from hydrogen or (1-3C)alkyl as defined herein.

"Aminocarbonyl" means a RR'NCO— radical where R and R' are independently hydrogen or (1-6C)alkyl as defined herein. Examples include $H_2NCO$—, dimethylaminocarbonyl, and the like.

"Aminocarbonyl(1-6C)alkyl" means a linear saturated hydrocarbon radical of one to six carbon atoms or a branched saturated monovalent hydrocarbon radical of three to six carbons wherein one of the carbon atoms is substituted with one aminocarbonyl group as defined herein, e.g., 2-aminocarbonylethyl, 1-, 2-, or 3-dimethylaminocarbonylpropyl, and the like.

"Aminocarbonyl(1-6C)alkoxy" means a (1-6C)alkoxy as defined herein, wherein one of the carbon atoms is substituted with one aminocarbonyl group as defined herein.

"(1-3C)Alkylamido(1-6C)alkoxy" means a (1-6C)alkoxy as defined herein, wherein one of the carbon atoms is substituted with one alkylamido group, i.e., substituted with a (1-3C)C(=O)NH— group.

"(1-4C alkyl)carboxy" means a R'—C(=O)O— group where R' is (1-4C)alkyl.

"(1-4C alkylsiloxy)(1-6C)alkoxy" means a (1-6C)alkoxy group as defined herein wherein one of the carbon atoms is substituted with one (1-4C alkyl)siloxy group, e.g., a (1-4C alkyl)Si—O— group such as a tert-butylsiloxy group.

"(1-3C)Alkylsulfonamido" means a (1-3C)alkyl $SO_2NH$— radical where (1-3C)alkyl is as defined herein.

"(1-3C Alkylsulfonamido)(1-6C)alkyl" means a linear saturated hydrocarbon radical of one to six carbon atoms or a branched saturated monovalent hydrocarbon radical of three to six carbons substituted with one (1-3C)alkylsulfonamido group as defined herein.

"(1-3C)Alkylsulfonamido(1-6C)alkoxy" means a (1-6C) alkoxy group as defined herein wherein one of the carbon atoms is substituted with one (1-3C)alkylsulfonamido group as defined herein.

"(1-3C)Alkylsulfonyl" means a —$SO_2R$ radical where R is (1-3C)alkyl as defined above, e.g., methylsulfonyl, and the like.

"(1-3C Alkylsulfonyl)(1-6C)alkoxy" means a (1-6C) alkoxy group as defined herein, wherein one of the carbon atoms is substituted with a (1-3C)alkylsulfonyl group.

"Hydroxycarbonyl" means HOC(=O)—.

"(1-4C alkyl)carboxy(1-6C)alkyl" means a (1-6C)alkyl group as defined herein wherein one of the carbon atoms is substituted with a (1-4C alkyl)carboxy group as defined herein.

"Cyano(1-6C)alkyl" means a linear saturated hydrocarbon radical of one to six carbon atoms or a branched saturated monovalent hydrocarbon radical of three to six carbons substituted with a cyano (CN) group.

"(3-6C)Cycloalkyl" means a cyclic saturated monovalent hydrocarbon radical of three to six carbon atoms, e.g., cyclopropyl, cyclobutyl, cyclopentyl, or cyclohexyl.

"Di(1-3C alkoxy)(1-6C)alkyl" means a (1-6C)alkyl group as defined herein, wherein two carbons are each substituted with one (1-3C)alkoxy group as defined herein.

"Dihydroxy(2-6C)alkyl" means a linear saturated hydrocarbon radical of two to six carbon atoms or a branched saturated monovalent hydrocarbon radical of three to six carbons substituted with two hydroxy (OH) groups, provided that two hydroxy groups are not both on the same carbon atom.

"Dihydroxy(2-6C)alkoxy" means a (2-6C)alkoxy group as defined herein, wherein two of the carbon atoms are substituted with a hydroxy group.

"Halogen" as used herein means F, Cl, Br or I.

"Heterocycle" refers to a saturated or partially unsaturated ring system having one or more ring heteroatoms as recited for the specific heterocyclic group, wherein the heterocycle is optionally substituted with substituents as defined for that particular heterocyclic group.

"Heteroaryl" refers to a 5-6 membered unsaturated ring system having one or more ring heteroatoms as recited for the specific heteroaryl group, wherein the heteroaryl is optionally substituted with substituents as defined for that particular heteroaryl group.

"hetCyc$^2$C(=O)(1-6C)alkoxy" means a (1-6C)alkoxy as defined herein, wherein one of the carbon atoms is substituted with a hetCyc$^2$C(=O) group, wherein hetCyc$^2$ is as defined herein.

"Hydroxy(1-6C)alkyl" and "hydroxy(1-4C)alkyl" means a linear saturated hydrocarbon radical of one to six carbon atoms or one to four carbon atoms, respectively, or a branched saturated monovalent hydrocarbon radical of three to six carbon atoms or three to four carbon atoms, respectively, wherein one of the carbon atoms is substituted with a hydroxy (OH) group.

"Hydroxy(1-6C)alkoxy" means a (1-6C)alkoxy group as defined herein, wherein one of the carbon atoms is substituted with a hydroxy group.

"Hydroxy(1-3C alkoxy)(1-6C)alkyl" means a (1-3C alkoxy)(1-6C)alkyl group as defined herein, wherein one of the carbons is substituted with a hydroxy group.

"Hydroxy(1-3C alkoxy)(1-6C)alkoxy" means a (1-3C alkoxy)(1-6C)alkoxy as defined herein, wherein one of the carbon atoms is substituted with a hydroxy group.

"Hydroxydifluoro(1-6C)alkyl" means a difluoro(1-6C) alkyl group as defined herein, wherein one of the carbon atoms is substituted with a hydroxy group.

"Hydroxytrifluoro(1-6C)alkoxy" means a trifluoro(1-6C) alkoxy group as defined herein, wherein one of the carbon atoms is substituted with a hydroxy group.

"Hydroxycarbonylalkyl" means a linear saturated hydrocarbon radical of one to six carbon atoms or a branched saturated monovalent hydrocarbon radical of three to six carbons substituted with one —COOH group. Examples include 2-hydroxycarbonylethyl, 1-, 2-, or 3-hydroxycarbonylpropyl, and the like.

"Isoindoline-1,3-dionyl(1-6C)alkoxy" means a (1-6C) alkoxy group as defined herein, wherein one of the carbon atoms is substituted with an isoindoline-1,3-dionyl group.

"(Trifluoromethoxy)(1-6C)alkyl" means a linear saturated hydrocarbon radical of one to six carbon atoms or a branched saturated monovalent hydrocarbon radical of three to six carbons substituted with one CF₃O— group.

"Trifluoro(1-3C alkyl)amido" means a (1-3C alkyl)C(=O)NH— group wherein one of the carbons is substituted with three fluoros.

"Trifluoro(1-6C)alkoxy" means a (1-6C)alkoxy group as defined herein, wherein one of the carbon atoms is substituted with three fluoros.

"Sulfamido(1-6C)alkyl" means a linear saturated hydrocarbon radical of one to six carbon atoms or a branched saturated monovalent hydrocarbon radical of three to six carbons substituted with one sulfamido (H₂NSO₂NH—) group.

It should be noted that compounds of the invention may contain groups that may exist in tautomeric forms, such as heteroatom substituted heteroaryl or heterocyclic groups and the like, which are illustrated in the following general and specific examples:

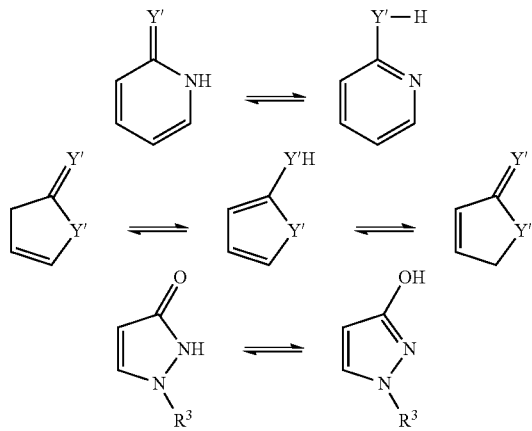

where Y'=O, S, or NR, and though one form is named, described, displayed and/or claimed herein, all the tautomeric forms are intended to be inherently included in such name, description, display and/or claim.

In one embodiment of Formula I, $R^a$, $R^b$, $R^c$ and $R^d$ are independently selected from H and methyl. In one embodiment, $R^a$, $R^b$, $R^c$ and $R^d$ are hydrogen. In one embodiment, $R^a$ is methyl and $R^b$, $R^c$ and $R^d$ are hydrogen. In one embodiment, $R^a$ and $R^b$ are methyl and $R^c$ and $R^d$ are hydrogen. In one embodiment, $R^a$, $R^b$ and $R^c$ are hydrogen and $R^d$ is methyl. In one embodiment, $R^a$ and $R^b$ are hydrogen and $R^c$ and $R^d$ are methyl.

In one embodiment, $R^c$ and $R^d$ are independently selected from H and (1-3C)alkyl, and $R^a$ and $R^b$ together with the atom to which they are attached form a cyclopropyl ring. In one embodiment, $R^c$ and $R^d$ are H, and $R^a$ and $R^b$ together with the atom to which they are attached form a cyclopropyl ring.

In one embodiment, X is O.

In one embodiment, X is S.

In one embodiment, X is NH.

In one embodiment, X is N—CN.

In one embodiment, $R^1$ is (1-3C alkoxy)(1-6C)alkyl, for example, methoxyethyl, methoxypropyl, ethoxyethyl and 2-methoxypropyl. Particular examples include 2-methoxyethyl and 2-methoxypropyl having the structures:

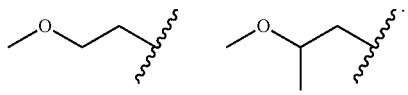

In one embodiment, $R^1$ is 2-methoxyethyl.

In one embodiment, $R^1$ is (trifluoromethoxy)(1-6C)alkyl, for example, trifluoromethoxyethyl, trifluoromethoxypropyl, and the like. A particular example is trifluoromethoxyethyl.

In one embodiment, $R^1$ is (1-3C sulfanyl)(1-6C)alkyl, for example methylsulfanylethyl, ethylsulfanylethyl, and the like. A particular example is methylsulfanylethyl.

In one embodiment, $R^1$ is monofluoro(1-6C)alkyl, difluoro(1-6C)alkyl or trifluoro(1-6C)alkyl. Particular examples include 1,3-difluoroprop-2-yl, 2,2-difluoroethyl, 4,4,4-trifluorobutyl and 2,2,2-trifluoroethyl having the structures:

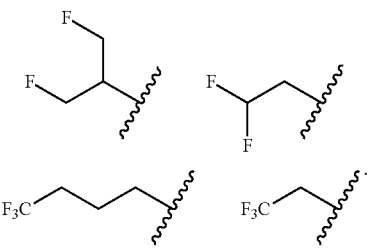

In one embodiment, $R^1$ is tetrafluoro(2-6C)alkyl or pentafluoro(2-6C)alkyl. A particular example is 3,3,4,4,4-pentafluorobutyl.

In one embodiment, $R^1$ is cyano(1-6C)alkyl. A particular example is 2-cyanoethyl.

In one embodiment, $R^1$ is aminocarbonyl(1-6C)alkyl. A particular example is aminocarbonylmethyl. Another example is methylaminocarbonylmethyl having the formula MeNHC(=O)CH₂—.

In one embodiment, $R^1$ is hydroxy(1-6C)alkyl. Particular examples include 2-hydroxyethyl and 2-hydroxypropyl.

In one embodiment, $R^1$ is dihydroxy(2-6C)alkyl. A particular example is the structure:

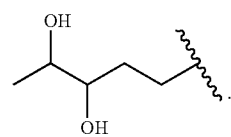 [SMILES: *CCC(O)C(C)O]

In one embodiment, $R^1$ is (1-6C)alkyl. Examples include methyl, ethyl, and propyl.

In one embodiment, $R^1$ is (1-3Calkylamino)(1-3C)alkyl, that is, a (1-3C)alkyl group which is substituted with a (1-3C alkyl)amino group, for example a (1-3Calkyl)NH— group such as methylamino. A particular example is (2-methylamino)ethyl.

In one embodiment, $R^1$ is (1-4C alkoxycarbonyl)(1-6C)alkyl. A particular example is methoxycarbonylmethyl, having the structure:

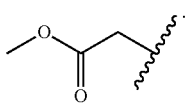

In one embodiment, $R^1$ is amino(1-6C)alkyl, such as methylamino(1-6C)alkyl. A particular example is 2-methylaminoethyl.

In one embodiment, $R^1$ is hydroxy(1-3C alkoxy)(1-6C)alkyl. Examples include hydroxymethoxy(1-6C)alkyl. Particular examples include the structures:

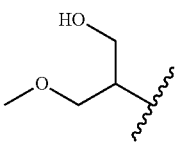 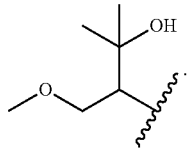

In one embodiment, $R^1$ is di(1-3C alkoxy)(1-6C)alkyl. Examples include dimethoxy(1-6C)alkyl. A particular example includes 1,3-dimethoxyprop-2-yl having the structure:

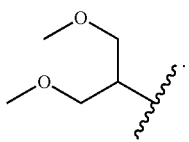 [SMILES: *C(COC)COC]

In one embodiment, $R^1$ is (1-3C alkoxy)trifluoro(1-6C)alkyl. Examples include methoxytrifluoro(1-6C)alkyl. A particular example includes 3,3,3-trifluoro-2-methoxypropyl.

In one embodiment, $R^1$ is hydroxytrifluoro(1-6C)alkyl. A particular example includes 3,3,3-trifluoro-2-hydroxypropyl.

In one embodiment, $R^1$ is (1-4C alkoxycarbonyl)(1-3C alkoxy)(1-6C)alkyl. Examples include (methoxycarbonyl)methoxy(1-6C)alkyl. A particular example includes the structure:

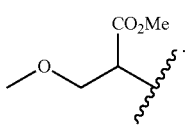 [SMILES: *C(COC)C(=O)OC]

In one embodiment, $R^1$ is hydroxycarbonyl(1-3C alkoxy)(1-6C)alkyl. Examples include (methoxycarbonyl)hydroxy(1-6C)alkyl. A particular example includes the structure:

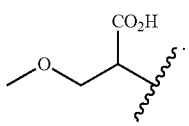 [SMILES: *C(COC)C(=O)O]

In one embodiment, $R^1$ is selected from (1-3C alkoxy)(1-6C)alkyl, difluoro(1-6C)alkyl and trifluoro(1-6C)alkyl.

In one embodiment, $R^2$ is H.
In one embodiment, $R^2$ is F.
In one embodiment, $R^2$ is OH.

In one embodiment of Formula I, Ring B is $Ar^1$, where $Ar^1$ is phenyl optionally substituted with one or more substituents independently selected from halogen, $CF_3$, $CF_3O-$, (1-4C)alkoxy, hydroxy(1-4C)alkyl, (1-6C)alkyl, and CN. In one embodiment, $Ar^1$ is phenyl optionally substituted with one or more substituents independently selected from halogen, $CF_3$, (1-4C)alkoxy and CN. In one embodiment, $Ar^1$ is phenyl optionally substituted with one or more substituents independently selected from F, Cl, $CF_3$, MeO and CN.

In one embodiment of Formula I, Ring B when represented by $Ar^1$ is phenyl, 2-fluorophenyl, 3-fluorophenyl, 4-fluorophenyl, 3,4-difluorophenyl, 3,5-difluorophenyl, 2,4-difluorophenyl, 2,5-difluorophenyl, 3,4,5-trifluorophenyl, 2-chlorophenyl, 3-chlorophenyl, 4-chlorophenyl, 3-trifluoromethylphenyl 3-methoxyphenyl, 3-chloro-4-fluorophenyl, 4-chloro-3-fluorophenyl, 3-chloro-5-fluorophenyl, 3-cyano-5-fluorophenyl, 2-cyanophenyl, 4-cyanophenyl or 3-cyano-4-fluorophenyl.

In one embodiment, Ring B is $Ar^1$, wherein $Ar^1$ is phenyl optionally substituted with one or more halogens. In one embodiment, $Ar^1$ is phenyl optionally substituted with one or more F or Cl. In one embodiment, $Ar^1$ is phenyl, 3-fluorophenyl, 4-fluorophenyl, 3,4-difluorophenyl, 3,5-difluorophenyl, 3,4,5-trifluorophenyl, 3-chloro-4-fluorophenyl, 3-chloro-5-fluorophenyl, or 4-chloro-3-fluorophenyl.

In one embodiment of Formula I, Ring B is $hetAr^1$, where $hetAr^1$ is a 5-6 membered heteroaryl having 1-3 ring heteroatoms independently selected from N, S and O, and is optionally substituted with one or more groups independently selected from (1-6C)alkyl, halogen, OH, $CF_3$, $NH_2$ and hydroxy(1-2C)alkyl. In one embodiment, Ring B is $hetAr^1$, wherein $hetAr^1$ is a 5-6 membered heteroaryl having 1-2 ring heteroatoms independently selected from N, S and O, and optionally substituted with 1-2 groups independently selected from (1-6C)alkyl, halogen, OH, $CF_3$, $NH_2$ and hydroxy(1-2C)alkyl. Examples of Ring B include pyridyl, thiophenyl, thiazolyl, oxazolyl, and isoxazolyl rings optionally substituted with 1-2 groups independently selected from (1-6C)alkyl, halogen, OH, $CF_3$, $NH_2$ and hydroxy(1-2C)alkyl. In one embodiment, Ring B is a pyridyl, thiophenyl, thiazolyl, oxazolyl, or isoxazolyl ring optionally substituted with 1-2 groups independently selected from halogen and (1-6C)alkyl.

Examples of Ring B when represented by $hetAr^1$ include pyrid-4-yl, pyrid-3-yl, pyrid-2-yl, 5-fluoropyrid-3-yl, thien-2-yl, thiazol-2-yl, 2,4-dimethylthiazol-5-yl, oxazol-5-yl, isoxazol-5-yl, 5-chloropyrid-3-yl, 5-fluoropyrid-2-yl, 3-fluoropyrid-4-yl and 1-methylpyrazol-4-yl having the structures:

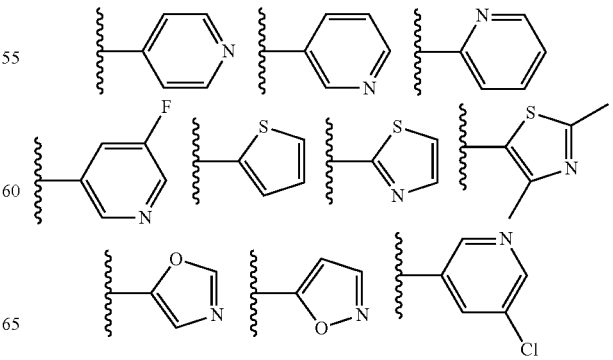

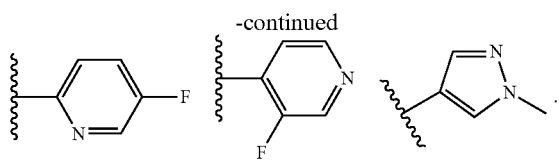

In one embodiment of Formula I, Ring B is a pyridyl ring optionally substituted with 1-2 groups independently selected from (1-6C)alkyl and halogen.

In one embodiment of Formula I, Ring C is formula C-1, C-2, C-3, C-4, C-5, C-6 or C-13, where $R^3$, $R^{3a}$, $R^4$, $R^{4a}$, $R^5$ and $R^{5a}$ are as defined for Formula I.

In one embodiment of Formula I, Ring C is formula C-1 or C-2

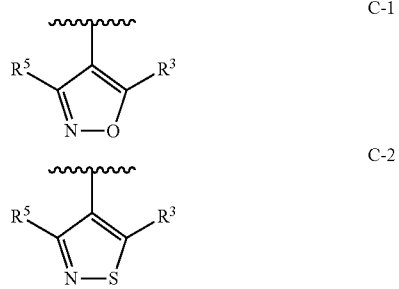

where $R^3$ and $R^5$ are as defined for Formula I.

In one embodiment of formula C-1 or C-2, $R^3$ is H.
In one embodiment of formula C-1 or C-2, $R^3$ is $NH_2$.
In one embodiment of formula C-1 or C-2, $R^3$ is CN.
In one embodiment of formula C-1 or C-2, $R^3$ is halogen.
In one embodiment of formula C-1 or C-2, $R^3$ is (1-3C) alkyl optionally substituted with 1 to 3 fluoros. In one embodiment, $R^3$ is methyl, ethyl, isopropyl, trifluoromethyl or 2,2,2-trifluoroethyl.

In one embodiment of formula C-1 or C-2, $R^3$ is $H_2NC(=O)$—, $(1\text{-}3Calkyl)NHC(=O)$— or $di(1\text{-}3Calkyl)NHC(=O)$—. In one embodiment, $R^3$ is $H_2NC(=O)$—.

In one embodiment of formula C-1 or C-2, $R^3$ is hydroxy (1-3C)alkyl. In one embodiment, $R^3$ is $HOCH_2CH_2$— or $HOC(CH_3)_2$—.

In one embodiment of formula C-1 or C-2, $R^3$ is $CH_3OCH_2CH_2$.

In one embodiment of formula C-1 or C-2, $R^3$ is (3-4C) cycloalkyl.

In one embodiment of formula C-1 or C-2, $R^3$ is (1-3C) alkoxy. In one embodiment, $R^3$ is methoxy or ethoxy.

In one embodiment of formula C-1 or C-2, $R^3$ is (1-3C) alkyl [optionally substituted with 1 to 3 fluoros] or $H_2NC(=O)$—. In one embodiment of Ring C-1 or C-2, $R^3$ is methyl or $H_2NC(=O)$—.

In one embodiment of formula C-1 or C-2, $R^5$ is H.
In one embodiment of formula C-1 or C-2, $R^5$ is (1-6C) alkyl [optionally substituted with 1-5 fluoros]. In one embodiment, $R^5$ is methyl, ethyl, isopropyl, trifluoromethyl, or 2,2,2-trifluoroethyl.

In one embodiment of formula C-1 or C-2, $R^5$ is halogen. In one embodiment, $R^5$ is F, Cl or Br.

In one embodiment of formula C-1 or C-2, $R^5$ is CN.
In one embodiment of formula C-1 or C-2, $R^5$ is (1-4C) alkoxy. In one embodiment, $R^5$ is methoxy or ethoxy.

In one embodiment of formula C-1 or C-2, $R^5$ is hydroxy (1-4C)alkyl. In one embodiment, $R^5$ is $HOCH_2$ or $HOCH_2CH_2$.

In one embodiment of formula C-1 or C-2, $R^5$ is (1-3C alkoxy)(1-4C)alkyl. In one embodiment, $R^5$ is $CH_3OCH_2CH_2$—.

In one embodiment of formula C-1 or C-2, $R^5$ is (1-4C alkyl)OC(=O)—. In one embodiment, $R^5$ is $CH_3OC(=O)$—.

In one embodiment of formula C-1 or C-2, $R^5$ is (1-6C) alkylthio. In one embodiment, $R^5$ is $CH_3S$— or $CH_3CH_2S$—.

In one embodiment of formula C-1 or C-2, $R^5$ is (3-4C) cycloalkyl.

In one embodiment of formula C-1 or C-2, $R^5$ is amino. In one embodiment, $R^5$ is $H_2N$—, $CH_3NH$—, or $(CH_3)_2N$—.

In one embodiment of formula C-1 or C-2, $R^5$ is aminocarbonyl. In one embodiment, $R^5$ is $H_2NC(=O)$—, $CH_3NHC(=O)$—, or $(CH_3)_2NC(=O)$—.

In one embodiment of formula C-1 or C-2, $R^5$ is trifluoro (1-3C alkyl)amido. In one embodiment, $R^5$ is $CF_3C(=O)NH$—.

In one embodiment of formula C-1 or C-2, $R^5$ is phenyl optionally substituted with one or more groups independently selected from halogen, (1-6C)alkyl and (1-6C)alkoxy. In one embodiment, $R^5$ is phenyl optionally substituted with one or more groups independently selected from F, Cl, Br, methyl, ethyl, methoxy and ethoxy. In one embodiment, $R^5$ is phenyl.

In one embodiment of formula C-1 or C-2, $R^5$ is (1-6C) alkyl [optionally substituted with 1-5 fluoros] or phenyl [optionally substituted with one or more groups independently selected from halogen, (1-6C)alkyl and (1-6C) alkoxy].

In one embodiment of formula C-1 or C-2, $R^5$ is methyl or phenyl.

In one embodiment of formula C-1 or C-2, $R^3$ is (1-3C) alkyl [optionally substituted with 1 to 3 fluoros] or $H_2NC(=O)$—; and $R^5$ is (1-6C)alkyl [optionally substituted with 1-5 fluoros] or phenyl [optionally substituted with one or more groups independently selected from halogen, (1-6C) alkyl and (1-6C)alkoxy].

In one embodiment of formula C-1 or C-2, $R^3$ is (1-3C) alkyl [optionally substituted with 1 to 3 fluoros] or $H_2NC(=O)$—; and $R^5$ is phenyl [optionally substituted with one or more groups independently selected from halogen, (1-6C) alkyl and (1-6C)alkoxy].

In one embodiment Ring C is formula C-1 or C-2 and is selected from the structures:

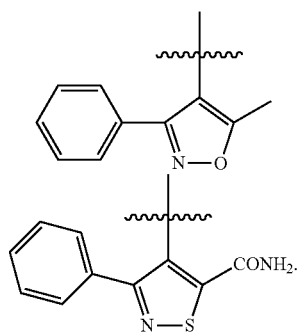

In one embodiment of Formula I, Ring C is formula C-3, C-4, C-5, C-6 or C-13

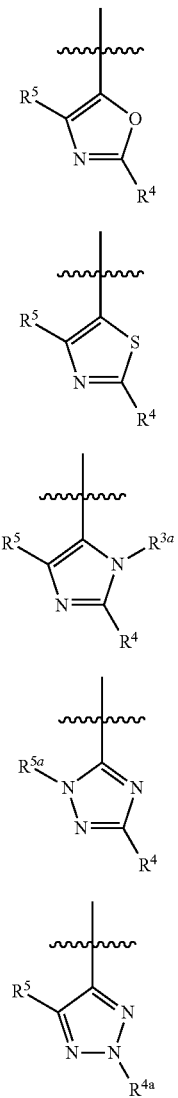

where $R^{3a}$, $R^4$, $R^{4a}$, $R^5$ and $R^{5a}$ are as defined for Formula I.

In one embodiment of formula C-5, $R^{3a}$ is H.

In one embodiment of formula C-5, $R^{3a}$ is (1-3C)alkyl.

In one embodiment of formula C-5, $R^{3a}$ is $CF_3CH_2CH_2$, $HCF_2CH_2CH_2$, $H_2FCCH_2CH_2$ or $CF_3CH_2$.

In one embodiment of formula C-5, $R^{3a}$ is $HOCH_2CH_2$.

In one embodiment of formula C-5, $R^{3a}$ is $MeOCH_2CH_2$.

In one embodiment of formula C-5, $R^{3a}$ is $H_2NC(=O)-$, $(1-3Calkyl)NHC(=O)-$, $di(1-3Calkyl)NHC(=O)-$. In one embodiment, $R^3$ is $H_2NC(=O)-$.

In one embodiment of formula C-5, $R^{3a}$ is (3-4C)cycloalkyl.

In one embodiment of formula C-3, C-4, C-5, C-6 or C-13, $R^5$ or $R^{5a}$ is H.

In one embodiment of formula C-3, C-4, C-5, or C-13, $R^5$ is (1-6C)alkyl optionally substituted with 1-5 fluoros. In one embodiment, $R^5$ is methyl, ethyl or isopropyl.

In one embodiment of formula C-6, $R^{5a}$ is (1-6C)alkyl, $CF_3CH_2CH_2$, $HCF_2CH_2CH_2$, $H_2FCCH_2CH_2$, or $CF_3CH_2$.

In one embodiment of formula C-3, C-4, C-5 or C-13, $R^5$ is halogen.

In one embodiment of formula C-3, C-4, C-5 or C-13, $R^5$ is CN.

In one embodiment of formula C-3, C-4, C-5 or C-13, $R^5$ is (1-4C)alkoxy. In one embodiment, $R^5$ is methoxy or ethoxy.

In one embodiment of formula C-3, C-4, C-5, C-6 or C-13, $R^5$ or $R^{5a}$ is hydroxy(1-4C)alkyl. In one embodiment, $R^5$ or $R^{5a}$ is $HOCH_2CH_2-$.

In one embodiment of formula C-3, C-4, C-5, C-6 or C-13, $R^5$ or $R^{5a}$ is (1-3C alkoxy)(1-4C)alkyl. In one embodiment, $R^5$ or $R^{5a}$ is $CH_3OCH_2CH_2-$.

In one embodiment of formula C-3, C-4, C-5 or C-13, $R^5$ is (1-4C alkyl)OC(=O)-. In one embodiment, $R^5$ is $CH_3OC(=O)-$.

In one embodiment of formula C-3, C-4, C-5 or C-13, $R^5$ is (1-6C)alkylthio. In one embodiment, $R^5$ is $CH_3S-$.

In one embodiment of formula C-3, C-4, C-5, C-6 or C-13, $R^5$ or $R^{5a}$ is (3-4C)cycloalkyl.

In one embodiment of formula C-3, C-4, C-5 or C-13, $R^5$ is amino. In one embodiment, $R^5$ is $NH_2$.

In one embodiment of formula C-3, C-4, C-5 or C-13, $R^5$ is aminocarbonyl or trifluoro(1-3C alkyl)amido.

In one embodiment of formula C-3, C-4, C-5, C-6 or C-13, $R^5$ or $R^{5a}$ is phenyl [optionally substituted with one or more groups independently selected from halogen, (1-6C) alkyl and (1-6C)alkoxy]. In one embodiment, $R^5$ or $R^{5a}$ is phenyl.

In one embodiment of formula C-3, C-4, C-5, C-6 or C-13, $R^4$ or $R^{4a}$ is H.

In one embodiment of formula C-3, C-4, C-5 or C-6, $R^4$ is OH.

In one embodiment of formula C-3, C-4, C-5 or C-6, $R^4$ is (1-6C)alkyl optionally substituted with 1-5 fluoros. In one embodiment, $R^4$ is methyl, ethyl, isopropyl, tert-butyl, fluoromethyl, 2-fluoroethyl, difluoromethyl and 2,2-difluoroethyl, trifluoromethyl, 2,2,2-trifluoroethyl, 3,3,3-trifluoropropyl, 2,2,3,3-tetrafluoropropyl or 2,2,3,3,3-pentafluoropropyl.

In one embodiment of formula C-13, $R^{4a}$ is (1-6C)alkyl, $CF_3CH_2CH_2$, $HCF_2CH_2CH_2$, $H_2FCCH_2CH_2$ or $CF_3CH_2$, In one embodiment of formula C-3, C-4, C-5, C-6 or C-13, $R^4$ or $R^{4a}$ is cyano(1-6C)alkyl. In one embodiment, $R^4$ or $R^{4a}$ is cyanomethyl or 2-cyanopropan-2-yl.

In one embodiment of formula C-3, C-4, C-5, C-6 or C-13, $R^4$ or $R^{4a}$ is hydroxy(1-6C)alkyl. In one embodiment, $R^4$ is hydroxymethyl, 2-hydroxyethyl, 2-hydroxypropyl, 2-hydroxy-2-methylpropyl or 1-hydroxy-2-methylpropan-2-yl. In one embodiment, $R^{4a}$ is 2-hydroxyethyl, 2-hydroxypropyl, 2-hydroxy-2-methylpropyl or 1-hydroxy-2-methylpropan-2-yl.

In one embodiment of formula C-3, C-4, C-5, C-6 or C-13, $R^4$ or $R^{4a}$ is dihydroxy(2-6C)alkyl. In one embodiment, $R^4$ or $R^{4a}$ is 2,3-dihydroxypropyl.

In one embodiment of formula C-3, C-4, C-5, C-6 or C-13, $R^4$ or $R^{4a}$ is (1-3C alkoxy)(1-6C)alkyl. In one embodiment, $R^4$ is methoxymethyl, 2-methoxyethyl or 3-methoxypropyl. In one embodiment, $R^{4a}$ is 2-methoxyethyl or 3-methoxypropyl.

In one embodiment of formula C-3, C-4, C-5, C-6 or C-13, $R^4$ or $R^{4a}$ is amino(1-6C)alkyl. In one embodiment, $R^4$ or $R^{4a}$ is aminomethyl, 2-aminoethyl or 3-aminopropyl.

In one embodiment of formula C-3, C-4, C-5, C-6 or C-13, $R^4$ or $R^{4a}$ is aminocarbonyl(1-6C)alkyl. In one embodiment, $R^4$ or $R^{4a}$ is aminocarbonylmethyl or 2-(aminocarbonyl)ethyl.

In one embodiment of formula C-3, C-4, C-5, C-6 or C-13, $R^4$ or $R^{4a}$ is (1-3C)alkylsulfonamido(1-6C)alkyl. In one embodiment, R⁴ is CH₃SO₂NHCH₂— or CH₃SO₂NHCH₂CH₂—. In one embodiment, R⁴ᵃ is CH₃SO₂NHCH₂CH₂—.

In one embodiment of formula C-3, C-4, C-5, C-6 or C-13, R⁴ or R⁴ᵃ is hydroxycarbonyl(1-6C)alkyl. In one embodiment, R⁴ or R⁴ᵃ is HOC(=O)CH₂— or HOC(=O)CH₂CH₂—.

In one embodiment of formula C-3, C-4, C-5, C-6 or C-13, R⁴ or R⁴ᵃ is hetAr³(1-6C)alkyl, where hetAr³ is a 5-membered heteroaryl ring having 1-3 ring atoms independently selected from N, S and O and optionally substituted with (1-6C)alkyl. In one embodiment, hetAr³ is a thienyl, furyl, imidazolyl, pyrazolyl, thiazolyl, isothiazolyl, oxazolyl, isoxazolyl, triazolyl, thiadiazolyl or oxadiazolyl ring optionally substituted with (1-6C)alkyl. In one embodiment, R⁴ or R⁴ᵃ when represented by hetAr³(1-6C)alkyl is (1-methyl-1H-1,2,4-triazol-3-yl)methyl or (5-methyl-1,3,4-oxadiazol-2-yl)methyl.

In one embodiment of formula C-3, C-4, C-5, C-6 or C-13, R⁴ or R⁴ᵃ is Ar³(1-6C)alkyl, where phenyl optionally substituted with (1-4C)alkoxy or hydroxy(1-4C)alkyl. In one embodiment, R⁴ or R⁴ᵃ is benzyl.

In one embodiment of formula C-3, C-4 or C-5 or C-6, R⁴ is (1-6C)alkoxy optionally substituted with 1-5 fluoros. In one embodiment, R⁴ is methoxy, ethoxy, fluoromethoxy, 2-fluoroethoxy, 2,2-difluoromethoxy, trifluoromethoxy, 2,2,2-trifluoroethoxy or 2,2-difluoroethoxy. In one embodiment, R⁴ is 2-fluoroethoxy.

In one embodiment of formula C-3, C-4, C-5 or C-6, R⁴ is cyano(1-6C)alkoxy. In one embodiment, R⁴ is cyanomethoxy or 2-cyanoethoxy.

In one embodiment of formula C-3, C-4, C-5 or C-6, R⁴ is hydroxy(1-6C)alkoxy. In one embodiment, R⁴ is 2-hydroxy-2-methylpropoxy, 2-hydroxyethoxy, 2-hydroxypropoxy, 2-hydroxy-2-methylpropoxy or 2-hydroxybutoxy.

In one embodiment of formula C-3, C-4, C-5 or C-6, R⁴ is dihydroxy(2-6C)alkoxy. In one embodiment, R⁴ is 2,3-dihydroxypropoxy or 3-hydroxy-2-(hydroxymethyl)propoxy.

In one embodiment of formula C-3, C-4, C-5 or C-6, R⁴ is amino(2-6C)alkoxy. In one embodiment, R⁴ is H₂NCH₂CH₂O—.

In one embodiment of formula C-3, C-4, C-5 or C-6, R⁴ is hetCyc²(1-6C)alkoxy, where hetCyc² is a 4-6 membered heterocyclic ring having 1-2 ring heteroatoms independently selected from N and O, wherein hetCyc² is optionally substituted with 1-2 groups independently selected from (1-6C)alkyl, (1-4C alkoxy)carbonyl, and (1-6C)acyl. In one embodiment, hetCyc² is oxetanyl, tetrahydrofuranyl, tetrahydropyranyl, azetidinyl, pyrrolidinyl, piperidinyl, piperazinyl, morpholinyl, or and 1,3-dioxolanyl optionally substituted with 1-2 groups independently selected from (1-6C)alkyl, (1-4C alkoxy)carbonyl and (1-6C)acyl. In one embodiment, R⁴ when represented by hetCyc²(1-6C)alkoxy is oxetan-2-ylmethoxy, 2-(oxetan-2-yl)propoxy, (2,2-dimethyl-1,3-dioxolan-4-yl)methoxy, (1,3-dioxolan-4-yl)methoxy, 2-morpholinoethoxy, piperazinylethyoxy or piperidinylethoxy optionally substituted with 1-2 groups independently selected from (1-6C)alkyl, (1-4C alkoxy)carbonyl and (1-6C)acyl. In one embodiment, R⁴ is represented by the structures:

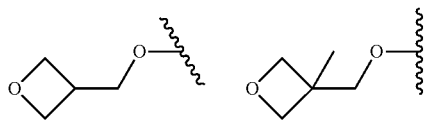

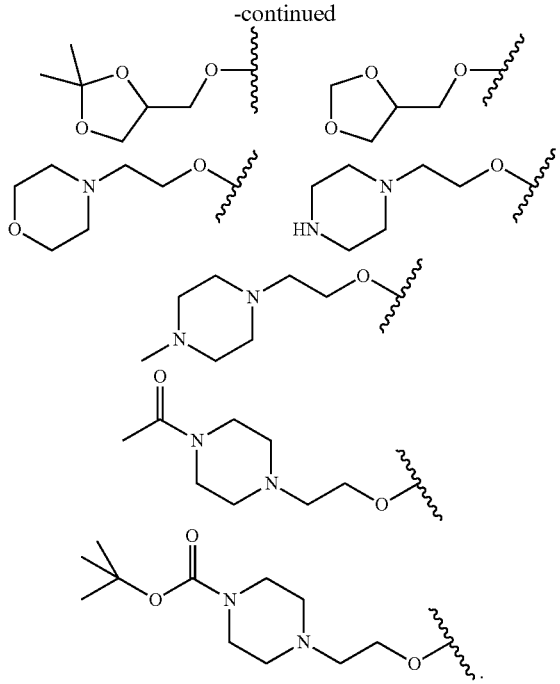

In one embodiment of formula C-3, C-4, C-5 or C-6, R⁴ is hetAr³(1-6C)alkoxy, where hetAr³ is a 5-membered heteroaryl ring having 1-3 ring atoms independently selected from N, S and O and optionally substituted with (1-6C)alkyl. In one embodiment, hetAr³ is a thienyl, furyl, imidazolyl, pyrazolyl, thiazolyl, isothiazolyl, oxazolyl, isoxazolyl, triazolyl, thiadiazolyl or oxadiazolyl ring optionally substituted with (1-6C)alkyl. In one embodiment, hetAr³ is triazolyl or oxadiazolyl ring optionally substituted with a (1-6C)alkyl group such as a methyl group. In one embodiment, R⁴ when represented by hetAr³(1-6C)alkoxy is (1-methyl-1H-1,2,4-triazol-3-yl)methoxy or (5-methyl-1,3,4-oxadiazol-2-yl)methoxy, which can be represented by the structures:

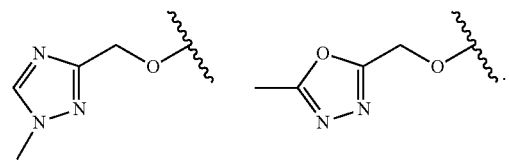

In one embodiment of formula C-3, C-4, C-5 or C-6, R⁴ is Ar³(1-6C)alkoxy, where Ar³ is phenyl optionally substituted with (1-4C)alkoxy. In one embodiment, R⁴ is phenylmethoxy or (4-methoxyphenyl)methoxy having the structures:

In one embodiment of formula C-3, C-4, C-5 or C-6, R⁴ is (1-4C alkoxy)(1-6C)alkoxy. In one embodiment, R⁴ is (2-methoxy)ethoxy having the structure:

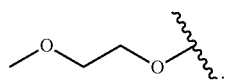 [SMILES: *OCCOC]

In one embodiment of formula C-3, C-4, C-5 or C-6, R⁴ is (1-3Calkylsulfonyl)(1-6C)alkoxy. In one embodiment, R⁴ is (2-methylsulfonyl)ethoxy having the structure:

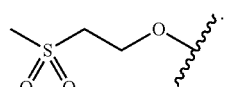

In one embodiment of formula C-3, C-4, C-5 or C-13, R⁴ or R⁴ᵃ is (3-6C)cycloalkyl optionally substituted with F, OH, (1-6C alkyl), (1-6C)alkoxy or (1-3C alkoxy)(1-6C)alkyl. Examples include cyclopropyl, cyclobutyl, cyclopentyl, cyclohexyl, 2-hydroxycyclobutyl. In one embodiment, R⁴ or R⁴ᵃ is cyclopropyl or 2-hydroxycyclobutyl. In one embodiment, R⁴ is cyclopropyl.

In one embodiment of formula C-3, C-4, C-5, C-6 or C-13, R⁴ or R⁴ᵃ is hetAr⁴, where hetAr⁴ is a 5-6 membered heteroaryl ring having 1-3 ring heteroatoms independently selected from N, S and O and optionally substituted with one or more substituents independently selected from (1-6C) alkyl, halogen, CN, hydroxy(1-6C)alkyl, trifluoro(1-6C) alkyl, difluoro(1-6C)alkyl, fluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C) alkylsulfonyl, NH₂, (1-6C alkyl)amino, di(1-6C alkyl) amino, (1-3C trifluoroalkoxy), fluoro(1-6C alkyl)amino, difluoro(1-6C alkyl)amino, trifluoro(1-6C alkyl)amino, and (3-4C cycloalkyl)amino.

In one embodiment of formula C-3, C-4, C-5, C-6 or C-13, R⁴ or R⁴ᵃ is hetAr⁴ where hetAr⁴ is pyridyl, pyrimidinyl pyridazinyl, pyrazolyl, imidazolyl, thienyl, 1,2,4-triazolyl, 1,2,3-triazolyl, thiazolyl, oxazolyl, 1,3,4-oxadiazolyl, or 1,2,4-oxadiazolyl optionally substituted with one or more substituents independently selected from (1-6C)alkyl, halogen, CN, hydroxy(1-6C)alkyl, trifluoro(1-6C)alkyl, difluoro(1-6C)alkyl, fluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy), fluoro(1-6C alkyl)amino, difluoro(1-6C alkyl) amino, trifluoro(1-6C alkyl)amino, and (3-4C cycloalkyl) amino.

In one embodiment of formula C-3, C-4, C-5, C-6 or C-13, R⁴ or R⁴ᵃ is hetAr⁴ where hetAr⁴ is pyridyl, pyrimidinyl pyridazinyl, pyrazolyl, imidazolyl, thienyl, 1,2,4-triazolyl, 1,2,3-triazolyl, thiazolyl, oxazolyl, 1,3,4-oxadiazolyl, or 1,2,4-oxadiazolyl optionally substituted with one or more substituents independently selected from (1-6C)alkyl, hydroxy(1-6C)alkyl, trifluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy)(1-3C)trifluoroalkyl and cyclopropylNH—.

In one embodiment of formula C-3, C-4, C-5, C-6 or C-13, R⁴ or R⁴ᵃ is hetAr⁴, where hetAr⁴ is pyridyl, pyrimidinyl pyridazinyl, pyrazolyl, imidazolyl, thionyl, triazolyl, thiazolyl, oxazolyl, 1,3,4-oxadiazolyl, or 1,2,4-oxadiazolyl optionally substituted with 1-3 substituents independently selected from fluoro, methyl, ethyl, isopropyl, cyclopropy-lmethyl, cyclopropyl, trifluoromethyl, 2,2,2-trifluoroethyl, methoxy, ethoxy, CN, H₂N—, (CH₃)₂N—, 2-hydroxyethyl, 2-methoxyethyl, 1-(2,2,2-trifluoroethoxy)-2,2,2-trifluoroethyl, cyclopropylcarbonyl, methylsulfonyl and cyclopropylNH—.

In one embodiment of formula C-3, C-4, C-5, C-6 or C-13, R⁴ or R⁴ᵃ is hetAr⁴, where hetAr⁴ is pyridyl, pyrimidinyl or pyridazinyl optionally substituted with 1-3 substituents independently selected from fluoro, methyl, ethyl, isopropyl, cyclopropylmethyl, cyclopropyl, trifluoromethyl, 2,2,2-trifluoroethyl, methoxy, ethoxy, CN, H₂N—, CH₃NH—, (CH₃)₂N—, and cyclopropylNH—. In one embodiment of formula C-3, C-4, C-5, C-6 or C-13, R⁴ or R⁴ᵃ is selected from the structures:

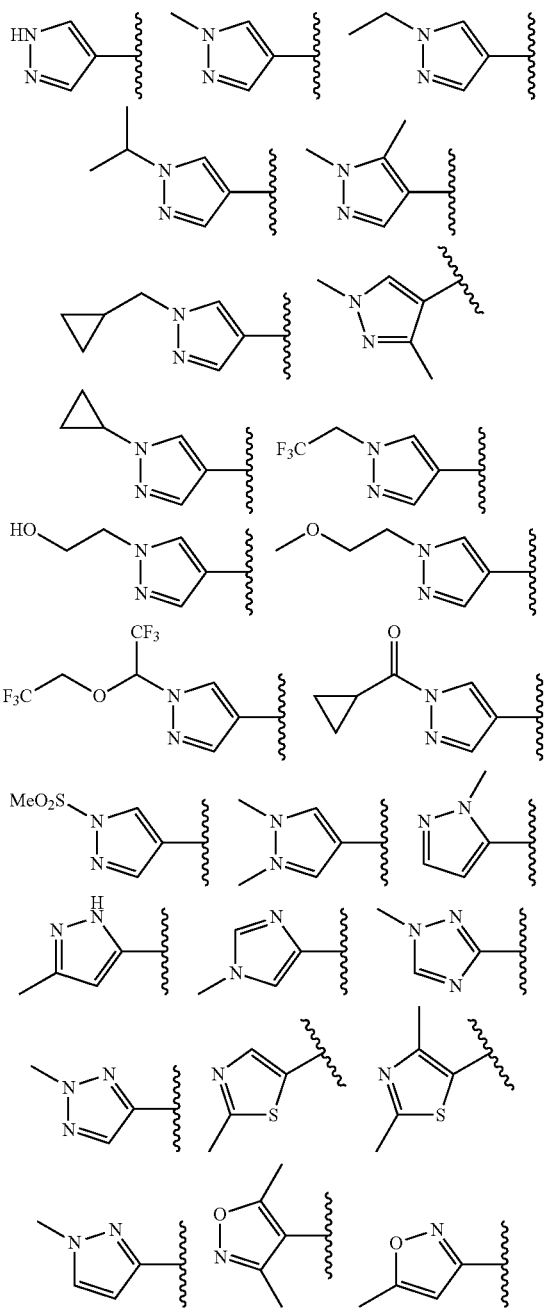

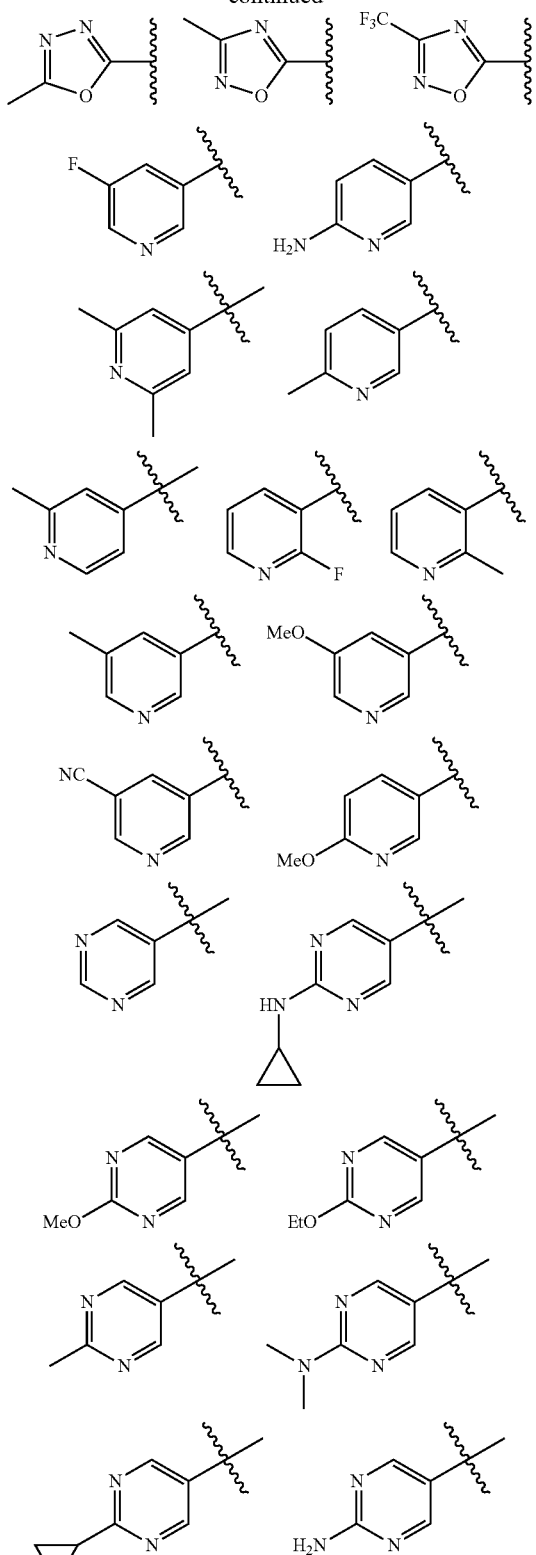
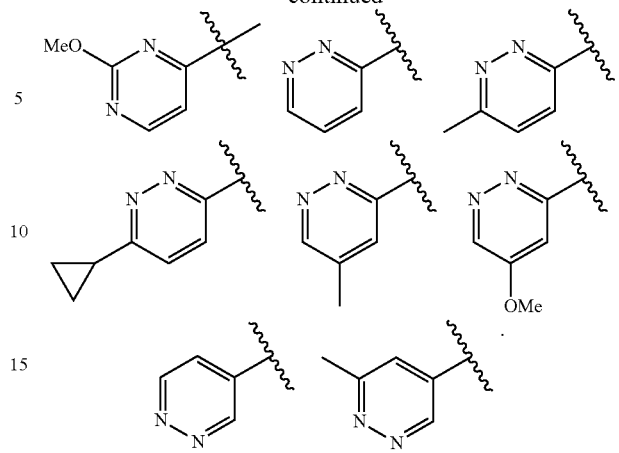

In one embodiment of formula C-3, C-4, C-5 or C-6, R[4] is hetAr[4]—O—. In one embodiment, R[4] is the structure:

In one embodiment of formula C-3, C-4, C-5, C-6 or C-13, R[4] or R[4a] is Ar[4], where Ar[4] is phenyl optionally substituted with one or more groups independently selected from (1-6C)alkyl, halogen, CN, CF$_3$, CF$_3$O—, (1-6C) alkoxy, (1-6Calkyl)OC(=O)—, aminocarbonyl, (1-6C) alkylthio, hydroxy(1-6C)alkyl, (1-6C alkyl)SO$_2$—, HOC(=O)— and (1-3C alkoxy)(1-3C alkyl)OC(=O)—. In one embodiment, Ar[4] is phenyl optionally substituted with one or more groups independently selected from methyl, F, Cl, CN, methoxy, CH$_3$OC(=O)—, aminocarbonyl, methylaminocarbonyl, dimethylaminocarbonyl, methylthio, CH$_3$SO$_2$—, HOC(=O)— and CH$_3$OCH$_2$CH$_2$OC(=O)—. In one embodiment, Ar[4] is phenyl optionally substituted with one or two of said substituents. In one embodiment, Ar[4] is selected from the structures:

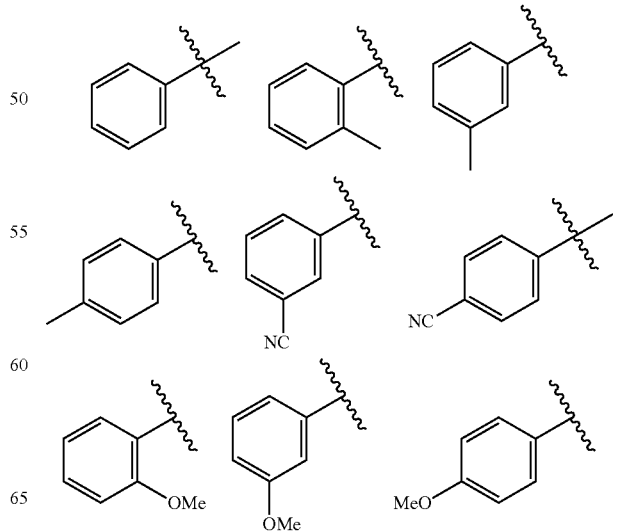

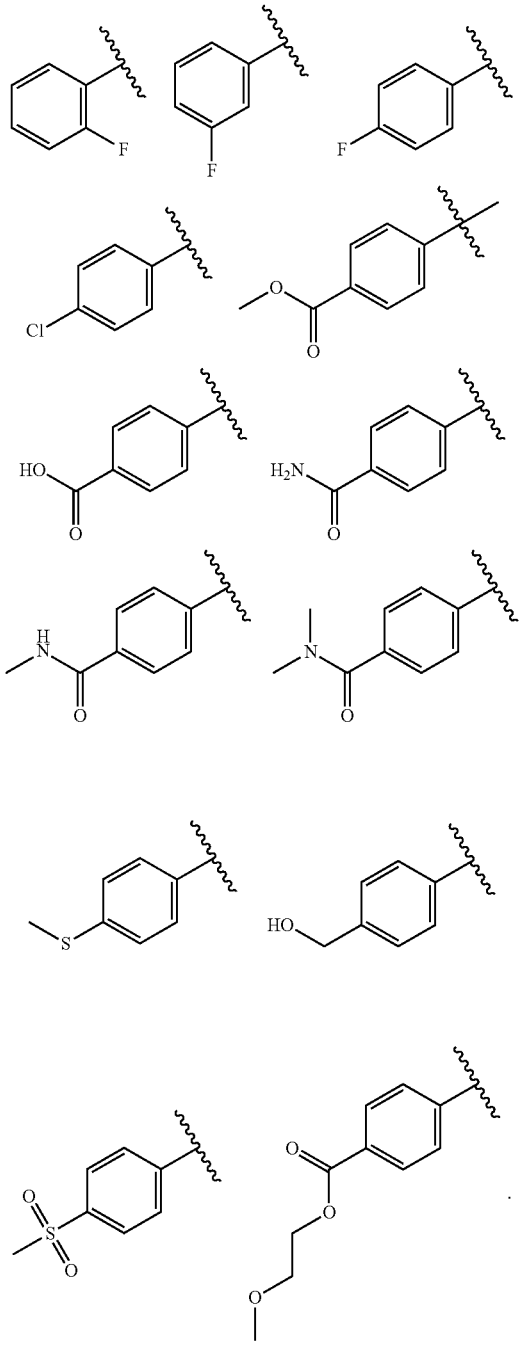

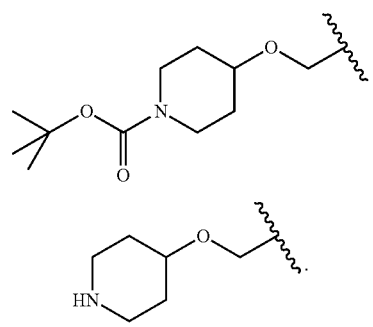

In one embodiment of formula C-3, C-4, C-5 or C-6, $R^4$ is (1-4C alkoxycarbonyl)(1-6C)alkoxy. In one embodiment, $R^4$ is methoxycarbonyl(1-6C)alkoxy or ethyoxycarbonyl(1-6C)alkoxy. A particular example is ethoxycarbonylmethoxy.

In one embodiment of formula C-3, C-4, C-5 or C-6, $R^4$ is hydroxycarbonyl(1-6C)alkoxy. In one embodiment, $R^4$ is hydroxycarbonylmethoxy.

In one embodiment of formula C-3, C-4, C-5 or C-6, $R^4$ is aminocarbonyl(1-6C)alkoxy. In one embodiment, $R^4$ is $H_2NC(=O)(1-6C)$alkoxy, (1-6C alkyl)NHC(=O)(1-6C)alkoxy, or di(1-6Calkyl)NC(=O)(1-6C)alkoxy. In one embodiment, $R^4$ is $CH_3CH_2NC(=O)CH_2O-$, $H_2NC(=O)CH_2O-$ or $H_2NC(=O)CH_2CH_2O-$.

In one embodiment of formula C-3, C-4, C-5 or C-6, $R^4$ is hetCyc$^2$C(=O)(1-6C)alkoxy, where hetCyc$^2$ is a 4-6 membered heterocyclic ring having 1-2 ring heteroatoms independently selected from N and O and optionally substituted with 1-2 groups independently selected from (1-6C)alkyl, (1-4C alkoxy)carbonyl, and (1-6C)acyl. In one embodiment, hetCyc$^2$ is oxetaynyl, tetrahydrofuranyl, tetrahydropyranyl, azetidinyl, pyrrolidinyl, piperidinyl, piperazinyl, morpholinyl, or 1,3-dioxolanyl optionally substituted with 1-2 groups independently selected from (1-6C)alkyl, (1-4C alkoxy)carbonyl and (1-6C)acyl. In one embodiment, hetCyc$^2$ is morpholinyl. In one embodiment, $R^4$ when represented by hetCyc$^2$C(=O)(1-6C)alkoxy has the structure:

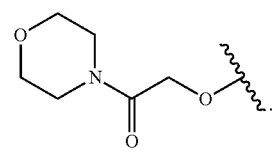 [SMILES: *OCC(=O)N1CCOCC1]

In one embodiment of formula C-3, C-4, C-5 or C-6, $R^4$ is hetCyc$^2$(O)CH$_2$, where hetCyc$^2$ is a 4-6 membered heterocyclic ring having 1-2 ring heteroatoms independently selected from N and O, wherein hetCyc$^2$ is optionally substituted with 1-2 groups independently selected from (1-6C)alkyl, (1-4C alkoxy)carbonyl, and (1-6C)acyl. Examples of hetCyc$^2$ include oxetaynyl, tetrahydrofuranyl, tetrahydropyranyl, azetidinyl, pyrrolidinyl, piperidinyl, piperazinyl, morpholinyl, and 1,3-dioxolanyl rings optionally substituted with 1-2 groups independently selected from (1-6C)alkyl, (1-4C alkoxy)carbonyl and (1-6C)acyl. In one embodiment, $R^4$ when represented by hetCyc$^2$(O)CH$_2$ is selected from the structures:

In one embodiment of formula C-3, C-4, C-5 or C-6, $R^4$ is hydroxy(1-3C alkoxy)(1-6C)alkoxy. In one embodiment, $R^4$ is 2-hydroxy-3-methoxypropoxy having the structure:

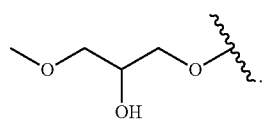 [SMILES: *OCC(O)COC]

In one embodiment of formula C-3, C-4, C-5 or C-6, $R^4$ is hydroxytrifluoro(1-6C)alkoxy. In one embodiment, $R^4$ is 3,3,3-difluoro-2-hydroxypropoxy having the structure:

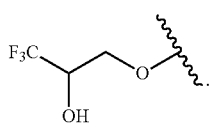

In one embodiment of formula C-3, C-4, C-5 or C-6, $R^4$ is (1-3C)alkylsulfonamido(1-6C)alkoxy. In one embodiment, $R^4$ is methanesulfonamido(1-6C)alkoxy. In one embodiment, $R^4$ is 2-methanesulfonamidoethoxy having the structure:

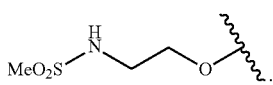

In one embodiment of formula C-3, C-4, C-5 or C-6, $R^4$ is (1-3C)alkylamido(1-6C)alkoxy. In one embodiment, $R^4$ is 2-(methylamido)ethoxy having the structure:

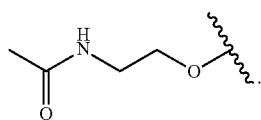 [SMILES: *OCCNC(C)=O]

In one embodiment of formula C-3, C-4, C-5 or C-6, $R^4$ is di(1-3C alkyl)aminocarboxy. In one embodiment, $R^4$ is dimethylaminocarboxy having the structure:

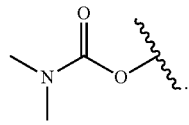 [SMILES: *OC(=O)N(C)C]

In one embodiment of formula C-3, C-4, C-5 or C-6, $R^4$ is hetCyc$^2$C(=O)O—, where hetCyc$^2$ is a 4-6 membered heterocyclic ring having 1-2 ring heteroatoms independently selected from N and O and optionally substituted with 1-2 groups independently selected from (1-6C)alkyl, (1-4C alkoxy)carbonyl and (1-6C)acyl. In one embodiment, hetCyc$^2$ is oxetaynyl, tetrahydrofuranyl, tetrahydropyranyl, azetidinyl, pyrrolidinyl, piperidinyl, piperazinyl, morpholinyl, or 1,3-dioxolanyl optionally substituted with 1-2 groups independently selected from (1-6C)alkyl, (1-4C alkoxy)carbonyl and (1-6C)acyl. In one embodiment, hetCyc$^2$ is morpholinyl. In one embodiment, $R^4$ when represented by hetCyc$^2$C(=O)O— is the structure:

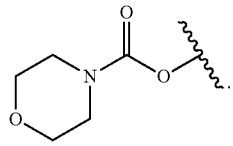 [SMILES: *OC(=O)N1CCOCC1]

In one embodiment of formula C-3, C-4, C-5, C-6 or C-13, $R^4$ or $R^{4a}$ is hydroxydifluoro(1-6C)alkyl. In one embodiment, $R^4$ or $R^{4a}$ is 2,2-difluoro-2-hydroxyethyl.

In one embodiment of formula C-3, C-4, C-5, C-6 or C-13, $R^4$ or $R^{4a}$ is (1-4C alkylcarboxy)(1-6C)alkyl. In one embodiment, $R^4$ or $R^{4a}$ is methylcarboxy(1-6C)alkyl. In one embodiment, $R^4$ or $R^{4a}$ is 2-(methylcarboxy)ethyl.

In one embodiment of formula C-3, C-4, C-5 or C-6, $R^4$ is (1-6C)alkoxycarbonyl. In one embodiment, $R^4$ is methoxycarbonyl or ethoxycarbonyl.

In one embodiment of formula C-3, C-4, C-5 or C-6, $R^4$ is hydroxycarbonyl.

In one embodiment of formula C-3, C-4, C-5 or C-6, $R^4$ is aminocarbonyl, that is, a RR'NCO— radical where R and R' are independently hydrogen or (1-6C)alkyl as defined herein. In one embodiment, $R^4$ is aminocarbonyl, methylaminocarbonyl, dimethylaminocarbonyl, ethylcarbonyl or isopropylaminocarbonyl.

In one embodiment of formula C-3, C-4, C-5 or C-6, $R^4$ is (1-3C alkoxy)aminocarbonyl. In one embodiment, $R^4$ is methoxyaminocarbonyl.

In one embodiment of formula C-3, C-4, C-5, C-6 or C-13, $R^4$ or $R^{4a}$ is hetCyc$^3$, where is a 4-7 membered heterocycle having 1-2 ring heteroatoms independently selected from N and O and optionally substituted with one or more substituents independently selected from F, CN, CF$_3$, (1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl. In one embodiment, hetCyc$^3$ is tetrahydropyranyl, piperidinyl, pyrrolidinyl or azetidinyl optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl. In one embodiment, hetCyc$^3$ is optionally substituted with one or two of said substituents. In one embodiment, hetCyc$^3$ is tetrahydropyranyl, piperidinyl, pyrrolidinyl or azetidinyl optionally substituted with CN, Me, CH$_3$C(=O)—, MeSO$_2$—, or CF$_3$SO$_2$—. In one embodiment of formula C-3, C-4, C-5, C-6 or C-13, $R^4$ or $R^{4a}$ when represented by hetCyc$^3$ is selected from the structures:

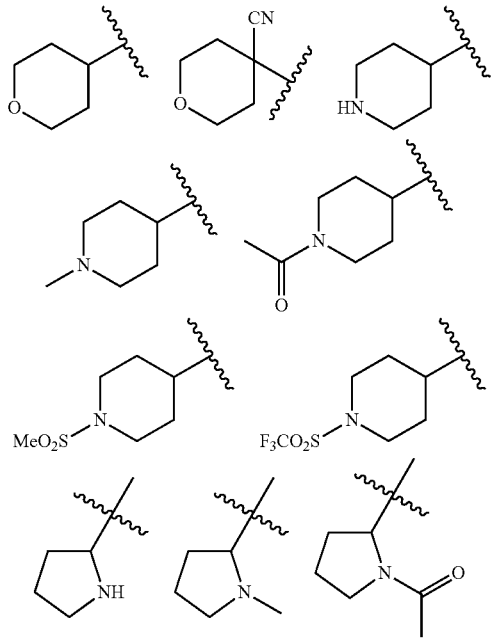

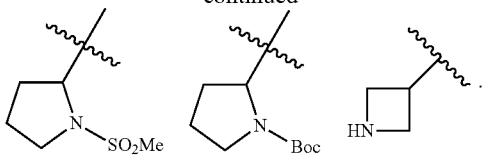

In one embodiment of formula C-3, C-4, C-5 or C-6, R⁴ is halogen. In one embodiment, R⁴ is Br.

In one embodiment of formula C-3, C-4, C-5 or C-6, R⁴ is CN.

In one embodiment of formula C-3, C-4, C-5 or C-6, R⁴ is trifluoromethylsulfonyl.

In one embodiment of formula C-3, C-4, C-5, C-6 or C-13, R⁴ or R⁴ᵃ is hetAr⁵, where hetAr⁵ is a group selected from the structures:

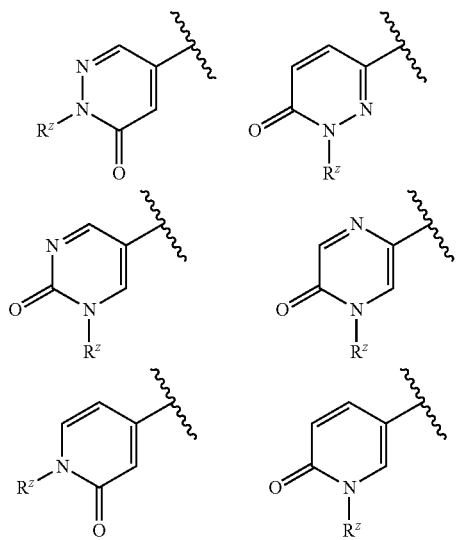

where R$^z$ is (3-4C)cycloalkyl or (1-3C)alkyl (optionally substituted with 1-3 fluoros), wherein each of said hetAr⁵ groups is optionally further substituted with one or more groups independently selected from F and (1-3C)alkyl optionally substituted with 1-3 fluoros.

In one embodiment of formula C-3, C-4, C-5, C-6 or C-13, R⁴ or R⁴ᵃ when represented by hetAr⁵ is selected from the structures:

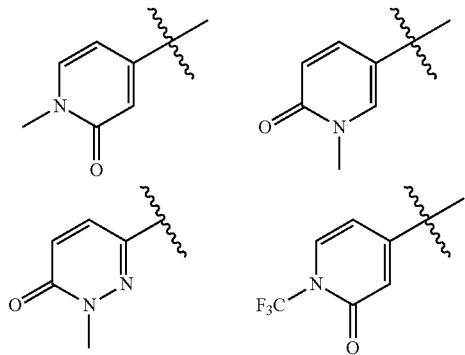

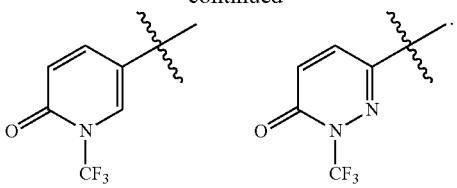

In one embodiment of formula C-3, C-4, C-5, C-6 or C-13, R⁴ or R⁴ᵃ is N-(1-3C alkyl)oxadiazolonyl. In one embodiment, R⁴ is represented by the structures:

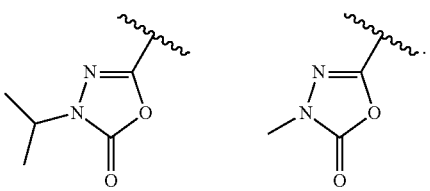

In one embodiment of formula C-3, C-4, C-5 or C-13, R⁴ is selected from H, (1-6C)alkyl, (1-6C)alkyl [optionally substituted with 1-5 fluoros], hydroxy(1-6C)alkyl, (1-3C alkoxy)(1-6C)alkyl, (3-6C)cycloalkyl, di(1-3C alkyl)aminocarboxy, hetAr⁴, hetAr⁴—O—, and hetAr⁵.

In one embodiment of formula C-6, R⁴ᵃ is selected from H, (1-6C)alkyl, CF₃CH₂CH₂, HCF₂CH₂CH₂, H₂FCCH₂CH₂, CF₃CH₂, (1-6C)alkyl, hydroxy(1-6C)alkyl, cyano(1-6C)alkyl, (1-3C alkoxy)(1-6C)alkyl, (3-6C)cycloalkyl, hetAr⁴, Ar⁴, and hetAr⁵.

In one embodiment of formula C-3, C-4, C-5, C-6 or C-13, R⁴ or R⁴ᵃ is selected from (1-6C)alkyl, hydroxy(1-6C)alkyl, hetAr⁴, Ar⁴, and hetAr⁵.

In one embodiment of formula C-3, C-4, C-5, C-6 or C-13, R⁴ or R⁴ᵃ is hetAr⁴, Ar⁴, or hetAr⁵.

In one embodiment of formula C-3, C-4, C-5, C-6 or C-13, R⁴ or R⁴ᵃ is hetAr⁴ or hetAr⁵.

In one embodiment of formula C-3, C-4, C-5, C-6 or C-13, R⁴ or R⁴ᵃ is hetAr⁵.

In one embodiment of formula C-3, C-4, C-5, C-6 or C-13, R⁴ or R⁴ᵃ is pyrazolyl optionally substituted with one or more groups independently selected from (1-6C)alkyl, or a hetAr⁵ group having the structure:

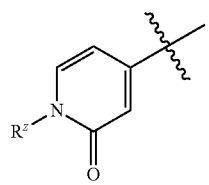

where R$^z$ is (3-4C)cycloalkyl or (1-3C)alkyl (optionally substituted with 1-3 fluoros), wherein said hetAr⁵ group is optionally further substituted with one or more groups independently selected from F and (1-3C)alkyl optionally substituted with 1-3 fluoros.

In one embodiment of Formula I, Ring C is formula C-3, C-4, C-5, C-6 or C-13, where R³ᵃ is (1-3C)alkyl; R⁴ is selected from (1-6C)alkyl, hydroxy(1-6C)alkyl, (1-6C) alkoxycarbonyl, aminocarbonyl, hetAr⁴, Ar⁴, and hetAr⁵; R⁴ᵃ is selected from (1-6C)alkyl, hydroxy(1-6C)alkyl, (1-6C)alkoxycarbonyl, aminocarbonyl, hetAr⁴, Ar⁴, and hetAr⁵; R⁵ is halogen or (1-6C)alkyl [optionally substituted with 1-5 fluoros] or phenyl [optionally substituted with one or more groups independently selected from halogen, (1-6C)alkyl and (1-6C)alkoxy], and R⁵ᵃ is (1-6C)alkyl, $CF_3CH_2CH_2$, $HCF_2CH_2CH_2$, $H_2FCCH_2CH_2$, $CF_3CH_2$, or phenyl [optionally substituted with one or more groups independently selected from halogen, (1-6C)alkyl and (1-6C)alkoxy].

In one embodiment of Formula I, formulas C-3, C-4, C-5, C-6 and C-13 are selected from the structures:

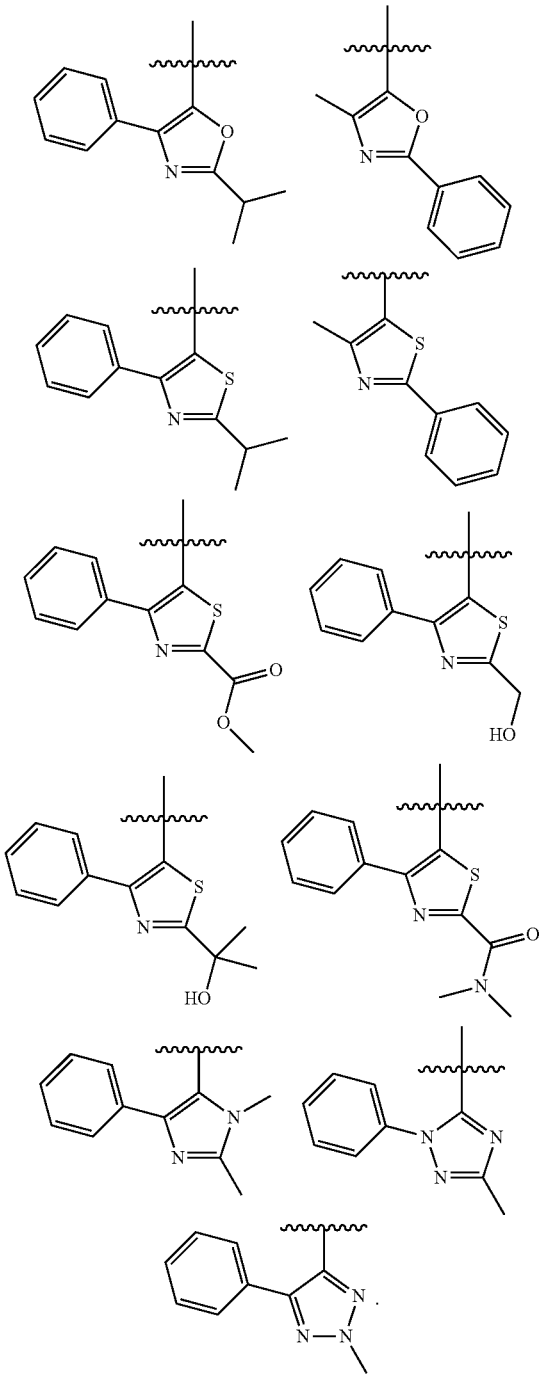

In one embodiment of Formula I, Ring C is formula C-7

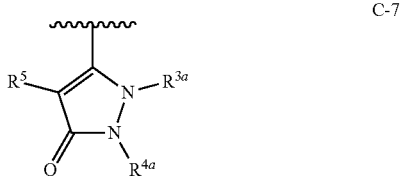

where $R^{3a}$, $R^{4a}$ and $R^5$ are as defined for Formula I.

In one embodiment of formula C-7, $R^{3a}$ is (1-3C)alkyl, $CF_3CH_2CH_2$, $HCF_2CH_2CH_2$, $H_2FCCH_2CH_2$, or $CF_3CH_2$.

In one embodiment of formula C-7, $R^{3a}$ is (1-3C)alkyl.

In one embodiment of formula C-7, $R^{3a}$ is $CF_3CH_2CH_2$, $HCF_2CH_2CH_2$, $H_2FCCH_2CH_2$, or $CF_3CH_2$.

In one embodiment of formula C-7, $R^{3a}$ is $HOCH_2CH_2$ or $MeOCH_2CH_2$.

In one embodiment of formula C-7, $R^{3a}$ is (3-4C)cycloalkyl.

In one embodiment of formula C-7, $R^5$ is any of the above described substituents as defined for formulas C-1 and C-2. In one embodiment of formula C-7, $R^5$ is phenyl optionally substituted with one or more groups independently selected from halogen, (1-6C)alkyl and (1-6C)alkoxy. In one embodiment of formula C-7, $R^5$ is phenyl optionally substituted with one or more groups independently selected from F, Cl, Br, methyl, ethyl, methoxy or ethoxy. In one embodiment, $R^5$ is phenyl.

In one embodiment of formula C-7, $R^{4a}$ is any of the above described substituents as defined for formula C-13. In one embodiment of formula C-7, $R^{4a}$ is (1-6C)alkyl, hetAr⁴, hetAr⁵ or Ar⁴. In one embodiment of formula C-7, $R^{4a}$ is (1-6C)alkyl.

In one embodiment, Ring C is formula C-7, wherein $R^{3a}$ is (1-3C)alkyl; $R^{4a}$ is (1-6C)alkyl; and $R^5$ is phenyl optionally substituted with one or more groups independently selected from halogen, (1-6C)alkyl and (1-6C)alkoxy.

In one embodiment, formula C-7 is selected from the structures:

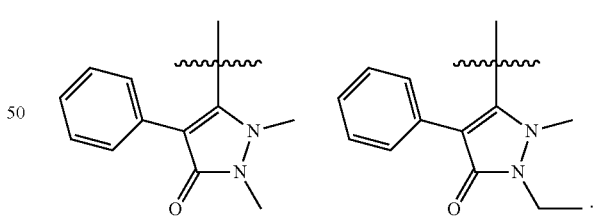

In one embodiment of Formula I, Ring C is formula C-8 or C-9

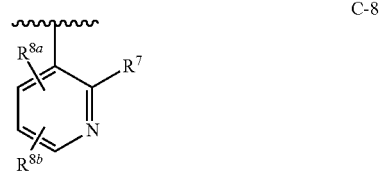

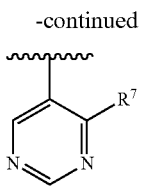

where $R^7$, $R^{8a}$ and $R^{8b}$ are as defined for Formula I.

In one embodiment of formula C-8 or C-9, $R^7$ is (1-6C)alkyl. In one embodiment, $R^7$ is methyl.

In one embodiment of formula C-8 or C-9, $R^7$ is (3-6C)cycloalkyl. In one embodiment, $R^7$ is cyclopropyl.

In one embodiment of formula C-8 or C-9, $R^7$ is phenyl optionally substituted with one or more groups independently selected from halogen, (1-6C)alkyl, (1-6C)alkoxy, (3-4C)cycloalkyl, amino, aminocarbonyl, and trifluoro(1-3C)alkylamido. In one embodiment of formula C-8 or C-9, $R^7$ is phenyl optionally substituted with one or two groups independently selected from halogen, (1-6C)alkyl, (1-6C)alkoxy, (3-4C)cycloalkyl, amino, aminocarbonyl, and trifluoro(1-3C)alkylamido. In one embodiment, $R^7$ is phenyl optionally substituted with one or more groups independently selected from F, Cl, methoxy, ethoxy, cyclopropyl, $NH_2$, $NH_2C(=O)$— and $CF_3C(=O)NH$—. In one embodiment, $R^7$ is phenyl.

In one embodiment of formula C-8 or C-9, $R^7$ is (1-6C)alkyl or phenyl.

In one embodiment of formula C-8, $R^{8a}$ and $R^{8b}$ are independently H, halogen, CN, $NH_2$, (1-6C)alkyl [optionally substituted with 1-5 fluoros], (1-6C)alkoxy, (1-3C alkoxy)(1-6C)alkyl, (1-3C alkoxy)(1-6C)alkoxy, (1-6C alkyl)sulfonyl, (3-6C cycloalkyl)sulfonyl, (3-4C)cycloalkyl, amino, (1-6CalkyONH—, phenyl [optionally substituted with (1-6C alkyl)$SO_2$—] or hetAr⁴, wherein only one of $R^{8a}$ and $R^{8b}$ can be phenyl [optionally substituted with (1-6C alkyl)$SO_2$—] or hetAr⁴; and $R^7$ is as defined for Formula I. In one embodiment, $R^7$ is (1-6C)alkyl or phenyl [optionally substituted with one or more groups independently selected from F, Cl, methoxy, ethoxy, cyclopropyl, $NH_2$, $NH_2C(=O)$— and $CF_3C(=O)NH$—].

In one embodiment of formula C-8, $R^{8a}$ is H, halogen, CN, $NH_2$, (1-6C)alkyl [optionally substituted with 1-5 fluoros], (1-6C)alkoxy, (1-3C alkoxy)(1-6C)alkyl, (1-3C alkoxy)(1-6C)alkoxy, (1-6C alkyl)sulfonyl, (3-6C cycloalkyl)sulfonyl, (3-4C)cycloalkyl, amino, (1-6Calkyl)NH—, phenyl [optionally substituted with (1-6C alkyl)$SO_2$—] or hetAr⁴; and $R^{8b}$ is H, halogen, (1-6C)alkyl, trifluoro(1-6C)alkyl or (1-6C)alkoxy; and $R^7$ is as defined for Formula I. In one embodiment, $R^7$ is (1-6C)alkyl or phenyl [optionally substituted with one or more groups independently selected from F, Cl, methoxy, ethoxy, cyclopropyl, $NH_2$, $NH_2C(=O)$— and $CF_3C(=O)NH$—].

In one embodiment of formula C-8, $R^{8a}$ is H, halogen, CN, $NH_2$, (1-6C)alkyl [optionally substituted with 1-5 fluoros], (1-6C)alkoxy, (1-3C alkoxy)(1-6C)alkyl, (1-3C alkoxy)(1-6C)alkoxy, (1-6C alkyl)sulfonyl, (3-6C cycloalkyl)sulfonyl, (3-4C)cycloalkyl, amino, (1-6Calkyl)NH—, phenyl [optionally substituted with (1-6C alkyl)$SO_2$—] or hetAr⁴; and $R^{8b}$ is H.

In one embodiment of formula C-8, $R^{8a}$ is H, halogen, (1-6C)alkyl [optionally substituted with 1-5 fluoros], (1-6C)alkoxy, (1-3C alkoxy)(1-6C)alkoxy, (1-6C alkyl)sulfonyl, (3-6C cycloalkyl)sulfonyl, phenyl or hetAr⁴; and $R^{8b}$ is H; and $R^7$ is as defined for Formula I. In one embodiment, $R^7$ is (1-6C)alkyl or phenyl [optionally substituted with one or more groups independently selected from F, Cl, methoxy, ethoxy, cyclopropyl, $NH_2$, $NH_2C(=O)$— and $CF_3C(=O)NH$—].

In one embodiment of formula C-8, $R^{8a}$ is H, halogen, (1-6C)alkyl [optionally substituted with 1-5 fluoros], (1-6C)alkoxy, (1-3C alkoxy)(1-6C)alkoxy, (1-6C alkyl)sulfonyl, (3-6C cycloalkyl)sulfonyl, phenyl or hetAr⁴; and $R^{8b}$ is H, where hetAr⁴ is a 6-membered heteroaryl having 1-2 ring nitrogen atoms and optionally substituted with one or more groups independently selected from (1-6C)alkyl [optionally substituted with 1-3 fluoros], halogen, (1-6C alkyl)amino, fluoro(1-6C alkyl)amino, difluoro(1-6C alkyl)amino, trifluoro(1-6C alkyl)amino, and (3-4C cycloalkyl)amino; and $R^7$ is as defined for Formula I. In one embodiment, $R^7$ is (1-6C)alkyl or phenyl [optionally substituted with one or more groups independently selected from F, Cl, methoxy, ethoxy, cyclopropyl, $NH_2$, $NH_2C(=O)$— and $CF_3C(=O)NH$—].

In one embodiment of formula C-8, $R^{8a}$ is H, Cl, Br, methyl, ethyl, isopropyl, methoxy, ethoxy, $CH_3OCH_2CH_2O$—, cyclopropylsulfonyl, $MeSO_2$, phenyl or pyridyl; and $R^{8b}$ is H; and $R^7$ is as defined for Formula I. In one embodiment, $R^7$ is (1-6C)alkyl or phenyl [optionally substituted with one or more groups independently selected from F, Cl, methoxy, ethoxy, cyclopropyl, $NH_2$, $NH_2C(=O)$— and $CF_3C(=O)NH$—].

In one embodiment of formula C-8, $R^{8b}$ is H, halogen, CN, $NH_2$, (1-6C)alkyl, trifluoro(1-6C)alkyl, (1-6C)alkoxy, (1-3C alkoxy)(1-6C)alkyl, (1-3C alkoxy)(1-6C)alkoxy, (1-6C alkyl)sulfonyl, (3-6C cycloalkyl)sulfonyl, (3-4C)cycloalkyl, amino, (1-6Calkyl)NH—, phenyl [optionally substituted with (1-6C alkyl)$SO_2$—] or hetAr⁴; and $R^{8a}$ is H, halogen, (1-6C)alkyl [optionally substituted with 1-5 fluoros], or (1-6C)alkoxy; and $R^7$ is as defined for Formula I. In one embodiment, $R^7$ is (1-6C)alkyl or phenyl [optionally substituted with one or more groups independently selected from F, Cl, methoxy, ethoxy, cyclopropyl, $NH_2$, $NH_2C(=O)$— and $CF_3C(=O)NH$—].

In one embodiment of formula C-8, $R^{8b}$ is H, halogen, CN, $NH_2$, (1-6C)alkyl [optionally substituted with 1-5 fluoros], (1-6C)alkoxy, (1-3C alkoxy)(1-6C)alkyl, (1-3C alkoxy)(1-6C)alkoxy, (1-6C alkyl)sulfonyl, (3-6C cycloalkyl)sulfonyl, (3-4C)cycloalkyl, amino, (1-6Calkyl)NH—, phenyl [optionally substituted with (1-6C alkyl)$SO_2$—] or hetAr⁴; and $R^{8a}$ is H.

In one embodiment of formula C-8, $R^{8b}$ is H, halogen, (1-6C)alkyl [optionally substituted with 1-5 fluoros], (1-6C)alkoxy, (1-3C alkoxy)(1-6C)alkoxy, (1-6C alkyl)sulfonyl, (3-6C cycloalkyl)sulfonyl, phenyl or hetAr⁴; and $R^{8a}$ is H; and $R^7$ is as defined for Formula I. In one embodiment, $R^7$ is (1-6C)alkyl or phenyl [optionally substituted with one or more groups independently selected from F, Cl, methoxy, ethoxy, cyclopropyl, $NH_2$, $NH_2C(=O)$— and $CF_3C(=O)NH$—].

In one embodiment of formula C-8, $R^{8b}$ is H, halogen, (1-6C)alkyl [optionally substituted with 1-5 fluoros], (1-6C)alkoxy, (1-3C alkoxy)(1-6C)alkoxy, (1-6C alkyl)sulfonyl, (3-6C cycloalkyl)sulfonyl, phenyl or hetAr⁴; and $R^{8a}$ is H, where hetAr⁴ is a 6-membered heteroaryl having 1-2 ring nitrogen atoms and optionally substituted with one or more groups independently selected from (1-6C)alkyl [optionally substituted with 1-3 fluoros], halogen, (1-6C alkyl)amino, fluoro(1-6C alkyl)amino, difluoro(1-6C alkyl)amino, trifluoro(1-6C alkyl)amino, and (3-4C cycloalkyl)amino; and $R^7$ is as defined for Formula I. In one embodiment, $R^7$ is (1-6C)alkyl or phenyl [optionally substituted with one or more groups independently selected from F, Cl, methoxy, ethoxy, cyclopropyl, NH$_2$, NH$_2$C(=O)— and CF$_3$C(=O)NH—].

In one embodiment of formula C-8, R$^{8b}$ is H, Cl, Br, methyl, ethyl, isopropyl, methoxy, ethoxy, CH$_3$OCH$_2$CH$_2$O—, cyclopropylsulfonyl, MeSO$_2$, phenyl or pyridyl; and R$^{8a}$ is H; and R$^7$ is as defined for Formula I. In one embodiment, R$^7$ is (1-6C)alkyl or phenyl [optionally substituted with one or more groups independently selected from F, Cl, methoxy, ethoxy, cyclopropyl, NH$_2$, NH$_2$C(=O)— and CF$_3$C(=O)NH—].

In one embodiment, formula C-8 has the structure:

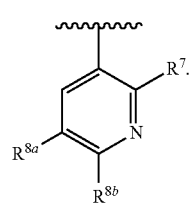

In one embodiment, formulas C-8 and C-9 are selected from the structures:

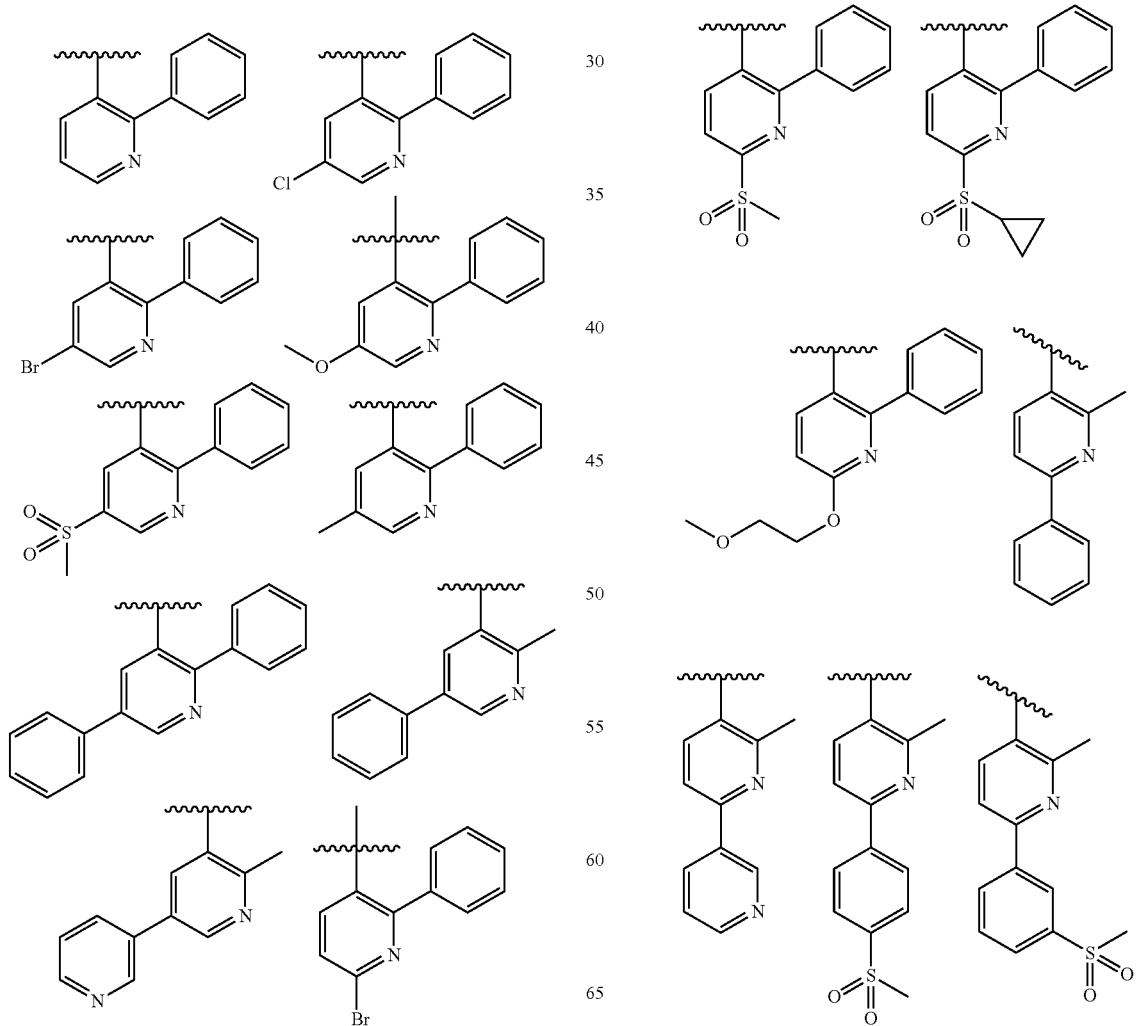

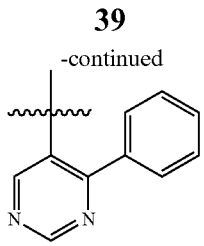

In one embodiment of Formula I, Ring C is formula C-10, C-11 or C-12

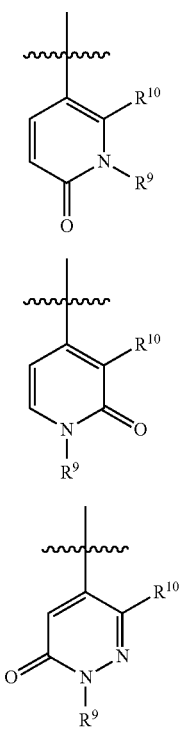

where R⁹ and R¹⁰ are as defined for Formula I.

In one embodiment of formula C-10, C-11 or C-12, $R^9$ is H.

In one embodiment of formula C-10, C-11 or C-12, $R^9$ is (1-6C)alkyl. In one embodiment, $R^9$ is methyl or ethyl.

In one embodiment of formula C-10, C-11 or C-12, $R^9$ is CF₃CH₂— or CF₃CH₂CH₂—.

In one embodiment of formula C-10, C-11 or C-12, $R^9$ is (1-3Calkoxy)(1-6C)alkyl. In one embodiment, $R^9$ is CH₃OCH₂—.

In one embodiment of formula C-10, C-11 or C-12, $R^9$ is (3-4C)cycloalkyl.

In one embodiment of formula C-10, C-11 or C-12, $R^{10}$ is (3-6C)cycloalkyl.

In one embodiment of formula C-10, C-11 or C-12, $R^{10}$ is phenyl optionally substituted with one or more substituents independently selected from halogen, (1-6C)alkyl, (1-6C)alkoxy, (3-4C)cycloalkyl, amino, aminocarbonyl and trifluoro(1-3C alkyl)amido. In one embodiment of formula C-10, C-11 or C-12, $R^{10}$ is phenyl optionally substituted with one or more substituents independently selected from halogen, (1-6C)alkyl, (1-6C)alkoxy, and amino. In one embodiment, $R^{10}$ is phenyl.

In one embodiment, formulas C-10, C-11 or C-12 are selected from the structures:

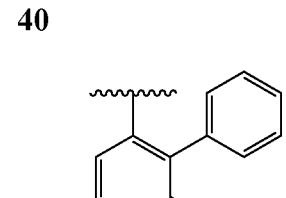

In one embodiment, Formula I comprises compounds of Formula I-a, wherein:
Ring B and the NH—C(=X)—NH moiety are in the trans configuration;
$R^a$, $R^b$, $R^c$ and $R^d$ are H;
X is O;
$R^1$ is (1-3C alkoxy)(1-6C)alkyl;
$R^2$ is H;
Ring B is $Ar^1$;
$Ar^1$ is phenyl optionally substituted with one or more substituents independently selected from halogen, CF₃, CF₃O—, (1-4C)alkoxy, hydroxy(1-4C)alkyl, (1-6C)alkyl and CN;
Ring C is selected from formulas C-1 through C-13; and $R^3$, $R^{3a}$, $R^4$, $R^{4a}$, $R^5$, $R^{5a}$, $R^7$, $R^{8a}$, $R^{8b}$, $R^9$ and $R^{10}$ are as defined for Formula I.

In one embodiment of Formula I-a,
$R^3$ is (1-3C)alkyl [optionally substituted with 1 to 3 fluoros] or H₂NC(=O)—;
$R^{3a}$ is H, (1-6C)alkyl, CF₃CH₂CH₂, HCF₂CH₂CH₂, H₂FCCH₂CH₂, or CF₃CH₂;
$R^4$ is selected from (1-6C)alkyl, hydroxy(1-6C)alkyl, (1-6C)alkoxycarbonyl, aminocarbonyl, hetAr⁴, Ar⁴, and hetAr⁵;
$R^{4a}$ is selected from (1-6C)alkyl, hydroxy(1-6C)alkyl, hetAr⁴, Ar⁴, and hetAr⁵;
$R^5$ is halogen (1-6C)alkyl [optionally substituted with 1-5 fluoros] or phenyl [optionally substituted with one or more groups independently selected from halogen, (1-6C)alkyl and (1-6C)alkoxy];
$R^{5a}$ is (1-6C)alkyl, CF₃CH₂CH₂, HCF₂CH₂CH₂, H₂FCCH₂CH₂, CF₃CH₂, or phenyl [optionally substituted with one or more groups independently selected from halogen, (1-6C)alkyl and (1-6C)alkoxy];
$R^7$ is (1-6C)alkyl or phenyl [optionally substituted with one or more groups independently selected from F, Cl, methoxy, ethoxy, cyclopropyl, NH₂, NH₂C(=O)— and CF₃C(=O)NH—]; and
$R^{8a}$ is H, halogen, CN, NH₂, (1-6C)alkyl [optionally substituted with 1-5 fluoros], (1-6C)alkoxy, (1-3C alkoxy)(1-6C)alkyl, (1-3C alkoxy)(1-6C)alkoxy, (1-6C alkyl)sulfonyl, (3-6C cycloalkyl)sulfonyl, (3-4C)cycloalkyl, amino, (1-6Calkyl)NH—, phenyl [optionally substituted with (1-6C alkyl)SO₂—] or hetAr⁴; and $R^{8b}$ is H, or
$R^{8''}$ is H, halogen, CN, NH₂, (1-6C)alkyl [optionally substituted with 1-5 fluoros], (1-6C)alkoxy, (1-3C alkoxy)(1-6C)alkyl, (1-3C alkoxy)(1-6C)alkoxy, (1-6C alkyl)sulfonyl, (3-6C cycloalkyl)sulfonyl, (3-4C)cycloalkyl, amino, (1-6Calkyl)NH—, phenyl [optionally substituted with (1-6C alkyl)SO₂—] or hetAr⁴; and R⁸ᵃ is H;
R⁹ is H, (1-6C)alkyl, CF₃CH₂—, CF₃CH₂CH₂—, (1-3Calkoxy)(1-6C)alkyl or (3-4C)cycloalkyl; and
R¹⁰ is phenyl optionally substituted with one or more substituents independently selected from halogen, (1-6C)alkyl, (1-6C)alkoxy, and amino.

In one embodiment, Formula I comprises compounds of Formula I-b, wherein:
Ring B and the NH—C(=X)—NH moiety are in the trans configuration;
Rᵃ, Rᵇ, Rᶜ and Rᵈ are H;
X is O;
R¹ is (1-3C alkoxy)(1-6C)alkyl;
R² is H;
Ring B is Ar¹;
Ar¹ is phenyl optionally substituted with one or more substituents independently selected from halogen, CF₃, CF₃O—, (1-4C)alkoxy, hydroxy(1-4C)alkyl, (1-6C)alkyl and CN;
Ring C is formula C-1 or C-2; and
R³ and R⁵ are as defined for Formula I.

In one embodiment of Formula I-b, R³ is (1-3C)alkyl [optionally substituted with 1 to 3 fluoros] or H₂NC(=O)—; and R⁵ is phenyl [optionally substituted with one or more groups independently selected from halogen, (1-6C)alkyl and (1-6C)alkoxy].

In one embodiment, Formula I comprises compounds of Formula I-c, wherein:
Ring B and the NH—C(=X)—NH moiety are in the trans configuration;
Rᵃ, Rᵇ, Rᶜ and Rᵈ are H;
X is O;
R¹ is (1-3C alkoxy)(1-6C)alkyl;
R² is H;
Ring B is Ar¹;
Ar¹ is phenyl optionally substituted with one or more substituents independently selected from halogen, CF₃, CF₃O—, (1-4C)alkoxy, hydroxy(1-4C)alkyl, (1-6C)alkyl and CN;
Ring C is formula C-3, C-4, C-5, C-6 or C-13; and
R³ᵃ, R⁴, R⁴ᵃ, R⁵, and R⁵ᵃ are as defined for Formula I.

In one embodiment of Formula I-c, R³ᵃ is (1-3C)alkyl; R⁴ is selected from (1-6C)alkyl, hydroxy(1-6C)alkyl, (1-6C)alkoxycarbonyl, aminocarbonyl, hetAr⁴, Ar⁴, and hetAr⁵; R⁴ᵃ is selected from (1-6C)alkyl, hydroxy(1-6C)alkyl, (1-6C)alkoxycarbonyl, aminocarbonyl, hetAr⁴, Ar⁴, and hetAr⁵; R⁵ is halogen, (1-6C)alkyl [optionally substituted with 1-5 fluoros] or phenyl [optionally substituted with one or more groups independently selected from halogen, (1-6C)alkyl and (1-6C)alkoxy]; and R⁵ᵃ is (1-6C)alkyl, CF₃CH₂CH₂, HCF₂CH₂CH₂, H₂FCCH₂CH₂, CF₃CH₂, or phenyl [optionally substituted with one or more groups independently selected from halogen, (1-6C)alkyl and (1-6C)alkoxy].

In one embodiment, Formula I comprises compounds of Formula I-d, wherein:
Ring B and the NH—C(=X)—NH moiety are in the trans configuration;
Rᵃ, Rᵇ, Rᶜ and Rᵈ are H;
X is O;
R¹ is (1-3C alkoxy)(1-6C)alkyl;
R² is H;
Ring B is Ar¹;
Ar¹ is phenyl optionally substituted with one or more substituents independently selected from halogen, CF₃, CF₃O—, (1-4C)alkoxy, hydroxy(1-4C)alkyl, (1-6C)alkyl and CN;
Ring C is formula C-7; and
R³ᵃ, R⁴ᵃ and R⁵ are as defined for Formula I.

In one embodiment of Formula I-d, R³ᵃ is (1-3C)alkyl, CF₃CH₂CH₂, HCF₂CH₂CH₂, H₂FCCH₂CH₂, or CF₃CH₂; R⁴ᵃ is (1-6C)alkyl; and R⁵ is phenyl optionally substituted with one or more groups independently selected from halogen, (1-6C)alkyl and (1-6C)alkoxy.

In one embodiment, Formula I comprises compounds of Formula I-e, wherein:
Ring B and the NH—C(=X)—NH moiety are in the trans configuration;
Rᵃ, Rᵇ, Rᶜ and Rᵈ are H;
X is O;
R¹ is (1-3C alkoxy)(1-6C)alkyl;
R² is H;
Ring B is Ar¹;
Ar¹ is phenyl optionally substituted with one or more substituents independently selected from halogen, CF₃, CF₃O—, (1-4C)alkoxy, hydroxy(1-4C)alkyl, (1-6C)alkyl and CN;
Ring C is formula C-8 or C-9; and
R⁷, R⁸ᵃ and R⁹ are as defined for Formula I.

In one embodiment of Formula I-e, R⁷ is (1-6C)alkyl or phenyl [optionally substituted with one or more groups independently selected from F, Cl, methoxy, ethoxy, cyclopropyl, NH₂, NH₂C(=O)— and CF₃C(=O)NH—].

In one embodiment of Formula I-e, R⁷ is (1-6C)alkyl or phenyl [optionally substituted with one or more groups independently selected from F, Cl, methoxy, ethoxy, cyclopropyl, NH₂, NH₂C(=O)— and CF₃C(=O)NH—]; R⁸ᵃ is H, halogen, CN, NH₂, (1-6C)alkyl [optionally substituted with 1-5 fluoros], (1-6C)alkoxy, (1-3C alkoxy)(1-6C)alkoxy, (1-3C alkoxy)(1-6C)alkoxy, (1-6C alkyl)sulfonyl, (3-6C cycloalkyl)sulfonyl, (3-4C)cycloalkyl, amino, (1-6Calkyl)NH—, phenyl [optionally substituted with (1-6C alkyl)SO₂—] or hetAr⁴; and R⁸ᵇ is H.

In one embodiment of Formula I-e, R⁷ is (1-6C)alkyl or phenyl [optionally substituted with one or more groups independently selected from F, Cl, methoxy, ethoxy, cyclopropyl, NH₂, NH₂C(=O)— and CF₃C(=O)NH—]; R⁸ᵃ is H, halogen, (1-6C)alkyl [optionally substituted with 1-5 fluoros], (1-6C)alkoxy, (1-3C alkoxy)(1-6C)alkoxy, (1-6C alkyl)sulfonyl, (3-6C cycloalkyl)sulfonyl, phenyl or hetAr⁴; and hetAr⁴ is a 6-membered heteroaryl having 1-2 ring nitrogen atoms and optionally substituted with one or more groups independently selected from (1-6C)alkyl [optionally substituted with 1-3 fluoros], halogen, (1-6C alkyl)amino, fluoro(1-6C alkyl)amino, difluoro(1-6C alkyl)amino, trifluoro(1-6C alkyl)amino, and (3-4C cycloalkyl)amino; and R⁸ᵇ is H.

In one embodiment of Formula I-e, R⁷ is (1-6C)alkyl or phenyl [optionally substituted with one or more groups independently selected from F, Cl, methoxy, ethoxy, cyclopropyl, NH₂, NH₂C(=O)— and CF₃C(=O)NH—]; R⁸ᵃ is H, Cl, Br, methyl, ethyl, isopropyl, methoxy, ethoxy, CH₃OCH₂CH₂O—, cyclopropylsulfonyl, MeSO₂, phenyl or pyridyl; and R⁸ᵇ is H.

In one embodiment of Formula I-e, R⁷ is (1-6C)alkyl or phenyl [optionally substituted with one or more groups independently selected from F, Cl, methoxy, ethoxy, cyclopropyl, NH₂, NH₂C(=O)— and CF₃C(=O)NH—]; R⁸ᵇ is H, halogen, CN, NH₂, (1-6C)alkyl [optionally substituted with 1-5 fluoros], (1-6C)alkoxy, (1-3C alkoxy)(1-6C)alkyl, (1-3C alkoxy)(1-6C)alkoxy, (1-6C alkyl)sulfonyl, (3-6C cycloalkyl)sulfonyl, (3-4C)cycloalkyl, amino, (1-6Calkyl) NH—, phenyl [optionally substituted with (1-6C alkyl) SO₂—] or hetAr⁴; and R$^{8a}$ is H.

In one embodiment of Formula I-e, R⁷ is (1-6C)alkyl or phenyl [optionally substituted with one or more groups independently selected from F, Cl, methoxy, ethoxy, cyclopropyl, NH₂, NH₂C(=O)— and CF₃C(=O)NH—]; R$^{8b}$ is H, halogen, (1-6C)alkyl [optionally substituted with 1-5 fluoros], (1-6C)alkoxy, (1-3C alkoxy)(1-6C)alkoxy, (1-6C alkyl)sulfonyl, (3-6C cycloalkyl)sulfonyl, phenyl or hetAr⁴; and hetAr⁴ is a 6-membered heteroaryl having 1-2 ring nitrogen atoms and optionally substituted with one or more groups independently selected from (1-6C)alkyl [optionally substituted with 1-3 fluoros], halogen, (1-6C alkyl)amino, fluoro(1-6C alkyl)amino, difluoro(1-6C alkyl)amino, trifluoro(1-6C alkyl)amino, and (3-4C cycloalkyl)amino; and R$^{8a}$ is H.

In one embodiment of Formula I-e, R⁷ is (1-6C)alkyl or phenyl [optionally substituted with one or more groups independently selected from F, Cl, methoxy, ethoxy, cyclopropyl, NH₂, NH₂C(=O)— and CF₃C(=O)NH—]; R$^{8b}$ is H, Cl, Br, methyl, ethyl, isopropyl, methoxy, ethoxy, CH₃OCH₂CH₂O—, cyclopropylsulfonyl, MeSO₂, phenyl or pyridyl; and R$^{8a}$ is H.

In one embodiment, Formula I comprises compounds of Formula I-f, wherein:

Ring B and the NH—C(=X)—NH moiety are in the trans configuration;

R$^a$, R$^b$, R$^c$ and R$^d$ are H;

X is O;

R¹ is (1-3C alkoxy)(1-6C)alkyl;

R² is H;

Ring B is Ar¹;

Ar¹ is phenyl optionally substituted with one or more substituents independently selected from halogen, CF₃, CF₃O—, (1-4C)alkoxy, hydroxy(1-4C)alkyl, (1-6C)alkyl and CN;

Ring C is formula C-10, C-11 or C-12; and

R⁹ and R¹⁰ are as defined for Formula I.

As noted, Ring B and the —NH—C(=X)—NH— moiety of Formulas I, IA and IB are in the trans configuration on the pyrrolidine ring, which relative stereochemistry can be illustrated by either generic structure A or B:

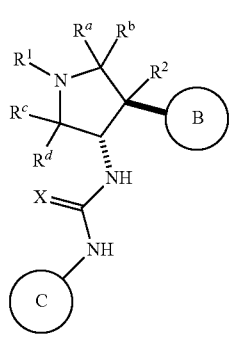

A

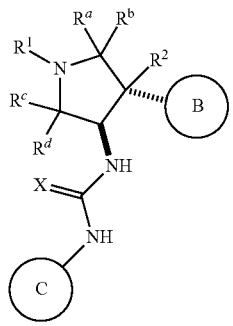

B in which the straight thick bars (━) and straight dashed bars (┅) indicate relative stereochemistry.

In one embodiment of Formulas I, IA and IB, Ring B and the —NH—C(=X)—NH— moiety trans in the absolute configuration which can be illustrated by generic structure C and D:

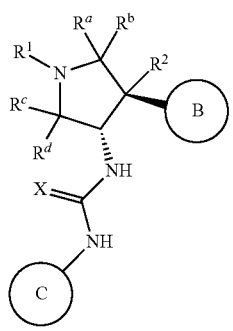

C

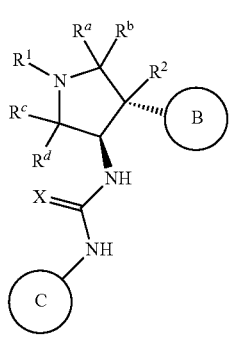

D in which the solid wedges (▬) and dashed wedges (┅) indicate absolute stereochemistry.

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention. For example, compounds of Formula I can exist in unsolvated as well as solvated forms with pharmaceutically acceptable solvents such as water, ethanol, and the like.

The compounds of Formula I include pharmaceutically acceptable salts thereof. In addition, the compounds of Formula I also include other salts of such compounds which are not necessarily pharmaceutically acceptable salts, and which are useful as intermediates for preparing and/or purifying compounds of Formula I and/or for separating enantiomers of compounds of Formula I. Particular examples of salts include hydrochloride salts, trifluoroacetate salts, and di-(trifluoroacetate) salts.

In one embodiment, the compounds of Formula I include the free base form of compounds of Examples 1-5, or pharmaceutically acceptable salts thereof In one embodiment, the compounds of Formula I include the hydrochloride salts of compounds of Examples 1-56.

In one embodiment, the compounds of Formula I include the trifluoroacetate salts of compounds of Examples 1-56.

In one embodiment, the compounds of Formula I include the di(trifluoroacetate) salts of compounds of Examples 1-56.

The term "pharmaceutically acceptable" indicates that the substance or composition is compatible chemically and/or toxicologically, with the other ingredients comprising a formulation, and/or the mammal being treated therewith.

The present invention also provides a process for the preparation of a compound of Formula I or a salt thereof as defined herein, which comprises:

(a) for a compound of Formula I where X is O, coupling a corresponding compound having the formula II

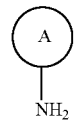

II with a corresponding compound having the formula III

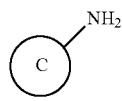

III in the presence carbonyldiimidazole or triphosgene and a base; or (b) for a compound of Formula I where X is S, coupling a corresponding compound having the formula II

II with a corresponding compound having the formula III

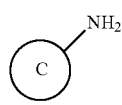

III in the presence di(1H-imidazol-2-yl)methanethione and a base; or (c) for a compound of Formula I where X is O, coupling a corresponding compound having the formula II

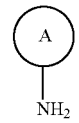

II with a corresponding compound having the formula IV

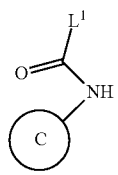

IV where $L^1$ is a leaving group, in the presence of a base; or (d) for a compound of Formula I where X is O, coupling a corresponding compound having the formula V

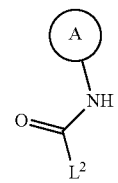

V where $L^2$ is a leaving group, with a corresponding compound having the formula III

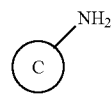

III in the presence of a base; or (e) for a compound of Formula I where X is O, activating a corresponding compound having the formula VI

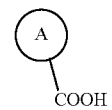

VI with diphenylphosphoryl azide followed by coupling the activated intermediate with a corresponding compound having the formula III

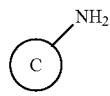

in the presence a base; or (f) for a compound of Formula I where X is O, coupling a corresponding compound having the formula II

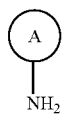

with a corresponding compound having the formula VII

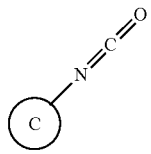

in the presence of a base; or (g) for a compound of Formula I where X is O, coupling a corresponding compound having the formula VIII

with a corresponding compound having the formula III

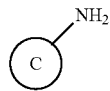

in the presence of a base; and optionally removing protecting groups and optionally preparing a pharmaceutically acceptable salt thereof.

In the above methods, the term "corresponding" means that the definitions for the "corresponding compound" are as defined for Formula I unless stated otherwise.

Referring to method (a), the base may be an amine base, such as triethylamine or diisopropylethylamine. Suitable solvents include dichloromethane, dichloroethane, THF, DMA and DMF. The reaction is conveniently performed at ambient temperature.

Referring to method (b), the base may be an amine base, such as triethylamine or diisopropylethylamine. Suitable solvents include dichloromethane, dichloroethane, THF, DMA and DMF. The reaction is conveniently performed at ambient temperature.

Referring to method (c), the leaving group may be, for example, phenoxy or 4-nitrophenoxy. The base may be an amine base, such as triethylamine or diisopropylethylamine. Suitable solvents include DMA, DMF and DCE. The reaction is conveniently performed at ambient temperature.

Referring to method (d), the leaving group may be, for example, phenoxy or 4-nitrophenoxy. The base may be an amine base, such as triethylamine or diisopropylethylamine. Suitable solvents include DCE, DMA and DMF. The reaction is conveniently performed at ambient temperature.

Referring to method (e), the base may be an amine base, such as triethylamine or diisopropylethylamine. Suitable solvents include toluene and DMF. The reaction is conveniently performed at elevated temperatures, for example the reflux temperature of the solvent.

Referring to methods (f) and (g), the base may be an amine base, such as triethylamine or diisopropylethylamine. Suitable solvents include DCM, DCE, DMF and THF. The reaction is conveniently performed at temperatures between about 0° C. and ambient temperature.

Amine groups in compounds described in any of the above methods may be protected with any convenient amine protecting group, for example as described in Greene & Wuts, eds., "Protecting Groups in Organic Synthesis", $2^{nd}$ ed. New York; John Wiley & Sons, Inc., 1991. Examples of amine protecting groups include acyl and alkoxycarbonyl groups, such as t-butoxycarbonyl (BOC), phenoxycarbonyl, and [2-(trimethylsilyl)ethoxy]methyl (SEM). Likewise, carboxyl groups may be protected with any convenient carboxyl protecting group, for example as described in Greene & Wuts, eds., "Protecting Groups in Organic Synthesis", $2^{nd}$ ed. New York; John Wiley & Sons, Inc., 1991. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", $2^{nd}$ ed. New York; John Wiley & Sons, Inc., 1991. Examples of alcohol protecting groups include benzyl, trityl, silyl ethers, and the like.

Amine groups in compounds described in any of the above methods may be protected with any convenient amine protecting group, for example as described in Greene & Wuts, eds., "Protecting Groups in Organic Synthesis", $2^{nd}$ ed. New York; John Wiley & Sons, Inc., 1991. Examples of amine protecting groups include acyl and alkoxycarbonyl groups, such as t-butoxycarbonyl (BOC) [2-(trimethylsilyl) ethoxy]methyl (SEM). Likewise, carboxyl groups may be protected with any convenient carboxyl protecting group, for example as described in Greene & Wuts, eds., "Protecting Groups in Organic Synthesis", $2^{nd}$ ed. New York; John Wiley & Sons, Inc., 1991. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", $2^{nd}$ ed. New York; John Wiley & Sons, Inc., 1991. Examples of alcohol protecting groups include benzyl, trityl, silyl ethers, and the like.

The compounds of the formulas II, III, IV, V, VI and VII are also provided as further aspects of the invention. In one embodiment, the compounds of the formulas II, III, IV, V, VI and VII are useful as intermediates for the preparation of compounds of Formula I.

In one embodiment of the above-described processes (a), (b), (c), and (f), where ring B is $Ar^1$ and $R^a$, $R^b$, $R^c$, $R^d$ and $R^2$ are hydrogen, a single enantiomer of intermediate II, namely enantiomer 1 of II-A is prepared by chiral crystallization prior to use. Accordingly, in one embodiment, a process for preparing enantiomer 1 of II-A comprises:

preparing racemic trans II-A

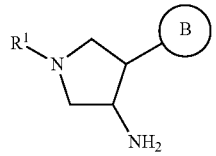

II-A where Ring B and the NH$_2$ group are in the trans configuration; Ring B is Ar$^1$ or hetAr$^1$; Ar$^1$ is phenyl optionally substituted with one or more substituents independently selected from halogen, CF$_3$, CF$_3$O—, (1-4C)alkoxy, hydroxy(1-4C)alkyl, (1-6C)alkyl and CN; and hetAr$^1$ is a 5-6 membered heteroaryl having 1-3 ring heteroatoms independently selected from N, S and O, and optionally substituted with 1-2 groups independently selected from (1-6C) alkyl, halogen, OH, CF$_3$, NH$_2$ and hydroxy(1-2C)alkyl; said method comprising:

treating racemic trans II-A with di-p-toluoyl-D-tartaric acid to provide the di-p-toluoyl-D-tartaric acid salt of racemic trans II-A;

recrystallizing the di-p-toluoyl-D-tartaric acid salt of trans II-A to provide the di-p-toluoyl-D-tartaric acid salt of enantiomer 1 of trans II-A; and treating the di-p-toluoyl-D-tartaric acid salt of enantiomer 1 of trans II-A with an inorganic base to provide free base of enantiomer 1 of trans II-A having the absolute configuration as illustrated:

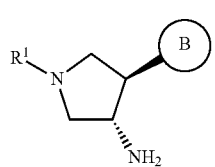

enantiomer 1 of II-A

In one embodiment of enantiomer 1 of trans II-A, R$^1$ is 2-methoxyethoxy and Ring B is 4-fluorophenyl, and racemic trans II-A is prepared by the process comprising:

reacting 4-fluorobenzaldehyde with nitromethane in the presence of acetic acid and ammonium acetate to provide (E)-1-fluoro-4-(2-nitrovinyl)benzene

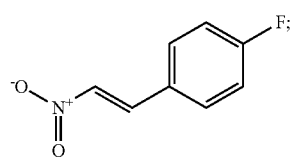

reacting (E)-1-fluoro-4-(2-nitrovinyl)benzene with 2-methoxy-N-(methoxymethyl)-N-(((trimethylsilyl)methyl) ethanamine in the presence of a catalytic amount of an acid (such as TFA) to provide trans-3-(4-fluorophenyl)-1-(2-methoxyethyl)-4-nitropyrrolidine

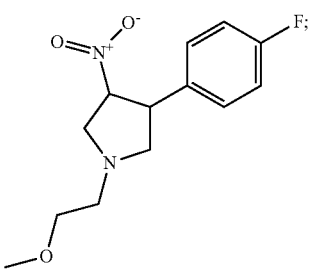 [SMILES: COCCN1CC(c2ccc(F)cc2)C([N+](=O)[O-])C1]

and treating trans-3-(4-fluorophenyl)-1-(2-methoxyethyl)-4-nitropyrrolidine with platinum (IV) oxide or Raney Nickel in a hydrogen atmosphere to provide trans-4-(4-fluorophenyl)-1-(2-methoxyethyl)pyrrolidin-3-amine

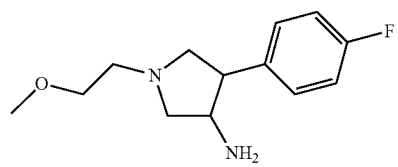 [SMILES: COCCN1CC(N)C(c2ccc(F)cc2)C1]

wherein the 4-fluorophenyl and amino group are in the trans configuration.

In one embodiment of enantiomer 1 of trans II-A, R$^1$ is 2-methoxyethoxy and Ring B is 3,4-difluorophenyl.

In one embodiment of the method for preparing racemic trans II-A, the inorganic base is an alkali metal hydroxide such as sodium hydroxide.

A similar process as above may be used utilizing di-p-toluoyl-L-tartaric acid to provide enantiomer 2 of II-A:

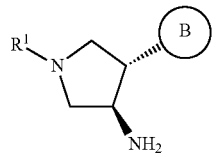

enantiomer 2 of II-A where R$^1$ and Ring B are as defined for Formula I. In one embodiment of enantiomer 2 of trans II-A, R$^1$ is 2-methoxyethoxy and Ring B is 4-fluorophenyl. In one embodiment of enantiomer 2 of trans II-A, R$^1$ is 2-methoxyethoxy and Ring B is 3,4-difluorophenyl.

The ability of compounds of the invention to act as TrkA inhibitors may be demonstrated by the assay described in Example A.

Compounds of Formula I are useful in the treatment of pain, cancer, inflammation/inflammatory diseases, neurodegenerative diseases, certain infectious diseases, Sjogren's syndrome, endometriosis, diabetic peripheral neuropathy, prostatitis or pelvic pain syndrome.

In one embodiment, compounds of Formula I are useful for treating pain, including chronic and acute pain. For example, compounds of Formula I are useful in the treatment of multiple types of pain including inflammatory pain, neuropathic pain, and pain associated with cancer, surgery or bone fracture.

In one embodiment, compounds of Formula I are useful for treating acute pain. Acute pain, as defined by the International Association for the Study of Pain, results from disease, inflammation, or injury to tissues. This type of pain generally comes on suddenly, for example, after trauma or surgery, and may be accompanied by anxiety or stress, and is confined to a given period of time and severity. In some instances, it can become chronic.

In one embodiment, compounds of Formula I are useful for treating chronic pain. Chronic pain, as defined by the International Association for the Study of Pain, is widely believed to represent a disease in itself. It can be made much worse by environmental and psychological factors. Chronic pain persists over a longer period than acute pain and is resistant to most medical treatments, generally over 3 months or more. It can and often does cause severe problems for patients.

Compounds of Formula I are also useful for treating cancer. Particular examples include neuroblastoma, ovarian, pancreatic, colorectal and prostate cancer.

Compounds of Formula I are also useful for treating inflammation and certain infectious diseases. For example, compounds of Formula I may be used to treat interstitial cystitis (IC), painful bladder syndrome (PBS), urinary incontinence, asthma, atopic dermatitis, and psoriasis.

Compounds of Formula I are also useful for treating a neurodegenerative disease in a mammal, comprising administering to said mammal one or more compounds of Formula I or a pharmaceutically acceptable salt thereof in an amount effective to treat said neurodegenerative disease. In one embodiment, compounds of Formula I may also be used to treat demyelination and dysmyelination by promoting myelination, neuronal survival, and oligodendrocyte differentiation via blocking Sp35-TrkA interaction. In one embodiment, the neurodegenerative disease is multiple sclerosis. In one embodiment, the neurodegenerative disease is Parkinson's disease. In one embodiment, the neurodegenerative disease is Alzheimer's disease.

Compounds of Formula I are also useful for treating certain infectious diseases such as *Trypanosoma cruzi* infection in a mammal.

Compounds of Formula I are also useful for treating Sjogren's syndrome in a mammal.

Compounds of Formula I are also useful for treating endometriosis in a mammal.

Compounds of Formula I are also useful for treating diabetic peripheral neuropathy in a mammal.

Compounds of Formula I are also useful for treating prostatitis in a mammal.

Compounds of Formula I are also useful for treating pelvic pain syndrome in a mammal.

Compounds of Formula I are also useful in treating diseases related to an imbalance of the regulation of bone remodeling, such as osteoporosis, rheumatoid arthritis, and bone metastases.

As used herein, terms "treat" or "treatment" refer to therapeutic or palliative measures. Beneficial or desired clinical results include, but are not limited to, alleviation, in whole or in part, of symptoms associated with a disorder or condition, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

In certain embodiments, compounds of Formula I are useful for preventing diseases and disorders as defined herein. The term "preventing" as used herein means the prevention of the onset, recurrence or spread, in whole or in part, of the disease or condition as described herein, or a symptom thereof, and includes to the administration of a compound of Formula I prior to the onset of symptoms.

Accordingly, one embodiment of this invention provides a method of treating pain in a mammal, comprising administering to said mammal in need thereof one or more compounds of Formula I or a pharmaceutically acceptable salt thereof in an amount effective to treat said pain. In one embodiment, the pain is chronic pain. In one embodiment, the pain is acute pain. In one embodiment, the pain is inflammatory pain, neuropathic pain, or pain associated with cancer, surgery, or bone fracture.

Another embodiment of this invention provides a method of preventing pain in a mammal, comprising administering to said mammal in need thereof one or more compounds of Formula I or a pharmaceutically acceptable salt thereof in an amount effective to prevent said pain. In one embodiment, the pain is chronic pain. In one embodiment, the pain is acute pain. In one embodiment, the pain is inflammatory pain, neuropathic pain, or pain associated with cancer, surgery, or bone fracture.

Another embodiment of this invention provides a method of treating cancer in a mammal, comprising administering to said mammal in need thereof one or more compounds of Formula I or a pharmaceutically acceptable salt thereof in an amount effective to treat said cancer.

In one embodiment, provided herein is a method for treating a patient diagnosed with a cancer having a dysregulation of TrkA, comprising administering to the patient a therapeutically effective amount of a compound of the invention or a pharmaceutically acceptable salt thereof.

In one embodiment, the dysregulation of TrkA comprises overexpression of wild-type TrkA (autocrine activation).

In one embodiment, the dysregulation of TrkA comprises one or more chromosome translocations or inversions resulting in TrkA gene fusions. In one embodiment, the dysregulation is a result of genetic translocations in which the expressed protein is a fusion protein containing residues from non-TrkA and TrkA proteins, and at a minimum the TrkA kinase domain. In one embodiment, the TrkA fusion protein is LMNA-TrkA, TFG-TrkA, TPM3-TrkA, CD74-TrkA, NFASC-TrkA, MPRIP-TrkA, BCAN-TrkA, or TPR-TrkA, where:
LMNA=Prelamin-A/C;
TFG=TRK-fused gene protein;
TPM3=Tropomysin alpha-3;
CD74=HLA class II histocompatibility antigen gamma chain;
NFASC=Neurofascin;
MPRIP=MPRIP protein;
BCAN=Brevican core protein; and
TPR=Nucleoprotein TPR In one embodiment, the dysregulation of TrkA comprises one or more deletions, insertions or mutations in the TrkA protein. In one embodiment, the dysregulation comprises a deletion of one or more residues from the TrkA protein, resulting in constitutive activity of TrkA kinase. In one embodiment the deletion includes deletion of residues 303-377 in TrkA Isoform 2.

In one embodiment, the dysregulation of TrkA comprises a splice variation in which the expressed protein is an alternatively spliced variant of TrkA having one or more residues deleted resulting in constitutive activity of TrkA kinase. In one embodiment, an alternatively spliced form of TrkA with constitutive activity has deletions of exons 8, 9, and 11 resulting in an expressed protein missing residues 192-284 and 393-398 relative to TrkA Isoform 2.

Cancers identified as having dysregulation of TrkA (see literature references below; also see www.cancer.gov and www.nccn.org) include:

(A) Cancers wherein the dysregulation of TrkA comprises one or more chromosome translocations or inversions resulting in TrkA gene fusions, including:

| Cancer | Literature reference(s) | Standard of Care |
|---|---|---|
| Non-Small Cell Lung Cancer | Vaishnavi et al. 2013: Nature Medicine 19, 1469-1472 | radiotherapy (e.g. radioiodide therapy, external-beam radiation, radium 223 therapy), chemotherapeutics as single agents (e.g. afatinib dimaleate, bevacizumab, carboplatin, cetuximab, cisplatin, crizotinib, erlotinib, gefitinib, gemcitabine, methotrexate, paclitaxel, pemetrexed) or combinations (e.g. carboplatin-paclitaxel, gemcitabine-paclitaxel, chemoradiation) |
| Papillary Thyroid Carcinoma | Caria et al. 2010: Cancer Genetics and Cytogenetics 203: 21-29 | Radiotherapies (e.g. radioiodide therapy, external-beam radiation) and chemotherapeutics (e.g. sorafenib, sunitinib, pazopanib) |
| Glioblastoma Multiforme | Frattini et al. 2013: Nature Genet. 45(10): 1141-9 | Chemotherapeutics (e.g. bevacizumab, everolimus, lomustine, temozolomide) |
| Colorectal Carcinoma | Martin-Zanca et al. 1986: Nature 319: 743 | Chemotherapeutics as single agents (aflibercept, bevacizumab, capecitabine, cetuximab, fluorouracil, irinotecan, leucovorin, oxaliplatin, panitumumab, regorafenib) or combinations (e.g. folfox, folfiri, capox, folfiri-bevacizumab, folfiri-cetuximab, xelox) |
| Melanoma | WO 2013/059740 A1 | Chemotherapeutics (e.g. aldesleukin, dabrafenib, dacarbazine, interferon alfa-2b, ipilimumab, peginterferon alfa-2b, trametinib, vemurafenib) |

(B) Cancers wherein the dysregulation of TrkA comprises one or more deletions, insertions or mutations in the TrkA protein, including:

| Cancer | Literature reference(s) | Standard of care |
|---|---|---|
| Acute Myeloid leukemia | Meyer 2007: Leukemia 21: 2171-2180 Reuther et al. 2000: Mol Cell Biol 20: 8655-8666 | Chemotherapeutics as single agents (e.g. arsenic trioxide, cyclophosphamide, cytarabine, daunorubicin, doxorubicin, vincristine) or combinations (e.g. ADE) |
| Large Cell Neuroendocrine Carcinoma | Marchetti et al 2008: Human Mutation 29(5): 609-616 | Radiotherapy (e.g. radioiodide therapy, external-beam radiation, radium 223 therapy) and/or chemotherapeutics (e.g. cisplatin, carboplatin, etoposide) |
| Neuroblastoma | Tacconelli et al 2004: Cancer Cell 6: 347 | Chemotherapeutics (e.g. cyclophosphamide, doxorubicin, vincristine) |

(C) Cancers driven by overexpression of wild-type TrkA (autocrine activation), including:

| Cancer | Literature Reference(s) | Standard of care |
|---|---|---|
| Prostate Carcinoma | Walch et al: Clinical & Experimental Metastasis 17: 307-314 Papatsoris et al 2007: Expert Opinion on Investigational Drugs 16(3): 303-309 | Radiotherapy (e.g. radium 223 therapy) or chemotherapeutics (e.g. abiraterone, cabazitaxel, degarelix, denosumab, docetaxel, enzalutamide, leuprolide, prednisone, sipuleucel-T) |
| Neuroblastoma | Van Noesel et al 2004: Gene 325: 1-15 | Chemotherapeutics (e.g. cyclophosphamide, doxorubicin, vincristine) |
| Pancreatic Carcinoma | Zhang et al 2005: Oncology Reports 14: 161-171 | Chemotherapeutics as single agents (e.g. erlotinib, fluorouracil, gemcitabine, mitomycin C) or combinations (e.g. gemcitabine-oxaliplatin) |
| Melanoma | Truzzi et al 2008: Journal of Investigative Dermatology 128(8): 2031 | Chemotherapeutics (e.g. aldesleukin, dabrafenib, dacarbazine, interferon alfa-2b, ipilimumab, peginterferon alfa-2b, trametinib, vemurafenib) |

| Cancer | Literature Reference(s) | Standard of care |
|---|---|---|
| Head and Neck Squamous Cell Carcinoma | Kolokythas et al 2010: Journal of Oral and Maxillofacial Surgery 68(6): 1290-1295 | Radiotherapy and/or chemotherapeutics (e.g. bleomycin, cetuximab, cisplatin, docetaxel, fluorouracil, methotrexate) |
| Gastric Carcinoma | Ni et al 2012: Asian Pacific Journal of Cancer Prevention 13: 1511 | Chemotherapeutics (e.g. docetaxel, doxorubucin, fluorouracil, mitomycin C, trastuzumab) |

In one embodiment, provided herein is a method for treating a patient diagnosed with a cancer having a dysregulation of TrkA, comprising administering to the patient a therapeutically effective amount of a compound of the invention, or a pharmaceutically acceptable salt thereof, wherein the cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

In one embodiment, the compounds of the present invention are useful for treating cancer in combination with one or more additional therapeutic agents or therapies that work by the same or a different mechanism of action.

In one embodiment, the additional therapeutic agent(s) is selected from receptor tyrosine kinase-targeted therapeutic agents, including cabozantinib, crizotinib, erlotinib, gefitinib, imatinib, lapatinib, nilotinib, pazopanib, pertuzumab, regorafenib, sunitinib, and trastuzumab.

In one embodiment, the additional therapeutic agent(s) is selected from signal transduction pathway inhibitors, including Ras-Raf-MEK-ERK pathway inhibitors (e.g. sorafenib, trametinib, vemurafenib), PI3K-Akt-mTOR-S6K pathway inhibitors (e.g. everolimus, rapamycin, perifosine, temsirolimus) and modulators of the apoptosis pathway (e.g. obataclax).

In one embodiment, the additional therapeutic agent(s) is selected from cytotoxic chemotherapeutics, including arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

In one embodiment, the additional therapeutic agent(s) is selected from angiogenesis-targeted therapies, including aflibercept and bevacizumab.

In one embodiment, the additional therapeutic agent(s) is selected from immune-targeted agents, including aldesleukin, ipilimumab, lambrolizumab, nivolumab, sipuleucel-T.

In one embodiment, the additional therapeutic agent(s) is selected from agents active against the TrkA pathway, including NGF-targeted biopharmaceuticals such as NGF antibodies, and panTrk inhibitors.

In one embodiment, the additional therapeutic agent or therapy is radiotherapy, including radioiodide therapy, external-beam radiation and radium 223 therapy.

In one embodiment, the additional therapeutic agent(s) includes any one of the above listed therapies or therapeutic agents which are standards of care in cancers wherein the cancer has a dysregulation of TrkA.

In one embodiment, provided herein is a method of treating cancer in a patient, comprising administering to said patient a compound of the invention or a pharmaceutically acceptable salt thereof, in combination with at least one additional therapy or therapeutic agent selected from radiotherapy (e.g. radioiodide therapy, external-beam radiation, radium 223 therapy), cytotoxic chemotherapeutics (e.g. arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, vincristine), tyrosine kinase targeted-therapeutics (e.g. afatinib, cabozantinib, cetuximab, crizotinib, dabrafenib, erlotinib, gefitinib, imatinib, lapatinib, nilotinib, pazopanib, panitumumab, pertuzumab, regorafenib, sunitinib, trastuzumab), apoptosis modulators and signal transduction inhibitors (e.g. everolimus, perifosine, rapamycin, sorafenib, temsirolimus, trametinib, vemurafenib), immune-targeted therapies (e.g. aldesleukin, interferon alfa-2b, ipilimumab, lambrolizumab, nivolumab, prednisone, sipuleucel-T) and angiogenesis-targeted therapies (e.g. aflibercept, bevacizumab), wherein the amount of the compound of the invention or a pharmaceutically acceptable salt thereof is, in combination with the additional therapy or therapeutic agent, is effective in treating said cancer. These additional therapeutic agents may be administered with one or more compounds of the invention as part of the same or separate dosage forms, via the same or different routes of administration, and on the same or different administration schedules according to standard pharmaceutical practice known to one skilled in the art.

Also provided herein is (i) a pharmaceutical combination for treating cancer in a patient in need thereof, which comprises (a) a compound of the invention or a pharmaceutically acceptable salt thereof, (b) an additional therapeutic agent and (c) optionally at least one pharmaceutically acceptable carrier for simultaneous, separate or sequential use for the treatment of a tumor disease, wherein the amounts of the compound or salt thereof and of the additional therapeutic agent are together effective in treating said cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer a patient in need thereof.

In one embodiment, the combination therapy is for treating a cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

Another embodiment of this invention provides a method of treating inflammation or an inflammatory disease or disorder in a mammal, comprising administering to said mammal in need thereof one or more compounds of Formula I or a pharmaceutically acceptable salt thereof in an amount effective to treat said inflammation. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

In one embodiment, the method of treating inflammation or an inflammatory disease or disorder comprises administering a compound of the invention in combination with one or more additional agents. Examples of additional agents include anti-TNF treatments (for example monoclonal antibody such as infliximab (Remicade), adalimumab (Humira), certolizumab pegol (Cimzia), and golimumab (Simponi), or a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348).

Another embodiment of this invention provides a method of treating *Trypanosoma cruzi* infection in a mammal, comprising administering to said mammal in need thereof one or more compounds of Formula I or a pharmaceutically acceptable salt thereof in an amount effective to treat said *Trypanosoma cruzi* infection.

Another embodiment of this invention provides a method of treating Sjogren's syndrome in a mammal, comprising administering to said mammal in need thereof one or more compounds of Formula I or a pharmaceutically acceptable salt thereof in an amount effective to treat said syndrome.

Another embodiment of this invention provides a method of treating endometriosis in a mammal, comprising administering to said mammal in need thereof one or more compounds of Formula I or a pharmaceutically acceptable salt thereof in an amount effective to treat said endometriosis.

Another embodiment of this invention provides a method of treating diabetic peripheral neuropathy in a mammal, comprising administering to said mammal in need thereof one or more compounds of Formula I or a pharmaceutically acceptable salt thereof in an amount effective to treat said diabetic peripheral neuropathy.

Another embodiment of this invention provides a method of treating prostatitis in a mammal, comprising administering to said mammal in need thereof one or more compounds of Formula I or a pharmaceutically acceptable salt thereof in an amount effective to treat said prostatitis.

Another embodiment of this invention provides a method of treating pelvic pain syndrome in a mammal, comprising administering to said mammal in need thereof one or more compounds of Formula I or a pharmaceutically acceptable salt thereof in an amount effective to treat said pelvic pain syndrome.

Another embodiment of this invention provides a method of treating a neurodegenerative disease in a mammal, comprising administering to said mammal in need thereof one or more compounds of Formula I or a pharmaceutically acceptable salt thereof in an amount effective to treat said neurodegenerative disease.

Another embodiment of this invention provides a method of treating diseases related to an imbalance of the regulation of bone remodeling in a mammal, comprising administering to said mammal in need thereof one or more compounds of Formula I or a pharmaceutically acceptable salt thereof in an amount effective to treat said disease. In one embodiment, the disease is osteoporosis, rheumatoid arthritis, and bone metastases.

In one embodiment, the method for treating diseases related to an imbalance of the regulation of bone remodeling in a mammal comprises administering a TrkA inhibitor of the invention in combination with one or more additional therapeutic agents or therapies. Examples of additional therapeutic agents or therapies include anti-TNF treatments (for example monoclonal antibody such as infliximab (Remicade), adalimumab (Humira), certolizumab pegol (Cimzia), and golimumab (Simponi), or with a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348).

As used herein, an "effective amount" means an amount of compound that, when administered to a mammal in need of such treatment, is sufficient to (i) treat a particular disease, condition, or disorder which can be treated with a compound of Formula I, or (ii) attenuate, ameliorate, or eliminate one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

The compounds of the present invention can be used in combination with one or more additional therapeutic agents that work by the same or a different mechanism of action. Examples of additional therapeutic agents include anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), and chemotherapeutic agents.

Also provided herein is a pharmaceutical combination comprising an effective amount of (a) at least one compound of Formula I; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), for use in the treatment of pain in a mammal, wherein (a) and (b) can be in separate dosage forms or in the same dosage form.

The term "pharmaceutical combination" as used herein refers to a pharmaceutical therapy resulting from the mixing or combining of more than one active ingredient and includes both fixed and non-fixed combinations of the active ingredients. The term "fixed combination" means that at least one of the compounds of Formula I, and at least one additional therapeutic agent are both administered to a patient simultaneously in the form of a single entity or dosage. The term "non-fixed combination" means that at least one of the compounds of Formula I, and at least one additional therapeutic agent, are administered to a patient as separate entities either simultaneously or sequentially with variable intervening time limits, wherein such administration provides effective levels of the two or more compounds in the body of the patient. These also apply to cocktail therapies, e.g. the administration of three or more active ingredients.

Also provided herein is a method of treating pain in a mammal, comprising co-administering to a mammal in need thereof an effective amount of: (a) at least one compound of Formula I; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), opioids (such as morphine), calcitonin gene-related peptide receptor antagonists, subtype-selective ion channel modulators, anticonvulsants (for example Pregabalin and gabapentin), dual serotonin-norepinephrin reuptake inhibitors (for example duloxetine, venlafaxine and milnacipran), and tricyclic antidepressants (such as amitriptyline, nortriptyline and desipramine).

The term "co-administering" is meant to encompass administration of the selected therapeutic agents to a single patient, and is intended to include treatment regimens in which the agents are administered by the same or different route of administration or at the same or different times. This term encompasses administration of two or more agents to a mammal so that both agents and/or their metabolites are present in the mammal at the same time. It includes simultaneous administration in separate compositions, administration at different times in separate compositions, and/or administration in a composition in which both agents are present. In some embodiments, the compound(s) of the invention and the other therapeutic agent(s) are administered in a single composition. In some embodiments, compound(s) of the invention and the other agent(s) are admixed in the composition.

Also provided herein is a medicament containing a compound of Formula I for treatment of pain in a mammal in combination with an additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine).

Also provided herein is a medicament containing a therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine) for treatment of pain in a mammal in combination with a compound of Formula I.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

Another formulation may be prepared by mixing a compound described herein and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

Accordingly, another aspect of the present invention provides a pharmaceutical composition, which comprises a compound of Formula I or a pharmaceutically acceptable salt thereof, as defined hereinabove, together with a pharmaceutically acceptable diluent or carrier.

According to another embodiment, the present invention provides a compound of Formula I or a pharmaceutically acceptable salt thereof, for use in the treatment of pain in a mammal. In one embodiment, the pain is chronic pain. In one embodiment the pain is acute pain. In one embodiment, the pain is inflammatory pain, neuropathic pain, or pain associated with cancer, surgery, or bone fracture.

According to another embodiment, the present invention provides a compound of Formula I or a pharmaceutically acceptable salt thereof, for use in the treatment of cancer in a mammal.

In another embodiment, the present invention provides a compound of Formula I or a pharmaceutically acceptable salt thereof, for use in the treatment of inflammation or an inflammatory disease or disorder in a mammal. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

In another embodiment, the present invention provides a compound of Formula I or a pharmaceutically acceptable salt thereof, for use in the treatment of infectious diseases, for example *Trypanosoma cruzi* infection, in a mammal.

In another embodiment, the present invention provides a compound of Formula I or a pharmaceutically acceptable salt thereof, for use in the treatment of Sjogren's syndrome in a mammal.

In another embodiment, the present invention provides a compound of Formula I or a pharmaceutically acceptable salt thereof, for use in the treatment of endometriosis in a mammal.

In another embodiment, the present invention provides a compound of Formula I or a pharmaceutically acceptable salt thereof, for use in the treatment of diabetic peripheral neuropathy in a mammal, In another embodiment, the present invention provides a compound of Formula I or a pharmaceutically acceptable salt thereof, for use in the treatment of prostatitis in a mammal, In another embodiment, the present invention provides a compound of Formula I or a pharmaceutically acceptable salt thereof, for use in the treatment of pelvic pain syndrome in a mammal, In another embodiment, the present invention provides a compound of Formula I or a pharmaceutically acceptable salt thereof, for use in the treatment of a neurodegenerative disease in a mammal.

According to a further aspect, the present invention provides the use of a compound of Formula I or a pharmaceutically acceptable salt thereof, in the manufacture of a medicament for the treatment of a condition selected from pain, cancer, inflammation, neurodegenerative disease or *Trypanosoma cruzi* infection. In one embodiment, the condition is chronic pain. In one embodiment, the condition is acute pain. In one embodiment, the pain is inflammatory pain, neuropathic pain, or pain associated with cancer, surgery, or bone fracture. In one embodiment, the condition is cancer. In one embodiment, the condition is inflammation. In one embodiment, the condition is a neurodegenerative disease. In one embodiment, the condition is *Trypanosoma cruzi* infection. In one embodiment, the condition is Sjogren's syndrome. In one embodiment, the condition is endometriosis. In one embodiment, the condition is diabetic peripheral neuropathy. In one embodiment, the condition is prostatitis. In one embodiment, the condition is pelvic pain syndrome.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel or C-18 reverse phase column, or on a silica SepPak cartridge (Waters).

Biological Assays

Example A-1

TrkA Kinase Binding Assay

TrkA binding activity was determined in a TrkA LanthaScreen™ Eu Kinase Binding Assay. 5 nM His-tagged recombinant human TrkA (6HIS tagged cytoplasmic domain from Invitrogen, Cat. No. PV3144) was incubated with 4 nM Alexa-Fluor® Tracer 236 (Invitrogen Cat. No. PV5592), 2 nM biotinylated anti-His (Invitrogen Cat. No. PV6090), and 2 nM europium-labeled Streptavidin (Invitrogen Cat. No. PV5899), in buffer (25 mM MOPS, pH 7.5, 5 mM $MgCl_2$, 0.005% Triton X-100). Three fold serial dilutions of compounds of the invention in DMSO were added to a final percentage of 2% DMSO. After 60-minute incubation at 22° C., the reaction was measured using the EnVision mutlimode plate reader (PerkinElmer) via TR-FRET dual wavelength detection at 615 nM and 665 nM. The percent of control was calculated using a ratiometric emission factor. The $IC_{50}$ values were determined by fitting a four parameter model to the percent of control data.

Table A provides averaged $IC_{50}$ values for compounds of the invention when tested in the assay of Example A, where A represents an averaged $IC_{50}$ value <100 nM; and B represents an averaged $IC_{50}$ value from 100 to 1,000 nM.

TABLE A

| Example # | TrkA Enzyme $IC_{50}$ (nM) |
|---|---|
| 1 | A |
| 2 | A |
| 3 | A |
| 4 | B |
| 5 | A |
| 6 | A |
| 7 | A |
| 8 | B |
| 9 | B |
| 10 | B |
| 11 | A |
| 12 | A |
| 13 | A |
| 14 | A |
| 15 | B |
| 16 | A |
| 17 | B |
| 18 | B |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | B |
| 34 | B |
| 35 | B |
| 36 | A |
| 37 | B |
| 38 | A |
| 39 | A |
| 40 | A |
| 41 | B |
| 42 | B |
| 43 | A |
| 44 | B |
| 45 | A |
| 46 | A |
| 47 | A |
| 48 | A |
| 49 | B |
| 50 | A |
| 51 | A |
| 52 | B |
| 53 | A |
| 54 | B |
| 55 | A |
| 56 | A |

Example A-2 p38 Kinase Binding Assay p38α binding activity was determined in a p38α LanthaScreen™ Eu Kinase Binding Assay. 5 nM of inactive, GST-tagged recombinant human p38α (GST-tagged cytoplasmic domain from Invitrogen, Catalog No. PV3305) was incubated with 5 nM Alexa-Fluor® Tracer 199 (Invitrogen Cat. No. PV5830), and 2 nM europium labeled anti-GST antibody (Invitrogen Cat. No. PV5594), in buffer (25 mM

[Na+] HEPES pH 7.3, 10 mM MgCl$_2$, 100 µM NaVO$_4$). Three fold serial dilutions of compounds of the invention in DMSO were added to a final percentage of 2% DMSO. After 60-minute incubation at 22° C., the reaction was measured using the EnVision multimode plate reader (PerkinElmer) via TR-FRET dual wavelength detection at 615 nM and 665 nM. The percent of control was calculated using a ratiometric emission factor. The IC$_{50}$ values were determined by fitting a four parameter model to the percent of control data. The compounds of Examples 1-56 were tested in this assay, and all compounds were found to be 1000 fold more potent against TrkA than p38α.

Example B

Off-Target Kinase Profiling

A representative compound of the invention (Example 48) was tested for off-target kinase activity at a concentration of 10 µM by Millipore, Inc. in their KinaseProfiler™ service against all the kinases available in their full kinase panel. The compound was run in duplicate at a concentration of ATP near the Km for each individual kinase according to Millipore's specifications. The results are shown in Table B. Data are reported as percent of control (POC) and are the average of the two replicates.

In the KinaseProfiler™ the representative compound showed remarkable and unexpected selectivity for inhibiting TrkA and TrkB versus other kinases in the panel. In fact, the compound was largely inactive against off-target kinases at a concentration of 10 µM, and thus would not be expected to inhibit off-target kinases at therapeutic doses in mammals. The ability of compounds of the invention to selectively inhibit the Trk pathway without inhibiting other off-target kinases could translate into drug profiles that are essentially free of side-effects related to inhibition of off-target kinases. Such a drug profile would represent a safer approach to treating pain, inflammation, cancer and certain skin diseases than has been previously reported.

TABLE B

| Kinase | Example 48 Avg POC |
|---|---|
| Abl2 | 124.5 |
| Abl-P | 147.5 |
| AKT1 | 117 |
| AKT2 | 148 |
| AKT3 | 106.5 |
| ALK | 125 |
| ALK4 | 88.5 |
| AMPK (A1/B1/G1) | 114.5 |
| ARK5 | 106 |
| AURKA | 133 |
| Axl | 113 |
| BLK_m | 107 |
| Bmx | 122 |
| BrSK1 | 123.5 |
| BrSK2 | 119.5 |
| BTK | 97.5 |
| CAMK1 | 104.5 |
| CAMK1d | 105 |
| CAMK2b | 90 |
| CAMK2d | 99 |
| CAMK2g | 116 |
| CAMK4 | 101.5 |
| CDK1/cyclinB | 106 |
| CDK2/cyclinA | 110 |
| CDK2/cyclinE | 113 |
| CDK3/cyclinE | 99.5 |
| CDK5/p25 | 110.5 |

TABLE B-continued

| Kinase | Example 48 Avg POC |
|---|---|
| CDK5/p35 | 109.5 |
| CDK6/cyclinD3 | 112.5 |
| CDK7/cyclinH/MAT1 | 112.5 |
| CDK9/cyclinT1 | 111.5 |
| CHK1 | 110 |
| CHK2 | 107.5 |
| CK1_y | 106 |
| CK1delta | 111.5 |
| CK1gamma1 | 116 |
| CK1gamma2 | 94.5 |
| CK1gamma3 | 110 |
| CK2 | 106 |
| CK2alpha2 | 113 |
| CLK2 | 116 |
| CLK3 | 101.5 |
| c-RAF | 106 |
| CSK | 108 |
| DAPK1 | 114.5 |
| DAPK2 | 99 |
| DAPK3 | 91 |
| DCAMKL2 | 142 |
| DDR2 | 101.5 |
| DMPK | 106 |
| DRAK1 | 104 |
| DYRK2 | 103.5 |
| eEF-2K | 116.5 |
| EGFR | 111 |
| EphA1 | 113.5 |
| EphA2 | 101 |
| EphA3 | 112 |
| EphA4 | 105.5 |
| EphA5 | 107 |
| EphA7 | 101 |
| EphA8 | 122.5 |
| EphB1 | 107.5 |
| EphB2 | 99.5 |
| EphB3 | 119 |
| EphB4 | 99 |
| ErbB4 | 97 |
| ERK1 | 100 |
| ERK2 | 101 |
| FAK | 107.5 |
| FAK2 | 107.5 |
| Fer | 91.5 |
| Fes | 86.5 |
| FGFR1 | 98 |
| FGFR2 | 106.5 |
| FGFR3 | 103.5 |
| FGFR4 | 102.5 |
| Fgr | 111.5 |
| Flt1 | 96.5 |
| Flt3 | 99 |
| Flt4 | 103 |
| Fms | 96 |
| Fyn | 108.5 |
| GRK5 | 106.5 |
| GRK6 | 101 |
| GRK7 | 122 |
| GSK3alpha | 120.5 |
| GSK3beta | 63 |
| Haspin | 117 |
| Hck | 115.5 |
| HIPK1 | 119.5 |
| HIPK2 | 103 |
| HIPK3 | 82 |
| IGF-1R | 85.5 |
| IGF-1R Activated | 102 |
| IKKalpha | 112 |
| IKKbeta | 96 |
| IR | 102 |
| IR Activated | 111.5 |
| IRAK1 | 100.5 |
| IRAK4 | 88 |
| IRR | 110.5 |
| ITK | 170.5 |
| JAK2 | 123.5 |
| JAK3 | 102.5 |

TABLE B-continued

| Kinase | Example 48 Avg POC |
|---|---|
| JNK1alpha1 | 106.5 |
| JNK2alpha2 | 93.5 |
| JNK3 | 106 |
| KDR | 104 |
| KIT | 100 |
| Lck | 102 |
| LIMK1 | 104 |
| LKB1 | 114.5 |
| LOK | 107.5 |
| Lyn | 108.5 |
| MAP3K5 | 102.5 |
| MAP4K2 | 110.5 |
| MAPKAP-K2 | 109.5 |
| MAPKAP-K3 | 75.5 |
| MAPKAP-K5 | 108 |
| MARK1 | 113 |
| MARK2 | 93 |
| MEK1 | 100 |
| MELK | 89 |
| Mer | 126.5 |
| Met | 109 |
| MINK | 117 |
| MKK4_m | 122 |
| MKK6 | 121 |
| MKK7beta | 98 |
| MKNK2 | 96 |
| MLK1 | 115 |
| MRCKalpha | 113.5 |
| MRCKbeta | 140.5 |
| MSK1 | 121.5 |
| MSK2 | 103.5 |
| MSSK1 | 94 |
| MST1 | 93.5 |
| MST2 | 109.5 |
| MST3 | 97 |
| mTOR | 99 |
| mTOR/FKBP12 | 111.5 |
| MuSK | 107.5 |
| MYLK | 107 |
| NEK11 | 105 |
| NEK2 | 112 |
| NEK3 | 129 |
| NEK6 | 121.5 |
| NEK7 | 107 |
| NLK | 108.5 |
| p38alpha | 108 |
| p38beta | 115 |
| p38delta | 108.5 |
| p38gamma | 120.5 |
| p70S6K | 107.5 |
| PAK2 | 101.5 |
| PAK4 | 134.5 |
| PAK5 | 113 |
| PAK6 | 94 |
| PASK | 103 |
| PDGFRalpha | 104.5 |
| PDGFRbeta | 103.5 |
| PDK1 | 85.5 |
| PhKgamma2 | 110 |
| Pim-1 | 134 |
| Pim-2 | 104 |
| Pim-3 | 140.5 |
| PKAC-alpha | 98.5 |
| PKCalpha | 106.5 |
| PKCbetaI | 97 |
| PKCbetaII | 97.5 |
| PKCdelta | 119.5 |
| PKCepsilon | 103.5 |
| PKCeta | 93 |
| PKCgamma | 93.5 |
| PKCiota | 120 |
| PKCtheta | 108.5 |
| PKCzeta | 108 |
| PKD1 | 94.5 |
| PKD2 | 115.5 |
| Plk1 | 93 |
| Plk2 | 99.5 |
| Plk3 | 113.5 |
| PRK2 | 111 |
| PRKG1alpha | 106 |
| PRKG1beta | 105 |
| PrKX | 122 |
| PTK5 | 107.5 |
| PTK6 | 99.5 |
| Ret | 125.5 |
| RIPK2 | 108 |
| ROCK-I | 103.5 |
| ROCK-II | 104.5 |
| Ron | 105.5 |
| Ros | 111 |
| Rse | 117 |
| Rsk1 | 121 |
| Rsk2 | 134 |
| Rsk3 | 108 |
| Rsk4 | 116 |
| SGK1 | 125 |
| SGK2 | 121.5 |
| SGK3 | 82 |
| SIK | 111 |
| SRC | 124 |
| SRPK1 | 115.5 |
| SRPK2 | 109 |
| STK33 | 110 |
| Syk | 86.5 |
| TAK1 | 104 |
| TAO1 | 101 |
| TAO2 | 100.5 |
| TAO3 | 105.5 |
| TBK1 | 96.5 |
| TEC Activated | 94 |
| Tie2 | 96 |
| TLK2 | 98 |
| TNK2 | 99.5 |
| TrkA | 2.5 |
| TrkB | 9 |
| TSSK1 | 99.5 |
| TSSK2 | 124 |
| Txk | 85.5 |
| ULK2 | 98.5 |
| ULK3 | 100 |
| VRK2 | 98 |
| WNK2 | 92.5 |
| WNK3 | 99.5 |
| Yes | 97.5 |
| ZAP-70 | 100.5 |

Preparation of Synthetic Intermediates

Preparation A

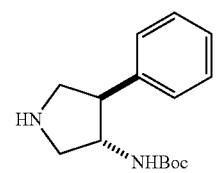

tert-butyl trans-4-phenylpyrrolidin-3-ylcarbamate

Step A: Preparation of
trans-1-benzyl-3-nitro-4-phenylpyrrolidine

To a DCM (2 L) solution of (E)-(2-nitrovinyl)benzene (149 g, 1.00 mol) was added TFA (19.5 mL, 0.250 mol), followed by cooling to −15° C. and then slow addition of a DCM (500 mL) solution of N-methoxymethyl-N-(trimethylsilylmethyl)benzylamine (274 g, 1.00 mol) over 3 hours, maintaining the reaction temperature between −15 and −10° C. The reaction was warmed up to ambient temperature and stirred for 18 hours, then washed with 2 N NaOH (500 mL) and treated with 2 N HCl (1 L). The resulting white suspension was stirred for 1 hour before being filtered and washed with DCM. DCM (1 L) and 2 N NaOH (750 mL) were then added to the collected white solid and stirred until all the solids dissolved. After phase-separation, the aqueous layer was extracted with DCM (2×1 L). The combined organic layers were dried with MgSO$_4$, filtered and concentrated to afford the title product as an off-white solid (205 g, 73% yield). MS (apci) m/z=283.1 (M+H).

Step B: Preparation of trans-1-benzyl-4-phenylpyrrolidin-3-amine

To a suspension of trans-1-benzyl-3-nitro-4-phenyl-pyrrolidine (93.9 g, 333 mmol) in EtOH (1.20 L) was added concentrated HCl (450 mL), followed by addition of zinc dust (173 g, 2.66 mol) in small portions over 1.5 hours while maintaining the temperature between 55-60° C. The reaction mixture was stirred at ambient temperature for 18 hours, then cooled in an ice/water bath followed by addition of concentrated NH$_4$OH (900 mL). The mixture (pH=10-11) was filtered and the collected zinc was washed with CHCl$_3$. The filtrate was then phase-separated, and the aqueous layer was extracted with CHCl$_3$ (2×400 mL). The combined organics was washed with H$_2$O, brine, dried with MgSO$_4$, filtered and concentrated to afford the title compound as an amber oil (85.0 g, 100% yield). MS (apci) m/z=253.2 (M+H).

Step C: Preparation of trans-(1-benzyl-4-phenyl-pyrrolidin-3-yl)-carbamic acid tert-butyl ester To a mixture of trans-1-benzyl-4-phenylpyrrolidin-3-amine (85.0 g, 333 mmol), THF (750 mL) and triethylamine (69.6 mL, 500 mmol), was slowly added (Boc)$_2$O (72.7 g, 333 mmol) in portions over 30 minutes. The reaction mixture was stirred at ambient temperature for 16 hours and was concentrated under vacuum. The residue was dissolved in CHCl$_3$ and was washed with aqueous Na$_2$CO$_3$ and brine. The organic layer was dried with MgSO$_4$, filtered and concentrated to afford the title compound as a pale-yellow solid (116 g, 99% yield). MS (apci) m/z=353.0 (M+H).

Step D: Preparation of tert-butyl trans-4-phenylpyrrolidin-3-ylcarbamate

A 2 gallon Parr reactor was charged with trans-(1-benzyl-4-phenyl-pyrrolidin-3-yl)-carbamic acid tert-butyl ester (114 g, 323 mmol), EtOH (2 L) and 10% Pd/C (50% wet, 11.0 g). The reactor was purged with N$_2$ several times, filled with H$_2$ to 56-57 psi and agitated at 80° C. When the reaction was complete according to HPLC analysis, the reaction mixture was filtered and the filtrate concentrated to provide the crude product as a yellow solid. The crude material was triturated from toluene to afford the title product as a white solid (68.4 g, 78% yield). MS (apci) m/z=262.9 (M+H).

Preparation B

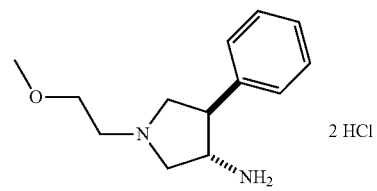 [SMILES: COCCN1C[C@@H](N)[C@H](c2ccccc2)C1]

trans-1-(2-methoxyethyl)-4-phenylpyrrolidin-3-amine dihydrochloride

Step A: Preparation of tert-butyl trans-1-(2-methoxyethyl)-4-phenylpyrrolidin-3-ylcarbamate To a solution of tert-butyl trans-4-phenylpyrrolidin-3-ylcarbamate (Preparation A, 4.82 g, 17.5 mmol) in dry DMF (50 mL) was added sequentially DIEA (9.12 mL, 52.4 mmol) and 1-bromo-2-methoxyethane (1.97 mL, 20.9 mmol). The mixture was stirred at ambient temperature for 46 hours and then poured into H$_2$O (300 mL). The mixture was extracted with EtOAc (3×150 mL) and the combined extracts were washed with brine, dried over MgSO$_4$/activated carbon, filtered through a SiO$_2$ plug capped with packed MgSO$_4$, and eluted with EtOAc. The solution was concentrated and dried under vacuum yielding the product as a white solid (5.15 g, 92% yield). MS (apci) m/z=321.1 (M+H).

Step B: Preparation of trans-1-(2-methoxyethyl)-4-phenylpyrrolidin-3-amine dihydrochloride To a solution of tert-butyl trans-1-(2-methoxyethyl)-4-phenylpyrrolidin-3-ylcarbamate (5.10 g, 15.9 mmol) in 2:1 EtOAc-MeOH (150 mL) was added 4 N HCl in dioxane (59.7 mL, 239 mmol). The mixture was stirred at ambient temperature for 90 minutes and then concentrated under vacuum. The resulting foam was treated with EtOAc (200 mL), sonicated for 5 minutes and stirred vigorously until a fine white suspension formed. The suspension was filtered, washed with EtOAc and dried under vacuum to afford the title compound as a white powder (5.10 g, 100% yield). MS (apci) m/z=221.1 (M+H).

Preparation C1

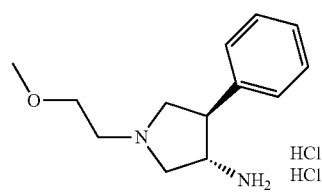 [SMILES: COCCN1C[C@@H](N)[C@H](c2ccccc2)C1]

(3S,4R)-1-(2-methoxyethyl)-4-phenylpyrrolidin-3-amine dihydrochloride

Step A: Preparation of (R)-3-cinnamoyl-4-phenyloxazolidin-2-one

A THF (50 mL) solution of (R)-4-phenyloxazolidin-2-one (5.90 g, 36.2 mmol) was cooled to −78° C. and treated with lithium bis(trimethylsilyl)amide (36.9 mL, 36.9 mmol, 1.0 M in THF) dropwise over 15 minutes. After stirring for 15 minutes at −78° C., a THF (10 mL) solution of cinnamoyl chloride (6.33 g, 38.0 mmol) was then introduced. The mixture was stirred for 1 hour at −78° C. and 2 hours at ambient temperature before it was quenched with saturated NaHCO$_3$ (50 mL) and stirred for 1 hour. The mixture was diluted with EtOAc (200 mL), washed with water and brine, dried over MgSO$_4$, filtered and concentrated to give the product as a pale yellow solid (10.6 g, 99.9% yield). MS (apci) m/z=293.9 (M+H).

Step B: Preparation of (R)-3-((3S,4R)-1-(2-methoxyethyl)-4-phenylpyrrolidine-3-carbonyl)-4-phenyloxazolidin-2-one A toluene (500 mL) solution of (R)-3-cinnamoyl-4-phenyloxazolidin-2-one (8.00 g, 27.3 mmol) and TFA (0.210 mL, 2.73 mmol) was first cooled to 5-10° C., followed by dropwise addition of a toluene (30 mL) solution of 2-methoxy-N-(methoxymethyl)-N-((trimethylsilyl)methyl) ethanamine (Preparation C, 8.40 g, 40.9 mmol). The resulting mixture was warmed up to ambient temperature and stirred for 3 hours, then washed with saturated NaHCO$_3$ and water, dried with MgSO$_4$, filtered and concentrated under vacuum. The crude material was purified by silica column chromatography, eluting with 16-20% EtOAc/hexanes, to afford the product (6.5 g, 60% yield). MS (apci) m/z=395.2 (M+H).

Step C: Preparation of (3S,4R)-1-(2-methoxyethyl)-4-phenylpyrrolidine-3-carboxylic acid To a 1M aqueous solution of LiOH (41.2 mL, 41.2 mmol) at 0° C. was added H$_2$O$_2$ (3.37 mL, 33.0 mmol, 30 wt %). The mixture was then added to solution of (R)-3-((3S,4R)-1-(2-methoxyethyl)-4-phenylpyrrolidine-3-carbonyl)-4-phenyloxazolidin-2-one (6.50 g, 16.5 mmol) in THF (100 mL) over 10 minutes at 0° C. After 1 hour stirring, 2.0 M aqueous Na$_2$SO$_3$ (33.0 mL, 65.9 mmol) was introduced at 0° C. and the reaction mixture was warmed to ambient temperature. After stirring for 10 minutes, the mixture was washed with EtOAc (50 mL). The aqueous layer was acidified with 1 N HCl until pH 3-5, then treated with NaCl (10 g), then extracted with 10% iPrOH/DCM. The organic layer was dried with MgSO$_4$, filtered and concentrated to give the product (4.11 g, 100% yield). MS (apci) m/z=250.1 (M+H).

Step D: Preparation of benzyl (3S,4R)-1-(2-methoxyethyl)-4-phenylpyrrolidin-3-ylcarbamate To a solution of (3S,4R)-1-(2-methoxyethyl)-4-phenylpyrrolidine-3-carboxylic acid (4.11 g, 16.5 mmol) in toluene (70 mL) was added TEA (5.74 mL, 41.2 mmol) followed by diphenyl phosphoryl azide (4.99 mL, 23.1 mmol). The mixture was stirred at ambient temperature for 1 hour and then heated to reflux for 1 hour. Benzyl alcohol (3.42 mL, 33.0 mmol) was then added and the reaction mixture was refluxed for 15 hours. The reaction mixture was treated with EtOAc, washed with water, dried over MgSO$_4$, filtered and concentrated under vacuum. The crude material was purified by silica column chromatography, eluting with 1% MeOH/DCM to afford the product (2.5 g, 43% yield). MS (apci) m/z=355.2 (M+H).

Step E: Preparation of (3S,4R)-1-(2-methoxyethyl)-4-phenylpyrrolidin-3-amine dihydrochloride Benzyl (3S,4R)-1-(2-methoxyethyl)-4-phenylpyrrolidin-3-ylcarbamate (0.257 g, 0.725 mmol) and TFA (3.91 mL, 50.8 mmol) were heated at 60° C. for 17 hours. The reaction mixture was concentrated under vacuum, using toluene to azeotrope, then treated with 2 N HCl in Et$_2$O and concentrated again to give the title compound (0.21 g, 100% yield) as an off-white solid. MS (apci) m/z=221.2 (M+H).

The following pyrrolidine intermediates were made according to the method of Preparation C1, using the appropriately substituted cinnamoyl chloride in Step A. The corresponding trifluoroacetate salts could be prepared by substituting HCl with TFA in an appropriate solvent such as DCM or CHCl$_3$ in Step E.

| Preparation # | Structure | Name | Data |
|---|---|---|---|
| C2 | 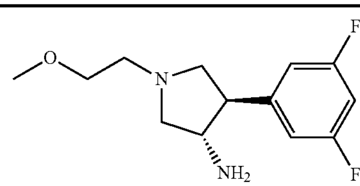 | (3S,4R)-4-(3,5-difluorophenyl)-1-(2-methoxyethyl)pyrrolidin-3-amine dihydrochloride | MS (apci) m/z = 257.1 (M + H) |
| C3 | 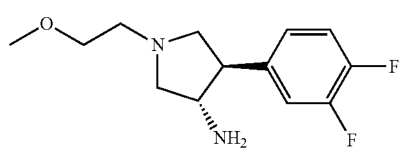 | (3S,4R)-4-(3,4-difluorophenyl)-1-(2-methoxyethyl)pyrrolidin-3-amine dihydrochloride | MS (apci) m/z = 257.1 (M + H) |
| C4 | 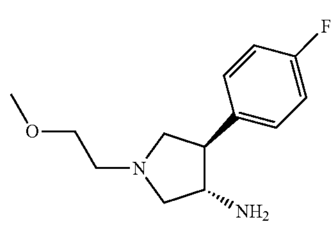 [SMILES: COCCN1C[C@@H](N)[C@H](c2ccc(F)cc2)C1] | (3S,4R)-4-(4-fluorophenyl)-1-(2-methoxyethyl)pyrrolidin-3-amine dihydrochloride | MS (apci) m/z = 239.1 (M + H). |

Preparation D

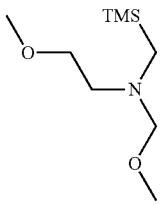

2-methoxy-N-(methoxymethyl)-N-((trimethylsilyl)methyl)ethanamine

Step A: Preparation of 2-methoxy-N-((trimethylsilyl)methyl)ethanamine

To a DMSO solution (15 mL) of 2-methoxyethanamine (14.2 mL, 163 mmol) at 90° C. was added a DMSO (10 mL) solution of (chloromethyl)trimethylsilane (11.4 mL, 81.5 mmol) by addition funnel over 40 minutes. The mixture was heated at 90° C. for 3.5 hours, then cooled to ambient temperature, diluted with H₂O (150 mL) and extracted with EtOAc (2×150 mL). The combined organic extracts were washed with brine (150 mL), dried with MgSO₄, filtered and concentrated to yield the product as a yellow oil (8.14 g, 62% yield). MS (apci) m/z=162.0 (M+H).

Step B: Preparation of 2-methoxy-N-(methoxymethyl)-N-((trimethylsilyl)methyl)ethanamine A MeOH (2.45 mL) solution of formaldehyde (37% aqueous, 4.91 g, 60.6 mmol) was cooled to 0° C., and treated with a dropwise addition of 2-methoxy-N-((trimethylsilyl)methyl)ethanamine (8.14 g, 50.5 mmol). The biphasic mixture was stirred at 0° C. for 3 hours, then K₂CO₃ (6.97 g, 50.5 mmol) was added and the mixture was stirred at 0° C. for 1 hour. The yellow oil was decanted onto K₂CO₃ (2.00 g, 14.4 mmol), and the mixture was stirred at ambient temperature for 2 hours. After the yellow oil was decanted, the solid K₂CO₃ was washed with Et₂O (2×10 mL), and the Et₂O washings were combined with the decanted yellow oil and concentrated on a rotary evaporator to yield the title compound as a yellow oil (9.92 g, 96% yield). ¹H NMR (CDCl₃) δ 4.00 (s, 2H), 3.37-3.43 (m, 2H), 3.29 (s, 3H), 3.19 (s, 3H), 2.77-2.82 (m, 2H), 2.18 (s, 2H), 0.00 (s, 9H).

Preparation E1

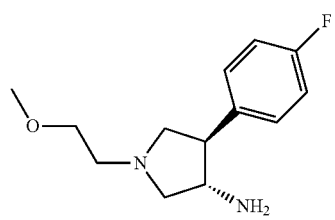

(3S,4R)-4-(4-fluorophenyl)-1-(2-methoxyethyl)pyrrolidin-3-amine

Step A: Preparation of (E)-1-fluoro-4-(2-nitrovinyl)benzene

Acetic acid (2.0 L, 35.5 mol) and ammonium acetate (310.5 g, 4.03 mol) were stirred at ambient temperature for 1 hour, then nitromethane (611 mL, 11.3 mol) and 4-fluorobenzaldehyde (200 g, 1.61 mol) were added and the reaction mixture was heated to 90° C. for 3 hours. The reaction was allowed to cool to ambient temperature, then H₂O (4 L) was added over 2 hours with mechanical stirring. The suspension was stirred 1 hour, then filtered and washed with 2:1 water/acetic acid (500 mL) The solids were dried in a vacuum oven (50° C.) to afford the title product as a pale yellow solid (238 g, 1.42 mol, 88% yield). ¹H NMR (CDCl₃) δ 7.98 (1H), 7.55 (3H), 7.16 (2H).

Step B: Preparation of trans-3-(4-fluorophenyl)-1-(2-methoxyethyl)-4-nitropyrrolidine To a suspension of (E)-1-fluoro-4-(2-nitrovinyl)benzene (201 g, 1.20 mol) in DCM (1.09 L) and TFA (9.3 mL, 120 mmol) was added dropwise over 30 minutes 2-methoxy-N-(methoxymethyl)-N-((trimethylsilyl)methyl)ethanamine (Preparation A; 383 g, 1.86 mol) and the internal reaction temperature was maintained between 23-36° C. by cooling in an ice bath. The reaction mixture was poured into aqueous phosphate buffer solution (pH 7, 500 mL) and diluted with DCM (300 mL). The phases were separated and the aqueous phase was extracted with DCM (400 mL). The organic phases were combined, washed with brine (300 mL), dried (MgSO₄), filtered and concentrated under reduced pressure. The crude oil was purified by silica column chromatography eluting with 40% EtOAc/heptane to afford the title compound as a yellow oil (245 g, 76% yield). MS (apci) m/z=269.1 (M+H).

Step C: Preparation of trans-4-(4-fluorophenyl)-1-(2-methoxyethyl)pyrrolidin-3-amine To a solution of trans-3-(4-fluorophenyl)-1-(2-methoxyethyl)-4-nitropyrrolidine (289 g, 1.08 mol) in EtOH (1 L) was added platinum(IV) oxide (24.5 g, 108 mmol) in a Parr vessel and installed into a Parr shaker. The vessel was evacuated and backfilled with nitrogen (3×), then evacuated and backfilled with hydrogen (60 psi). The vessel was recharged with hydrogen as needed until the reaction was complete. The reaction mixture was filtered through Celite® and rinsed with MeOH (50 mL), then concentrated under reduced pressure to afford the title compound as a yellow oil (243 g, 95% yield). MS (apci) m/z=239.1 (M+H).

Step D: Preparation of (3S,4R)-4-(4-fluorophenyl)-1-(2-methoxyethyl)pyrrolidin-3-amine (2S,3S)-2,3-bis(4-methylbenzoyloxy)succinate To a solution of (3S,4R)-4-(4-fluorophenyl)-1-(2-methoxyethyl)pyrrolidin-3-amine (120 g, 504 mmol) in THF (3.0 L) and H₂O (333 mL) was added di-p-toluoyl-D-tartaric acid (195 g, 504 mmol). The mixture was stirred at ambient temperature for 1 hour, then placed in a freezer (−11° C.) for 18 hours. The mixture was stirred to give a slurry, filtered, and rinsed with Et₂O (4×100 mL). The solid was dried in vacuum oven (40° C.) for 4 hours, then recrystallized twice by the following procedure: the solid was dissolved in THF (1.06 mL) and H₂O (118 mL) with heating to 45° C., then allowing to cool to ambient temperature over 2 hours, then placed in a freezer (−11° C.) for 18 hours; the mixture was stirred to give a slurry, filtered, and rinsed with Et₂O (4×100 mL). After two recrystallizations, the solid was dried in vacuum oven (40° C.) for 18 hours to afford the title compound as a white crystalline solid (96 g, 31% yield). MS (apci) m/z=239.2 (M+H).

Step E: Preparation of (3S,4R)-4-(4-fluorophenyl)-1-(2-methoxyethyl)pyrrolidin-3-amine (3S,4R)-4-(4-fluorophenyl)-1-(2-methoxyethyl)pyrrolidin-3-amine (2S,3S)-2,3-bis(4-methylbenzoyloxy)succinate (20 g, 32.0 mmol) was dissolved in DCM (300 mL) and washed with 1M NaOH (2×200 mL). The combined aqueous phases were extracted with DCM (200 mL). The combined organic extracts were washed with brine (200 mL), dried (MgSO₄), filtered and concentrated, then dried under vacuum to afford the title compound as a yellow oil (6.17 g, 81%, >99% ee). MS (apci) m/z=239.1 (M+H).

The following pyrrolidine intermediates were made according to the method of Preparation E1, using the appropriate benzaldehyde in Step A and replacing EtOH and platinum(IV) oxide with MeOH and Raney nickel respectively in Step C. For preparation E3, the 90% THF/H₂O in Step D was replaced with 85% MeOH/H₂O.

lithium bis(trimethylsilyl)amide (36.9 mL, 36.9 mmol, 1.0 M in THF) dropwise over 15 minutes. After 15-minute stirring at −78° C., a THF (10 mL) solution of cinnamoyl chloride (6.33 g, 38.0 mmol) was then introduced. The mixture was stirred for 1 hour at −78° C. and 2 hours at ambient temperature before it was quenched with saturated NaHCO₃ (50 mL) and stirred for 1 hour. The mixture was diluted with EtOAc (200 mL), washed with water and brine, dried over MgSO₄, filtered and concentrated to give the product as a pale yellow solid (10.6 g, 99.9% yield). MS (apci) m/z=293.9 (M+H).

Step B: Preparation of (R)-3-(3S,4R)-1-(2-methoxyethyl)-4-phenylpyrrolidine-3-carbonyl)-4-phenyloxazolidin-2-one A toluene (500 mL) solution of (R)-3-cinnamoyl-4-phenyloxazolidin-2-one (8.00 g, 27.3 mmol) and TFA (0.210 mL, 2.73 mmol) was first cooled to 5-10° C., followed by dropwise addition of a toluene (30 mL) solution of 2-methoxy-N-(methoxymethyl)-N-((trimethylsilyl)methyl)ethanamine (Preparation C, 8.40 g, 40.9 mmol). The resulting mixture was warmed up to ambient temperature and stirred for 3 hours, then washed with saturated NaHCO₃ and water, dried with MgSO₄, filtered and concentrated in vacuo. The crude material was purified by silica column chroma-

| Preparation # | Structure | Name | Data |
|---|---|---|---|
| E2 | 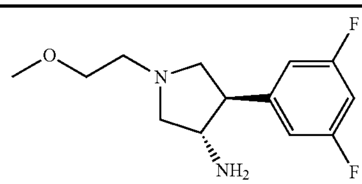 | (3S,4R)-4-(3,5-difluorophenyl)-1-(2-methoxyethyl)pyrrolidin-3-amine | MS (apci) m/z = 257.1 (M + H) |
| E3 | 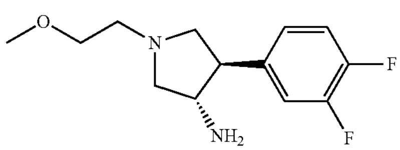 [SMILES: COCCN1C[C@@H](N)[C@H](c2ccc(F)c(F)c2)C1] | (3S,4R)-4-(3,4-difluorophenyl)-1-(2-methoxyethyl)pyrrolidin-3-amine (2S,3S)-2,3-bis(4-methylbenzoyloxy)succinate | MS (apci) m/z = 257.1 (M + H) |

Preparation D-100

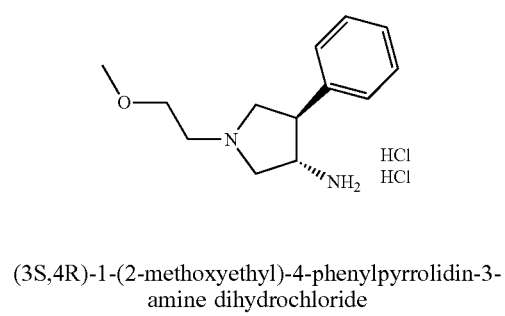

(3S,4R)-1-(2-methoxyethyl)-4-phenylpyrrolidin-3-amine dihydrochloride

Step A: Preparation of (R)-3-cinnamoyl-4-phenyloxazolidin-2-one

A THF (50 mL) solution of (R)-4-phenyloxazolidin-2-one (5.90 g, 36.2 mmol) was cooled to −78° C. and treated with tography, eluting with 16-20% EtOAc/hexanes, to afford the product (6.5 g, 60% yield). MS (apci) m/z=395.2 (M+H).

Step C: Preparation of (3S,4R)-1-(2-methoxyethyl)-4-phenylpyrrolidine-3-carboxylic acid To a 1M aqueous solution of LiOH (41.2 mL, 41.2 mmol) at 0° C. was added H₂O₂ (3.37 mL, 33.0 mmol, 30 wt %). The mixture was then added to solution of (R)-3-((3S,4R)-1-(2-methoxyethyl)-4-phenylpyrrolidine-3-carbonyl)-4-phenyloxazolidin-2-one (6.50 g, 16.5 mmol) in THF (100 mL) over 10 minutes at 0° C. After 1 hour stirring, 2.0 M aqueous Na₂SO₃ (33.0 mL, 65.9 mmol) was introduced at 0° C. and the reaction mixture was warmed to ambient temperature. After stirring for 10 minutes, the mixture was washed with EtOAc (50 mL). The aqueous layer was acidified with 1 N HCl until pH 3-5, then treated with NaCl (10 g), then extracted with 10% iPrOH/DCM. The organic layer was dried with MgSO₄, filtered and concentrated to give the product (4.11 g, 100% yield). MS (apci) m/z=250.1 (M+H).

Step D: Preparation of benzyl (3S,4R)-1-(2-methoxyethyl)-4-phenylpyrrolidin-3-ylcarbamate To a solution of (3S,4R)-1-(2-methoxyethyl)-4-phenylpyrrolidine-3-carboxylic acid (4.11 g, 16.5 mmol) in toluene (70 mL) was added TEA (5.74 mL, 41.2 mmol) followed by diphenyl phosphoryl azide (4.99 mL, 23.1 mmol). The mixture was stirred at ambient temperature for 1 hour and then heated to reflux for 1 hour. Benzyl alcohol (3.42 mL, 33.0 mmol) was then added and the reaction mixture was refluxed for 15 hours. The reaction mixture was treated with EtOAc, washed with water, dried over MgSO₄, filtered and concentrated in vacuo. The crude material was purified by silica column chromatography, eluting with 1% MeOH/DCM to afford the product (2.5 g, 43% yield). MS (apci) m/z=355.2 (M+H).

Step E: Preparation of (3S,4R)-1-(2-methoxyethyl)-4-phenylpyrrolidin-3-amine dihydrochloride Benzyl (3S,4R)-1-(2-methoxyethyl)-4-phenylpyrrolidin-3-ylcarbamate (0.257 g, 0.725 mmol) and TFA (3.91 mL, 50.8 mmol) were heated at 60° C. for 17 hours. The reaction mixture was concentrated in vacuo, using toluene to azeotrope, then treated with 2 N HCl in Et₂O and concentrated again to give the title compound (0.21 g, 100% yield) as an off-white solid. MS (apci) m/z=221.2 (M+H).

Preparation G-100

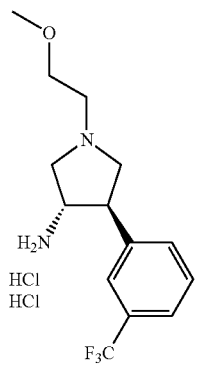 [SMILES: COCCN1C[C@@H](N)[C@H](c2cccc(C(F)(F)F)c2)C1]

(3S,4R)-1-(2-methoxyethyl)-4-(3-(trifluoromethyl)phenyl)pyrrolidin-3-amine dihydrochloride

Step A: Preparation of tert-butyl (3S,4R)-1-(2-methoxyethyl)-4-(3-(trifluoromethyl)-phenyl)pyrrolidin-3-ylcarbamate A solution of tert-butyl (3S,4R)-4-(3-(trifluoromethyl)phenyl)-pyrrolidin-3-ylcarbamate (100 mg, 0.303 mmol, commercially available), N,N-diethylpropan-2-amine (0.145 mL, 0.908 mmol) and 1-bromo-2-methoxyethane (0.0361 mL, 0.363 mmol) in DMF (1 mL) was stirred at ambient temperature for 2 hours, then heated to 60° C. for 4 hours, then cooled to ambient temperature overnight. After partitioning between EtOAc and saturated NaHCO₃ (10 mL each), the organic layer was washed with water and brine (2×10 mL each), dried over Na₂SO₄, filtered and concentrated to yield the crude product as white solid (80 mg, 68% yield). LCMS (apci) m/z=389.1 (M+H).

Step B: Preparation of (3S,4R)-1-(2-methoxyethyl)-4-(3-(trifluoromethyl)phenyl)-pyrrolidin-3-amine dihydrochloride A solution of tert-butyl (3S,4R)-1-(2-methoxyethyl)-4-(3-(trifluoromethyl)phenyl)pyrrolidin-3-ylcarbamate (80.0 mg, 0.206 mmol) in 5-6 N HCl in IPA (4.12 mL, 20.6 mmol) was stirred at ambient temperature for 1 hour, followed by concentrating in vacuo and triturating with Et₂O to afford the product as beige solid (74 mg, 99.5% yield). LCMS (apci) m/z=289.1 (M+H).

Preparation H-100

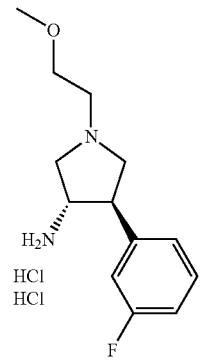 [SMILES: COCCN1C[C@@H](N)[C@H](c2cccc(F)c2)C1]

(3S,4R)-4-(3-fluorophenyl)-1-(2-methoxyethyl)pyrrolidin-3-amine dihydrochloride

Prepared according to the method of Preparation G-100, replacing tert-butyl (3S,4R)-4-(3-(trifluoromethyl)phenyl)-pyrrolidin-3-ylcarbamate with tert-butyl (3S,4R)-4-(3-fluorophenyl)pyrrolidin-3-ylcarbamate to afford the title compound. LCMS (apci) m/z=239.1 (M+H).

Preparation I-100

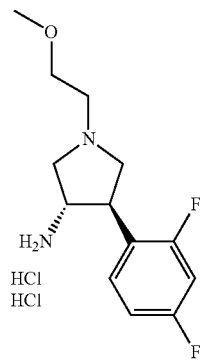 [SMILES: COCCN1C[C@@H](N)[C@H](c2ccc(F)cc2F)C1]

(3S,4R)-4-(2,4-difluorophenyl)-1-(2-methoxyethyl)pyrrolidin-3-amine dihydrochloride Prepared according to the method of Preparation G-100, replacing tert-butyl (3S,4R)-4-(3-(trifluoromethyl)phenyl)-pyrrolidin-3-ylcarbamate with tert-butyl (3S,4R)-4-(2,4 di-fluoro-phenyl)pyrrolidin-3-ylcarbamate to afford the title compound. LCMS (apci) m/z=257.1 (M+H).

Preparation J-100

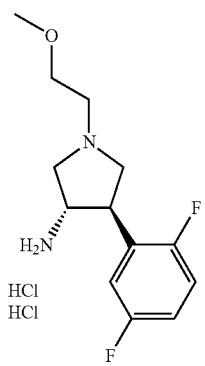

(3S,4R)-4-(2,5-difluorophenyl)-1-(2-methoxyethyl) pyrrolidin-3-amine dihydrochloride Prepared according to the method of Preparation G-100, replacing tert-butyl (3S,4R)-4-(3-(trifluoromethyl)phenyl)-pyrrolidin-3-ylcarbamate with tert-butyl (3S,4R)-4-(2,5 di-fluoro-phenyl)pyrrolidin-3-ylcarbamate to afford the title compound. LCMS (apci) m/z=257.1 (M+H).

Preparation K-100

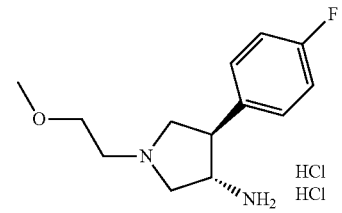 [SMILES: COCCN1C[C@@H](N)[C@H](c2ccc(F)cc2)C1]

(3S,4R)-4-(4-fluorophenyl)-1-(2-methoxyethyl)pyrrolidin-3-amine dihydrochloride

Prepared according to the method described in Preparation D-100, replacing cinnamoyl chloride with (E)-3-(4-fluorophenyl)acryloyl chloride. MS (apci) m/z=239.1 (M+H).

The following pyrrolidine intermediates were made according to the method of Preparation E1, using the appropriate benzaldehyde in Step A and replacing EtOH and platinum(IV) oxide with MeOH and Raney nickel respectively in Step C.

| Preparation # | Structure | Name | Data |
|---|---|---|---|
| L-100 | 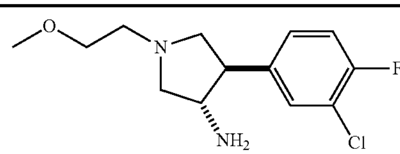 | trans-4-(3-chloro-4-fluoro-phenyl)-1-(2-methoxyethyl) pyrrolidin-3-amine | MS (apci) m/z = 273.1 (M + H) |
| L-101 | 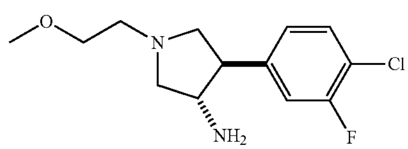 [SMILES: COCCN1C[C@@H](N)[C@H](c2ccc(Cl)c(F)c2)C1] | trans-4-(4-chloro-3-fluoro-phenyl)-1-(2-methoxyethyl) pyrrolidin-3-amine | MS (apci) m/z = 273.1 (M + H) |
| L-102 | 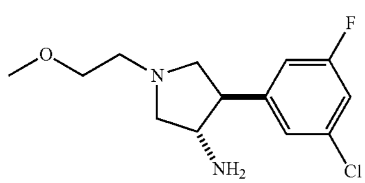 [SMILES: COCCN1C[C@@H](N)[C@H](c2cc(F)cc(Cl)c2)C1] | trans-4-(3-chloro-5-fluoro-phenyl)-1-(2-methoxyethyl) pyrrolidin-3-amine | MS (apci) m/z = 273.1 (M + H) |
| L-103 | 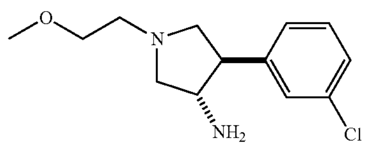 [SMILES: COCCN1C[C@@H](N)[C@H](c2cccc(Cl)c2)C1] | trans-4-(3-chlorophenyl)-1-(2-methoxyethyl)pyrrolidin-3-amine | MS (apci) m/z = 255.1 (M + H) |
| L-104 | 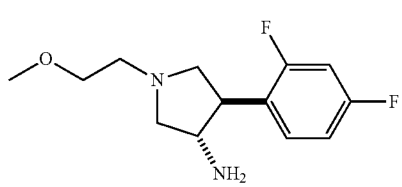 [SMILES: COCCN1C[C@@H](N)[C@H](c2ccc(F)cc2F)C1] | trans-4-(2,4-difluorophenyl)-1-(2-methoxyethyl)pyrrolidin-3-amine | MS (apci) m/z = 256.1 (M + H) |

| Preparation # | Structure | Name | Data |
|---|---|---|---|
| L-105 | 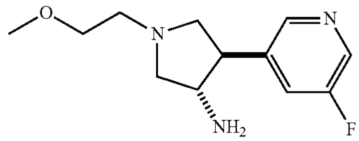 [SMILES: COCCN1C[C@@H](N)[C@H](c2cncc(F)c2)C1] | trans-4-(5-fluoropyridin-3-yl)-1-(2-methoxyethyl)pyrrolidin-3-amine | MS (apci) m/z = 240.1 (M + H) |
| L-106 | 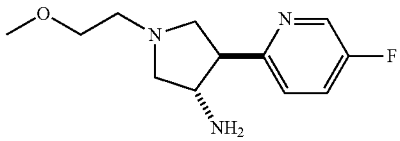 [SMILES: COCCN1C[C@@H](N)[C@H](c2ccc(F)cn2)C1] | trans-4-(5-fluoropyridin-2-yl)-1-(2-methoxyethyl)pyrrolidin-3-amine | $^1$H NMR consistent with expected product |
| L-107 | 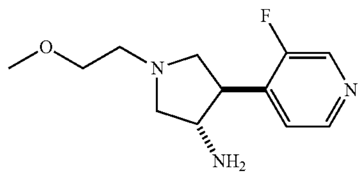 [SMILES: COCCN1C[C@@H](N)[C@H](c2ccncc2F)C1] | trans-4-(3-fluoropyridin-4-yl)-1-(2-methoxyethyl)pyrrolidin-3-amine | Not available |
| L-108 | 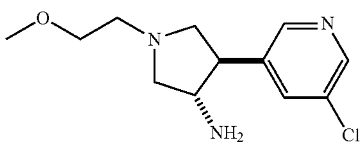 [SMILES: COCCN1C[C@@H](N)[C@H](c2cncc(Cl)c2)C1] | trans-4-(5-chloropyridin-3-yl)-1-(2-methoxyethyl)pyrrolidin-3-amine | MS (apci) m/z = 256.1 (M + H) |
| L-109 | 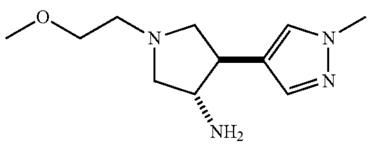 | trans-1-(2-methoxyethyl)-4-(1-methyl-1H-pyrazol-4-yl)pyrrolidin-3-amine | $^1$H NMR consistent with expected product |
| L-110 | 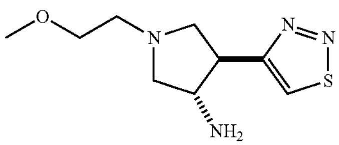 | trans-1-(2-methoxyethyl)-4-(1,2,3-thiadiazol-4-yl)pyrrolidin-3-amine | Not available |

Preparation L-111

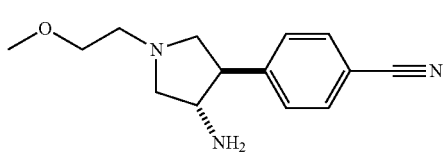

4-(trans-4-amino-1-(2-methoxyethyl)pyrrolidin-3-yl)benzonitrile

Prepared according to the method described in Preparation E1, Steps A to C, replacing 4-fluorobenzaldehyde with 4-formylbenzonitrile in Step A and replacing EtOH and platinum(IV) oxide with MeOH, Zn (dust) and saturated NH$_4$Cl, respectively in Step C. MS (apci) m/z=246.1 (M+H).

Preparation L-112

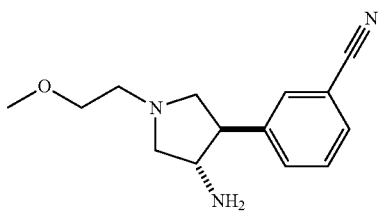 [SMILES: COCCN1C[C@@H](N)[C@H](c2cccc(C#N)c2)C1]

3-(trans-4-amino-1-(2-methoxyethyl)pyrrolidin-3-yl)benzonitrile

Prepared according to the method described in Preparation E1, Steps A to C, replacing 4-fluorobenzaldehyde with 3-formylbenzonitrile in Step A, and replacing EtOH and platinum(IV) oxide with MeOH, Zn (dust) and saturated NH$_4$Cl, respectively, in Step C. MS (apci) m/z=246.2 (M+H).

Preparation M-100

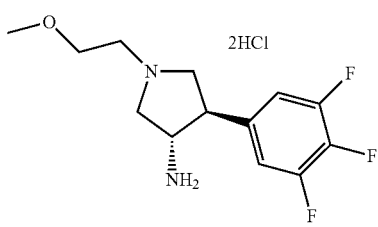 [SMILES: COCCN1C[C@@H](N)[C@H](c2cc(F)c(F)c(F)c2)C1]

(3S,4R)-1-(2-methoxyethyl)-4-(3,4,5-trifluorophenyl)pyrrolidin-3-amine dihydrochloride Prepared according to the method described in Preparation D-100, replacing cinnamoyl chloride with (E)-3-(3,4,5-trifluorophenyl)acryloyl chloride. $^1$H NMR (D$_2$O) δ 7.06-7.10 (m, 2H), 4.13-4.20 (m, 1H), 3.92-3.99 (m, 2H), 3.71-3.74 (m, 1H), 3.57-3.63 (m, 3H), 3.41-3.49 (m, 3H), 3.25 (s, 3H).

Preparation N-100

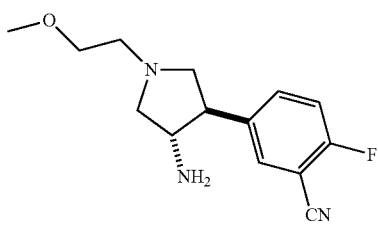 [SMILES: COCCN1C[C@@H](N)[C@H](c2ccc(F)c(C#N)c2)C1]

Trans-5-(4-amino-1-(2-methoxyethyl)pyrrolidin-3-yl)-2-fluorobenzonitrile

Step A: (E)-2-fluoro-5-(2-nitrovinyl)benzonitrile

To a solution of 2-fluoro-5-formylbenzonitrile (3.84 g, 25.0 mmol) in 3:1 CH$_3$NO$_2$/CH$_3$CN (25 mL) was added DMAP (0.305 g, 2.50 mmol) and the mixture stirred at ambient temperature for 23 hours. The mixture was cooled on an ice bath and Ac$_2$O (3.54 mL, 37.5 mmol) was added. The mixture was stirred for 5 minutes, allowed to reach ambient temperature and stirred for 1 hour. The mixture was concentrated to a yellow solid. The solid was suspended in iPrOH (70 mL) and stirred for 10 minutes. The suspension was collected via vacuum filtration, the cake washed with iPrOH and dried in vacuum to afford the title compound as a light tan powder (3.36 g, 70%). $^1$H NMR (CDCl$_3$) δ 7.96 (d, 1H), 7.79-7.88 (m, 2H), 7.57 (d, 1H), 7.36 (t, 1H).

Step B: Trans-2-fluoro-5-(1-(2-methoxyethyl)-4-nitropyrrolidin-3-yl)benzonitrile Using (E)-2-fluoro-5-(2-nitrovinyl)benzonitrile in Step B of the procedure describe in Preparation E1, the title compound was prepared as light gold syrup (1.56 g, 53%). MS (apci) m/z=294.1 (M+H).

Step C: Trans-5-(4-amino-1-(2-methoxyethyl)pyrrolidin-3-yl)-2-fluorobenzonitrile A solution of trans-2-fluoro-5-(1-(2-methoxyethyl)-4-nitropyrrolidin-3-yl)benzonitrile (450 mg, 1.53 mmol) in MeOH (6.0 mL) was cooled to 0°. Zn dust (1.00 mg, 15.3 mmol) and saturated aqueous NH$_4$Cl (1.0 mL) were added sequentially and the mixture was stirred for 5 minutes. The mixture was allowed to reach ambient temperature and stirred until complete by LCMS analysis. The mixture was filtered through packed Celite® using MeOH for rinsing and elution and the filtrate was concentrated to a colorless syrup. The syrup was treated with 1M K$_2$CO$_3$ (15 mL), mixed and extracted with CH$_2$Cl$_2$ (3×). The combined CH$_2$Cl$_2$ extracts were dried over Na$_2$SO$_4$, filtered and concentrated to provide the title compound as a colorless syrup (412 mg, 100%). MS (apci) m/z=264.1 (M+H).

Preparation O-100

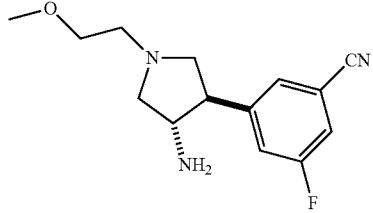 [SMILES: COCCN1C[C@@H](N)[C@H](c2cc(F)cc(C#N)c2)C1]

Trans-3-(4-amino-1-(2-methoxyethyl)pyrrolidin-3-yl)-5-fluorobenzonitrile

Step A: 3-fluoro-5-formylbenzonitrile

A solution of 3-bromo-5-fluorobenzonitrile (5.00 g, 25.0 mmol) in dry THF (25 mL) was cooled to 0° C. and 2M iPrMgCl (15.0 mL, 30.0 mmol) in THF was added dropwise over 5 minutes. The mixture was stirred at 0° C. for 15 minutes then at ambient temperature for 1 hour. The mixture was cooled to 0° C. and dry DMF (5.81 mL, 75.0 mmol) was added. The mixture was stirred for 17 hours during which time the temperature reached ambient temperature after 2 hours. The mixture was added to ice water (150 mL) and Et$_2$O (100 mL) The biphasic mixture was stirred and treated with 6M HCl to aqueous pH=3. The organic layer was removed and the aqueous layer extracted with Et$_2$O (2×). The combined Et$_2$O fractions were washed with saturated NaCl and dried over MgSO$_4$/activated carbon. The dried solution was filtered through a SiO$_2$ plug eluting with Et$_2$O. The filtrate was concentrated to give the title compound as a yellow solid that was dried in vacuum (3.68 g, 99%). $^1$H NMR (CDCl$_3$) δ 10.0 (s, 1H), 8.00 (s, 1H), 7.81-7.86 (m, 1H), 7.62-7.67 (m, 1H).

Step B: Trans-3-(4-amino-1-(2-methoxyethyl)pyrrolidin-3-yl)-5-fluorobenzonitrile The tile compound was prepared using 3-fluoro-5-formylbenzonitrile in the procedure described for the preparation of trans-5-(4-amino-1-(2-methoxyethyl)pyrrolidin-3-yl)-2-fluorobenzonitrile (Preparation N-100). The compound was isolated as a colorless syrup (542 mg, 93%). MS (apci) m/z=264.1 (M+H).

Preparation P-100

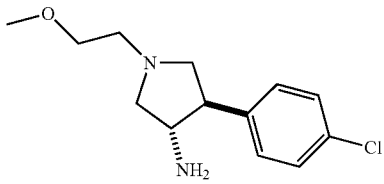 [SMILES: COCCN1C[C@@H](N)[C@H](c2ccc(Cl)cc2)C1]

Trans-1-(2-methoxyethyl)-4-(4-chlorophenyl)pyrrolidin-3-amine

Step A: Trans-3-(4-chlorophenyl)-1-(2-methoxyethyl)-4-nitropyrrolidine

Using (E)-1-chloro-4-(2-nitrovinyl)benzene in Step B of the procedure describe in Preparation E1, the title compound was prepared as viscous colorless oil (5.10 g, 64%). MS (apci) m/z=285.0 (M+H).

Step B: Trans-1-(2-methoxyethyl)-4-(4-chlorophenyl)pyrrolidin-3-amine

To a suspension of 2800 Raney Nickel (50 wt % in H$_2$O, 0.873 g, 5.10 mmol) in MeOH (25 mL) was added trans-3-(4-chlorophenyl)-1-(2-methoxyethyl)-4-nitropyrrolidine (2.90 g, 10.2 mmol) in MeOH (25 mL). The mixture was flushed with H$_2$ gas and stirred under a balloon atmosphere of H$_2$ for 16 hours. The mixture was purged with N$_2$ gas and filtered through packed Celite® using MeOH for rinsing and elution. The filtrate was concentrated to a cloudy oil. The oil was dissolved in CH$_2$Cl$_2$ and dried over Na$_2$SO$_4$/activated carbon. The solution was filtered and concentrated to provide the title compound as a light gold oil that was dried in vacuum (2.46 g, 95%). MS (apci) m/z=255.1 (M+H).

Preparation of Synthetic Examples

Example 1

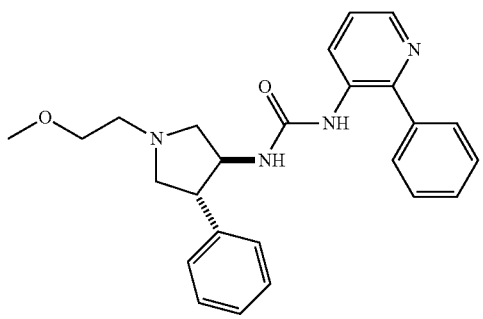 [SMILES: COCCN1C[C@@H](NC(=O)Nc2cccnc2-c2ccccc2)[C@H](c2ccccc2)C1]

1-(trans-1-(2-methoxyethyl)-4-phenylpyrrolidin-3-yl)-3-(2-phenylpyridin-3-yl)urea

Step A: Preparation of 2-phenylpyridin-3-amine

Phenyl boronic acid (92 mg, 0.75 mmol), K$_2$CO$_3$ (320 mg, 2.31 mmol) and Pd(PPh$_3$)$_4$ (67 mg, 0.06 mmol) were combined in toluene (3 mL), water (1.5 mL) and EtOH (0.75 mL) then treated with 2-bromopyridin-3-amine (100 mg, 0.58 mmol). The mixture was warmed to 95° C. in a sealed tube for 16 hours then cooled and partitioned between EtOAc (20 mL) and water (20 mL). The aqueous layer was extracted with EtOAc (2×10 mL) and the combined organic phases were washed with brine (10 mL), dried over Na$_2$SO$_4$, filtered and concentrated under vacuum. The residue was purified by silica column chromatography eluting with 9:1 to 4:1 hexanes/EtOAc, to afford 2-phenylpyridin-3-amine (83 mg, 84% yield) as a pale yellow gum. MS (apci) m/z=171.2 (M+H).

Step B: Preparation of phenyl (2-phenylpyridin-3-yl)carbamate

To a solution of 2-phenylpyridin-3-amine (83 mg, 0.49 mmol) in EtOAc (2 mL) was added 2 M NaOH (488 µL, 0.97 mmol) followed by phenyl chloroformate (86 µL, 0.68 mmol). The mixture was stirred vigorously for 16 hours then partitioned between EtOAc (10 mL) and water (10 mL). The aqueous layer was extracted with EtOAc (2×10 mL) and the combined organic phases were washed with saturated NaHCO$_3$ (10 mL) and brine (10 mL) then dried over Na$_2$SO$_4$, filtered and concentrated under vacuum to afford phenyl (2-phenylpyridin-3-yl)carbamate (121 mg, 85% yield) as a white foam. MS (apci) m/z=291.1 (M+H).

Step C: Preparation of 1-(trans-1-(2-methoxyethyl)-4-phenylpyrrolidin-3-yl)-3-(2-phenylpyridin-3-yl)urea To a solution of trans-1-(2-methoxyethyl)-4-phenylpyrrolidin-3-amine dihydrochloride [Preparation B] (50 mg, 0.17 mmol) and phenyl (2-phenylpyridin-3-yl)carbamate (54.5 mg, 0.19 mmol) in DMA (2 mL) was added DIEA (104 µL, 0.60 mmol). The mixture was stirred at ambient temperature for 16 hours then partitioned between saturated NH$_4$Cl (20 mL) and EtOAc (10 mL). The aqueous layer was extracted with EtOAc (2×10 mL) and the combined organic phases were washed with water (5×10 mL) and brine (10 mL) then dried over Na$_2$SO$_4$, filtered and concentrated under vacuum. The residue was purified by silica column chromatography eluting with 2-4% MeOH/DCM to afford the title product (47 mg, 66% yield) as a white foam. MS (apci) m/z=417.2 (M+H).

Example 2

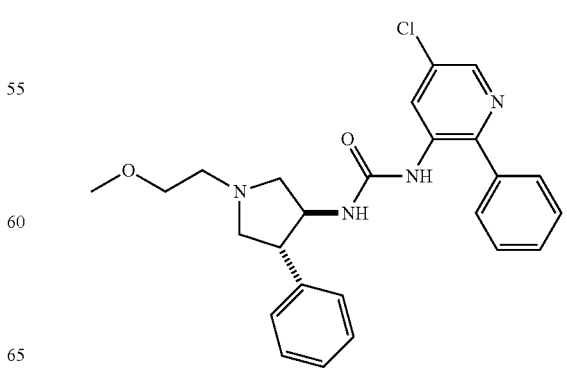

1-(5-chloro-2-phenylpyridin-3-yl)-3-(trans-1-(2-methoxyethyl)-4-phenylpyrrolidin-3-yl)urea Prepared according to the procedure of Example 1, replacing 2-bromopyridin-3-amine with 2-bromo-5-chloropyridin-3-amine in Step A. Material was purified by silica column chromatography eluting with 2% MeOH/DCM to afford the title compound (75 mg, 61% yield) as a colorless glass. MS (apci) m/z=451.3 (M+H).

Example 3

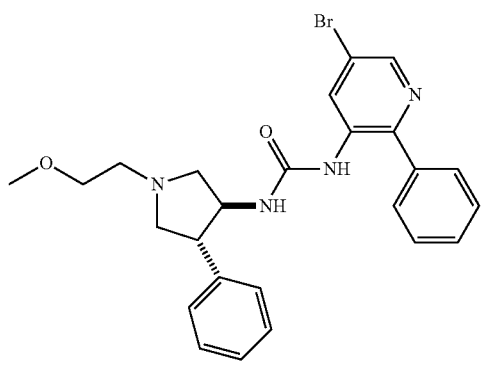 [SMILES: COCCN1C[C@@H](NC(=O)Nc2cc(Br)cnc2-c2ccccc2)[C@H](c2ccccc2)C1]

1-(5-bromo-2-phenylpyridin-3-yl)-3-(trans)-1-(2-methoxyethyl)-4-phenylpyrrolidin-3-yl)urea Prepared according to the procedure of Example 1, replacing 2-bromopyridin-3-amine with 2,5-dibromopyridin-3-amine in Step A. Material was purified by silica column chromatography eluting with 2% MeOH/DCM to afford the title compound (57 mg, 75% yield) as a white foam. MS (apci) m/z=495.1 (M+).

Example 4

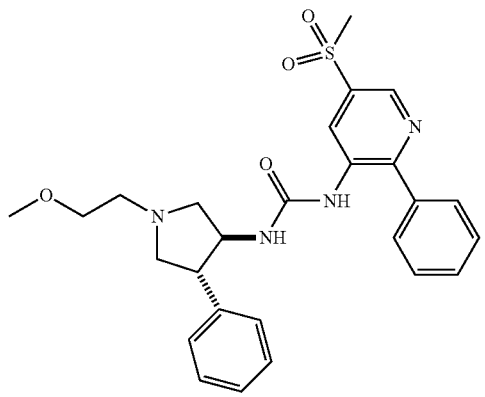 [SMILES: COCCN1C[C@@H](NC(=O)Nc2cc(S(C)(=O)=O)cnc2-c2ccccc2)[C@H](c2ccccc2)C1]

1-(trans-1-(2-methoxyethyl)-4-phenylpyrrolidin-3-yl)-3-(5-(methylsulfonyl)-2-phenylpyridin-3-yl)urea 1-(5-Bromo-2-phenylpyridin-3-yl)-3-(trans)-1-(2-methoxyethyl)-4-phenylpyrrolidin-3-yl)urea [Example 3] (50 mg, 0.1 mmol), methane sulfinic acid, sodium salt (41.2 mg, 0.4 mmol) and copper iodide (21.1 mg, 0.11 mmol) were combined in DMSO (1 mL) and purged with argon for 5 minutes. The mixture was stirred at 100° C. in a sealed tube for 16 hours then treated with copper iodide (40 mg) and stirred at 100° C. for 6 hours. The cooled mixture was partitioned between water (10 mL) and EtOAc (10 mL) and a few drops of NH$_4$OH were added. The aqueous layer was extracted with EtOAc (2×10 mL) and the combined organic phases were washed with water (5×10 mL) and brine (10 mL) then dried over Na$_2$SO$_4$, filtered and concentrated under vacuum. The residue was purified by silica column chromatography eluting with 2-5% MeOH/DCM to afford the title compound (6 mg, 12% yield) as a pale yellow gum. MS (apci) m/z=495.3 (M+H).

Example 5

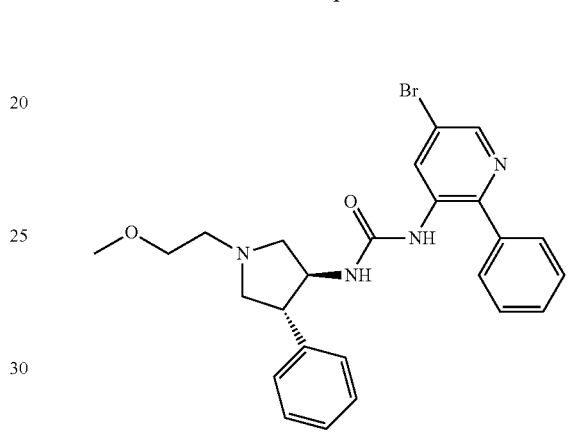

1-(5-bromo-2-phenylpyridin-3-yl)-3-((3S,4R)-1-(2-methoxyethyl)-4-phenylpyrrolidin-3-yl)urea Prepared according to the procedure of Example 1, replacing trans-1-(2-methoxyethyl)-4-phenylpyrrolidin-3-amine dihydrochloride [Preparation B] with (3S,4R)-1-(2-methoxyethyl)-4-phenylpyrrolidin-3-amine dihydrochloride [Preparation C1] in Step C. The crude material was purified by silica column chromatography eluting with 2% MeOH/DCM to afford the title compound (46 mg, 60% yield) as a white foam. MS (apci) m/z=497.2 (M+H).

Example 6

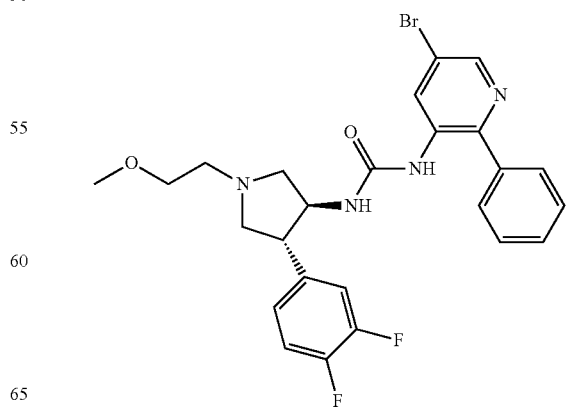

87

1-(5-bromo-2-phenylpyridin-3-yl)-3-((3S,4R)-4-(3,4-difluorophenyl)-1-(2-methoxyethyl)pyrrolidin-3-yl)urea Prepared according to the procedure of Example 1, replacing trans-1-(2-methoxyethyl)-4-phenylpyrrolidin-3-amine dihydrochloride [Preparation B] with (3S,4R)-4-(3,4-difluorophenyl)-1-(2-methoxyethyl)pyrrolidin-3-amine dihydrochloride [Preparation C3] in Step C. The crude material was purified by silica column chromatography eluting with 2% MeOH/DCM to afford the title compound (49 mg, 56% yield) as a colorless glass. MS (apci) m/z=533.2 (M+H).

Example 7

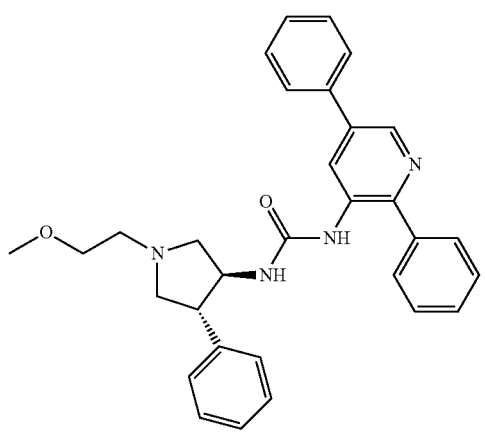 [SMILES: COCCN1C[C@@H](NC(=O)Nc2cc(-c3ccccc3)cnc2-c2ccccc2)[C@H](c2ccccc2)C1]

1-(2,5-diphenylpyridin-3-yl)-3-((3S,4R)-1-(2-methoxyethyl)-4-phenylpyrrolidin-3-yl)urea Prepared according to the procedure of Example 1, replacing 2-bromopyridin-3-amine with 2,5-dibromopyridin-3-amine in Step A (isolating 2,5-diphenylpyridin-3-amine) and trans-1-(2-methoxyethyl)-4-phenylpyrrolidin-3-amine dihydrochloride [Preparation B] with (3S,4R)-1-(2-methoxyethyl)-4-phenylpyrrolidin-3-amine dihydrochloride [Preparation C1] in Step C. The crude material was purified by silica column chromatography eluting with 2% MeOH/DCM to afford the title compound (20 mg, 61% yield) as a colorless glass. MS (apci) m/z=493.2 (M+).

88

Example 8

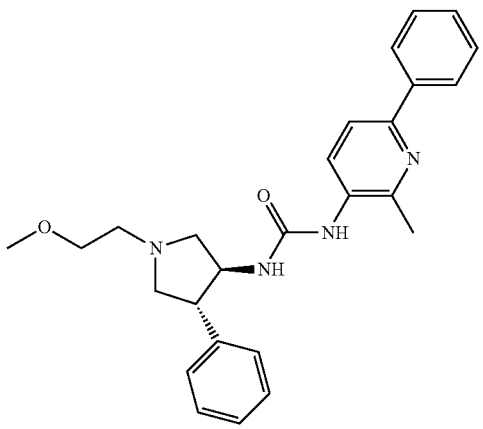 [SMILES: COCCN1C[C@@H](NC(=O)Nc2ccc(-c3ccccc3)nc2C)[C@H](c2ccccc2)C1]

1-((3S,4R)-1-(2-methoxyethyl)-4-phenylpyrrolidin-3-yl)-3-(2-methyl-6-phenylpyridin-3-yl)urea Prepared according to the procedure of Example 1, replacing 2-bromopyridin-3-amine with 6-bromo-2-methylpyridin-3-amine in Step A and trans-1-(2-methoxyethyl)-4-phenylpyrrolidin-3-amine dihydrochloride [Preparation B] with (3S,4R)-1-(2-methoxyethyl)-4-phenylpyrrolidin-3-amine dihydrochloride [Preparation C1] in Step C. The crude material was purified by silica column chromatography eluting with 2% MeOH/DCM to afford the title compound (18 mg, 63% yield) as a colorless glass. MS (apci) m/z=431.0 (M+H).

Example 9

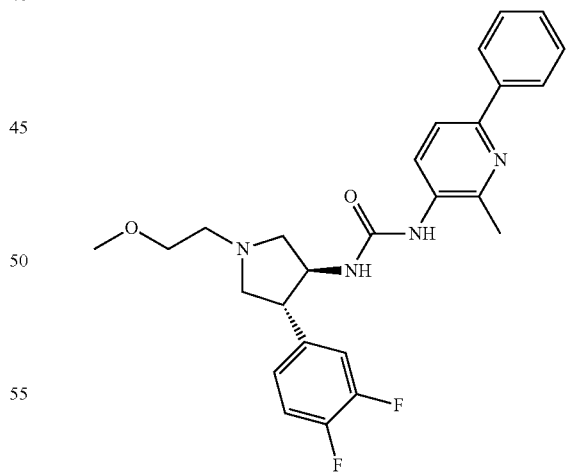

1-((3S,4R)-4-(3,4-difluorophenyl)-1-(2-methoxyethyl)pyrrolidin-3-yl)-3-(2-methyl-6-phenylpyridin-3-yl)urea Prepared according to the procedure of Example 8, replacing (3S,4R)-1-(2-methoxyethyl)-4-phenylpyrrolidin-3-amine dihydrochloride [Preparation C1] with (3S,4R)-4-(3, 4-difluorophenyl)-1-(2-methoxyethyl)pyrrolidin-3-amine dihydrochloride [Preparation C3] in Step C. Material was purified by silica column chromatography eluting with 2% MeOH/DCM to afford the title compound (19 mg, 66% yield) as a white solid. MS (apci) m/z=467.2 (M+H).

Example 10

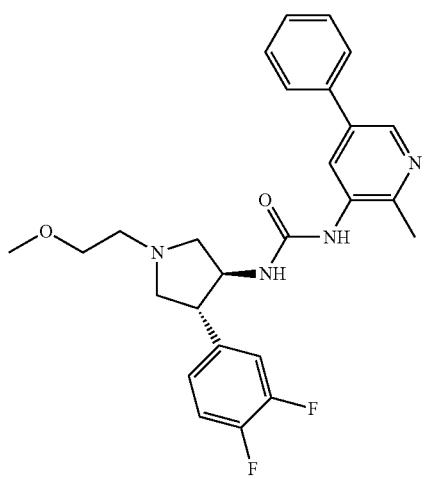

1-((3S,4R)-4-(3,4-difluorophenyl)-1-(2-methoxyethyl)pyrrolidin-3-yl)-3-(2-methyl-5-phenylpyridin-3-yl)urea Prepared according to the procedure of Example 1, replacing 2-bromopyridin-3-amine with 5-bromo-2-methylpyridin-3-amine in Step A and trans-1-(2-methoxyethyl)-4-phenylpyrrolidin-3-amine dihydrochloride [Preparation B] with (3S,4R)-4-(3,4-difluorophenyl)-1-(2-methoxyethyl)pyrrolidin-3-amine dihydrochloride [Preparation C3] in Step C. Material was purified by silica column chromatography eluting with 2-5% MeOH/DCM to afford the title compound (16 mg, 55% yield) as a colorless glass. MS (apci) m/z=467.2 (M+H).

Example 11

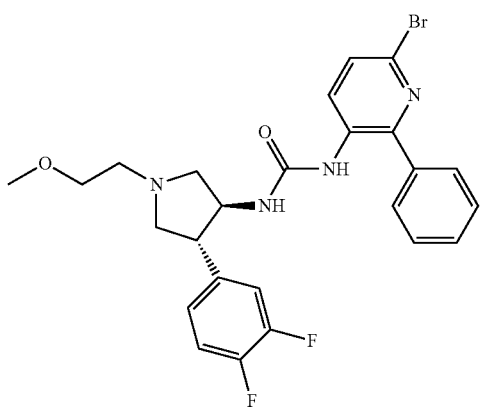

1-(6-bromo-2-phenylpyridin-3-yl)-3-((3S,4R)-4-(3,4-difluorophenyl)-1-(2-methoxyethyl)pyrrolidin-3-yl)urea Prepared according to the procedure of Example 1, replacing 2-bromopyridin-3-amine with 2,6-dibromopyridin-3-amine in Step A and trans-1-(2-methoxyethyl)-4-phenylpyrrolidin-3-amine dihydrochloride [Preparation B] with (3S,4R)-4-(3,4-difluorophenyl)-1-(2-methoxyethyl)pyrrolidin-3-amine dihydrochloride [Preparation C3] in Step C. Material was purified by silica column chromatography eluting with 2% MeOH/DCM to afford the title compound (58 mg, 62% yield) as a white solid. MS (apci) m/z=533.0 (M+H).

Example 12

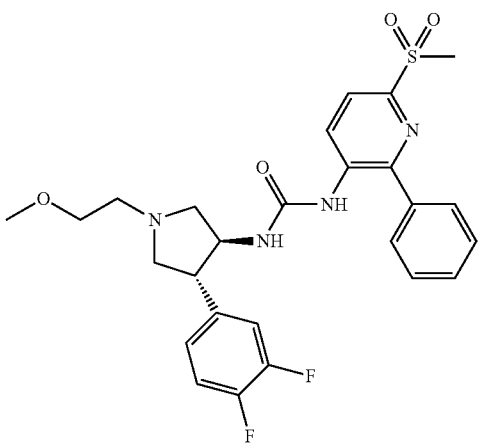 [SMILES: COCCN1C[C@@H](NC(=O)Nc2ccc(S(C)(=O)=O)nc2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(6-(methylsulfonyl)-2-phenylpyridin-3-yl)urea Step A: Preparation of 6-bromo-2-phenylpyridin-3-amine Prepared according to the procedure of Example 1, Step A, replacing 2-bromopyridin-3-amine with 2,6-dibromopyridin-3-amine. MS (apci) m/z=249.1 (M+).

Step B: Preparation of 6-(methylsulfonyl)-2-phenylpyridin-3-amine

6-Bromo-2-phenylpyridin-3-amine (50 mg, 0.20 mmol), methane sulfinic acid, sodium salt (82 mg, 0.80 mmol) and copper iodide (42 mg, 0.22 mmol) were combined in DMSO (1 mL) and purged with argon for 5 minutes. The mixture was stirred at 100° C. in a sealed tube for 3.5 hours then cooled and partitioned between water (10 mL) and EtOAc (10 mL) and a few drops of NH$_4$OH. The aqueous layer was extracted with EtOAc (2×10 mL) and the combined organic phases were washed with water (5×10 mL) and brine (10 mL) then dried over Na$_2$SO$_4$, filtered and concentrated under vacuum. The residue was purified by silica column chromatography eluting with 1% MeOH/DCM to afford 6-(methylsulfonyl)-2-phenylpyridin-3-amine (39 mg, 78% yield) as a colorless glass. MS (apci) m/z=249.1 (M+).

Step C: Preparation of 1-((3S,4R)-4-(3,4-difluoro-phenyl)-1-(2-methoxyethyl)pyrrolidin-3-yl)-3-(6-(methylsulfonyl)-2-phenylpyridin-3-yl)urea Prepared according to the procedure of Example 1, replacing 2-phenylpyridin-3-amine with 6-(methylsulfonyl)-2-phenylpyridin-3-amine in Step B and trans-1-(2-methoxyethyl)-4-phenylpyrrolidin-3-amine dihydrochloride [Preparation B] with (3S,4R)-4-(3,4-difluorophenyl)-1-(2-methoxyethyl)pyrrolidin-3-amine dihydrochloride [Preparation C3] in Step C. The crude material was purified by silica column chromatography eluting with 2% MeOH/DCM to afford the title compound (34 mg, 52% yield) as a white foam. MS (apci) m/z=531.0 (M+H).

Example 13

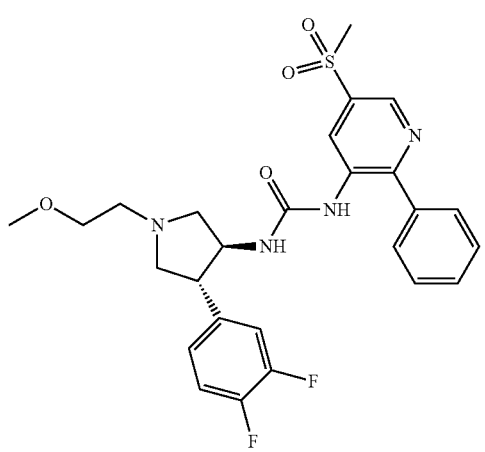 [SMILES: COCCN1C[C@@H](NC(=O)Nc2cc(S(C)(=O)=O)cnc2-c2ccccc2)[C@H](c2ccc(F)c(F)c2)C1]

1-((3S,4R)-4-(3,4-difluorophenyl)-1-(2-methoxy-ethyl)pyrrolidin-3-yl)-3-(5-(methylsulfonyl)-2-phenylpyridin-3-yl)urea 1-(5-Bromo-2-phenylpyridin-3-yl)-3-((3S,4R)-4-(3,4-difluorophenyl)-1-(2-methoxyethyl)pyrrolidin-3-yl)urea [Example 6] (30 mg, 0.06 mmol), methane sulfinic acid, sodium salt (23 mg, 0.23 mmol) and copper iodide (12 mg, 0.06 mmol) were combined in DMSO (1 mL) and purged with argon for 5 minutes. The mixture was stirred at 100° C. in a sealed tube for 16 hours then cooled and partitioned between water (10 mL) and EtOAc (10 mL) and a few drops of NH₄OH. The aqueous layer was extracted with EtOAc (2×10 mL) and the combined organic phases were washed with water (5×10 mL) and brine (10 mL) then dried over Na₂SO₄, filtered and concentrated under vacuum. The residue was purified by silica column chromatography eluting with 2% MeOH/DCM to afford the title compound (6 mg, 20% yield) as a white solid. MS (apci) m/z=531.0 (M+H).

Example 14

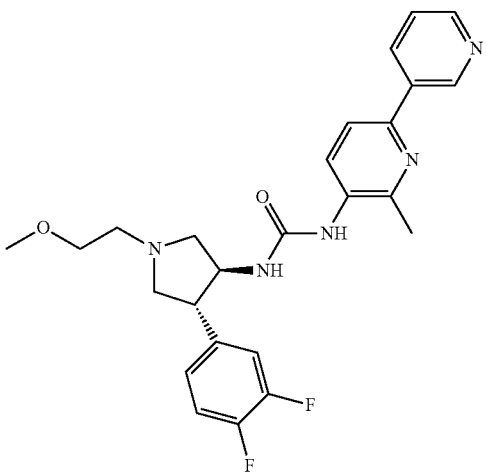 [SMILES: COCCN1C[C@@H](NC(=O)Nc2ccc(-c3cccnc3)nc2C)[C@H](c2ccc(F)c(F)c2)C1]

1-((3S,4R)-4-(3,4-difluorophenyl)-1-(2-methoxy-ethyl)pyrrolidin-3-yl)-3-(6-methyl-[2,3'-bipyridin]-5-yl)urea Prepared according to the procedure of Example 9, replacing phenyl boronic acid with pyridin-3-ylboronic acid in Step A. Material was purified by silica column chromatography eluting with 2-10% MeOH/DCM to afford the title compound (38 mg, 61%) as a white solid. MS (apci) m/z=468.1 (M+H).

Example 15

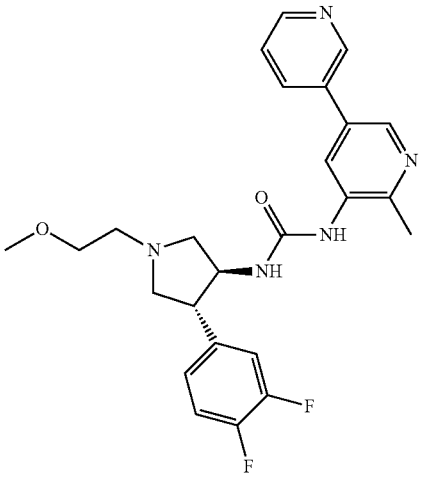

1-((3S,4R)-4-(3,4-difluorophenyl)-1-(2-methoxy-ethyl)pyrrolidin-3-yl)-3-(6-methyl-[3,3'-bipyridin]-5-yl)urea Prepared according to the procedure of Example 10, replacing phenyl boronic acid with pyridin-3-ylboronic acid in Step A. The crude material was purified by silica column chromatography eluting with 5-10% MeOH/DCM to afford the title compound (14 mg, 24%) as a white solid. MS (apci) m/z=468.1 (M+H).

Example 16

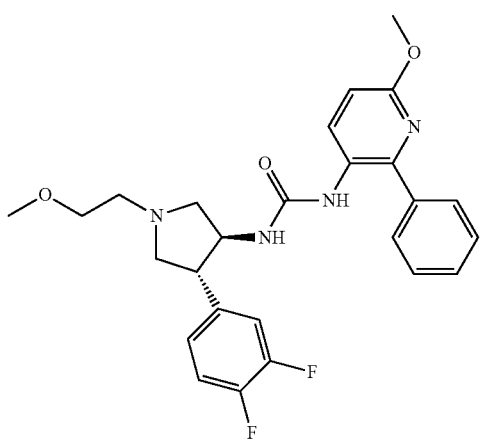 [SMILES: COCCN1C[C@@H](NC(=O)Nc2ccc(OC)nc2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(6-methoxy-2-phenylpyridin-3-yl)urea Prepared according to the procedure of Example 1, replacing 2-bromopyridin-3-amine with 2-bromo-6-methoxypyridin-3-amine in Step A and trans-1-(2-methoxyethyl)-4-phenylpyrrolidin-3-amine dihydrochloride [Preparation B] with (3S,4R)-4-(3,4-difluorophenyl)-1-(2-methoxyethyl)pyrrolidin-3-amine dihydrochloride [Preparation C3] in Step C. The crude material was purified by silica column chromatography eluting with 2% MeOH/DCM to afford the title compound (109 mg, 63% yield) as a white solid. MS (apci) m/z=483.0 (M+H).

Example 17

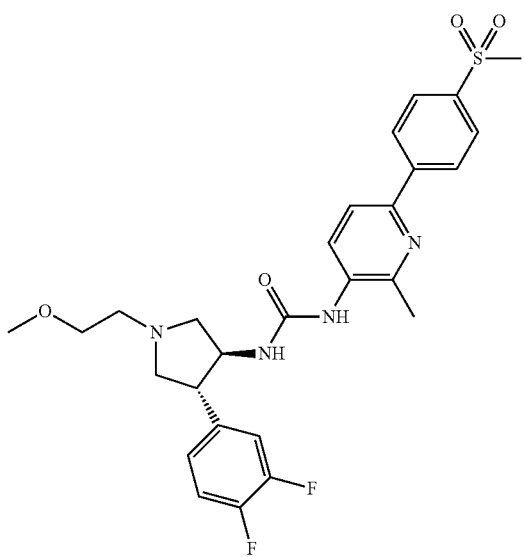

1-((3S,4R)-4-(3,4-difluorophenyl)-1-(2-methoxyethyl)pyrrolidin-3-yl)-3-(2-methyl-6-(4-(methylsulfonyl)phenyl)pyridin-3-yl)urea Prepared according to the procedure of Example 9, replacing phenyl boronic acid with 4-(methylsulfonyl)phenylboronic acid in Step A. Material was purified by silica column chromatography eluting with 2-6% MeOH/DCM to afford the title compound (34 mg, 50%) as a colorless glass. MS (apci) m/z=545.0 (M+H).

Example 18

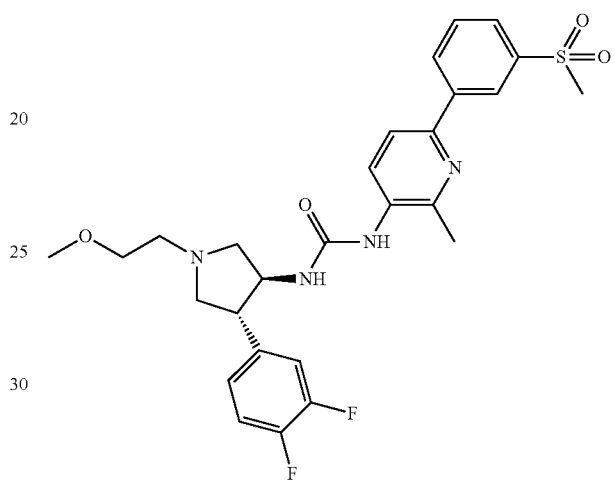

1-((3S,4R)-4-(3,4-difluorophenyl)-1-(2-methoxyethyl)pyrrolidin-3-yl)-3-(2-methyl-6-(3-(methylsulfonyl)phenyl)pyridin-3-yl)urea Prepared according to the procedure of Example 9, replacing phenyl boronic acid with 3-(methylsulfonyl)phenylboronic acid in Step A. Material was purified by silica column chromatography eluting with 2-6% MeOH/DCM to afford the title compound (31 mg, 46%) as a white foam. MS (apci) m/z=545.0 (M+H).

Example 19

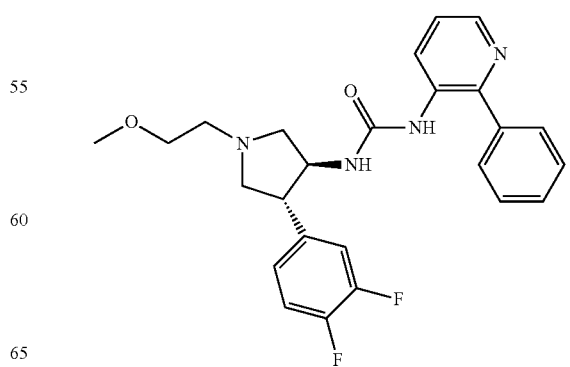

1-((3S,4R)-4-(3,4-difluorophenyl)-1-(2-methoxy-
ethyl)pyrrolidin-3-yl)-3-(2-phenylpyridin-3-yl)urea Prepared according to the procedure of Example 1, replacing trans-1-(2-methoxyethyl)-4-phenylpyrrolidin-3-amine dihydrochloride [Preparation B] with (3S,4R)-1-(2-methoxyethyl)-4-phenylpyrrolidin-3-amine dihydrochloride [Preparation C1] in Step C. Material was purified by silica column chromatography eluting with 2.5% MeOH/DCM to afford the title compound (19 mg, 25% yield) as a colorless gum. MS (apci) m/z=453.0 (M+H).

Example 20

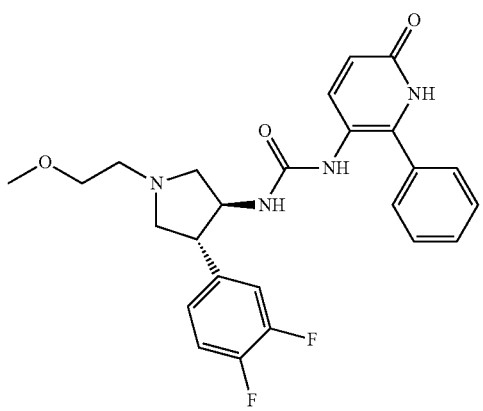 [SMILES: COCCN1C[C@@H](NC(=O)Nc2ccc(=O)[nH]c2-c2ccccc2)[C@H](c2ccc(F)c(F)c2)C1]

1-((3S,4R)-4-(3,4-difluorophenyl)-1-(2-methoxy-
ethyl)pyrrolidin-3-yl)-3-(6-oxo-2-phenyl-1,6-dihy-
dropyridin-3-yl)urea A suspension of 1-((3S,4R)-4-(3,4-difluorophenyl)-1-(2-methoxyethyl)pyrrolidin-3-yl)-3-(6-methoxy-2-phenylpyridin-3-yl)urea [Example 16] (20 mg, 0.04 mmol) in 4N HCl/dioxanes (1 mL) was heated to 100° C. in a sealed tube for 1.5 hours. The cooled mixture was concentrated and the residue partitioned between 1N NaOH (15 mL) and DCM (15 mL). The aqueous layer was extracted with DCM (2×10 mL) and the combined organic phases were washed with brine (10 mL), dried over $Na_2SO_4$, filtered and concentrated under vacuum. The residue was purified by silica column chromatography eluting with 5-10% MeOH/DCM to afford the title compound (4 mg, 21% yield) as a white solid. MS (apci) m/z=469.1 (M+H).

Example 21

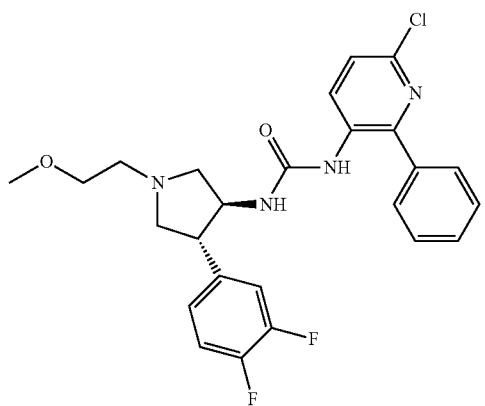 [SMILES: COCCN1C[C@@H](NC(=O)Nc2ccc(Cl)nc2-c2ccccc2)[C@H](c2ccc(F)c(F)c2)C1]

1-(6-chloro-2-phenylpyridin-3-yl)-3-((3S,4R)-4-(3,4-
difluorophenyl)-1-(2-methoxyethyl)pyrrolidin-3-yl)
urea Prepared according to the procedure of Example 1, replacing 2-bromopyridin-3-amine with 2-bromo-6-chloropyridin-3-amine in Step A and trans-1-(2-methoxyethyl)-4-phenylpyrrolidin-3-amine dihydrochloride [Preparation B] with (3S,4R)-4-(3,4-difluorophenyl)-1-(2-methoxyethyl)pyrrolidin-3-amine dihydrochloride [Preparation C3] in Step C. The crude material was purified by silica column chromatography eluting with 2% MeOH/DCM to afford the title compound (95 mg, 63% yield) as a cream foam. MS (apci) m/z=487.0 (M+H).

Example 22

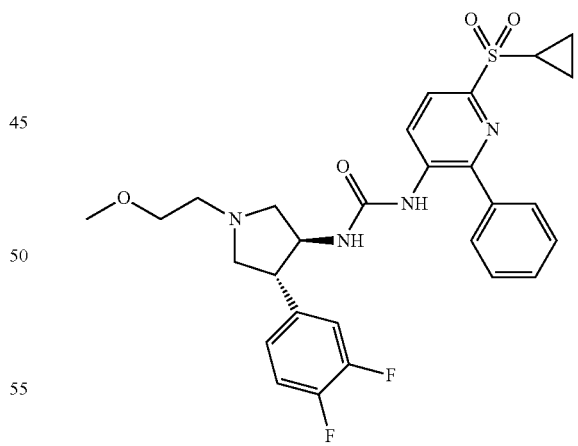

1-(6-(cyclopropylsulfonyl)-2-phenylpyridin-3-yl)-3-
((3S,4R)-4-(3,4-difluorophenyl)-1-(2-methoxyethyl)
pyrrolidin-3-yl)urea Prepared according to the procedure of Example 12, replacing methane sulfinic acid, sodium salt with sodium cyclopropanesulfinate in Step B. Material was purified by silica column chromatography eluting with 2% MeOH/

DCM to afford the title compound (14 mg, 35% yield) as a white foam. MS (apci) m/z=557.0 (M+H).

Example 23

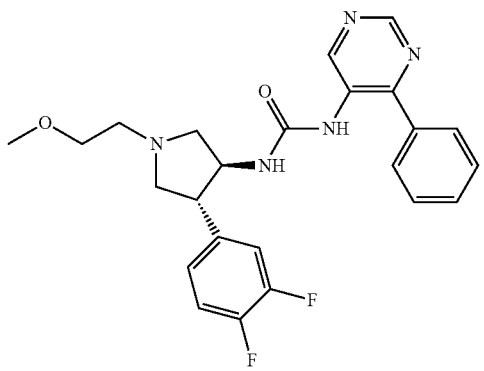 [SMILES: COCCN1C[C@@H](NC(=O)Nc2cncnc2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(4-phenylpyrimidin-5-yl) urea Step A: Preparation of 4-phenylpyrimidin-5-amine Prepared according to the procedure of Example 1, Step A, replacing 2-bromopyridin-3-amine with 4-bromopyrimidin-5-amine. Material was purified by silica column chromatography eluting with 2% MeOH/DCM to afford 4-phenylpyrimidin-5-amine (60 mg, 61% yield) as a yellow solid. MS (apci) m/z=172.0 (M+H).

Step B: Preparation of 1-((3S,4R)-4-(3,4-difluorophenyl)-1-(2-methoxyethyl)pyrrolidin-3-yl)-3-(4-phenylpyrimidin-5-yl)urea To a solution of 4-phenylpyrimidin-5-amine (37 mg, 0.22 mmol) and CDI (74 mg, 0.45 mmol) in DMF (1 mL) was added DIEA (151 µL, 0.86 mmol) and the solution stirred at ambient temperature for 16 hours. To this mixture was added a solution of (3S,4R)-4-(3,4-difluorophenyl)-1-(2-methoxyethyl)pyrrolidin-3-amine dihydrochloride [Preparation C3] (149 mg, 0.45 mmol) and DIEA (151 µL, 0.86 mmol) in DMF (1 mL) and stirring was continued for 16 hours. The mixture was partitioned between saturated NH₄Cl (20 mL) and EtOAc (20 mL) and the aqueous layer extracted with EtOAc (2×10 mL). The combined organic phases were washed with water (5×10 mL) and brine (10 mL) then dried over Na₂SO₄, filtered and concentrated under vacuum. The residue was purified by silica column chromatography eluting with 2% MeOH/DCM to afford the title compound (26 mg, 27% yield) as a pale yellow foam. MS (apci) m/z=454.0 (M+H).

Example 24

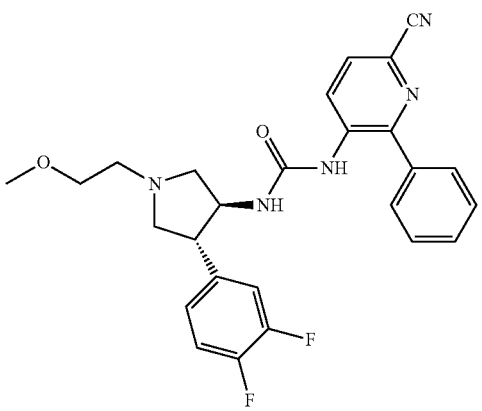 [SMILES: COCCN1C[C@@H](NC(=O)Nc2ccc(C#N)nc2-c2ccccc2)[C@H](c2ccc(F)c(F)c2)C1]

1-(6-cyano-2-phenylpyridin-3-yl)-3-((3S,4R)-4-(3,4-difluorophenyl)-1-(2-methoxyethyl)pyrrolidin-3-yl) urea Prepared according to the procedure of Example 1, replacing 2-bromopyridin-3-amine with 5-amino-6-bromopicolinonitrile in Step A and trans-1-(2-methoxyethyl)-4-phenylpyrrolidin-3-amine dihydrochloride [Preparation B] with (3S,4R)-4-(3,4-difluorophenyl)-1-(2-methoxyethyl)pyrrolidin-3-amine dihydrochloride [Preparation C3] in Step C. The crude material was purified by silica column chromatography eluting with 2% MeOH/DCM to afford the title compound (82 mg, 57% yield) as a white foam. MS (apci) m/z=478.0 (M+H).

Example 25

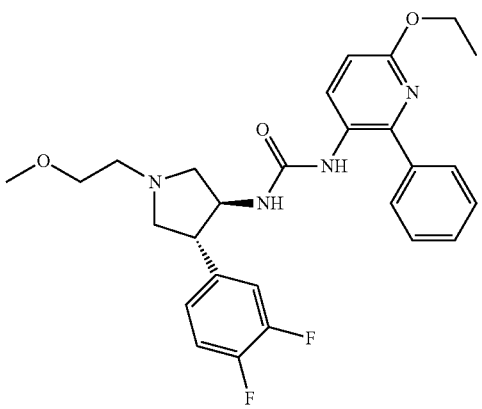 [SMILES: CCOc1ccc(NC(=O)N[C@@H]2CN(CCOC)C[C@H]2c2ccc(F)c(F)c2)c(-c2ccccc2)n1]

1-((3S,4R)-4-(3,4-difluorophenyl)-1-(2-methoxyethyl)pyrrolidin-3-yl)-3-(6-ethoxy-2-phenylpyridin-3-yl urea Step A: Preparation of 2-bromo-6-ethoxypyridin-3-amine To a solution of 6-ethoxypyridin-3-amine (100 mg, 0.72 mmol) in acetonitrile (2 mL) was added N-bromosuccinimide (129 mg, 0.72 mmol). The mixture was stirred at ambient temperature for 3 hours then concentrated under vacuum. The residue was purified by silica column chromatography eluting with 4:1 hexanes/EtOAc to afford 2-bromo-6-ethoxypyridin-3-amine (68 mg, 43% yield) as a dark orange/brown oil. MS (apci) m/z=216.9 (M+).

Step B: Preparation of 1-((3S,4R)-4-(3,4-difluorophenyl)-1-(2-methoxyethyl)pyrrolidin-3-yl)-3-(6-ethoxy-2-phenylpyridin-3-yl)urea Prepared according to the procedure of Example 1, replacing 2-bromopyridin-3-amine with 2-bromo-6-ethoxypyridin-3-amine in Step A and trans-1-(2-methoxyethyl)-4-phenylpyrrolidin-3-amine dihydrochloride [Preparation B] with (3S,4R)-4-(3,4-difluorophenyl)-1-(2-methoxyethyl)pyrrolidin-3-amine dihydrochloride [Preparation C3] in Step C. The crude material was purified by silica column chromatography eluting with 2% MeOH/DCM to afford the title compound (66 mg, 76% yield) as a white solid. MS (apci) m/z=497.1 (M+H).

Example 26

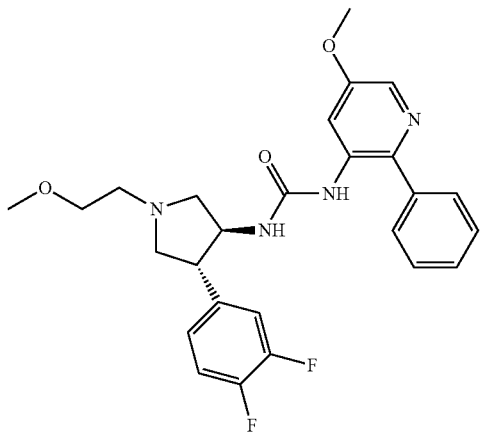 [SMILES: COCCN1C[C@@H](NC(=O)Nc2cc(OC)cnc2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(5-methoxy-2-phenylpyridin-3-yl)urea Prepared according to the procedure of Example 1, replacing 2-bromopyridin-3-amine with 2-bromo-5-methoxypyridin-3-amine in Step A and trans-1-(2-methoxyethyl)-4-phenylpyrrolidin-3-amine dihydrochloride [Preparation B] with (3S,4R)-4-(3,4-difluorophenyl)-1-(2-methoxyethyl)pyrrolidin-3-amine dihydrochloride [Preparation C3] in Step C. Material was purified by silica column chromatography eluting with 2% MeOH/DCM to afford the title compound (46 mg, 59% yield) as a white solid. MS (apci) m/z 483.1 (M+H).

Example 27

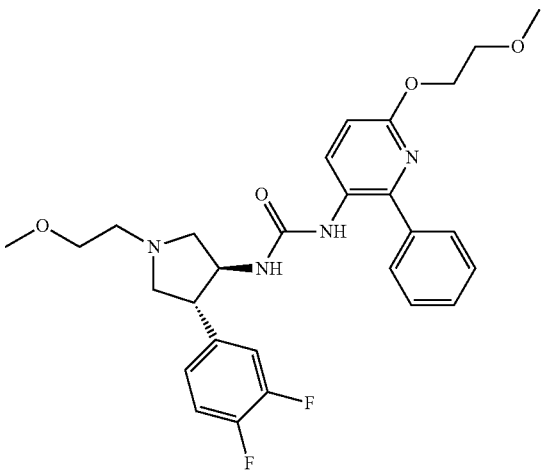

1-((3S,4R)-4-(3,4-difluorophenyl)-1-(2-methoxyethyl)pyrrolidin-3-yl)-3-(6-(2-methoxyethoxy)-2-phenylpyridin-3-yl)urea Prepared according to the procedure of Example 25, replacing 6-ethoxypyridin-3-amine with 6-(2-methoxyethoxy)pyridin-3-amine in Step A. The crude material was purified by silica column chromatography eluting with 2% MeOH/DCM to afford the title compound (50 mg, 63% yield) as a colorless glass. MS (apci) m/z 527.1 (M+H).

Example 28

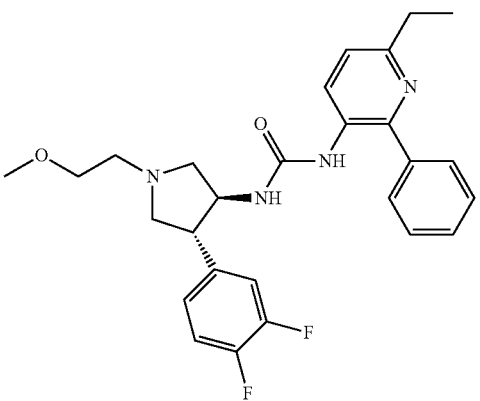 [SMILES: CCc1ccc(NC(=O)N[C@@H]2CN(CCOC)C[C@H]2c2ccc(F)c(F)c2)c(-c2ccccc2)n1]

1-((3S,4R)-4-(3,4-difluorophenyl)-1-(2-methoxyethyl)pyrrolidin-3-yl)-3-(6-ethyl-2-phenylpyridin-3-yl)urea Step A: Preparation of 6-ethyl-2-phenylpyridin-3-amine 6-Bromo-2-phenylpyridin-3-amine [Example 11, Step A] (85 mg, 0.34 mmol), Pd(PPh$_3$)$_4$ (39 mg, 0.034 mmol) and ethyl boronic acid (252 mg, 3.41 mmol) were combined in dioxane (3 mL) in a sealed vessel then treated with K$_2$CO$_3$ (0.68 mL, 2M, 1.36 mmol). The mixture was stirred at 110° C. for 16 hours then cooled and partitioned between water (20 mL) and EtOAc (20 mL). The aqueous layer was extracted with EtOAc (2×10 mL) and the combined organic phases were washed with brine (10 mL), dried over $Na_2SO_4$, filtered and concentrated under vacuum. The residue was purified by silica column chromatography eluting with 4:1 hexanes/EtOAc to afford 6-ethyl-2-phenylpyridin-3-amine (18 mg, 27% yield) as a colorless gum. MS (apci) m/z 199.1 (M+H).

Step B: Preparation of 1-((3S,4R)-4-(3,4-difluorophenyl)-1-(2-methoxyethyl)pyrrolidin-3-yl)-3-(6-ethyl-2-phenylpyridin-3-yl)urea Prepared according to the procedure of Example 1, replacing 2-bromopyridin-3-amine with 6-ethyl-2-phenylpyridin-3-amine in Step A and trans-1-(2-methoxyethyl)-4-phenylpyrrolidin-3-amine dihydrochloride [Preparation B] with (3S,4R)-4-(3,4-difluorophenyl)-1-(2-methoxyethyl)pyrrolidin-3-amine dihydrochloride [Preparation C3] in Step C. The crude material was purified by silica column chromatography eluting with 2% MeOH/DCM to afford the title compound (21 mg, 53% yield) as a white solid. MS (apci) m/z=481.1 (M+H).

Example 29

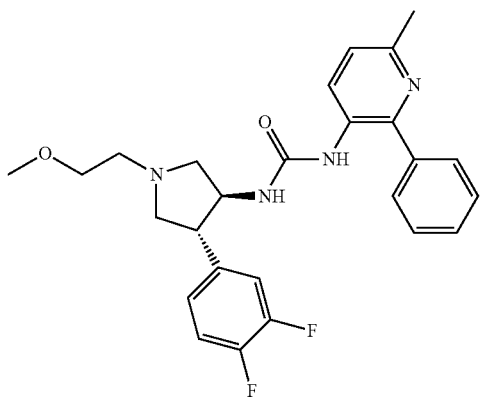 [SMILES: COCCN1C[C@@H](NC(=O)Nc2ccc(C)nc2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(6-methyl-2-phenylpyridin-3-yl)urea Prepared according to the procedure of Example 28, replacing ethyl boronic acid with methyl boronic acid in Step A. The crude material was purified by silica column chromatography eluting with 2% MeOH/DCM to afford the title compound (21 mg, 76% yield) as a white solid. MS (apci) m/z=467.1 (M+H).

Example 30

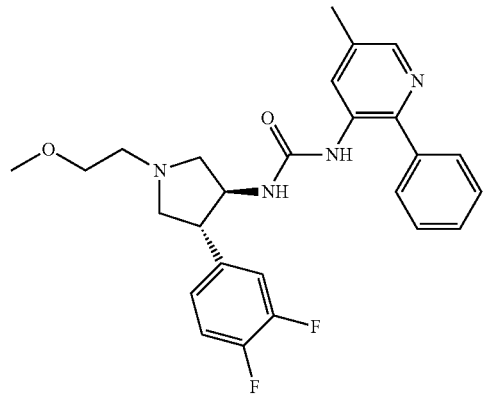 [SMILES: COCCN1C[C@@H](NC(=O)Nc2cc(C)cnc2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(5-methyl-2-phenylpyridin-3-yl)urea Step A: Preparation of 2-bromo-5-methylpyridin-3-amine Acetic acid (5 mL) was added dropwise to iron powder (1.11 g, 19.8 mmol) and the mixture was warmed to 80° C. A solution of 2-bromo-5-methyl-3-nitropyridine (1.0 g, 4.61 mmol) in AcOH (5 mL) was then added dropwise over 20 minutes and the mixture stirred for a further 30 minutes. The mixture was stirred at ambient temperature for 16 hours then diluted with EtOAc (20 mL) and filtered through Celite®. The Celite® pad was washed well with EtOAc and the filtrate concentrated under vacuum. The residue was slowly treated with saturated $NaHCO_3$ solution (50 mL) followed by portions of solid $NaHCO_3$ until all the AcOH was neutralized. The mixture was then extracted with EtOAc (3×30 mL) and the combined organic phases were washed with brine (20 mL), dried over $Na_2SO_4$, filtered and concentrated to afford 2-bromo-5-methylpyridin-3-amine (799 mg, 93% yield) as a bright yellow crystalline solid which darkened to a green color after drying under vacuum. MS (apci) m/z=188.9 (M+H).

Step B: Preparation of 1-((3S,4R)-4-(3,4-difluorophenyl)-1-(2-methoxyethyl)pyrrolidin-3-yl)-3-(5-methyl-2-phenylpyridin-3-yl)urea Prepared according to the procedure of Example 1, replacing 2-bromopyridin-3-amine with 2-bromo-5-methylpyridin-3-amine in Step A and trans-1-(2-methoxyethyl)-4-phenylpyrrolidin-3-amine dihydrochloride [Preparation B] with (3S,4R)-4-(3,4-difluorophenyl)-1-(2-methoxyethyl)pyrrolidin-3-amine dihydrochloride [Preparation C3] in Step C. The crude material was purified by silica column chromatography eluting with 2% MeOH/DCM to afford the title compound (51 mg, 72% yield) as a white foam. MS (apci) m/z=467.1 (M+H).

Example 31

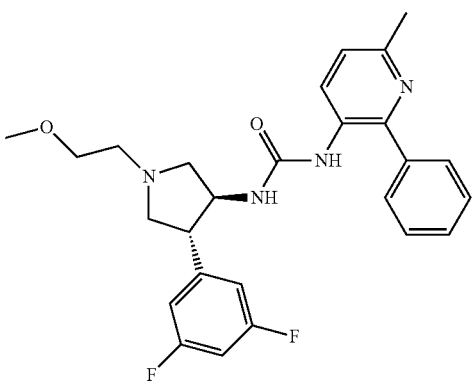 [SMILES: COCCN1C[C@@H](NC(=O)Nc2ccc(C)nc2-c2ccccc2)[C@H](c2cc(F)cc(F)c2)C1]

1-((3S,4R)-4-(3,5-difluorophenyl)-1-(2-methoxy-
ethyl)pyrrolidin-3-yl)-3-(6-methyl-2-phenylpyridin-
3-yl)urea Prepared according to the procedure of Example 29, replacing (3S,4R)-4-(3,4-difluorophenyl)-1-(2-methoxyethyl)pyrrolidin-3-amine dihydrochloride [Preparation C3] with (3S,4R)-4-(3,5-difluorophenyl)-1-(2-methoxyethyl)pyrrolidin-3-amine dihydrochloride [Preparation C2] in Step C. The crude material was purified by silica column chromatography eluting with 2% MeOH/DCM to afford the title compound (37 mg, 52% yield) as a white foam. MS (apci) m/z=467.2 (M+H).

Example 32

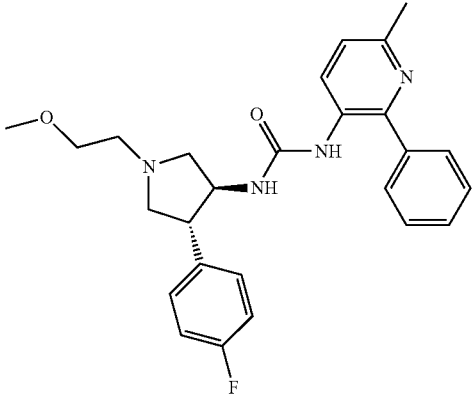 [SMILES: COCCN1C[C@@H](NC(=O)Nc2ccc(C)nc2-c2ccccc2)[C@H](c2ccc(F)cc2)C1]

1-((3S,4R)-4-(4-fluorophenyl)-1-(2-methoxyethyl)
pyrrolidin-3-yl)-3-(6-methyl-2-phenylpyridin-3-yl)
urea Prepared according to the procedure of Example 29, replacing (3S,4R)-4-(3,4-difluorophenyl)-1-(2-methoxyethyl)pyrrolidin-3-amine dihydrochloride [Preparation C3] with (3S,4R)-4-(4-fluorophenyl)-1-(2-methoxyethyl)pyrrolidin-3-amine dihydrochloride [Preparation C4] in Step C. The crude material was purified by silica column chromatography eluting with 2% MeOH/DCM to afford the title compound (40 mg, 55% yield) as a cream solid. MS (apci) m/z=449.2 (M+H).

Example 33

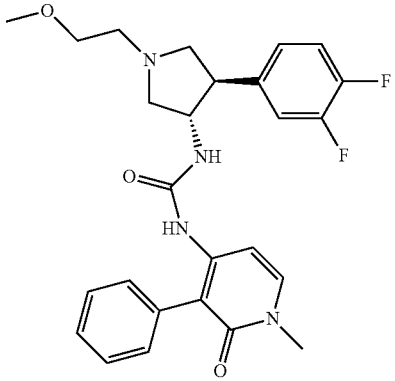 [SMILES: COCCN1C[C@@H](NC(=O)Nc2ccn(C)c(=O)c2-c2ccccc2)[C@H](c2ccc(F)c(F)c2)C1]

1-((3S,4R)-4-(3,4-difluorophenyl)-1-(2-methoxy-
ethyl)pyrrolidin-3-yl)-3-(1-methyl-2-oxo-3-phenyl-
1,2-dihydropyridin-4-yl)urea

Step A: Preparation of 4-amino-1-methylpyridin-2(1H)-one

4-Amino-1-methylpyridin-2(1H)-one hydrochloride (500 mg, 3.11 mmol) was suspended in DCM (30 mL) and methanol (1 mL) added. The resulting solution was treated with MP-carbonate (3.23 g, 2.89 mmol/g, 9.34 mmol) and gently stirred for 4 hours. The mixture was filtered, resin washed well with DCM and the filtrate carefully concentrated (no heat) to afford 4-amino-1-methylpyridin-2(1H)-one (317 mg, 82% yield) as a fluffy white solid. $^1$H NMR (CDCl$_3$) δ 7.07 (d, J=7.3 Hz, 1H), 5.74 (dd, J=7.3, 2.5 Hz, 1H), 5.64 (d, J=2.5 Hz, 1H), 3.43 (s, 3H), 2.82 (s, 2H) ppm.

Step B: Preparation of 4-amino-3-bromo-1-methylpyridin-2(1H)-one

To a solution of 4-amino-1-methylpyridin-2(1H)-one (50 mg, 0.40 mmol) in ACN (2 mL) was added N-bromosuccinimide (72 mg, 0.40 mmol). The mixture was stirred at ambient temperature for 3 hours then concentrated under vacuum. The residue was purified by silica column chromatography eluting with 2% MeOH/DCM to afford 4-amino-3-bromo-1-methylpyridin-2(1H)-one (56 mg, 68% yield) as a white solid. MS (apci) m/z=202.9 (M+).

Step C: Preparation of 4-amino-1-methyl-3-phenylpyridin-2(1H)-one 4-amino-3-bromo-1-methylpyridin-2(1H)-one (56 mg, 0.28 mmol), phenyl boronic acid (44 mg, 0.36 mmol), K$_2$CO$_3$ (152 mg, 1.1 mmol) and Pd(PPh$_3$)$_4$ (32 mg, 0.03 mmol) were combined in toluene (1 mL), water (0.5 mL) and EtOH (0.25 mL) The mixture was warmed to 95° C. in a sealed tube for 16 hours then cooled and partitioned between EtOAc (10 mL) and saturated NH$_4$Cl (10 mL). The aqueous layer was extracted with EtOAc (2×10 mL) and the combined organic phases were washed with brine (10 mL), dried over Na₂SO₄, filtered and concentrated under vacuum. The residue was purified by silica column chromatography eluting with 2% MeOH/DCM to afford 4-amino-1-methyl-3-phenylpyridin-2(1H)-one (24 mg, 43% yield) as a white solid. MS (apci) m/z=201.1 (M+H).

Step D: Preparation of 1-((3S,4R)-4-(3,4-difluorophenyl)-1-(2-methoxyethyl)pyrrolidin-3-yl)-3-(1-methyl-2-oxo-3-phenyl-1,2-dihydropyridin-4-yl)urea To a solution of 4-amino-1-methyl-3-phenylpyridin-2(1H)-one (24 mg, 0.12 mmol) in DCM (1 mL) was added triphosgene (18 mg, 0.06 mmol) followed by DIEA (62 μL, 0.36 mmol). The mixture was stirred at ambient temperature for 30 minutes then treated with (3S,4R)-4-(3,4-difluorophenyl)-1-(2-methoxyethyl)pyrrolidin-3-amine dihydrochloride [Preparation C3] (39 mg, 0.12 mmol) and DIEA (62 μL, 0.36 mmol). After stirring for a further 16 hours the mixture was partitioned between saturated NH₄Cl (10 mL) and DCM (10 mL) and the aqueous layer extracted with DCM (2×10 mL). The combined organic phases were washed with brine (10 mL), dried over Na₂SO₄ and concentrated under vacuum. The residue was purified by silica column chromatography eluting with 2.5-5% MeOH/DCM to 5% to afford the title compound (22 mg, 38% yield) as a white solid. MS (apci) m/z=483.2 (M+H).

Example 34

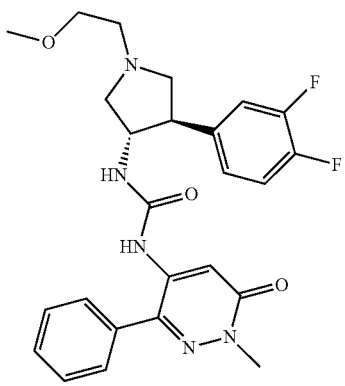 [SMILES: COCCN1C[C@@H](NC(=O)Nc2cc(=O)n(C)nc2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(1-methyl-6-oxo-3-phenyl-1,6-dihydropyridazin-4-yl)urea Step A: Preparation of 3,4-dichloro-5-phenylfuran-2(5H)-one To a suspension of AlCl₃ (10.0 g, 75.0 mmol) in dry benzene (50 mL) was added 3,4-dichloro-5-hydroxyfuran-2(5H)-one (8.45 g, 50.0 mmol) in portions over 5 minutes (immediate deep orange color). The mixture was stirred at ambient temperature for 2.5 hours and was poured into an ice-water slurry (300 mL). The mixture was stirred until ambient temperature was reached and extracted with Et₂O (3×). The combined extracts were washed with H₂O and saturated NaHCO₃ (3×). The Et₂O solution was dried over MgSO₄ and filtered through a SiO₂ plug eluting with Et₂O. The filtrate was concentrated to provide the title compound a colorless syrup that solidified upon drying to a white solid (8.72 g, 76% yield). ¹H NMR (CDCl₃) δ 7.47-7.42 (m, 3H), 7.31-7.28 (m, 2H), 5.85 (s, 1H) ppm.

Step B: Preparation of 5-chloro-2-methyl-6-phenylpyridazin-3(2H)-one

A solution of 3,4-dichloro-5-phenylfuran-2(5H)-one (1.00 g, 4.37 mmol) in absolute EtOH (15 mL) was cooled to 0° C. and methylhydrazine (0.511 mL, 9.60 mmol) was added. The mixture was stirred for 3 hours during which time the temperature gradually became ambient. The mixture was heated at reflux for 16 hours, cooled to ambient temperature and diluted with ice-water (50 mL). The resulting suspension was stirred for 30 minutes and the suspension collected by vacuum filtration. The solid was washed with H₂O then Et₂O and dried in vacuum to afford the title compound a light tan powder (378 mg, 39%). ¹H NMR (DMSOd₆) δ 7.57-7.54 (m, 2H), 7.51-7.48 (m, 3H), 7.40 (s, 1H), 3.70 (s, 3H) ppm.

Step C: Preparation of 5-azido-2-methyl-6-phenylpyridazin-3(2H)-one

To a solution of 5-chloro-2-methyl-6-phenylpyridazin-3(2H)-one (360 mg, 1.63 mmol) in dry DMF (2 mL) was added NaN₃ (318 mg, 4.89 mmol) in one portion. The mixture was heated at 60° C. for 1.5 hours then at 80° C. for 1 hour. The mixture was cooled to ambient temperature and treated with ice-water (15 mL) The resulting suspension was stirred for 5 minutes, the solid collected by vacuum filtration, washed with H₂O and dried in vacuum to provide the title compound as a tan powder (262 mg, 71%). ¹H NMR (DMSOd₆) δ 7.62-7.58 (m, 2H), 7.48-7.44 (m, 3H), 6.91 (s, 1H), 3.69 (s, 3H) ppm.

Step D: Preparation of 5-amino-2-methyl-6-phenylpyridazin-3(2H)-one

To a solution of 5-azido-2-methyl-6-phenylpyridazin-3(2H)-one (250 mg, 1.10 mmol) in dry MeOH (5 mL) was added 10 wt. % Pd on carbon (234 mg, 0.110 mmol, 50 wt. % H₂O). The reaction flask was purged with H₂ gas for 2 minutes and the mixture was stirred under a balloon of H₂ at ambient temperature for 4 hours. The mixture was purged with N₂ gas, diluted with Et₂O (5 mL) and filtered through packed Celite® layer eluting and rinsing with EtOAc. The filtrate was concentrated to a white foam that was washed with dry Et₂O. The resulting granular white solid was dried in vacuum to furnish the title compound (188 mg, 85% yield). ¹H NMR (DMSOd₆) δ 7.48 (br s, 5H), 5.94 (br s, 2H), 5.80 (s, 1H), 3.54 (s, 3H) ppm.

Step E: Preparation of phenyl 1-methyl-6-oxo-3-phenyl-1,6-dihydropyridazin-4-ylcarbamate A fine suspension of 5-amino-2-methyl-6-phenylpyridazin-3(2H)-one (175 mg, 0.870 mmol) in EtOAc (3 mL) was cooled to 0° C. and 2M NaOH (1.30 mL, 2.61 mmol) was added. The mixture was stirred for 5 minutes (solid dissolved) and phenylchloroformate (163 μL, 1.30 mmol) was added. The mixture was allowed to reach ambient temperature and was stirred for 16 hours. The mixture was diluted with EtOAc (2 mL), washed with H₂O (2×) and saturated NaCl and dried over MgSO₄/activated charcoal. The dried solution was filtered through packed Celite® (EtOAc elution), concentrated and the residue purified by silica column chromatography (50% EtOAc-hexanes) to provide the title compound as a white solid (26 mg, 9.3%). $^1$H NMR (CDCl$_3$) δ 7.72 (s, 1H), 7.64-7.48 (m, 5H), 7.38 (t, J=7.7 Hz, 2H), 7.30-7.22 (m, 2H), 7.12 (d, J=7.8 Hz, 2H), 6.93 (s, 1H), 3.81 (s, 3H) ppm.

Step F: 1-((3S,4R)-4-(3,4-difluorophenyl)-1-(2-methoxyethyl)pyrrolidin-3-yl)-3-(1-methyl-6-oxo-3-phenyl-1,6-dihydropyridazin-4-yl)urea A mixture of phenyl 1-methyl-6-oxo-3-phenyl-1,6-dihydropyridazin-4-ylcarbamate (25.0 mg, 0.078 mmol) and (3S,4R)-4-(3,4-difluorophenyl)-1-(2-methoxyethyl)pyrrolidin-3-amine dihydrochloride (Preparation C3, 38.4 mg, 0.117 mmol) in dry DCM (1.0 mL) was treated with DIEA (54.4 µL, 0.311 mmol) and the resulting homogeneous solution was stirred at ambient temperature for 17 hours. The mixture was diluted with DCM (3 mL) and was washed with H$_2$O (2×), 1M NaOH (3×) and H$_2$O. The DCM solution was dried over Na$_2$SO$_4$ and was eluted through a short SiO$_2$ column eluting with 50% EtOAc-hexanes, EtOAc then 10% MeOH-EtOAc. The 10% MeOH-EtOAc product pool was concentrated to a cloudy film. The film was treated with 1:1 Et$_2$O-DCM and concentrated. The residual solid was dried in vacuum to provide the title compound (29 mg, 77% yield) as a white solid. MS (apci) m/z=484.2 (M+H).

Example 35

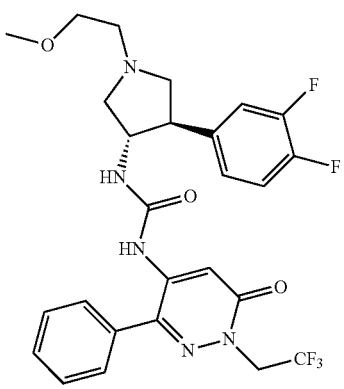 [SMILES: COCCN1C[C@@H](NC(=O)Nc2cc(=O)n(CC(F)(F)F)nc2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(6-oxo-3-phenyl-1-(2,2,2-trifluoroethyl)-1,6-dihydropyridazin-4-yl)urea Step A: Preparation of 5-chloro-6-phenylpyridazin-3(2H)-one To a solution of 3,4-dichloro-5-phenylfuran-2(5H)-one (Example 34 Step A, 4.00 g, 17.5 mmol) in absolute EtOH (35 mL) was added hydrazine (1.65 mL, 52.4 mmol) by syringe over 1-2 minutes. The mixture was stirred at ambient temperature for 15 minutes then heated at reflux for 3 hours. The mixture was cooled to ambient temperature, treated with ice-water (50 mL) and mixed for 5 minutes. The resulting suspension was collected by vacuum filtration, the solid washed with H$_2$O and Et$_2$O and dried in vacuum to afford the title compound (2.22 g, 61% yield) as a light peach colored powder. $^1$H NMR (DMSOd$_6$) δ 13.4 (br s, 1H), 7.56-7.54 (m, 2H), 7.50-7.47 (m, 3H), 7.33 (s, 1H) ppm.

Step B: Preparation of 5-azido-6-phenylpyridazin-3(2H)-one

To a solution of 5-chloro-6-phenylpyridazin-3(2H)-one (2.10 g, 10.2 mmol) in dry DMF (9 mL) was added NaN$_3$ (1.98 g, 30.5 mmol) and the mixture was heated at 60° C. for 3 hours. The mixture was cooled to ambient temperature and treated with ice-water (50 mL). The resulting suspension was stirred for 10 minutes, the solid collected, washed with H$_2$O and dried in vacuum to afford the title compound as light peach colored powder (2.10 g, 97%). $^1$H NMR (DMSOd$_6$) δ 13.2 (br s, 1H), 7.61-7.55 (m, 2H), 7.48-7.43 (m, 3H), 6.82 (s, 1H) ppm.

Step C: Preparation of 5-azido-6-phenyl-2-(2,2,2-trifluoroethyl)pyridazin-3(2H)-one A suspension of 5-azido-6-phenylpyridazin-3(2H)-one (300 mg, 1.41 mmol) in dry DMF (4 mL) was cooled to 0° C. and NaH (53.3 mg, 2.11 mmol) was added in one portion. The ice bath was removed and the mixture was stirred at ambient temperature for 15 minutes. The resulting thick, pink slurry was treated with 2,2,2-trifluoroethyl trifluoromethanesulfonate (505 mg, 2.11 mmol) and the mixture was stirred for 3 hours. The deep orange reaction mixture was diluted with ice-water (25 mL) and the resulting orange suspension was stirred for 10 minutes at ambient temperature. The solid was collected by filtration, the cake washed with H$_2$O and 1:1 Et$_2$O-hexanes. The solid was recrystalized from MTBE to give the title compound as a light peach-colored solid (125 mg, 30%). $^1$H NMR (DMSOd$_6$) δ 7.65-7.58 (m, 2H), 7.53-7.44 (m, 3H), 7.03 (s, 1H); 5.00 (q, J=9.1 Hz, 2H) ppm.

Step D: Preparation of 5-amino-6-phenyl-2-(2,2,2-trifluoroethyl)pyridazin-3(2H)-one To a fine suspension of 5-azido-6-phenyl-2-(2,2,2-trifluoroethyl)pyridazin-3(2H)-one (110 mg, 0.373 mmol) in dry MeOH (3 mL) was added 10 wt. % Pd on carbon (79.3 mg, 0.0373 mmol, 50 wt. % H$_2$O). The reaction flask was purged with H$_2$ gas for 2 minutes and the mixture was stirred under a balloon of H$_2$ at ambient temperature for 20 hours. The reaction mixture was purged with N$_2$ gas, diluted with Et$_2$O (3 mL) and filtered through packed Celite® eluting and rinsing with EtOAc. The filtrate was concentrated and the residual solid was dried in vacuum to provide the title compound (89 mg, 89%) as white solid. $^1$H NMR (DMSOd$_6$) δ 7.51 (br s, 5H), 6.29 (br s, 2H), 5.82 (s, 1H), 4.82 (q, J=9.0 Hz, 2H) ppm.

Step E: Preparation of 1-((3S,4R)-4-(3,4-difluorophenyl)-1-(2-methoxyethyl)pyrrolidin-3-yl)-3-(6-oxo-3-phenyl-1-(2,2,2-trifluoroethyl)-1,6-dihydropyridazin-4-yl)urea To solution of triphosgene (35.4 mg, 0.117 mmol) in dry DCM (1.0 mL) was added a solution of 5-amino-6-phenyl-2-(2,2,2-trifluoroethyl)pyridazin-3(2H)-one (85 mg, 0.316 mmol) and DIEA (165 µL, 0.947 mmol) in dry DCM (2.0 mL) dropwise over 30 minutes. The mixture was stirred for 30 minutes and (3S,4R)-4-(3,4-difluorophenyl)-1-(2-methoxyethyl)pyrrolidin-3-amine dihydrochloride (Preparation C3, 156 mg, 0.474 mmol) and DIEA (110 µL, 0.631 mmol) were sequentially added. The reaction mixture was stirred at ambient temperature for 18 hours. Additional (3S,4R)-4-(3,4-difluorophenyl)-1-(2-methoxyethyl)pyrrolidin-3-amine dihydrochloride (Preparation C3, 60 mg) and DIEA (100 μL) were added and the mixture heated at reflux for 4 hours. The mixture was cooled to ambient temperature, washed with H₂O (3×) and dried over Na₂SO₄. The dried solution was filtered through packed Celite®, concentrated and the crude residue was purified by silica column chromatography (50% EtOAc-hexanes, EtOAc, 5% MeOH-EtOAc step gradient elution) to provide the title compound as a white solid (18 mg, 10% yield). MS (apci) m/z=552.2 (M+H).

Example 36

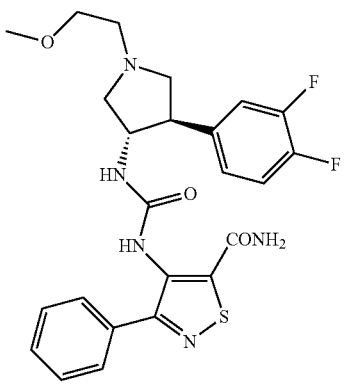 [SMILES: COCCN1C[C@@H](NC(=O)Nc2c(-c3ccccc3)nsc2C(N)=O)[C@H](c2ccc(F)c(F)c2)C1]

4-(3-((3S,4R)-4-(3,4-difluorophenyl)-1-(2-methoxyethyl)pyrrolidin-3-yl)ureido)-3-phenylisothiazole-5-carboxamide Step A: Preparation of (Z)—N-(tosyloxy)benzimidoyl cyanide A solution of (Z)—N-hydroxybenzimidoyl cyanide (3.01 g, 20.0 mmol) and triethylamine (5.58 mL, 40.0 mmol) in dry DCM (40 mL) was cooled to 0° C. and tosyl chloride (4.19 g, 22.0 mmol) was added in one portion. The mixture was stirred for 16 hours during which time the temperature increased to ambient after 2 hours. The mixture was diluted with chilled 1M HCl (80 mL) and stirred for 15 minutes. The organic layer was separated and was washed with H₂O and saturated NaHCO₃. The solution was dried over Na₂SO₄ and eluted through a thin SiO₂ plug capped with a layer of MgSO₄ using DCM for elution. The eluate was concentrated and the residual solid dried in vacuum to furnish the title compound as a white crystalline solid (6.10 g, 102% yield). MS (apci) m/z=299.1 (M−H).

Step B: Preparation of methyl 4-amino-3-phenylisothiazole-5-carboxylate

To a suspension of (Z)—N-(tosyloxy)benzimidoyl cyanide (3.16 g, 10.0 mmol) in dry MeOH (30 mL) was added methyl 2-mercaptoacetate (1.05 mL, 11.0 mmol) followed by triethylamine (3.07 mL, 22.0 mmol). The mixture was stirred at ambient temperature for 3 hours and was added to chilled H₂O (150 mL) with stirring. The resulting suspension was stirred for 15 minutes, the solid collected by vacuum filtration and the cake washed with H₂O and hexanes. The solid was dissolved in DCM and dried over Na₂SO₄/activated charcoal. The dried solution was eluted through a thin SiO₂ plug capped with a layer of MgSO₄ (DCM elution) and concentrated. The residual white solid was dried in vacuum to give the title compound (1.43 g, 61% yield). ¹H NMR (CDCl₃) δ 7.73-7.70 (m, 2H), 7.53-7.44 (m, 3H), 5.40 (br s, 2H), 3.91 (s, 3H) ppm.

Step C: Preparation of 4-amino-3-phenylisothiazole-5-carboxamide

In a glass pressure vessel, methyl 4-amino-3-phenylisothiazole-5-carboxylate (300 mg, 1.28 mmol) was dissolved in 7M NH₃ (11 mL, 76.8 mmol) in MeOH and the solution was purged with NH₃ gas for 5 minutes. The reaction vessel was sealed and the mixture heated at 100° C. for 24 hours. The mixture was cooled to ambient temperature, concentrated and the residual solid was washed thoroughly with Et₂O. The solid was dried in vacuum to give the title compound as a white solid (98 mg, 35% yield). ¹H NMR (DMSOd₆) δ 7.75 (d, J=8.0 Hz, 2H), 7.58 (br s, 2H), 7.57-7.46 (m, 3H), 6.19 (s, 2H) ppm.

Step D: Preparation of 4-(3-((3S,4R)-4-(3,4-difluorophenyl)-1-(2-methoxyethyl)pyrrolidin-3-yl)ureido)-3-phenylisothiazole-5-carboxamide A solution of triphosgene (44.3 mg, 0.142 mmol) in dry DCM (1 mL) was cooled to 0° C. and a solution of (3S,4R)-4-(3,4-difluorophenyl)-1-(2-methoxyethyl)pyrrolidin-3-amine dihydrochloride (Preparation C3, 139 mg, 0.421 mmol) and DIEA (220 μL, 1.26 mmol) in dry DCM (0.5 mL) was added dropwise over 40 minutes. The mixture was stirred for 1 hour during which time temperature increased to ambient. 4-amino-3-phenylisothiazole-5-carboxamide (84.0 mg, 0.383 mmol) was added in one portion and the mixture stirred at ambient temperature for 10 minutes. The DCM was evaporated under a stream of N₂ gas and the residue treated with dry CH₃CN (2 mL). The mixture was heated at 40° C. for 6 hours, cooled to ambient temperature and diluted with chilled H₂O (4 mL). The cold mixture (pH=3) was treated with 2M NaOH to pH=10. The mixture was extracted with EtOAc (3×) and the combined extracts were washed with H₂O and saturated NaCl. The EtOAc solution was dried over MgSO₄ and eluted through a short SiO₂ column eluting with EtOAc then 10% MeOH/EtOAc. The product pool was concentrated to a colorless glass. The glass was treated with Et₂O and agitated until a granular suspension formed. The solvent was decanted and the residual solid was washed with Et₂O (2×) and dried in vacuum to afford the title compound as a white solid (120 mg, 63% yield). MS (apci) m/z=502.1 (M+H).

Example 37

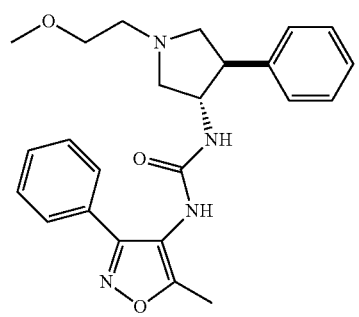

1-((trans)-1-(2-methoxyethyl)-4-phenylpyrrolidin-3-yl)-3-(5-methyl-3-phenylisoxazol-4-yl)urea To a DCM (512 µL) solution of 5-methyl-3-phenylisoxazol-4-amine (18 mg, 0.10 mmol) [purchased from Maybridge TL01028DA, CAS 21169-65-3] was added CDI (17 mg, 0.10 mmol), followed by DIEA (71 µL, 0.41 mmol). After stirring at ambient temperature for 3 days, (trans)-1-(2-methoxyethyl)-4-phenylpyrrolidin-3-amine dihydrochloride [Preparation B] (30 mg, 0.10 mmol) was added to the reaction mixture in one portion and stirred for 16 hours. The reaction mixture was directly purified by reverse-phase chromatography (C18, eluent acetonitrile/water 5 to 54%) to yield the product as white solid (25 mg, 58% yield). MS (apci) m/z=421.0 (M+H).

Example 38

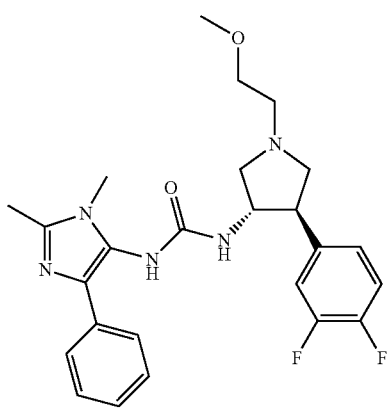 [SMILES: COCCN1C[C@@H](NC(=O)Nc2c(-c3ccccc3)nc(C)n2C)[C@H](c2ccc(F)c(F)c2)C1]

1-((3S,4R)-4-(3,4-difluorophenyl)-1-(2-methoxyethyl)pyrrolidin-3-yl)-3-(1,2-dimethyl-4-phenyl-1H-imidazol-5-yl)urea To a mixture of 1,2-dimethyl-4-phenyl-1H-imidazol-5-amine (25 mg, 0.13 mmol) [purchased from Nanjing Chemlin 1040040-76-3, CAS 1040040-76-3] in DCM (1 mL) at 0° C. was added DIEA (0.047 ml, 0.27 mmol) followed by triphosgene (16 mg, 0.053 mmol) in one portion. The reaction was allowed to warm up to ambient temperature and stirred for 2 hours. It was then added to a mixture of (3S,4R)-4-(3,4-difluorophenyl)-1-(2-methoxyethyl)pyrrolidin-3-amine dihydrochloride (Preparation C3, 30 mg, 0.0911 mmol) and N-ethyl-N-isopropylpropan-2-amine (79.4 µL). After stirring at room temperature for 1 hour, the reaction mixture was directly purified by reverse-phase chromatography (C18, eluent 5 to 52% acetonitrile/water) to yield the product as white solid (15 mg, 32% yield). MS (apci) m/z=470.0 (M+H).

Example 39

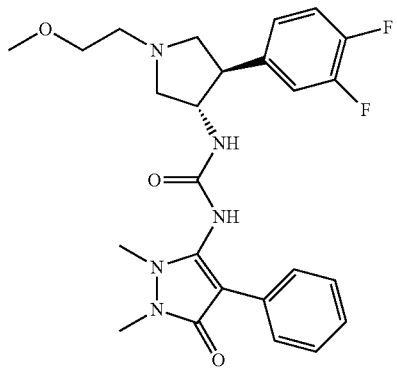 [SMILES: COCCN1C[C@@H](NC(=O)Nc2c(-c3ccccc3)c(=O)n(C)n2C)[C@H](c2ccc(F)c(F)c2)C1]

1-((3S,4R)-4-(3,4-difluorophenyl)-1-(2-methoxyethyl)pyrrolidin-3-yl)-3-(1,2-dimethyl-5-oxo-4-phenyl-2,5-dihydro-1H-pyrazol-3-yl)urea Step A: Preparation of 5-amino-1-methyl-4-phenyl-1H-pyrazol-3(2H)-one To a suspension of ethyl 2-cyano-2-phenylacetate (2.56 g, 13.3 mmol) in EtOH (10 mL) was added dropwise methylhydrazine (1.09 mL, 19.9 mmol). The reaction was heated at 85° C. for 16 hours. The reaction mixture was cooled to 0° C. and filtered. The solid was washed with cold EtOH (20 mL) and Et$_2$O (20 mL) to give final product (2.1 g, 84%). $^1$H NMR (d$_6$-DMSO) δ 9.46 (br s, 1H), 7.48-7.52 (m, 2H), 7.24-7.30 (m, 2H), 7.01-7.06 (m, 1H), 5.72 (br s, 2H), 3.23 (s, 3H).

Step B: Preparation of 5-amino-1,2-dimethyl-4-phenyl-1H-pyrazol-3(2H)-one

To a suspension of 5-amino-1-methyl-4-phenyl-1H-pyrazol-3(2H)-one (208 mg, 1.10 mmol) and K$_2$CO$_3$ (456 mg, 3.30 mmol) in DMF (5 mL) was added dropwise iodomethane (172 mg, 1.21 mmol). The reaction was stirred at ambient temperature for 16 hours. The solvent was removed under reduced pressure and the residue was purified by silica column chromatography eluting with 1:2 EtOAc/hexanes to yield the desired product (lower Rf, 136 mg, 61%) and a side-product 3-methoxy-1-methyl-4-phenyl-1H-pyrazol-5-amine (higher Rf, 68 mg, 30%). MS (apci) m/z=204.1 (M+H).

Step C: Preparation of 1-((3S,4R)-4-(3,4-difluorophenyl)-1-(2-methoxyethyl)pyrrolidin-3-yl)-3-(1,2-dimethyl-5-oxo-4-phenyl-2,5-dihydro-1H-pyrazol-3-yl)urea To a suspension of 5-amino-1,2-dimethyl-4-phenyl-1H-pyrazol-3(2H)-one (85 mg, 0.418 mmol) in dichloroethane (5 mL) at 0° C. was added portionwise bis(trichloromethyl) carbonate (62.1 mg, 0.209 mmol), followed by dropwise addition of triethylamine (87.4 µL, 0.627 mmol). Cold bath was then removed and the reaction was stirred at ambient temperature for two hours. The solvent was then removed under reduced pressure, and to the residue was added DMF (5 mL), triethylamine (87.4 µL, 0.627 mmol) and (3S,4R)-4-(3,4-difluorophenyl)-1-(2-methoxyethyl)pyrrolidin-3- amine dihydrochloride (Preparation C3, 138 mg, 0.418 mmol). The reaction mixture was stirred at ambient temperature for two hours then concentrated under vacuum. The residue was purified by silica column chromatography eluting with 10% MeOH/DCM to yield the title product. MS (apci) m/z=486.0 (M+H).

Example 40

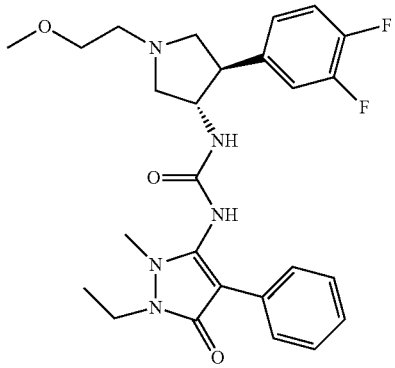 [SMILES: CCn1c(=O)c(-c2ccccc2)c(NC(=O)N[C@@H]2CN(CCOC)C[C@H]2c2ccc(F)c(F)c2)n1C]

1-((3S,4R)-4-(3,4-difluorophenyl)-1-(2-methoxyethyl)pyrrolidin-3-yl)-3-(1-ethyl-2-methyl-5-oxo-4-phenyl-2,5-dihydro-1H-pyrazol-3-yl)urea Step A: Preparation of 5-amino-2-ethyl-1-methyl-4-phenyl-1H-pyrazol-3(2H)-one To a suspension of 5-amino-1-methyl-4-phenyl-1H-pyrazol-3(2H)-one (465 mg, 2.46 mmol) and K$_2$CO$_3$ (1.02 g, 7.37 mmol) in DMF (10 mL) was added dropwise iodoethane (218 μL, 2.70 mmol). The reaction was stirred for 16 hours then concentrated under vacuum. The residue was purified by silica column chromatography eluting with 1:2 EtOAc/hexanes to yield the desired product (lower Rf, 220 mg, 41%) and a side-product 3-ethoxy-1-methyl-4-phenyl-1H-pyrazol-5-amine (higher Rf, 230 mg, 43%). MS (apci) m/z=218.1 (M+H).

Step B: Preparation of 1-((3S,4R)-4-(3,4-difluorophenyl)-1-(2-methoxyethyl)pyrrolidin-3-yl)-3-(1-ethyl-2-methyl-5-oxo-4-phenyl-2,5-dihydro-1H-pyrazol-3-yl)urea To a suspension of 5-amino-2-ethyl-1-methyl-4-phenyl-1H-pyrazol-3(2H)-one (75 mg, 0.345 mmol) in dichloroethane (5 mL) at 0° C. was added portionwise bis(trichloromethyl) carbonate (51.2 mg, 0.173 mmol), followed by dropwise addition of triethylamine (72.2 μL, 0.518 mmol). Cold bath was then removed and the reaction was stirred at ambient temperature for two hours. The solvent was then removed under reduced pressure, and to the residue was added DMF (5 mL), triethylamine (72.2 μL, 0.518 mmol) and (3S,4R)-4-(3,4-difluorophenyl)-1-(2-methoxyethyl)pyrrolidin-3-amine dihydrochloride (Preparation C3, 114 mg, 0.345 mmol). The reaction mixture was stirred at ambient temperature for two hours then concentrated under vacuum. The residue was purified by silica column chromatography eluting with 10% MeOH/DCM to yield the title product. MS (apci) m/z=500.0 (M+H).

Example 41

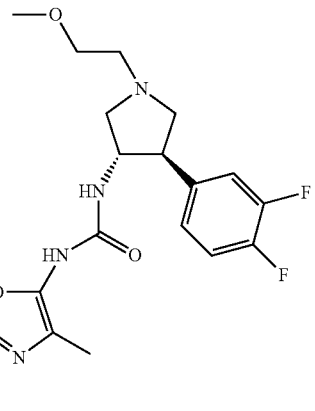

1-((3S,4R)-4-(3,4-difluorophenyl)-1-(2-methoxyethyl)pyrrolidin-3-yl)-3-(2-methyl-4-phenyloxazol-5-yl)urea Step A: Preparation of 2-aminopropanenitrile Acetaldehyde (15.9 mL, 316 mmol) was added slowly to a slurry of NH$_4$Cl (16.9 g, 316 mmol) and KCN (19.5 g, 300 mmol) in 150 mL of concentrated ammonium hydroxide. The reaction was stirred for 30 minutes and transferred to a liquid-liquid extraction apparatus containing DCM (1 L). TsOH (54.3 g, 316 mmol) was added to the collection flask and liquid-liquid extraction was performed for 34 hours. The collected suspension was extracted with 1N NaOH (500 mL) and brine, dried over MgSO$_4$, filtered and concentrated to provide the title compound (15.9 g, 71.9% yield) as yellowish oil. $^1$H NMR (D4-MeOH) 3.80-3.86 (m, 1H), 1.43 (d, J=7.1 Hz, 3H).

Step B: Preparation of N-(1-cyanoethyl)benzamide

2-Aminopropanenitrile (1.65 g, 23.5 mmol), 4-methylbenzenesulfonic acid (3.68 g, 21.3 mmol) and benzoyl chloride (3.00 g, 21.3 mmol) were combined in NMP (20 mL) and stirred at ambient temperature for 4 days. The reaction was poured into a mixture of 1N NaOH (50 mL) and ice (50 g), extracted with EtOAc (2×100 mL), dried over MgSO$_4$, filtered and concentrated to afford the title compound (3.33 g, 89.6% yield) as a brownish oil. MS (apci) m/z=175.1 (M+H).

Step C: Preparation of 4-methyl-2-phenyloxazol-5-amine

N-(1-cyanoethyl)benzamide (1.8 g, 10.3 mmol) was dissolved in 20 mL of dioxane and hydrogen chloride (20.7 mL, 82.7 mmol) in dioxane added. The reaction was stirred at ambient temperature overnight, concentrated, taken up in DCM (20 mL) and sonicated. The obtained brown solid was collected and partitioned between EtOAc (50 mL) and 1N NaOH (30 mL). The EtOAc layer was washed with brine, dried over MgSO$_4$, filtered and concentrated to provide a mixture of the title compound with 4-methyl-2-phenyloxazol-5(4H)-imine (1.20 g, 66.7% yield) as a brown solid. MS (apci) m/z=349.0 (dimer+H).

Step D: Preparation of phenyl 4-methyl-2-phenyloxazol-5-ylcarbamate

To a suspension of 4-methyl-2-phenyloxazol-5-amine hydrochloride (300 mg, 1.42 mmol) in EtOAc (5 mL) was added NaOH (2848 µL, 2.85 mmol) followed by phenyl carbonochloridate (177 µL, 1.42 mmol). The reaction was stirred for 5 hours, adding additional phenyl carbonochloridate (177 µL, 1.42 mmol) after 2 hours. The reaction was treated with EtOAc (50 mL), washed with water (10 mL) and brine (10 mL), dried over MgSO$_4$, filtered and concentrated under vacuum. The residue was purified by silica column chromatography eluting with 25% EtOAc-hexanes to provide the title compound (255 mg, 60.8% yield) as a white solid. MS (apci) m/z=295.0 (M+H).

Step E: Preparation of 1-((3S,4R)-4-(3,4-difluorophenyl)-1-(2-methoxyethyl)pyrrolidin-3-yl)-3-(4-methyl-2-phenyloxazol-5-yl)urea Phenyl 4-methyl-2-phenyloxazol-5-ylcarbamate (6.1 mg, 0.021 mmol), (3S,4R)-4-(3,4-difluorophenyl)-1-(2-methoxyethyl)pyrrolidin-3-amine bis(2,2,2-trifluoroacetate) (10 mg, 0.021 mmol) and DIEA (18 µL, 0.10 mmol) were combined in 0.2 mL of DMF and stirred at ambient temperature for 1 hour. The mixture was loaded onto a samplet and purified by reverse-phase column chromatography, eluting with 0-55% acetonitrile/water, to afford the title compound (5.9 mg, 62% yield). MS (apci) m/z=457.0 (M+H).

Example 42

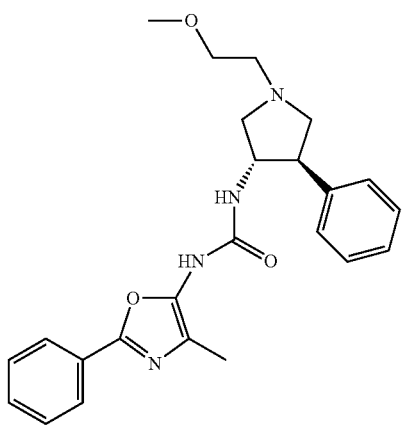 [SMILES: COCCN1C[C@@H](NC(=O)Nc2oc(-c3ccccc3)nc2C)[C@H](c2ccccc2)C1]

1-((3S,4R)-1-(2-methoxyethyl)-4-phenylpyrrolidin-3-yl)-3-(4-methyl-2-phenyloxazol-5-yl)urea Prepared according to the procedure of Example 41, Step E using (3S,4R)-1-(2-methoxyethyl)-4-phenylpyrrolidin-3-amine bis(2,2,2-trifluoroacetate) instead of (3S,4R)-4-(3,4-difluorophenyl)-1-(2-methoxyethyl)pyrrolidin-3-amine bis(2,2,2-trifluoroacetate). The material was purified by reverse-phase column chromatography using 0-60% acetonitrile/H$_2$O as the eluent to provide the title compound (4.1 mg, 47% yield). MS (apci) m/z=421.1 (M+H).

Example 43

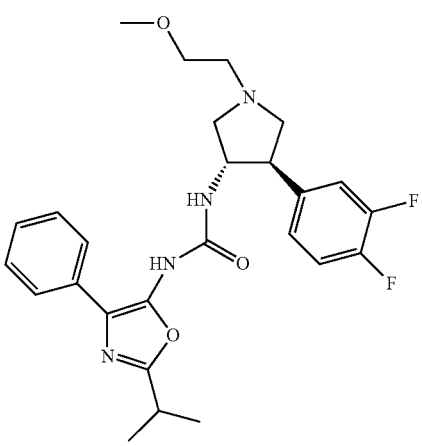 [SMILES: COCCN1C[C@@H](NC(=O)Nc2oc(C(C)C)nc2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(2-isopropyl-4-phenyloxazol-5-yl)urea

Step A: Preparation of N-(cyano(phenyl)methyl)isobutyramide 2-amino-2-phenylacetonitrile hydrochloride (2.00 g, 11.9 mmol), DIEA (5.16 mL, 29.7 mmol) and isobutyryl chloride (1.20 g, 11.3 mmol) were combined in DCM (40 mL) and stirred at ambient temperature for 16 hours. Brine (25 mL) was added and the reaction was extracted with DCM (2×50 mL). The combined organic extracts were dried over MgSO$_4$, filtered and concentrated to afford the title compound (2.1 g, 96.3% yield). MS (apci) m/z=405.1 (dimer+H).

Step B: Preparation of 1-((3S,4R)-4-(3,4-difluorophenyl)-1-(2-methoxyethyl)pyrrolidin-3-yl)-3-(2-isopropyl-4-phenyloxazol-5-yl)urea Prepared from N-(cyano(phenyl)methyl)isobutyramide using the procedures described in Example 41, Steps C-E. The final product was purified by reverse-phase column chromatography, eluting with 0-60% acetonitrile/water, to afford the title compound (5.2 mg, 25% yield for 3 steps). MS (apci) m/z=485.1 (M+H).

Example 44

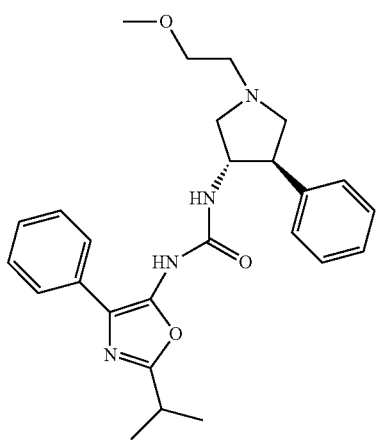 [SMILES: COCCN1C[C@@H](NC(=O)Nc2oc(C(C)C)nc2-c2ccccc2)[C@H](c2ccccc2)C1]

11-(2-isopropyl-4-phenyloxazol-5-yl)-3-((3S,4R)-1-(2-methoxyethyl)-4-phenylpyrrolidin-3-yl)urea Prepared according to the procedure of Example 43, using (3S,4R)-1-(2-methoxyethyl)-4-phenylpyrrolidin-3-amine bis(2,2,2-trifluoroacetate) instead of (3S,4R)-4-(3,4-difluorophenyl)-1-(2-methoxyethyl)pyrrolidin-3-amine bis(2,2,2-trifluoroacetate). The material was purified by reverse-phase column chromatography using 0-60% acetonitrile/H₂O as the eluent to provide the title compound (4.7 mg, 55% yield). MS (apci) m/z=449.1 (M+H).

Example 45

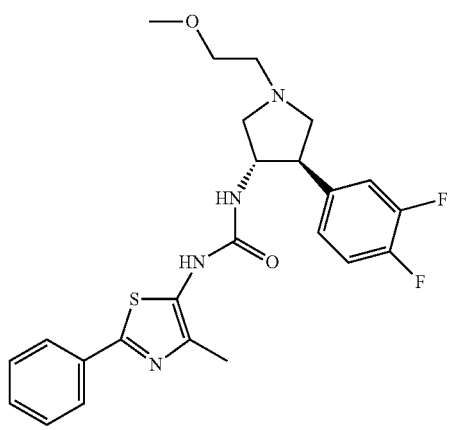 [SMILES: COCCN1C[C@@H](NC(=O)Nc2sc(-c3ccccc3)nc2C)[C@H](c2ccc(F)c(F)c2)C1]

11-((3S,4R)-4-(3,4-difluorophenyl)-1-(2-methoxyethyl)pyrrolidin-3-yl)-3-(4-methyl-2-phenylthiazol-5-yl)urea

Step A: Preparation of 4-methyl-2-phenylthiazol-5-amine

N-(1-cyanoethyl)benzamide (500 mg, 2.87 mmol, prepared as described in Example 41, Step B) and Lawesson's Reagent (1277 mg, 3.16 mmol) were combined in 2 mL of toluene in a sealed vessel and heated at 100° C. for 2 days. The reaction was cooled, concentrated and purified by silica column chromatography eluting with 10-25% EtOAc-hexanes to provide the title compound (148 mg, 27.1% yield). MS (apci) m/z=191.0 (M+H).

Step B: Preparation of 11-((3S,4R)-4-(3,4-difluorophenyl)-1-(2-methoxyethyl)pyrrolidin-3-yl)-3-(4-methyl-2-phenylthiazol-5-yl)urea Prepared from 4-methyl-2-phenylthiazol-5-amine using the procedures described in Example 41, Steps D-E. The final product was purified by reverse-phase column chromatography, eluting with 0-60% acetonitrile/water, to afford the title compound (6.2 mg, 52% yield for 2 steps). MS (apci) m/z=473.0 (M+H).

Example 46

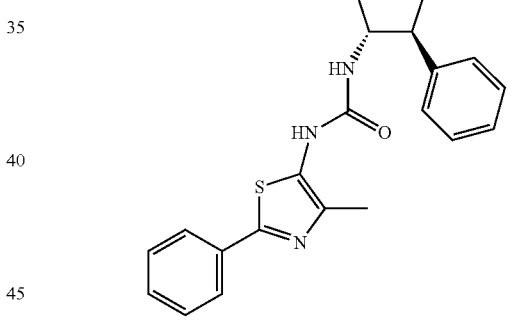

1-((3S,4R)-1-(2-methoxyethyl)-4-phenylpyrrolidin-3-yl)-3-(4-methyl-2-phenylthiazol-5-yl)urea Prepared according to the procedure of Example 45, step B using (3S,4R)-1-(2-methoxyethyl)-4-phenylpyrrolidin-3-amine bis(2,2,2-trifluoroacetate) instead of (3S,4R)-4-(3,4-difluorophenyl)-1-(2-methoxyethyl)pyrrolidin-3-amine bis(2,2,2-trifluoroacetate). The final product was purified by reverse-phase column chromatography using 0-60% acetonitrile/H₂O as the eluent to provide the title compound (6.3 mg, 73% yield). MS (apci) m/z=437.0 (M+H).

Example 47

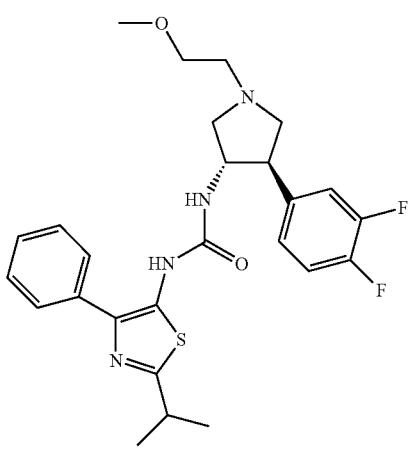 [SMILES: COCCN1C[C@@H](NC(=O)Nc2sc(C(C)C)nc2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(2-isopropyl-4-phenylthiazol-5-yl)urea Prepared from N-(cyano(phenyl)methyl)isobutyramide (prepared as described in Example 43, Step A) using the procedures described in Example 45, Steps A-B. The final product was purified by reverse-phase column chromatography, eluting with 0-70% acetonitrile/water, to afford the title compound (4.5 mg, 19% yield for 3 steps). MS (apci) m/z=501.0 (M+H).

Example 48

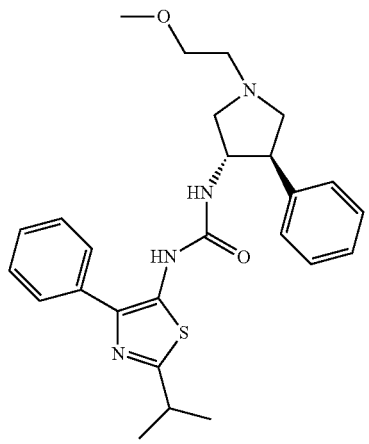 [SMILES: COCCN1C[C@@H](NC(=O)Nc2sc(C(C)C)nc2-c2ccccc2)[C@H](c2ccccc2)C1]

1-(2-isopropyl-4-phenylthiazol-5-yl)-3-((3S,4R)-1-(2-methoxyethyl)-4-phenylpyrrolidin-3-yl)urea Prepared according to the procedure of Example 47, using (3S,4R)-1-(2-methoxyethyl)-4-phenylpyrrolidin-3-amine bis(2,2,2-trifluoroacetate) instead of (3S,4R)-4-(3,4-difluorophenyl)-1-(2-methoxyethyl)pyrrolidin-3-amine bis(2,2,2-trifluoroacetate). The final product was purified by reverse-phase column chromatography using 0-60% acetonitrile/ H$_2$O as the eluent to provide the title compound (3.7 mg, 44% yield). MS (apci) m/z=465.1 (M+H).

Example 49

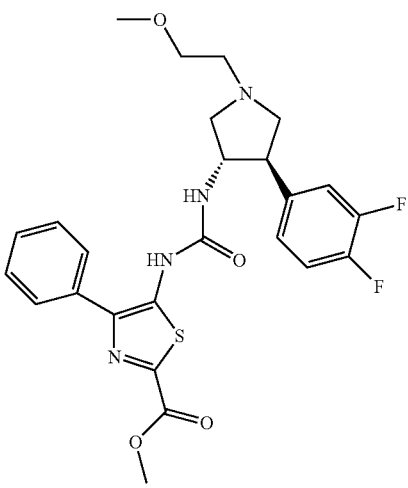 [SMILES: COCCN1C[C@@H](NC(=O)Nc2sc(C(=O)OC)nc2-c2ccccc2)[C@H](c2ccc(F)c(F)c2)C1]

methyl 5-(3-((3S,4R)-4-(3,4-difluorophenyl)-1-(2-methoxyethyl)pyrrolidin-3-yl)ureido)-4-phenylthiazole-2-carboxylate Prepared according to the procedure of Example 47, using methyl 2-chloro-2-oxoacetate instead of isobutyryl chloride. The final compound was purified by reverse-phase column chromatography using 5-80% acetonitrile/H$_2$O as the eluent to provide the title compound (53 mg, 2% yield for 4 steps). MS (apci) m/z=517.2 (M+H).

Example 50

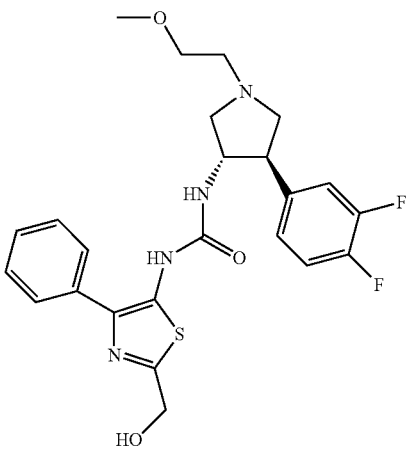 [SMILES: COCCN1C[C@@H](NC(=O)Nc2sc(CO)nc2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(2-(2-hydroxypropan-2-yl)-4-phenylthiazol-5-yl)urea Methyl 5-(3-((3S,4R)-4-(3,4-difluorophenyl)-1-(2-methoxyethyl)pyrrolidin-3-yl)ureido)-4-phenylthiazole-2- carboxylate (40 mg, 0.0774 mmol, prepared as described in Example 49) was dissolved in 3 mL of THF and cooled to 0° C. LiAlH₄ (1M in THF, 96.8 µL, 0.194 mmol) was added dropwise and the reaction was allowed to warm to ambient temperature. Additional THF (5 mL) was added followed by Na₂SO₄×10H₂O (249 mg, 0.774 mmol). The reaction was stirred at ambient temperature for 16 hours, filtered, concentrated and purified by reverse-phase column chromatography using 5-70% acetonitrile/H₂O as the eluent to provide the title compound (8.96 mg, 23.6% yield). MS (apci) m/z=489.2 (M+H)

Example 51

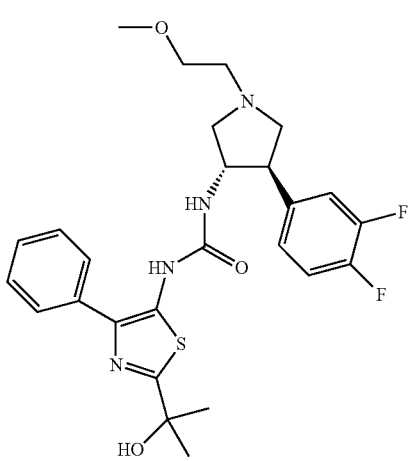 [SMILES: COCCN1C[C@@H](NC(=O)Nc2sc(C(C)(C)O)nc2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(2-(2-hydroxypropan-2-yl)-4-phenylthiazol-5-yl)urea Methyl 5-(3-((3S,4R)-4-(3,4-difluorophenyl)-1-(2-methoxyethyl)pyrrolidin-3-yl)ureido)-4-phenylthiazole-2-carboxylate (20 mg, 0.039 mmol) was dissolved in 1 mL of THF and cooled to 0° C. MeMgBr (1M in THF, 116 µL, 0.12 mmol) was added and the reaction was allowed to warm to ambient temperature, quenched with brine (1 mL), extracted with several portions of DCM in a PS frit and concentrated. The crude product was purified by reverse-phase column chromatography using 10-80% acetonitrile/H₂O as the eluent to provide the title compound (2.8 mg, 14% yield). MS (apci) m/z=517.2 (M+H).

Example 52

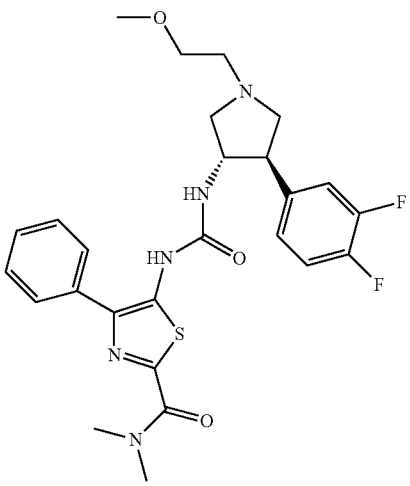 [SMILES: COCCN1C[C@@H](NC(=O)Nc2sc(C(=O)N(C)C)nc2-c2ccccc2)[C@H](c2ccc(F)c(F)c2)C1]

5-(3-((3S,4R)-4-(3,4-difluorophenyl)-1-(2-methoxyethyl)pyrrolidin-3-yl)ureido)-N,N-dimethyl-4-phenylthiazole-2-carboxamide Step A: 5-(3-((3S,4R)-4-(3,4-difluorophenyl)-1-(2-methoxyethyl)pyrrolidin-3-yl)ureido)-4-phenylthiazole-2-carboxylic acid Methyl 5-(3-((3S,4R)-4-(3,4-difluorophenyl)-1-(2-methoxyethyl)pyrrolidin-3-yl)ureido)-4-phenylthiazole-2-carboxylate (200 mg, 0.387 mmol) was dissolved in 2 mL of MeOH and NaOH (103 mg, 0.774 mmol) was added. The reaction was stirred at ambient temperature for 16 hours and HCl (5N in IPA, 310 µL, 1.55 mmol) added. The reaction was concentrated, taken up in acetone (5 mL) and filtered through Celite®. The Celite® was washed with several portions of acetone and the combined acetone solutions were concentrated to afford the title compound containing about 50%/weight of NaCl (359 mg, 92.3% yield). MS (apci) m/z=503.1 (M+H).

Step B: Preparation of 5-(3-((3S,4R)-4-(3,4-difluorophenyl)-1-(2-methoxyethyl)pyrrolidin-3-yl)ureido)-N,N-dimethyl-4-phenylthiazole-2-carboxamide 5-(3-((3S,4R)-4-(3,4-difluorophenyl)-1-(2-methoxyethyl)pyrrolidin-3-yl)ureido)-4-phenylthiazole-2-carboxylic acid (50% pure, 25 mg, 0.025 mmol), HBTU (23 mg, 0.060 mmol), dimethylamine hydrochloride (12 mg, 0.15 mmol) and DIEA (52 µL, 0.30 mmol) were combined in 0.5 mL of DMF and stirred at ambient temperature for 2 days. The reaction was loaded onto a samplet and purified by reverse-phase column chromatography, eluting with 0-80% acetonitrile/water, to afford the title compound (5.4 mg, 40% yield). MS (apci) m/z=530.2 (M+H).

Example 53

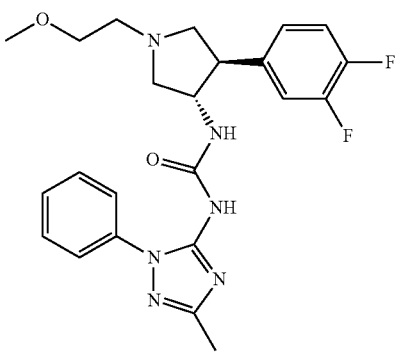 [SMILES: COCCN1C[C@@H](NC(=O)Nc2nc(C)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(3-methyl-1-phenyl-1H-1,2,4-triazol-5-yl)urea

Step A: Preparation of 3-methyl-1-phenyl-1H-1,2,4-triazol-5-amine

To a solution of methyl N-cyanoacetimidate (100 mg, 1.019 mmol) in MeOH (4 mL) was added phenylhydrazine (0.121 mL, 1.223 mmol). The reaction mixture was refluxed for 4 hours, then cooled to ambient temperature. The reaction mixture was purified by silica column chromatography eluting with 0-80% acetone/hexane, to afford the title compound as a white solid (147 mg, 83% yield). MS (apci) m/z=175.1 (M+H).

Step B: Preparation of 1-((3S,4R)-4-(3,4-difluorophenyl)-1-(2-methoxyethyl)pyrrolidin-3-yl)-3-(3-methyl-1-phenyl-1H-1,2,4-triazol-5-yl)urea To a solution of 3-methyl-1-phenyl-1H-1,2,4-triazol-5-amine (15 mg, 0.086 mmol) in DCM (1 mL) was added CDI (14 mg, 0.086 mmol), followed by addition of DIEA (0.030 mL, 0.172 mmol). The reaction mixture was stirred at ambient temperature for 5 hours, and a solution of (3S,4R)-4-(3,4-difluorophenyl)-1-(2-methoxyethyl)pyrrolidin-3-amine (2S,3S)-2,3-bis((4-methylbenzoyl)oxy)succinate [Preparation E3] (58 mg, 0.090 mmol) and DIEA (0.030 mL, 0.172 mmol) in DCM (1 mL) was added. The reaction mixture was stirred at ambient temperature for 16 hour, then was diluted with $H_2O$ (20 mL) and extracted with DCM (3×20 mL). The combined organic phases were dried ($MgSO_4$), filtered and concentrated. The crude product was purified by reverse-phase column chromatography, eluting with 5-70% acetonitrile/water, to afford the title compound as a colorless glass (20.6 mg, 52% yield). MS (apci) m/z=457.2 (M+H).

Example 54

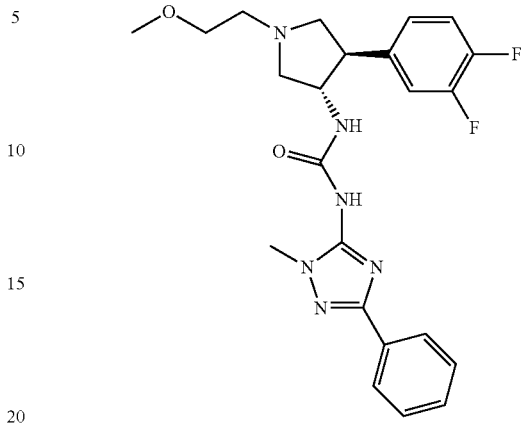

1-((3S,4R)-4-(3,4-difluorophenyl)-1-(2-methoxyethyl)pyrrolidin-3-yl)-3-(1-methyl-3-phenyl-1H-1,2,4-triazol-5-yl)urea Prepared according to the procedure for Example 54, Step B, replacing 3-methyl-1-phenyl-1H-1,2,4-triazol-5-amine with 1-methyl-3-phenyl-1H-1,2,4-triazol-5-amine hydrochloride hydrate (ChemBridge, 25 mg, 0.109 mmol), to afford the title compound as a white solid (27.3 mg, 55% yield). MS (apci) m/z=457.2 (M+H).

Example 55

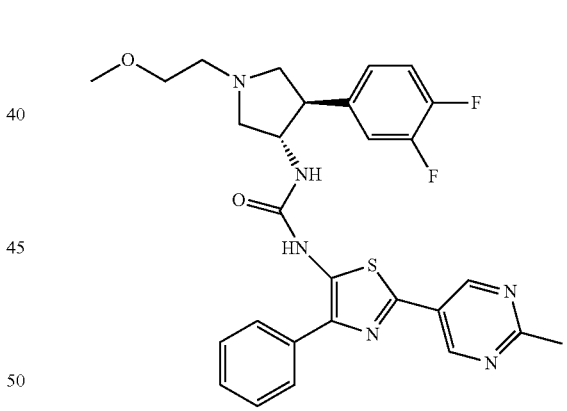

1-((3S,4R)-4-(3,4-difluorophenyl)-1-(2-methoxyethyl)pyrrolidin-3-yl)-3-(2-(1-methyl-1H-pyrazol-4-yl)-4-phenylthiazol-5-yl)urea

Step A: Preparation of ethyl 2-amino-4-phenylthiazole-5-carboxylate

A suspension of ethyl 2-bromo-3-oxo-3-phenylpropanoate (4.9 g, 18.1 mmol) and thiourea (1.38 g, 18.1 mmol) in ethanol (50 mL) was warmed to reflux and stirred for 4 hours. After standing at ambient temperature for 16 hours the mixture was concentrated under reduced pressure. The residue was partitioned between DCM (100 mL) and saturated $NaHCO_3$ (100 mL) and the aqueous layer was extracted with DCM (2×50 mL). The combined organic phases were washed with brine (50 mL), dried over Na₂SO₄, filtered and concentrated. The resulting solid was triturated with DCM, filtered and dried under vacuum to afford ethyl 2-amino-4-phenylthiazole-5-carboxylate (3.09 g, 69% yield) as a solid. MS (apci) m/z=249.1 (M+H).

Step B: Preparation of ethyl 2-bromo-4-phenylthiazole-5-carboxylate

A suspension of copper bromide (3.34 g, 14.9 mmol) in anhydrous acetonitrile (50 mL) was degassed with N₂ for 10 minutes and cooled to 0° C., then treated with t-butyl nitrite (2.2 mL, 18.7 mmol). This mixture was treated with a suspension of ethyl 2-amino-4-phenylthiazole-5-carboxylate (3.09 g, 12.4 mmol) in acetonitrile (50 mL) and the dark mixture was allowed to warm slowly to ambient temperature over 16 hours. The mixture was concentrated and the residue was dissolved in EtOAc (100 mL) and washed with NaHCO₃ (100 mL). The aqueous layer was extracted with EtOAc (2×50 mL), and the combined organic phases were washed with water and brine, dried over Na₂SO₄, filtered and concentrated to afford ethyl 2-bromo-4-phenylthiazole-5-carboxylate (3.8 g, 98% yield) as a brown, crystalline solid. MS (apci) m/z=312.0 (M+).

Step C: Preparation of 2-bromo-4-phenylthiazole-5-carboxylic acid

To a solution of ethyl 2-bromo-4-phenylthiazole-5-carboxylate (3.80 g, 12.17 mmol) in THF (100 mL) was added water (30 mL) followed by potassium hydroxide (908 mg, 16.2 mmol). The mixture was stirred at ambient temperature for 16 hours then acidified with 1N HCl and extracted with EtOAc. The combined organic phases were washed with brine, dried over Na₂SO₄, filtered and concentrated to afford 2-bromo-4-phenylthiazole-5-carboxylic acid (3.4 g, 98% yield) as a yellow solid. MS (apci) m/z=285.9 (M+H).

Step D: Preparation of 2-(2-methylpyrimidin-5-yl)-4-phenylthiazole-5-carboxylic acid 2-Bromo-4-phenylthiazole-5-carboxylic acid (300 mg, 1.06 mmol), 2-methyl-5-(4,4,5,5,-tetramethyl-1,3,2-dioxaborolan-2-yl)pyrimidine (465 mg, 2.11 mmol), K₂CO₃ (584 mg, 4.22 mmol) and Pd(PPh₃)₄ (122 mg, 0.11 mmol) were combined in toluene (2 mL), water (1 mL) and EtOH (0.5 mL) and warmed to 95° C. in a sealed vessel for 16 hours. The cooled mixture was filtered through GF paper and the filtrate partitioned between water (10 mL) and EtOAc (10 mL). The aqueous layer was extracted with EtOAc and then adjusted to pH 5 with 1N HCl. The resulting solids were filtered, washed with water and Et₂O and then dried under vacuum to afford 2-(2-methylpyrimidin-5-yl)-4-phenylthiazole-5-carboxylic acid (195 mg, 62% yield) as a cream solid. MS (apci) m/z=298.1 (M+H).

Step E: Preparation of tert-butyl (2-(2-methylpyrimidin-5-yl)-4-phenylthiazol-5-ylcarbamate 2-(2-Methylpyrimidin-5-yl)-4-phenylthiazole-5-carboxylic acid (195 mg, 0.66 mmol) was suspended in t-BuOH (5 mL) and treated with DPPA (142 µL, 0.66 mmol) followed by Et₃N (91 µL, 0.66 mmol). The mixture was warmed to reflux and stirred for 16 hours. The cooled mixture was concentrated and then partitioned between EtOAc (10 mL) and water (10 mL), followed by addition of 1N NaOH and a small amount of MeOH. The aqueous layer was extracted with EtOAc (2×10 mL) and the combined organic phases were washed with brine, dried over Na₂SO₄, filtered and concentrated. The residue was purified by silica column chromatography eluting with hexanes:EtOAc, 4:1, to afford tert-butyl (2-(2-methylpyrimidin-5-yl)-4-phenylthiazol-5-ylcarbamate (80 mg, 33% yield) as a pale pink solid. MS (apci) m/z=369.1 (M+H).

Step F: Preparation of 2-(2-methylpyrimidin-5-yl)-4-phenylthiazol-5-amine

To a solution of tert-butyl (2-(2-methylpyrimidin-5-yl)-4-phenylthiazol-5-ylcarbamate (80 mg, 0.22 mmol) in anhydrous DCM (5 mL) was added TFA (2 mL) The solution was stirred at ambient temperature for 3.5 hours, then concentrated and partitioned between 2N NaOH (10 mL) and DCM (10 mL). The aqueous layer was extracted with DCM and the combined organic phases were washed with brine (10 mL), dried over Na₂SO₄, filtered and concentrated to afford 2-(2-methylpyrimidin-5-yl)-4-phenylthiazol-5-amine (42 mg, 72% yield) as a yellow solid. MS (apci) m/z=269.1 (M+H).

Step G: Preparation of 1-((3S,4R)-4-(3,4-difluorophenyl)-1-(2-methoxyethyl)pyrrolidin-3-yl)-3-(2-(1-methyl-1H-pyrazol-4-yl)-4-phenylthiazol-5-yl)urea To a solution of 2-(2-methylpyrimidin-5-yl)-4-phenylthiazol-5-amine (42 mg, 0.16 mmol) in DCM (2 mL) was added triphosgene (23 mg, 0.08 mmol) followed by DIEA (82 µL, 0.47 mmol). The mixture was stirred for 30 minutes at ambient temperature. The mixture was then treated with (3S,4R)-4-(3,4-difluorophenyl)-1-(2-methoxyethyl)pyrrolidin-3-amine [Preparation C1] (50 mg, 0.19 mmol) and DIEA (82 µL, 0.47 mmol) and stirred for 16 hours. The mixture was partitioned between water (10 mL) and DCM (10 mL) and the aqueous layer was extracted with DCM. The combined organic phases were washed with brine (10 mL), dried over Na₂SO₄, filtered and concentrated. The residue was purified by silica column chromatography eluting with 2.5% MeOH/DCM. The fractions containing the desired product were then purified by reverse phase HPLC (5-95% ACN/H₂O/0.1% TFA over 20 minutes). Clean fractions containing the desired product were combined and concentrated, and the residue was worked up with 2N NaOH/DCM to afford the title compound (8 mg, 9% yield) as a white solid. MS (apci) m/z=551.2 (M+H).

Example 56

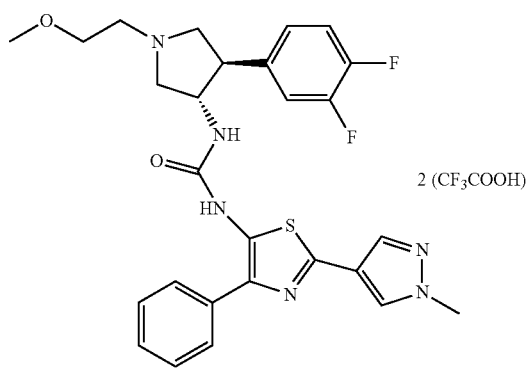

2 (CF₃COOH)

1-((3S,4R)-4-(3,4-difluorophenyl)-1-(2-methoxy-ethyl)pyrrolidin-3-yl)-3-(2-(1-methyl-1H-pyrazol-4-yl)-4-phenylthiazol-5-yl)urea di(trifluoroacetate)

Step A: Preparation of 2-(1-methyl-1H-pyrazol-4-yl)-4-phenylthiazole-5-carboxylic acid Prepared according to the procedure for Example 55, substituting 2-methyl-5-(4,4,5,5,-tetramethyl-1,3,2-dioxaborolan-2-yl)pyrimidine for 1-methyl-4-(4,4,5,5-tetramethyl-1,3,2-dioxaborolan-2-yl)-1H-pyrazole in Step D, to provide the title compound (500 mg, 99% yield) as a cream solid. MS (apci) m/z=286.0 (M+H).

Step B: Preparation of 1-((3S,4R)-4-(3,4-difluorophenyl)-1-(2-methoxyethyl)pyrrolidin-3-yl)-3-(2-(1-methyl-1H-pyrazol-4-yl)-4-phenylthiazol-5-yl)urea di(trifluoroacetate)

2-(1-Methyl-1H-pyrazol-4-yl)-4-phenylthiazole-5-carboxylic acid (50 mg, 0.18 mmol) and (3S,4R)-4-(3,4-difluorophenyl)-1-(2-methoxyethyl)pyrrolidin-3-amine [Preparation C1] (135 mg, 0.53 mmol) were combined in toluene (3 mL) and treated with DPPA (53 µL, 0.25 mmol) followed by Et₃N (98 µL, 0.70 mmol). The mixture was warmed to reflux, stirred for 16 h then cooled and partitioned between water (10 mL) and EtOAc (10 mL). The aqueous layer was extracted with EtOAc (2×10 mL) and the combined organic phases were washed with brine (10 mL), dried over Na₂SO₄, filtered and concentrated. The residue was purified by silica column chromatography eluting with 2% MeOH/DCM, then by reverse phase HPLC (5-95% ACN/water/0/1% TFA over 20 min) to afford the title compound as the di-trifluoroacetate salt (17 mg, 13% yield) as a colorless glass. MS (apci) m/z=539.2 (M+H).

What is claimed is:
1. A compound of Formula I:

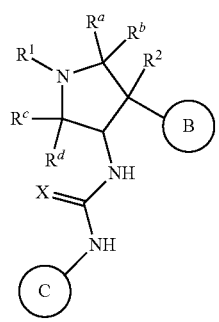

I or stereoisomers, tautomers, or pharmaceutically acceptable salts thereof, wherein:
Ring B and the NH—C(═X)—NH moiety are in the trans configuration;
$R^a$, $R^b$, $R^c$ and $R^d$ are independently selected from H and (1-3C)alkyl,
or $R^c$ and $R^d$ are independently selected from H and (1-3C)alkyl, and $R^a$ and $R^b$ together with the atom to which they are attached form a cyclopropyl ring;
X is O, S, NH or N—CN;
$R^1$ is (1-3C alkoxy)(1-6C)alkyl, (trifluoromethoxy)(1-6C)alkyl, (1-3C sulfanyl)(1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, cyano(1-6C)alkyl, aminocarbonyl(1-6C)alkyl, hydroxy(1-6C)alkyl, dihydroxy(2-6C)alkyl, (1-6C)alkyl, (1-3Calkylamino)(1-3C)alkyl, (1-4C alkoxycarbonyl)(1-6C)alkyl, amino(1-6C)alkyl, hydroxy(1-3C alkoxy)(1-6C)alkyl, di(1-3C alkoxy)(1-6C)alkyl, (1-3C alkoxy)trifluoro(1-6C)alkyl, hydroxytrifluoro(1-6C)alkyl, (1-4C alkoxycarbonyl)(1-3C alkoxy)(1-6C)alkyl, or hydroxycarbonyl (1-3C alkoxy)(1-6C)alkyl;
$R^2$ is H, F, or OH;
Ring B is $Ar^1$ or $hetAr^1$;
$Ar^1$ is phenyl optionally substituted with one or more substituents independently selected from halogen, $CF_3$, $CF_3O$—, (1-4C)alkoxy, hydroxy(1-4C)alkyl, (1-6C) alkyl and CN;
$hetAr^1$ is a 5-6 membered heteroaryl having 1-3 ring heteroatoms independently selected from N, S and O, and optionally substituted with one or more groups independently selected from (1-6C)alkyl, halogen, OH, $CF_3$, $NH_2$ and hydroxy(1-2C)alkyl;
Ring C is selected from formulas C-1 through C-13:

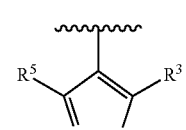

C-1

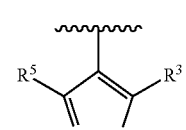

C-2

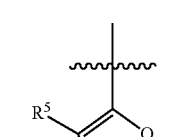

C-3

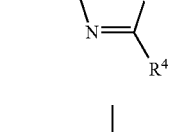

C-4

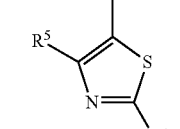

C-5

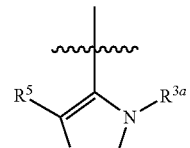

C-6

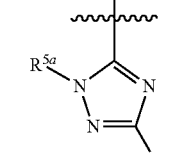

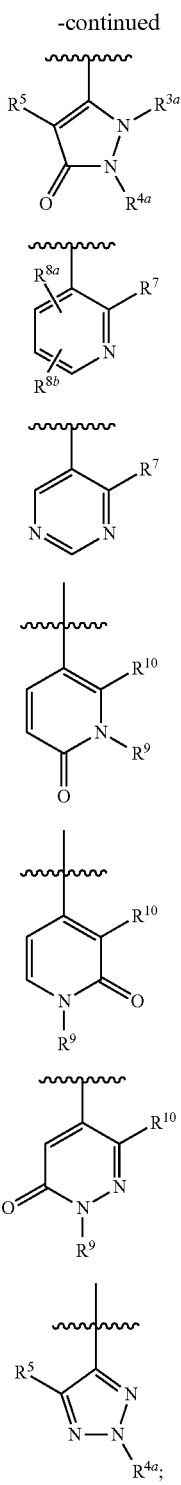

R³ is H, NH₂, CN, halogen, (1-3C)alkyl wherein said (1-3C)alkyl is optionally substituted with 1 to 3 fluoros, H₂NC(=O)—, (1-3Calkyl)NHC(=O)—, di(1-3Calkyl)NHC(=O)—, hydroxy(1-3C)alkyl, CH₃OCH₂CH₂, (3-4C)cycloalkyl or (1-3C)alkoxy;

R³ᵃ is H, (1-3C)alkyl, CF₃CH₂CH₂, HCF₂CH₂CH₂, H₂FCCH₂CH₂, CF₃CH₂, HOCH₂CH₂, MeOCH₂CH₂, or (3-4C)cycloalkyl;

R⁴ is H, OH, (1-6C)alkyl wherein said (1-6C)alkyl is optionally substituted with 1-5 fluoros, cyano(1-6C) alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl (1-6C)alkyl, hetAr³ (1-6C)alkyl, Ar³ (1-6C)alkyl, (1-6C)alkoxy wherein said (1-6C)alkoxy is optionally substituted with 1-5 fluoros, cyano(1-6C)alkoxy, hydroxy(1-6C)alkoxy, dihydroxy(2-6C)alkoxy, amino (2-6C)alkoxy, hydroxyl-carbonyl(1-6C)alkoxy, hetCyc²(1-6C)alkoxy, hetAr³(1-6C)alkoxy, Ar³(1-6C)alkoxy, (1-4C alkoxy)(1-6C)alkoxy, (1-3C alkylsulfonyl)(1-6C)alkoxy, (3-6C)cycloalkyl wherein said (3-6C)cycloalkyl is optionally substituted with a substituent selected from F, OH, (1-6C alkyl), (1-6C) alkoxy, and (1-3C alkoxy)(1-6C)alkyl, hetAr⁴, hetAr⁴—O—, Ar⁴, hetCyc²(O)CH₂—, (1-4C alkoxycarbonyl)(1-6C)alkoxy, hydroxycarbonyl(1-6C) alkoxy, aminocarbonyl(1-6C)alkoxy, hetCyc²C(=O) (1-6C)alkoxy, hydroxy(1-3C alkoxy)(1-6C)alkoxy, hydroxytrifluoro(1-6C)alkoxy, (1-3C)alkylsulfonamido(1-6C)alkoxy, (1-3C)alkylamido(1-6C)alkoxy, di(1-3C alkyl)amino-carboxy, hetCyc²C(=O)O—, hydroxydifluoro(1-6C)alkyl, (1-4C alkylcarboxy)(1-6C)alkyl, (1-6C)alkoxycarbonyl, hydroxylcarbonyl, aminocarbonyl, (1-3C alkoxy)aminocarbonyl, hetCyc³, halogen, CN, trifluoromethylsulfonyl, N-(1-3C alkyl) oxadiazolonyl, or hetAr⁵;

R⁴ᵃ is H, (1-6C)alkyl, CF₃CH₂CH₂, HCF₂CH₂CH₂, H₂FCCH₂CH₂, CF₃CH₂, cyano(1-6C)alkyl, hydroxy (1-6C)alkyl, dihydroxy(2-6C)alkyl, (1-3C alkoxy)(1-6C)alkyl, amino(1-6C)alkyl, aminocarbonyl(1-6C) alkyl, (1-3C)alkyl sulfonamido(1-6C)alkyl, sulfamido (1-6C)alkyl, hydroxycarbonyl(1-6C)alkyl, hetAr³(1-6C)alkyl, Ar³(1-6C)alkyl, (3-6C)cycloalkyl wherein said (3-6C)cycloalkyl is optionally substituted with a substituent selected from F, OH, (1-6C alkyl), (1-6C) alkoxy, and (1-3C alkoxy)(1-6C)alkyl, hetAr⁴, Ar⁴, hydroxydifluoro(1-6C)alkyl, (1-4C alkylcarboxy)(1-6C)alkyl, hetCyc³, N-(1-3C alkyl)oxadiazolonyl, or hetAr⁵;

hetCyc² is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, and (1-6C)acyl;

hetCyc³ is a 4-7 membered heterocycle having 1-2 ring heteroatoms independently selected from N and O and optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, (1-6C)alkyl sulfonyl, trifluoromethylsulfonyl and (1-4C alkoxy)carbonyl;

hetAr³ is a 5-membered heteroaryl ring having 1-3 ring atoms independently selected from N, O and S and optionally substituted with (1-6C)alkyl;

Ar³ is phenyl optionally substituted with (1-4C)alkoxy;

hetAr⁴ is independently a 5-6 membered heteroaryl ring having 1-3 ring heteroatoms independently selected from N, S and O and optionally substituted with one or more substituents independently selected from (1-6C) alkyl wherein said (1-6C)alkyl is optionally substituted with 1-3 fluoros, halogen, CN, hydroxy(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl) amino, di(1-6C alkyl)amino, (1-3C trifluoroalkoxy), fluoro(1-6C alkyl)amino, difluoro(1-6C alkyl)amino, trifluoro(1-6C alkyl)amino, and (3-4C cycloalkyl)amino;

hetAr⁵ is a group selected from the structures:

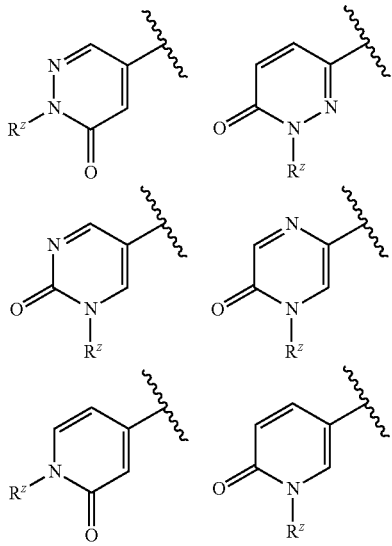

where R$^z$ is (3-4C)cycloalkyl or (1-3C)alkyl wherein said alkyl is optionally substituted with 1-3 fluoros, wherein each of said hetAr⁵ groups is optionally further substituted with one or more groups independently selected from F and (1-3C)alkyl optionally substituted with 1-3 fluoros;

Ar⁴ is phenyl optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—;

R⁵ is H, (1-6C)alkyl wherein said (1-6C)alkyl is optionally substituted with 1-5 fluoros, halogen, CN, (1-4C) alkoxy, hydroxy(1-4C)alkyl, (1-3C alkoxy)(1-4C) alkyl, (1-4C alkyl)OC(=O)—, (1-6C)alkylthio, (3-4C) cycloalkyl, amino, aminocarbonyl, trifluoro(1-3C alkyl)amido, or phenyl wherein said phenyl is optionally substituted with one or more groups independently selected from the group consisting of halogen, (1-6C) alkyl and (1-6C)alkoxy;

R$^{5a}$ is H, (1-6C)alkyl, CF₃CH₂CH₂, HCF₂CH₂CH₂, H₂FCCH₂CH₂, CF₃CH₂, hydroxy(1-4C)alkyl, (1-3C alkoxy)(1-4C)alkyl, (3-4C)cycloalkyl, or phenyl wherein said phenyl is optionally substituted with one or more groups independently selected from the group consisting of halogen, (1-6C)alkyl and (1-6C)alkoxy;

R⁷ is (1-6C)alkyl, (3-6C)cycloalkyl, or phenyl wherein said phenyl is optionally substituted with one or more groups independently selected from the group consisting of halogen, (1-6C)alkyl, (1-6C)alkoxy, (3-4C)cycloalkyl, amino, aminocarbonyl, and trifluoro(1-3C) alkylamido;

R$^{8a}$ and R$^{8b}$ are independently H, halogen, CN, NH₂, (1-6C)alkyl wherein said (1-6C)alkyl is optionally substituted with 1-5 fluoros, (1-6C)alkoxy, (1-3C alkoxy)(1-6C)alkyl, (1-3C alkoxy)(1-6C)alkyl, (1-6C alkyl)sulfonyl, (3-6C cycloalkyl)sulfonyl, (3-4C)cycloalkyl, amino, (1-6Calkyl)NH—, phenyl wherein said phenyl is optionally substituted with (1-6C alkyl)SO₂—, or hetAr⁴, wherein only one of R$^{8a}$ and R$^{8b}$ can be phenyl optionally substituted with (1-6C alkyl)SO₂—, or hetAr⁴;

R⁹ is H, (1-6C)alkyl, CF₃CH₂—, CF₃CH₂CH₂—, (1-3Calkoxy)(1-6C)alkyl or (3-4C)cycloalkyl; and R¹⁰ is (3-6C)cycloalkyl or phenyl wherein said phenyl is optionally substituted with one or more substituents independently selected from the group consisting of halogen, (1-6C)alkyl, (1-6C)alkoxy, (3-4C)cycloalkyl, amino, aminocarbonyl and trifluoro(1-3C alkyl)amido.

2. A compound according to claim 1, wherein X is O.

3. A compound according to claim 1, wherein R¹ is (1-3C alkoxy)(1-6C)alkyl.

4. A compound according to claim 1, wherein Ring B is Ar¹.

5. A compound according to claim 1, wherein Ring C is formula C-1 or C-2.

6. A compound according to claim 1, wherein Ring C is formula C-3, C-4, C-5, C-6 or C-13.

7. A compound according to claim 1, wherein Ring C is formula C-7.

8. A compound according to claim 1, wherein Ring C is formula C-8 or C-9.

9. A compound according to claim 1, wherein Ring C is formula C-10, C-11 or C-12.

10. A compound according to claim 1, wherein R² is H.

11. A compound according to claim 1, wherein R$^a$, R$^b$, R$^c$ and R$^d$ are H.

12. A compound according to claim 1, wherein Ring B and the —NH—C(=X)—NH— moiety of Formula I are trans in the absolute configuration shown in structure C:

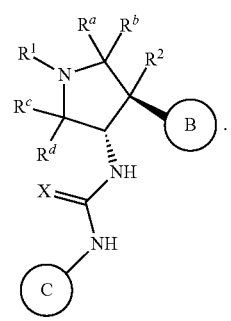

13. A compound according to claim 1, wherein ring B and the —NH—C(=X)—NH— moiety of Formula I are trans in the absolute configuration shown in structure D:

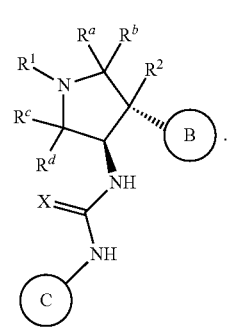

14. A compound of claim 1, selected from
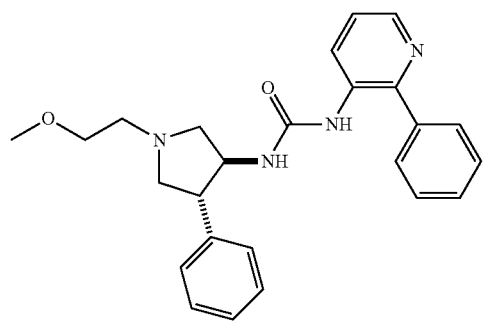
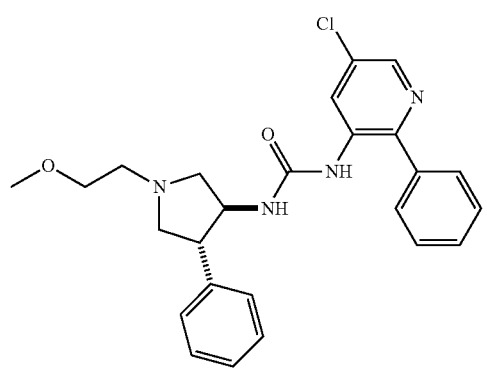
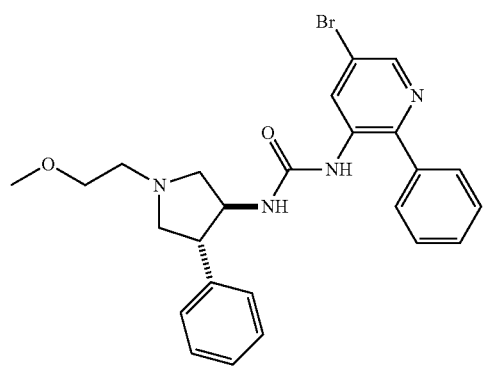
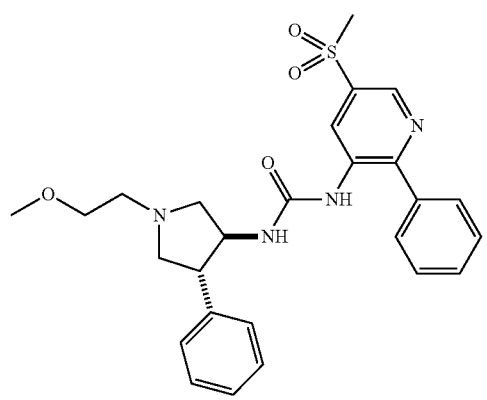
-continued
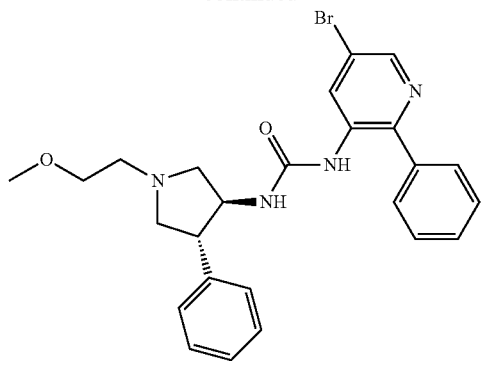
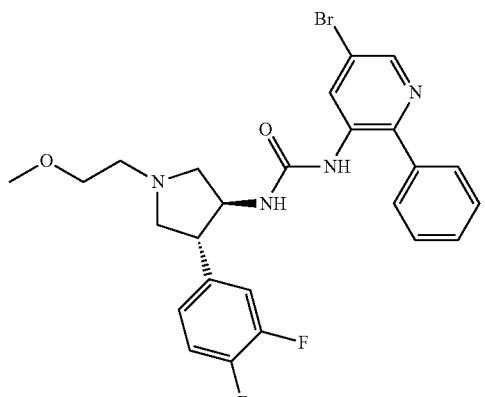
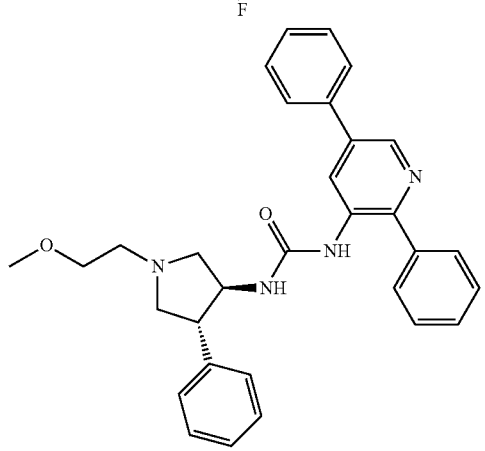
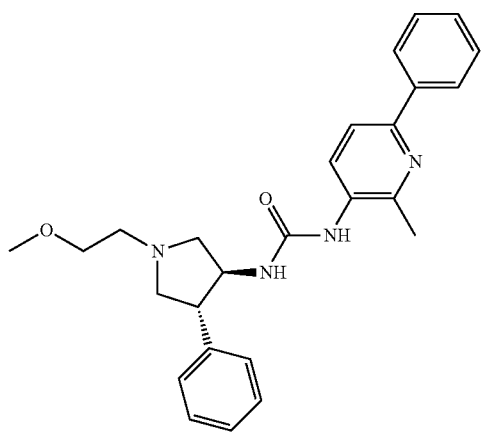

135
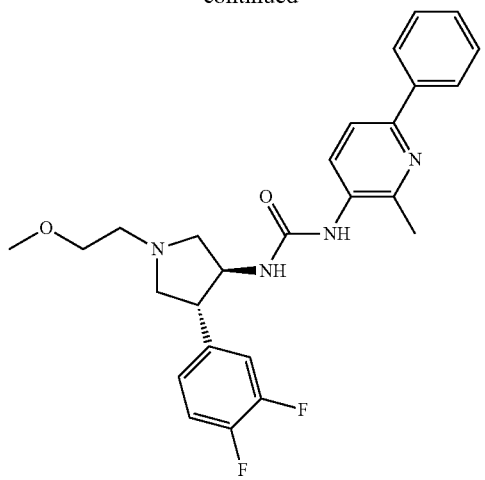
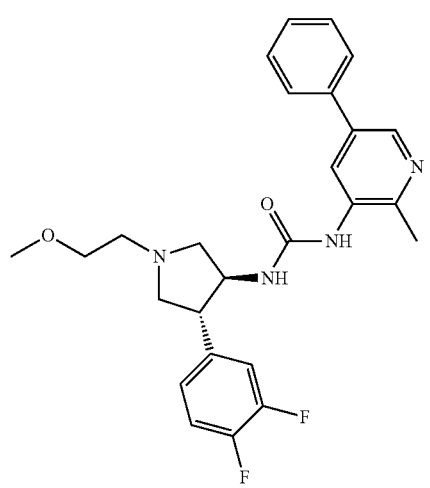
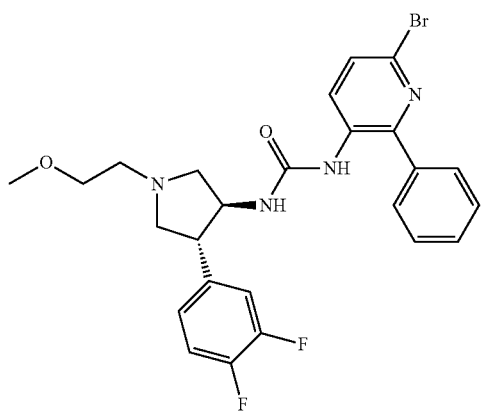
136
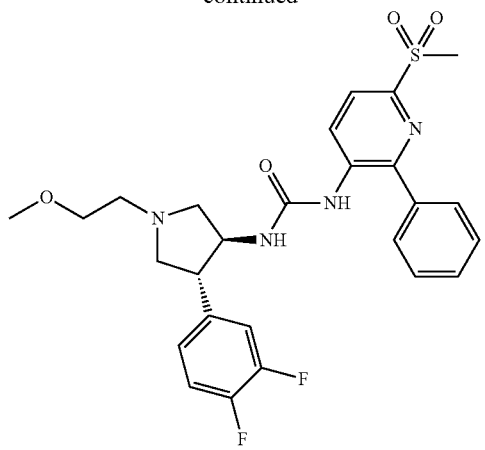
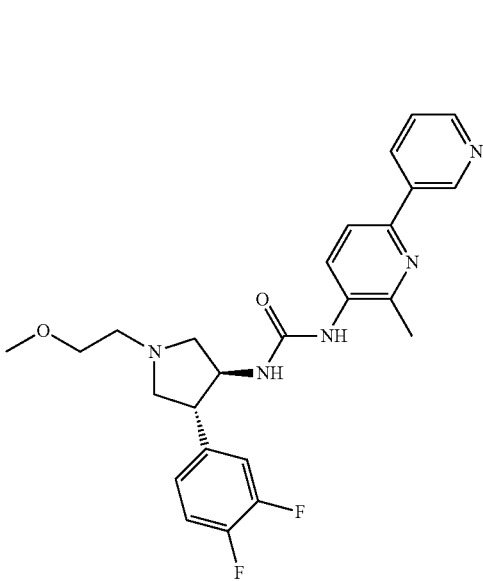

137
-continued
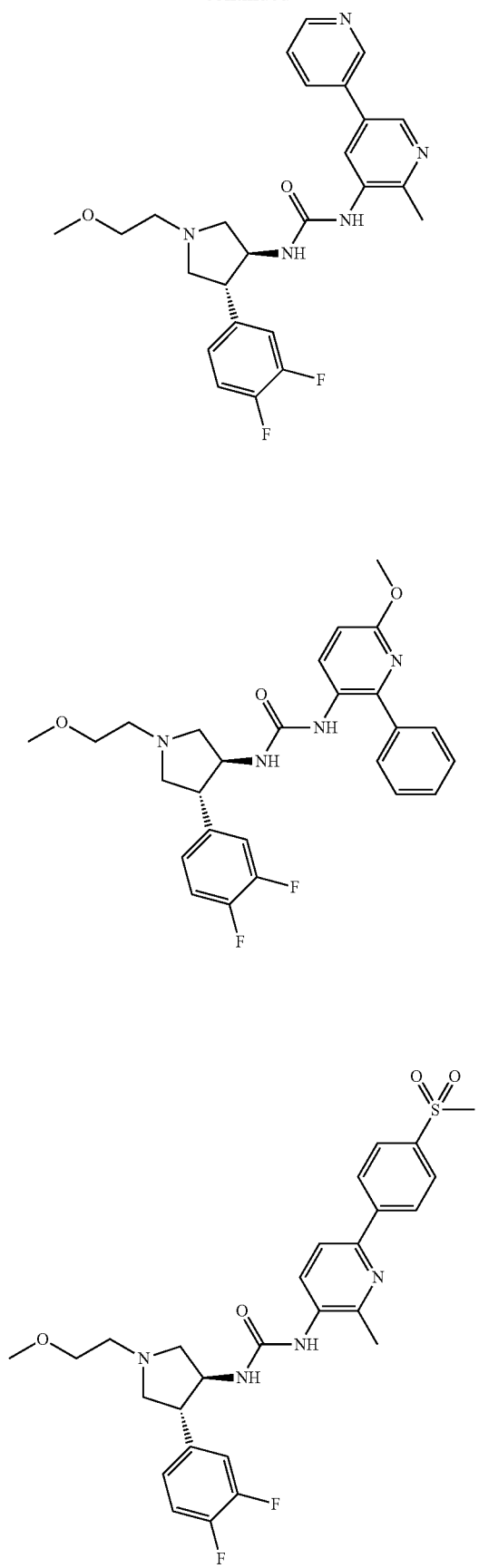
138
-continued
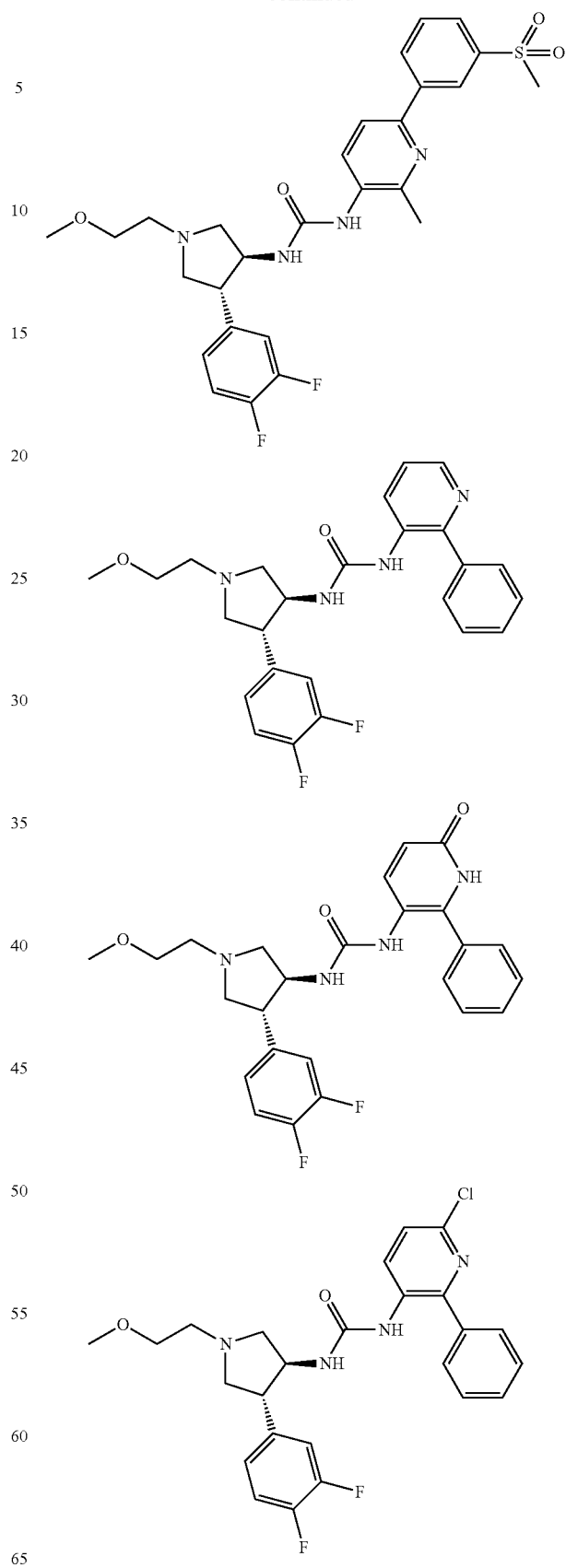

139
-continued
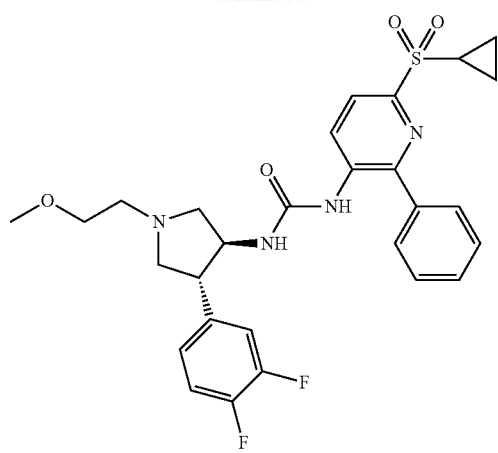
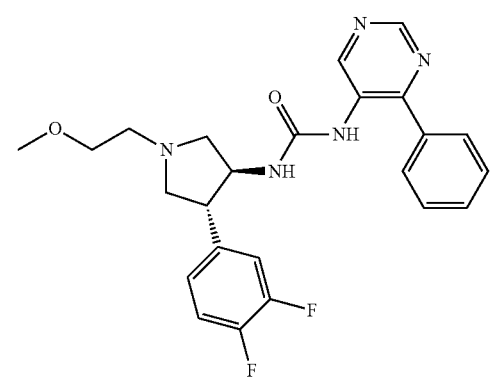
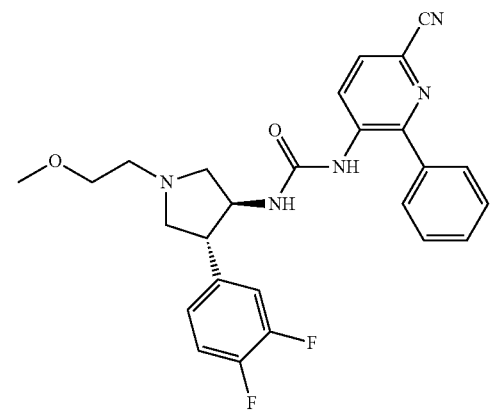
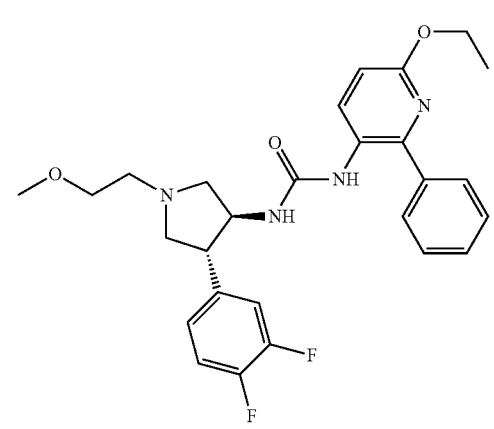
140
-continued
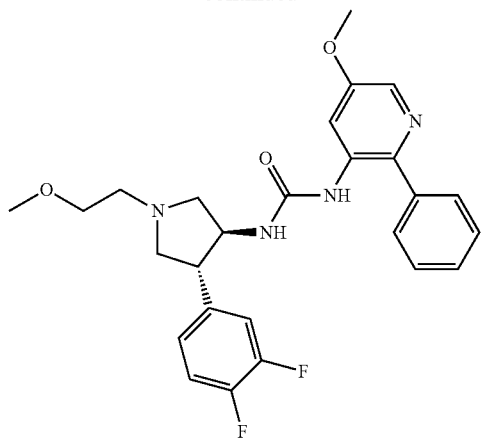
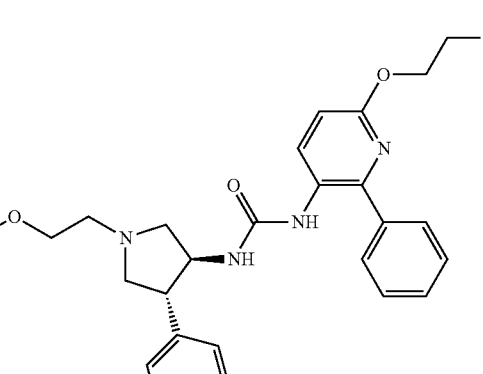
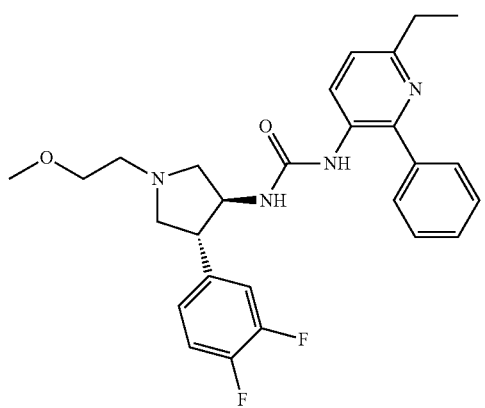
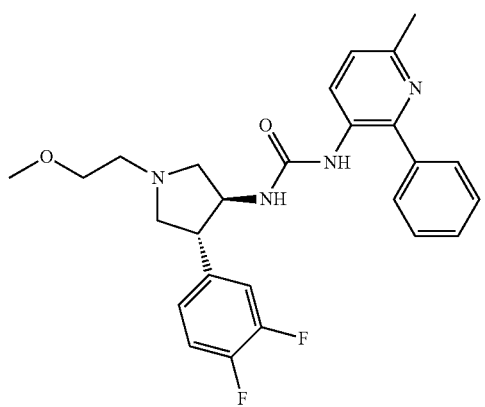

-continued
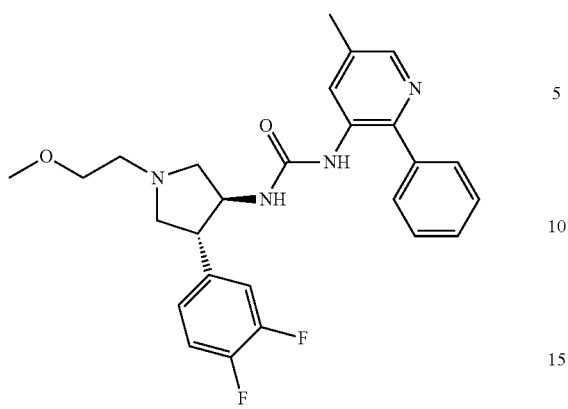
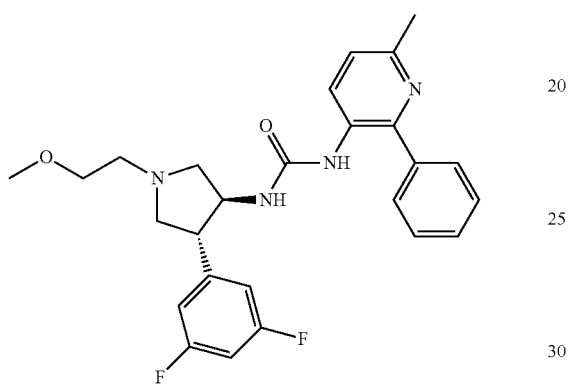
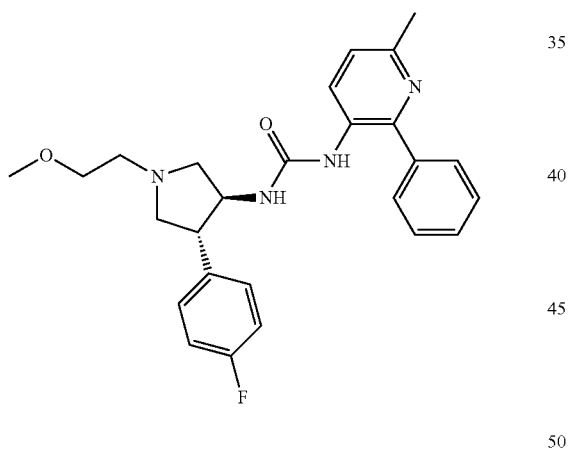
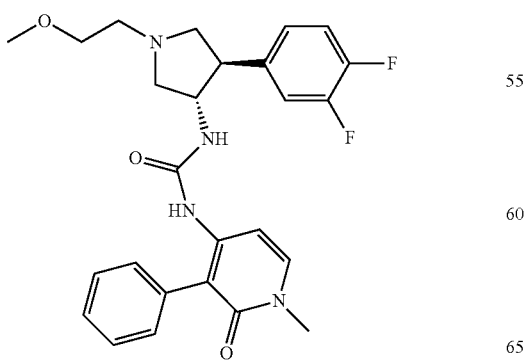
-continued
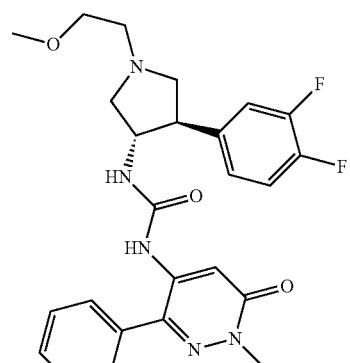
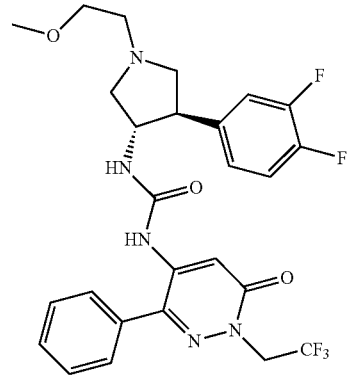
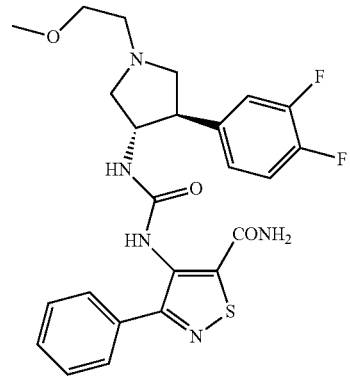
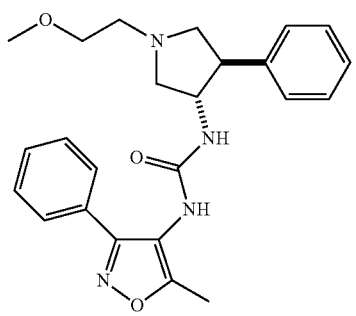

143
-continued
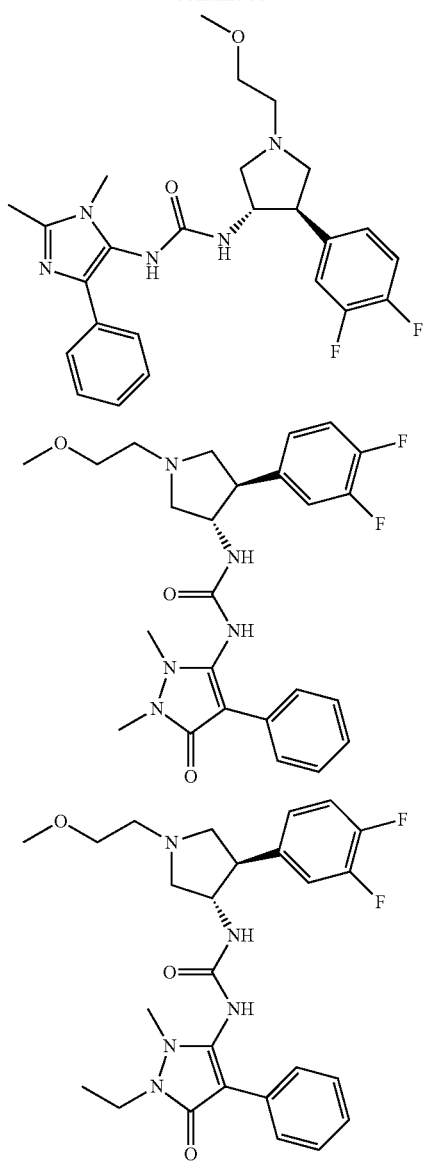
144
-continued
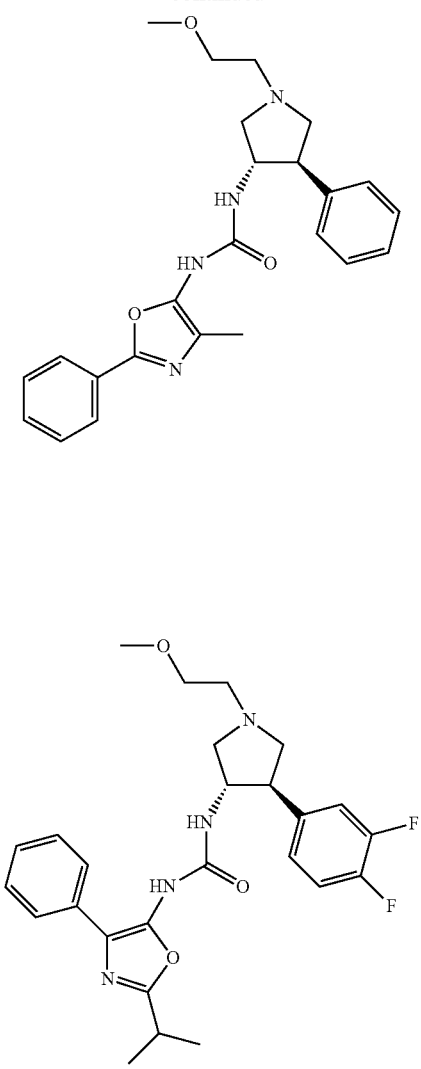
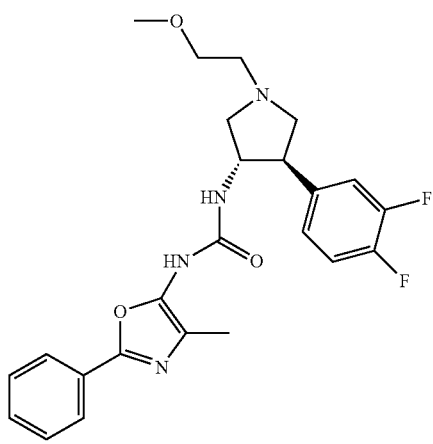
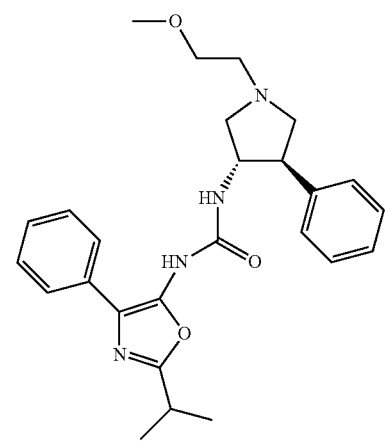

145
-continued
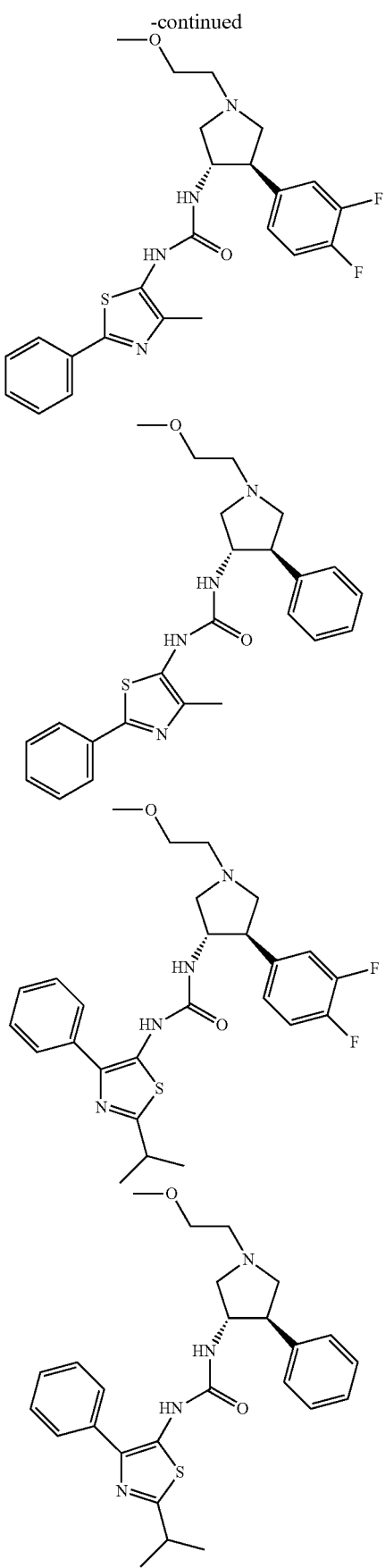
146
-continued
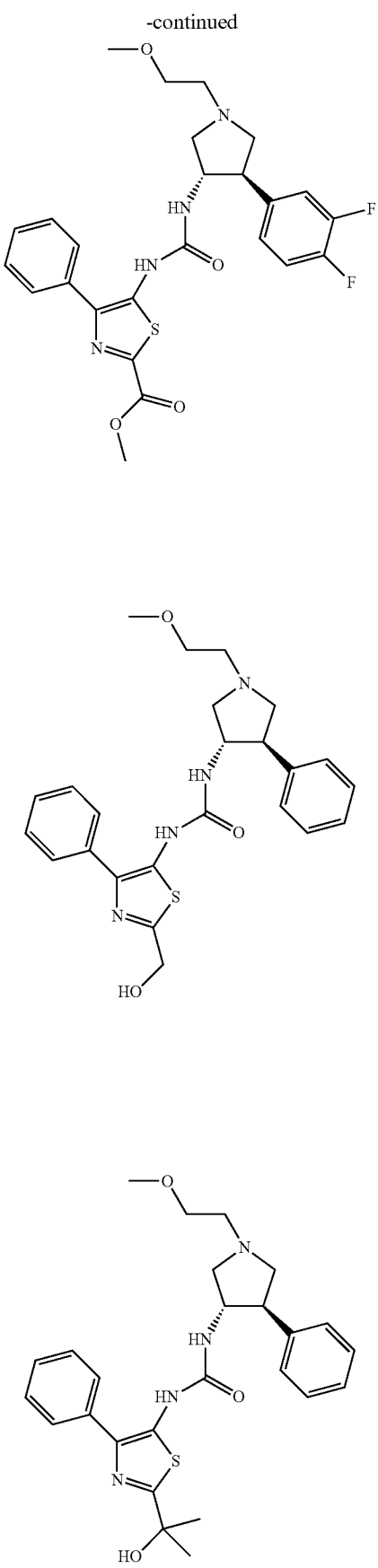

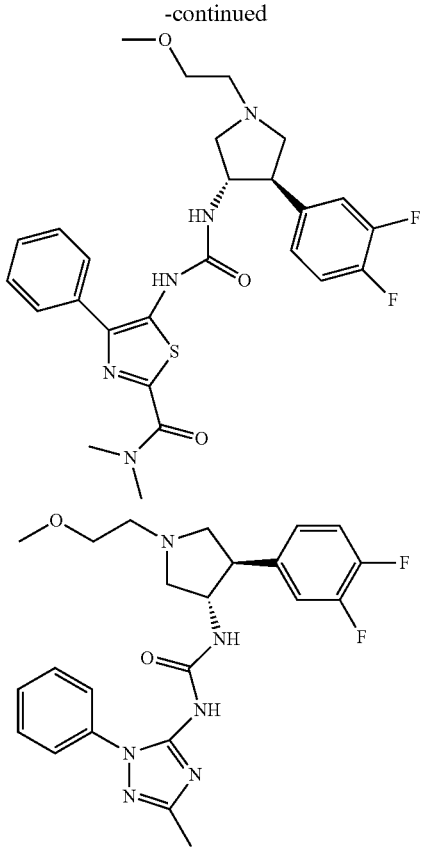
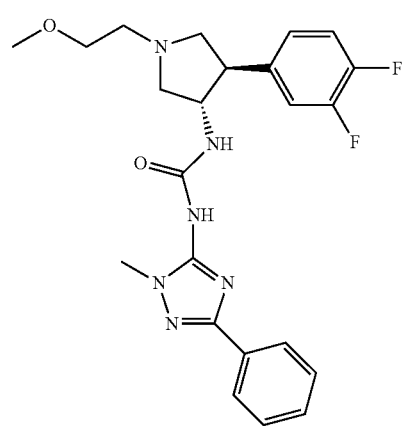
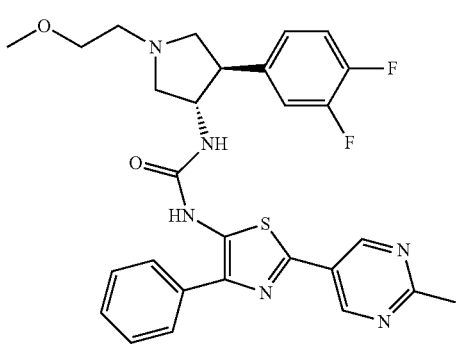

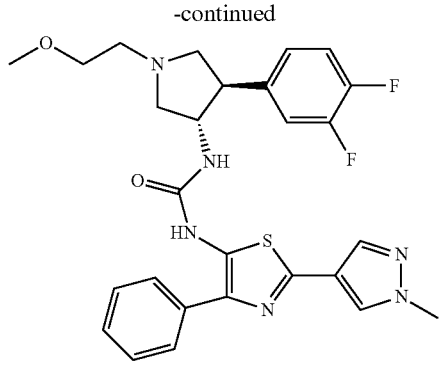

or a pharmaceutically acceptable salt thereof.

15. A pharmaceutical composition, which comprises a compound of Formula I as defined in claim 1 or a pharmaceutically acceptable salt thereof, and a pharmaceutically acceptable diluent or carrier.

16. A method for treating pain in a mammal, which comprises administering to said mammal a therapeutically effective amount of a compound of Formula I as defined in claim 1, or a pharmaceutically acceptable salt thereof.

17. A process for the preparation of a compound of claim 1, which comprises:

(a) for a compound of Formula I where X is O, coupling a corresponding compound having the formula II

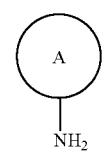

II with a corresponding compound having the formula III

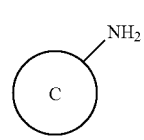

III where Ring C is as defined in claim 1, in the presence carbonyldiimidazole or triphosgene and a base; or (b) for a compound of Formula I where X is S, coupling a corresponding compound having the formula II

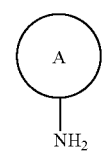

II with a corresponding compound having the formula III

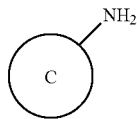

where Ring C is as defined in claim 1, in the presence di(1H-imidazol-2-yl)methanethione and a base; or
(c) for a compound of Formula I where X is O, coupling a corresponding compound having the formula II

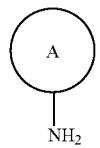

with a corresponding compound having the formula IV

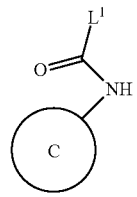

where Ring C is as defined in claim 1 and $L^1$ is a leaving group, in the presence of a base; or
(d) for a compound of Formula I where X is O, coupling a corresponding compound having the formula V

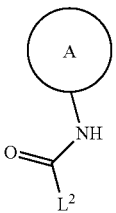

where $L^2$ is a leaving group, with a corresponding compound having the formula III

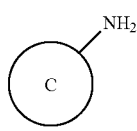

where Ring C is as defined in claim 1, in the presence of a base; or
(e) for a compound of Formula I where X is O, activating a corresponding compound having the formula VI

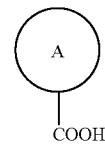

with diphenylphosphoryl azide followed by coupling the activated intermediate with a corresponding compound having the formula III

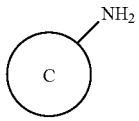

where Ring C is as defined in claim 1, in the presence a base; or
(f) for a compound of Formula I where X is O, coupling a corresponding compound having the formula II

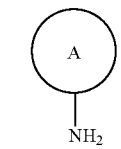

with a corresponding compound having the formula VII

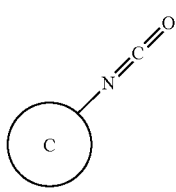

where Ring C is as defined in claim 1, in the presence of a base; or
(g) for a compound of Formula I where X is O, coupling a corresponding compound having the formula VIII

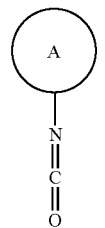

with a corresponding compound having the formula III

III where Ring C is as defined in claim 1, in the presence of a base; and optionally removing protecting groups and optionally preparing a pharmaceutically acceptable salt thereof;

wherein in any of the above methods (a), (b), (c), (d), (e), (f), or (g), the ring A is

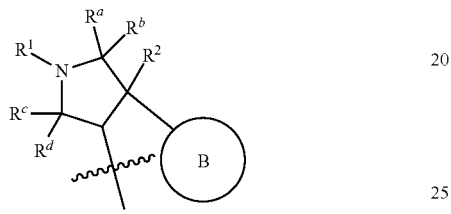

where $R^1$, $R^2$, Ring B, $R^a$, $R^b$, $R^c$ and $R^d$ are as defined in claim 1.

* * * * *

UNITED STATES PATENT AND TRADEMARK OFFICE
CERTIFICATE OF CORRECTION

PATENT NO. : 9,828,360 B2  
APPLICATION NO. : 14/442522  
DATED : November 28, 2017  
INVENTOR(S) : Shelley Allen et al.

Page 1 of 1

It is certified that error appears in the above-identified patent and that said Letters Patent is hereby corrected as shown below:

In the Claims

Column 130, Line 5, Claim 1, please delete "hetAr$^3$ (1-6C)alkyl," and insert -- hetAr$^3$(1-6C)alkyl, --;

Column 130, Line 5, Claim 1, please delete "Ar$^3$ (1-6C)alkyl," and insert -- Ar$^3$(1-6C)alkyl, --;

Column 130, Line 64, Claim 1, please delete "cycloalkyl)CH$_2$- (3-6C" and insert -- cycloalkyl)CH$_2$-(3-6C -- therefor.

Signed and Sealed this  
Twenty-fourth Day of April, 2018

Andrei Iancu  
*Director of the United States Patent and Trademark Office*